US010301360B2

(12) United States Patent
Deverman et al.

(10) Patent No.: US 10,301,360 B2
(45) Date of Patent: May 28, 2019

(54) SELECTIVE RECOVERY

(71) Applicant: California Institute of Technology, Pasadena, CA (US)

(72) Inventors: Benjamin E. Deverman, Pasadena, CA (US); Paul H. Patterson, Altadena, CA (US); Viviana Gradinaru, La Canada-Flintridge, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/422,259

(22) Filed: Feb. 1, 2017

(65) Prior Publication Data

US 2017/0240885 A1    Aug. 24, 2017

Related U.S. Application Data

(62) Division of application No. 14/485,024, filed on Sep. 12, 2014, now Pat. No. 9,585,971.

(60) Provisional application No. 61/877,506, filed on Sep. 13, 2013, provisional application No. 61/983,624, filed on Apr. 24, 2014, provisional application No. 62/020,658, filed on Jul. 3, 2014, provisional application No. 62/034,060, filed on Aug. 6, 2014.

(51) Int. Cl.

| | | |
|---|---|---|
| *A61K 39/12* | (2006.01) | |
| *C07K 14/005* | (2006.01) | |
| *A61K 38/17* | (2006.01) | |
| *A61K 38/20* | (2006.01) | |
| *A61K 38/47* | (2006.01) | |
| *A61K 38/48* | (2006.01) | |
| *A61K 38/50* | (2006.01) | |
| *A61K 39/395* | (2006.01) | |
| *A61K 48/00* | (2006.01) | |
| *C12N 7/00* | (2006.01) | |
| *C12N 15/86* | (2006.01) | |
| *C07K 7/06* | (2006.01) | |
| *C12N 15/10* | (2006.01) | |
| *A61K 38/00* | (2006.01) | |

(52) U.S. Cl.
CPC ........ *C07K 14/005* (2013.01); *A61K 38/1709* (2013.01); *A61K 38/2093* (2013.01); *A61K 38/47* (2013.01); *A61K 38/4813* (2013.01); *A61K 38/50* (2013.01); *A61K 39/3955* (2013.01); *A61K 48/005* (2013.01); *A61K 48/0058* (2013.01); *C07K 7/06* (2013.01); *C12N 7/00* (2013.01); *C12N 15/1068* (2013.01); *C12N 15/86* (2013.01); *A61K 38/00* (2013.01); *C07K 2319/33* (2013.01); *C12N 2750/14122* (2013.01); *C12N 2750/14143* (2013.01); *C12N 2750/14145* (2013.01); *C12N 2810/6027* (2013.01); *C12Y 304/14009* (2013.01); *C12Y 305/01015* (2013.01)

(58) Field of Classification Search
None
See application file for complete search history.

(56) References Cited

U.S. PATENT DOCUMENTS

| | | |
|---|---|---|
| 5,919,676 A | 7/1999 | Graham et al. |
| 6,228,646 B1 | 5/2001 | Hardy |
| 6,274,354 B1 | 8/2001 | Wilson et al. |
| 6,379,943 B1 | 4/2002 | Graham et al. |
| 6,410,271 B1 | 6/2002 | Zhu et al. |
| 9,018,138 B2 | 4/2015 | Lupold et al. |
| 2002/0058325 A1* | 5/2002 | Hardy ...................... C12N 7/00 435/235.1 |
| 2009/0042257 A1* | 2/2009 | Rodriguez ............... C12N 7/00 435/91.4 |
| 2009/0202490 A1 | 8/2009 | Schaffer et al. |
| 2013/0142764 A1 | 6/2013 | Davidson et al. |
| 2013/0195801 A1 | 8/2013 | Gao et al. |
| 2015/0079038 A1 | 3/2015 | Deverman et al. |
| 2015/0315612 A1 | 11/2015 | Wilson et al. |
| 2017/0166926 A1 | 6/2017 | Deverman et al. |
| 2017/0204144 A1 | 7/2017 | Deverman et al. |

FOREIGN PATENT DOCUMENTS

| | | |
|---|---|---|
| JP | 2014-518614 | 8/2014 |
| WO | WO 2005/017101 | 2/2005 |
| WO | WO 2012/145601 A2 | 10/2012 |
| WO | WO 2017/100671 A1 | 6/2017 |

OTHER PUBLICATIONS

Deverman et al., "Cre-dependent selection yields AAV variants for widespread gene transfer to the adult brain," Nature Biotechnology, Feb. 1, 2016, vol. 34, No. 2, pp. 204-209.
International Search Report and Written Opinion dated Mar. 28, 2017 for International Patent Application No. PCT/US2016/065969 filed Dec. 9, 2016, 18 pages.
Albert et al., "Site-specific integration of DNA into wild-type and mutant lox sites placed in the plant genome," The Plant Journal: for cell and molecular biology, 1995, vol. 7(4), pp. 649-659.
Araki, K. et al., "Targeted integration of DNA using mutant lox sites in embryonic stem cells," Nucleic Acids Res, 1997, vol. 25, pp. 868-872.
Aschauer, D.F. et al., "Analysis of transduction efficiency, tropism and axonal transport of AAV serotypes 1, 2, 5, 6, 8 and 9 in the mouse brain," 2013, PLoS One 8(9), e76310, 16 pages, doi:10.1371/journal.pone.0076310.
Asokan, A. et al., "The AAV Vector Toolkit: Poised at the Clinical Crossroads," Molecular Therapy : the Journal of the American Society of Gene Therapy, 2012, 20(4):699-708.
Asokan, A., "Reengineered AAV vectors: old dog, new tricks," Discovery medicine, 2010, vol. 9, pp. 399-403.

(Continued)

*Primary Examiner* — Benjamin P Blumel
(74) *Attorney, Agent, or Firm* — Knobbe, Martens, Olson & Bear LLP

(57) ABSTRACT

Provided herein are methods of selective screening. In addition, various targeting proteins and sequences, as well as methods of their use, are also provided.

17 Claims, 65 Drawing Sheets

Specification includes a Sequence Listing.

(56) References Cited

OTHER PUBLICATIONS

Ayuso, E. et al., "High AAV vector purity results in serotype- and tissue-independent enhancement of transduction efficiency," Gene Therapy, 2010, vol. 17(4), pp. 503-510, doi:10.1038/gt.2009.157.
Balazs, A.B. et al., Antibody-based protection against HIV infection by vectored immunoprophylaxis, Nature, 2011, vol. 481, No. 7379, pp. 81-84, doi:doi:10.1038/nature10660.
Balazs, A.B. et al., "Broad protection against influenza infection by vectored immunoprophylaxis in mice," Nature Biotechnology, Jul. 2013 31(7):647-52. doi:10.1038/nbt.2618.
Bartel, M. et al., "Enhancing the Clinical Potential of AAV Vectors by Capsid Engineering to Evade Pre-Existing Immunity," Frontiers in Microbiology, 2011, vol. 2, Article 204, 10 pages, doi 10.3389/fmicb.2011.00204.
Callaway, E.M., "Transneuronal circuit tracing with neurotropic viruses," Curr Opin Neurobiol, 2008, vol. 18, pp. 617-623.
Castle et al., "Long-distance axonal transport of AAV9 is driven by dynein and kinesin-2 and is trafficked in a highly motile Rab7-positive compartment," Molecular Therapy, 2014, vol. 22, pp. 554-566.
Castle, M.J. et al., "Adeno-Associated Virus Serotypes 1, 8, and 9 Share Conserved Mechanisms for Anterograde and Retrograde Axonal Transport," Hum Gene Ther., 2014, 25(8), pp. 705-720.
Cearley, C.N. et al., "A single injection of an adeno-associated virus vector into nuclei with divergent connections results in widespread vector distribution in the brain and global correction of a neurogenetic disease," The Journal of Neuroscience : the official journal of the Society for Neuroscience, 2007, vol. 27, pp. 9928-9940.
Chung, K. et al., "CLARITY for mapping the nervous system," Nat Methods, 2013, vol. 10, No. 6, pp. 508-513.
Dalkara, D. et al., "In vivo-directed evolution of a new adeno-associated virus for therapeutic outer retinal gene delivery from the vitreous," Science translational medicine, 2013, vol. 5, No. 189, pp. 189ra176, doi: 10.1126/scitranslmed.3005708.
Duque, S. et al., "Intravenous Administration of Self-complementary AAV9 Enables Transgene Delivery to Adult Motor Neurons," Molecular therapy : the journal of the American Society of Gene Therapy, 2009, vol. 17, pp. 1187-1196.
Excoffon, K.J.D.A. et al., "Directed evolution of adeno-associated virus to an infectious respiratory virus," Proceedings of the National Academy of Sciences of the United States of America, 2009, vol. 106, No. 10, pp. 3865-3870, doi:10.1073/pnas.0813365106.
Farris et al., "Improved splicing of adeno-associated viral (AAV) capsid protein-supplying pre-mRNAs leads to increased recombinant AAV vector production," Human Gene Therapy, 2008, vol. 19, pp. 1421-1427.
Fenno, L. et al., "The development and application of optogenetics," Annual review of neuroscience, 2011, vol. 34, pp. 389-412.
Fenno, L.E. et al., "Targeting cells with single vectors using multiple-feature Boolean logic," Nat Methods, 2014, vol. 11, pp. 763-772.
Flotte et al., "Adeno-associated virus vectors for gene therapy of cystic fibrosis," Methods Enzymol, 1998, vol. 292, pp. 717-732.
Foust, K.D. et al., "Intravascular AAV9 preferentially targets neonatal neurons and adult astrocytes," Nature biotechnology, 2009, vol. 27, pp. 59-65.
Foust, K.D. et al., "Rescue of the spinal muscular atrophy phenotype in a mouse model by early postnatal delivery of SMN," Nat Biotechnol, 2010, vol. 28, pp. 271-274, doi:10.1038/nbt.1610.
Foust, K.D. et al., "Therapeutic AAV9-mediated Suppression of Mutant SOD1 Slows Disease Progression and Extends Survival in Models of Inherited ALS," Molecular therapy: the journal of the American Society of Gene Therapy, 2013, vol. 21, No. 12, pp. 2148-2159, doi:10.1038/mt.2013.211.
Garcia, A.D.R. et al., "GFAP-expressing progenitors are the principal source of constitutive neurogenesis in adult mouse forebrain," Nature neuroscience, 2004, vol. 7, pp. 1233-1241, doi:10.1038/nn1340.

Garg, S.K. et al., "Systemic Delivery of MeCP2 Rescues Behavioral and Cellular Deficits in Female Mouse Models of Rett Syndrome," The Journal of neuroscience : the official journal of the Society for Neuroscience, 2013, vol. 33, pp. 13612-13620, doi:10.1523/JNEUROSCI.1854-13.2013.
Gaudet, D. et al., "Review of the clinical development of alipogene tiparvovec gene therapy for lipoprotein lipase deficiency," Atherosclerosis Supplements 2010, vol. 11, pp. 55-60, doi:10.1016/j.atherosclerosissup.2010.03.004.
Gibson et al., "Enzymatic assembly of DNA molecules up to several hundred kilobases," Nature Methods, 2009, vol. 6(5), pp. 343-345.
Gray, S.J. et al., "Directed Evolution of a Novel Adeno-associated Virus (AAV) Vector That Crosses the Seizure-compromised Blood-Brain Barrier (BBB)," Molecular therapy : the journal of the American Society of Gene Therapy, 2009, vol. 18, pp. 570-578.
Gray, S.J. et al., "Preclinical Differences of Intravascular AAV9 Delivery to Neurons and Glia: A Comparative Study of Adult Mice and Nonhuman Primates," Molecular therapy : the journal of the American Society of Gene Therapy, 2011, vol. 19, pp. 1058-1069.
Gray, S. J. et al., "Production of recombinant adeno-associated viral vectors and use in in vitro and in vivo administration," Current Protocols in Neuroscience / Editorial Board, Jacqueline N. Crawley . . . [Et Al.], 2011, Chapter 4, Unit 4.17, pp. 4.17.1-4.17.30, doi:10.1002/0471142301.ns0417s57.
Grieger, J. C. et al., "Production and characterization of adeno-associated viral vectors," Nature Protocols, 2006, vol. 1(3), pp. 1412-1428, doi:10.1038/nprot.2006.207.
Grimm, D. et al., "In vitro and in vivo gene therapy vector evolution via multispecies interbreeding and retargeting of adeno-associated viruses," Journal of virology, 2008, vol. 82, pp. 5887-5911.
Hirt, B., "Selective extraction of polyoma DNA from infected mouse cell cultures," Journal of Molecular Biology, 1967, vol. 26(2), pp. 365-369.
Hutson, T.H. et al., "Corticospinal tract transduction: a comparison of seven adeno-associated viral vector serotypes and a non-integrating lentiviral vector," Gene therapy, 2012, vol. 19, pp. 49-60.
Inagaki, K. et al., "Frequency and spectrum of genomic integration of recombinant adeno-associated virus serotype 8 vector in neonatal mouse liver," J Virol, 2008, vol. 82, pp. 9513-9524.
International Preliminary Report on Patentability dated Mar. 15, 2016 for International Patent Application No. PCT/US2014/055490 filed Sep. 12, 2014, 10 pages.
International Search Report and Written Opinion dated Dec. 24, 2014 for International Patent Application No. PCT/US2014/055490 filed Sep. 12, 2014, 18 pages.
Kaeppel, C. et al., "A largely random AAV integration profile after LPLD gene therapy," Nat Med, 2013, vol. 19, pp. 889-891.
Kaplitt et al., "Long-term gene expression and phenotypic correction using adeno-associated virus vectors in the mammalian brain," Nature, 1994, vol. 8, pp. 148-154.
Kaplitt, M.G. et al., "Safety and tolerability of gene therapy with an adeno-associated virus (AAV) borne GAD gene for Parkinsons disease: an open label, phase I trial," Lancet, 2007, vol. 369, pp. 2097-2105.
Kessler et al., "Gene delivery to skeletal muscle results in sustained expression and systemic delivery of a therapeutic protein," Proceedings of the National Academy of Sciences USA, 1996, vol. 93, pp. 14082-14087.
Knipe, D. et al., "Fields of virology," edition (2006), 2007, Section 57, vol. II (Lippincott Williams & Wilkins), pp. 2107-2185.
Koerber, J.T. et al., "Construction of diverse adeno-associated viral libraries for directed evolution of enhanced gene delivery vehicles," Nature protocols, 2006, vol. 1, pp. 701-706.
Levitt, N. et al., "Definition of an efficient synthetic poly(A) site," Genes and Development, 1989, vol. 3, pp. 1019-1025.
Limber's, M.P. et al., "Intranasal antibody gene transfer in mice and ferrets elicits broad protection against pandemic influenza," Sci Transl Med, 2013, 5(187):187ra72, 10 pages.
Lisowski, L. et al., "Selection and evaluation of clinically relevant AAV variants in a xenograft liver model," Nature, 2014, vol. 506, pp. 382-386.

(56) References Cited

OTHER PUBLICATIONS

Low, K. et al., "Direct and retrograde transduction of nigral neurons with AAV6, 8, and 9 and intraneuronal persistence of viral particles," Human gene therapy, 2013, vol. 24, pp. 613-629.
Luo, L. et al., "Genetic dissection of neural circuits," Neuron, 2008, vol. 57, pp. 634-660.
Maguire, A.M. et al., "Safety and efficacy of gene transfer for Leber's congenital amaurosis," N Engl J Med, 2008, vol. 358, pp. 2240-2248, doi:10.1056/NEJMoa0802315.
Maguire, C. A. et al., Directed evolution of adeno-associated virus for glioma cell transduction, Journal of neuro-oncology, 2010, vol. 96, No. 3, pp. 337-347, doi:10.1007/s11060-009-9972-7.
Maheshri, N. et al., "Directed evolution of adeno-associated virus yields enhanced gene delivery vectors," Nature biotechnology, 2006, vol. 24, No. 2, pp. 198-204, doi:10.1038/nbt1182.
Marshel, J.H. et al., "Targeting single neuronal networks for gene expression and cell labeling in vivo," Neuron, 2010, vol. 67, pp. 562-574.
Martino, a.T. et al., "The genome of self-complementary adeno-associated viral vectors increases Toll-like receptor 9-dependent innate immune responses in the liver," Blood, 2011, vol. 117, pp. 6459-6468.
McBride, J.L. et al., "Preclinical safety of RNAi-mediated HTT suppression in the rhesus macaque as a potential therapy for Huntingtons disease," Molecular Therapy : the Journal of the American Society of Gene Therapy, 2011, vol. 19, pp. 2152-2162.
McCarty, D.M., "Self-complementary AAV vectors; advances and applications," Molecular Therapy : the Journal of the American Society of Gene Therapy, 2008, vol. 16, pp. 1648-1656.
MGI Mouse Genome Informatics Web Site. Available at http://www.informatics.jax.org in some form no later than Aug. 6, 2014. While no copy of the website as it existed on Aug. 6, 2014 is in Applicant's possession, Applicant has provided a copy of the website that was printed on Jan. 22, 2015, 1 page.
Mittermeyer, G. et al., "Long-term evaluation of a phase 1 study of AADC gene therapy for Parkinson's disease," Hum Gene Ther, 2012, vol. 23, pp. 377-381.
Nathwani, A. C. et al., "Adenovirus-associated virus vector-mediated gene transfer in hemophilia B, "The New England Journal of Medicine, 2011, vol. 365, No. 25, pp. 2357-2365, doi:10.1056/NEJMoa1108046.
Nathwani, A.G. et al., "Long-term safety and efficacy following systemic administration of a self-complementary AAV vector encoding human FIX pseudotyped with serotype 5 and 8 capsid proteins," Molecular therapy : the journal of the American Society of Gene Therapy, 2011, vol. 19, pp. 876-885, doi:10.1038/mt.2010.274.
National Institute of Health. Advisory Committee to the Director, Interim Report: Brain Research Through Advancing Innovation Neurotechnologies (BRAIN) Working Group, Sep. 16, 2013, pp. 1-58.
Nowrouzi, A. et al., "Integration frequency and intermolecular recombination of rAAV vectors in non-human primate skeletal muscle and liver," Mol Ther, 2012, vol. 20, pp. 1177-1186.
Osakada, F. et al., "New rabies virus variants for monitoring and manipulating activity and gene expression in defined neural circuits," Neuron, 2011, vol. 71, pp. 617-631.
Pulicherla, N. et al., "Engineering Liver-detargeted AAV9 Vectors for Cardiac and Musculoskeletal Gene Transfer," Molecular Therapy: the Journal of the American Society of Gene Therapy, 2011, vol. 19, pp. 1070-1078, doi:10.1038/mt.2011.22.
Qiu et al., "Characterization of the Transcription Profile of Adeno-Associated Virus Type 5 Reveals a Number of Unique Features Compared to Previously Characterized Adeno-Associated Viruses," Journal of Virology., 2002, vol. 76, pp. 12435-12447.
Salegio, E.A. et al., "Axonal transport of adeno-associated viral vectors is serotype-dependent," Gene Ther, 2013, vol. 20, pp. 348-352.
Samaranch et al., "AAV9 Transduction in the Central Nervous System of Non-Human Primates," Human gene therapy, 2011, vol. 22, pp. 329-337.
Samaranch, L. et al., "Adeno-associated virus serotype 9 transduction in the central nervous system of nonhuman primates," Hum Gene Ther, 2012, vol. 23, pp. 382-389, doi:10.1089/hum.2011.200.
Sambrook et al., "Molecular Cloning: A Laboratory Manual," 2nd Ed., Cold Spring Harbor Laboratory Press, Cold Spring Harbor, N.Y., 1989, 39 pages.
Savitt et al., "Bcl-x Is Required for Proper Development of the Mouse Substantia Nigra," The Journal of Neuroscience, 2005, vol. 25, pp. 6721-6728.
Schaffer, D.V. et al., "Molecular Engineering of Viral Gene Delivery Vehicles," Annual Review of Biomedical Engineering, 2008, vol. 10, pp. 169-194.
Simonelli, F. et al., "Gene Therapy for Leber's Congenital Amaurosis is Safe and Effective Through 1.5 Years After Vector Administration," Molecular Therapy : the Journal of the American Society of Gene Therapy, 2009, vol. 18(3), pp. 643-650, doi:10.1038/mt.2009.277.
Smith, A.D. et al., "The neural network of the basal ganglia as revealed by the study of synaptic connections of identified neurones," Trends Neurosci, 1990, vol. 13, pp. 259-265.
Sonntag, F. et al., "A viral assembly factor promotes AAV2 capsid formation in the nucleolus," Proceedings of the National Academy of Sciences of the United States of America, 2010, vol. 107, pp. 10220-10225, doi:10.1073/pnas.1001673107.
Southwell, A.L. et al., "Intrabody gene therapy ameliorates motor, cognitive, and neuropathological symptoms in multiple mouse models of Huntington's disease," The Journal of Neuroscience : the official journal of the Society for Neuroscience, 2009, vol. 29, No. 43, pp. 13589-13602, doi:110.1523/JNEUROSCI.4286-09.2009.
Tang et al., "Role of ornithine decarboxylase antizyme inhibitor in vivo", Genes to Cells, Dec. 10, 2008, vol. 14, No. 1, pp. 79-87, XP055324401.
Tomer, R. et al., "Advanced CLARITY for rapid and high-resolution imaging of intact tissues," Nat Protoc, 2014, vol. 9, pp. 1682-1697.
Valori, C.F. et al., "Systemic delivery of scAAV9 expressing SMN prolongs survival in a model of spinal muscular atrophy," Sci Transl Med, 2010, 2(35):35ra42, 9 pages, doi:10.1126/scitranslmed.3000830.
VanDendriessche, T. et al., "Efficacy and safety of adeno-associated viral vectors based on serotype 8 and 9 vs. lentiviral vectors for hemophilia B gene therapy," Journal of thrombosis and haemostasis : JTH, 2007, vol. 5, pp. 16-24.
Wagner et al., "Efficient and persistent gene transfer of AAV-CFTR in maxillary sinus," Lancet, 1998, vol. 351, Issue 9117, pp. 1702-1703.
Wall, N.R. et al., "Differential innervation of direct- and indirect-pathway striatal projection neurons," Neuron, 2013, vol. 79, pp. 347-360.
Wang, J. et al., "Existence of transient functional double-stranded DNA intermediates during recombinant AAV transduction," Proceedings of the National Academy of Sciences of the United States of America, 2007, vol. 104, No. 32, pp. 13104-13109, doi:10.1073/pnas.0702778104.
Wu et al., "Mutational analysis of the adeno-associated virus type 2 (AAV2) capsid gene and construction of AAV2 vectors with altered tropism," Journal of Virology, 2000, vol. 74, No. 18, pp. 8635-8647.
Wu, T. et al., "Self-complementary AAVs induce more potent transgene product-specific immune responses compared to a single-stranded genome," Mol Ther, 2012, vol. 20, pp. 572-579.
Yang, B. et al., Global CNS Transduction of Adult Mice by Intravenously Delivered rAAVrh.8 and rAAVrh.10 and Nonhuman Primates by rAAVrh.10, Molecular Therapy, 2014a, vol. 22, pp. 1299-1309.
Yang, B. et al., "Single-Cell Phenotyping within Transparent Intact Tissue through Whole-Body Clearing," Cell, 2014, vol. 158, pp. 945-958. doi:10.1016/j.cell.2014.07.017.
Yang, L. et al., "A myocardium tropic adeno-associated virus (AAV) evolved by DNA shuffling and in vivo selection," Proceedings of the National Academy of Sciences of the United States of America, 2009, vol. 106, pp. 3946-3951.

(56) References Cited

OTHER PUBLICATIONS

Zariwala et al., "A Cre-dependent GCaMP3 reporter mouse for neuronal imaging in vivo", J. Neurosci., Feb. 29, 2012, vol. 32, No. 9, pp. 3131-3141.
Zolotukhin, S. et al., "Recombinant adeno-associated virus purification using novel methods improves infectious titer and yield," Gene therapy, 1999, vol. 6, pp. 973-985, doi:10.1038/sj.gt.3300938.
Bartlett, J.S. et al., "Selective and rapid uptake of adeno-associated virus type 2 in brain," Human Gene Therapy, Mar. 1998, vol. 9, No. 8, pp. 1181-1186, doi:10.1089/hum.1998.9.8-1181.
Bartlett, J.S. et al., "Targeted adeno-associated virus vector transduction of nonpermissive cells mediated by a bispecific F(ab'gamma)2 antibody," Nat Biotechnol, 1999, vol. 17, pp. 181-186, doi:10.1038/6185.
Betley, J.N. et al., "Adeno-associated viral vectors for mapping, monitoring, and manipulating neural circuits," Hum Gene Ther, 2011, vol. 22, pp. 669-677, doi:10.1087/hum.2010.204.
Bevan, A.K. et al., "Systemic gene delivery in large species for targeting spinal cord, brain, and peripheral tissues for pediatric disorders," Molecular therapy : the journal of the American Society of Gene Therapy, 2011, vol. 19, pp. 1971-1980, doi:10.1038/mt.2011.157.
Borel, F. et al., "Recombinant AAV as a platform for translating the therapeutic potential of RNA interference," Molecular Therapy : the Journal of the American Society of Gene Therapy, 2014, vol. 22, pp. 692-701, doi:10.1038/mt.2013.285.
Boudreau, R.L. et al., "Nonallele-specific silencing of mutant and wild-type huntingtin demonstrates therapeutic efficacy in Huntington's disease mice," Molecular therapy : the journal of the American Society of Gene Therapy, 2009, vol. 17, pp. 1053-1063, doi:10.1038/mt.2009.17.
Boutin, S. et al., "Prevalence of serum IgG and neutralizing factors against adeno-associated virus (AAV) types 1, 2, 5, 6, 8, and 9 in the healthy population: implications for gene therapy using AAV vectors," Hum Gene Ther, 2010, vol. 21, pp. 704-712, doi:10.1089/hum.2009.182.
Calcedo, R. et al., "Worldwide epidemiology of neutralizing antibodies to adeno-associated viruses," J Infect Dis, 2009, vol. 199, pp. 381-390, doi:10.1086/595830.
Chakrabarty, P., et al., "Capsid serotype and timing of injection determines AAV transduction in the neonatal mice brain," PLoS One, 2013, vol. 8, pp. e67680, doi:10.1371/journal.pone.0067680.
Chiorini, J.A. et al., Cloning and characterization of adeno-associated virus type, J. Virol., 1999, vol. 73, pp. 1309-1319.
Dufour, B.D., et al., "Intrajugular vein delivery of AAV9-RNAi prevents neuropathological changes and weight loss in Huntington's disease mice," Molecular therapy : the journal of the American Society of Gene Therapy, 2014, vol. 22, pp. 797-810, doi:10.1038/mt.2013.289.
European Search Report dated Jan. 20, 2017 for European Patent Application No. 14843244.6, in 6 pages.
Guenthner, C.J., et al., "Permanent genetic access to transiently active neurons via TRAP: targeted recombination in active populations," Neuron, 2013, vol. 78, pp. 773-784, doi:10.1016/j.neuron.2013.03.025.
Hancock, J.F. et al., "A CAAX or a CAAL motif and a second signal are sufficient for plasma membrane targeting of ras proteins," EMBO J., 1991, vol. 10, pp. 4033-4039.
High, K.H., et al., "Current status of haemophilia gene therapy," Haemophilia : the official journal of the World Federation of Hemophilia, 2014, 20 Suppl. 4, pp. 43-49, doi:10.1111/hae.12411.
Inagaki, K. et al., "Robust systemic transduction with AAV9 vectors in mice: efficient global cardiac gene transfer superior to that of AAV8," Molecular therapy : the journal of the American Society of Gene Therapy, 2006, vol. 14, pp. 45-53, doi:10.1016/j.ymthe.2006.03.014.
Izpisua Belmonte, J.C., et al., "Brains, genes, and primates," Neuron, 2015, vol. 86, pp. 617-631, doi:10.1016/j.neuron.2015.03.021.
Kawashima, T., et al., "Functional labeling of neurons and their projections using the synthetic activity-dependent promoter E-SARE," Nat Methods, 2013, vol. 10, pp. 889-895, doi:10.1038/nmeth.2559.
Maguire, C.A., et al., "Gene therapy for the nervous system: challenges and new strategies," Neurotherapeutics, 2014, vol. 11, pp. 817-839, doi:10.1007/s13311-014-0299-5.
Muller, O.J., et al., "Random peptide libraries displayed on adeno-associated virus to select for targeted gene therapy vectors," Nat Biotechnol, 2003, vol. 21, pp. 1040-1046, doi:10.1038/nbt856.
Ojala, D.S., et al., "Adeno-associated virus vectors and neurological gene therapy," Neuroscientist, 2015, vol. 21, pp. 84-98, doi:10.1177/1073858414521870.
Pasca, A.M., et al., "Functional cortical neurons and astrocytes from human pluripotent stem cells in 3D culture," Nature methods, 2015, vol. 12, pp. 671-678, doi:10.1038/nmeth.3415.
Perdomini, M. et al., "Prevention and reversal of severe mitochondrial cardiomyopathy by gene therapy in a mouse model of Friedreich's ataxia," Nat. Med., 2014, vol. 20, pp. 542-547, doi:10.1038/nm.3510.
Schuster, D.J. et al., "Biodistribution of adeno-associated virus serotype 9 (AAV9) vector after intrathecal and intravenous delivery in mouse," Front Neuroanat, 2014, vol. 8, Article 42, 14 pages, doi:10.3389/fnana.2014.00042.
Shaner, N.C. et al., "A bright monomeric green fluorescent protein derived from Branchiostoma lanceolatum," Nat Methods, 2013, vol. 10, pp. 407-409.
Van Der Marel, S., et al., "Neutralizing antibodies against adeno-associated viruses in inflammatory bowel disease patients: implications for gene therapy," Inflamm Bowel Dis, 2011, vol. 17, pp. 2436-2442, doi:10.1002/ibd.21673.
Wall, N.R., et al., "Monosynaptic circuit tracing in vivo through Cre-dependent targeting and complementation of modified rabies virus," Proc Natl Acad Sci USA, 2010, vol. 107, pp. 21848-21853, doi:10.1073/pnas.1011756107.
Wang, H., et al., "Widespread spinal cord transduction by intrathecal injection of rAAV delivers efficacious RNAi therapy for amyotrophic lateral sclerosis," Hum Mol Genet, 2014, vol. 23, pp. 668-681, doi:10.1093/hmg/ddt454.
Wobus, C.E., et al., "Monoclonal antibodies against the adeno-associated virus type 2 (AAV-2) capsid: epitope mapping and identification of capsid domains involved in AAV-2-cell interaction and neutralization of AAV-2 infection," J Virol, 2000, vol. 74, pp. 9281-9293.
Wu, Z., et al., "Adeno-associated virus serotypes: vector toolkit for human gene therapy," Molecular therapy : the journal of the American Society of Gene Therapy, 2006, vol. 14, pp. 316-327, doi:10.1016/j.ymthe.2006.05.009.
Xie, et al., "MicroRNA-regulated, Systemically Delivered rAAV9: A step closer to CNS-restricted transgene expression," Molecular therapy, 2010, vol. 19, pp. 526-535, doi:10.1038/mt.2010.279.
Ying, Y., et al., "Heart-targeted adeno-associated viral vectors selected by in vivo biopanning of a random viral display peptide library," Gene therapy, 2010, vol. 17, pp. 980-990, doi:10.1038/gt.2010.44.
Bartel et al., "Directed evolution of novel adeno-associated viruses for therapeutic gene delivery," Gene Therapy, 2012, vol. 19(6), pp. 694-700, http://doi.org/10.1038/gt.2012.20.
Groth et al., "A phage integrase directs efficient site-specific integration in human cells," Proceedings of the National Academy of Sciences of the United States of America, 2000, vol. 97(11), pp. 5995-6000, http://doi.org/10.1073/pnas.090527097.
Huser et al., "Kinetics and frequency of adeno-associated virus site-specific integration into human chromosome 19 monitored by quantitative real-time PCR," The Journal of Virology, 2002, vol. 76(15), pp. 7554-7559, http://doi.org/DOI: 10.1128/JVI.76.15.7554-7559.2002.
Koerber et al., "DNA shuffling of adeno-associated virus yields functionally diverse viral progeny," Molecular Therapy: the Journal of the American Society of Gene Therapy, 2008, vol. 16(10), pp. 1703-1709, http://doi.org/10.1038/mt.2008.167.
Koerber et al., "Molecular Evolution of Adeno-associated Virus for Enhanced Glial Gene Delivery," Molecular Therapy: the Journal of

(56) References Cited

OTHER PUBLICATIONS the American Society of Gene Therapy, 2009, vol. 17(12), pp. 2088-2095, http://doi.org/10.1038/mt.2009.184.
Schaffer et al., "Directed evolution of AAV mutants for enhanced gene delivery," Conference Proceedings: .Annual International Conference of the IEEE Engineering in Medicine and Biology Society. IEEE Engineering in Medicine and Biology Society. Conference, 5, 2004, pp. 3520-3523, http://doi.org/10.1109/IEMBS.2004.1403990.
Varadi et al., "Novel random peptide libraries displayed on AAV serotype 9 for selection of endothelial cell-directed gene transfer vectors," Gene Therapy, 2012, vol. 19(8), pp. 800-809, http://doi.org/10.1038/gt.2011.143.
Waterkamp et al., "Isolation of targeted AAV2 vectors from novel virus display libraries," The Journal of Gene Medicine, 2006, vol. 8(11), pp. 1307-1319, http://doi.org/10.1002/jgm.967.
Communication pursuant to Article 94(3) EPC dated Sep. 8, 2018 in European Patent Application No. 14843244.6.
Office Action dated Sep. 6, 2017 in U.S. Appl. No. 15/422,237, filed Feb. 1, 2017.
Communication pursuant to Article 94(3) EPC dated Aug. 9, 2018 in European Patent Application No. 14843244.6.

\* cited by examiner

Capsid amino Acid sequences for variants G2B-13, G2B-26, TH1.1-32 and TH1.1-35

G2B-13
```
MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF    100
QERLKEDTSFGGNLGRAVFQAKKRLLEPLGLVEEAAKTAPGKKRPVEQSPQEPDSSAGIGKSGAQPAKKRLNFGQTGDTESVPDPQPIGEPPAAPSGVGS    200
LTMASGGGAPVADNNEGADGVGSSSGNWHCDSQWLGDRVITTSTVQVFTDSDYQLPYVLGSAHEGCLPPFPADVFMIPQYGYLTLNDGSQAVGRSSFYCLEYF    300
LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF    400
PSQMLRTGNNFQFSYEFENVPFHSSYAHSQSLDRLMNPLIDQYLYLSRTIQSSQTPRQTLKFSVAGPSNMAVQGRNYIPGPSYRQQRVSTTVTQNNNSE    500
FAWPGASSWALNGRNSLMNPGPAMASHKEGEDRFFPLSGSLIFGKQGTGRDNVDADKVMITNEEEIKTTNPVATESYGQVATNHQSAQAQTGWVQNQG    600
ILPGMVWQDRDVYLQGPIWAKIPHTDGNFHPSPLMGGFGMKHPPPQILKNTPVPADPPTAFNKDKLNSFITQYSTGQVSVEIEWELQKENSKRWNPEIQ    700
YTSNYYKSNNVEFAVNTEGVYSEPRPIGTRYLTRNL        SEQ ID NO: 12
```

G2B-26
```
MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF    100
QERLKEDTSFGGNLGRAVFQAKKRLLEPLGLVEEAAKTAPGKKRPVEQSPQEPDSSAGIGKSGAQPAKKRLNFGQTGDTESVPDPQPIGEPPAAPSGVGS    200
LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR    300
PSQMLRTGNNFQFSYEFENVPFHSSYAHSQSLDRLMNPLIDQYLYLSRTINGSGQNQQTLKFSVAGPSNMAVQGRNYIPGPSYRQQRVSTTVTQNNNSE    400
FAWPGASSWALNGRNSLMNPGPAMASHKEGEDRFFPLSGSLIFGKQGTGRDNVDADKVMITNEEEIKTTNPVATESYGQVATNHQSAQTLAVPFKAQAQT    500
GWVQNQGILPGMVWQDRDVYLQGPIWAKIPHTDGNFHPSPLMGGFGMKHPPPQILKNTPVPADPPTAFNKDKLNSFITQYSTGQVSVEIEWELQKENSK    600
RWNPEIQYTSNYYKSNNVEFAVNTEGVYSEPRPIGTRYLTRNL        SEQ ID NO: 13    700
```

TH1.1-32
```
MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF    100
QERLKEDTSFGGNLGRAVFQAKKRLLEPLGLVEEAAKTAPGKKRPVEQSPQEPDSSAGIGKSGAQPAKKRLNFGQTGDTESVPDPQPIGEPPAAPSGVGS    200
LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR    300
PSQMLRTGNNFQFSYEFENVPFHSSYAHSQSLDRLMNPLIDQYLYLSRTIILGTGTSQTLKFSVAGPSNMAVQGRNYIPGPSYRQQRVSTTVTQNNNSE    400
FAWPGASSWALNGRNSLMNPGPAMASHKEGEDRFFPLSGSLIFGKQGTGRDNVDADKVMITNEEEIKTTNPVATESYGQVATNHQSAQTRTNPEAAQAQT    500
GWVQNQGILPGMVWQDRDVYLQGPIWAKIPHTDGNFHPSPLMGGFGMKHPPPQILKNTPVPADPPTAFNKDKLNSFITQYSTGQVSVEIEWELQKENSK    600
RWNPEIQYTSNYYKSNNVEFAVNTEGVYSEPRPIGTRYLTRNL        SEQ ID NO: 14    700
```

TH1.1-35
```
MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF    100
QERLKEDTSFGGNLGRAVFQAKKRLLEPLGLVEEAAKTAPGKKRPVEQSPQEPDSSAGIGKSGAQPAKKRLNFGQTGDTESVPDPQPIGEPPAAPSGVGS    200
LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR    300
PSQMLRTGNNFQFSYEFENVPFHSSYAHSQSLDRLMNPLIDQYLYLSRTIILGTGTSQTLKFSVAGPSNMAVQGRNYIPGPSYRQQRVSTTVTQNNNSE    400
FAWPGASSWALNGRNSLMNPGPAMASHKEGEDRFFPLSGSLIFGKQGTGRDNVDADKVMITNEEEIKTTNPVATESYGQVATNHQSAQNGGTSSSAQAQT    500
GWVQNQGILPGMVWQDRDVYLQGPIWAKIPHTDGNFHPSPLMGGFGMKHPPPQILKNTPVPADPPTAFNKDKLNSFITQYSTGQVSVEIEWELQKENSK    600
RWNPEIQYTSNYYKSNNVEFAVNTEGVYSEPRPIGTRYLTRNL        SEQ ID NO: 14    700
```

FIG. 1A

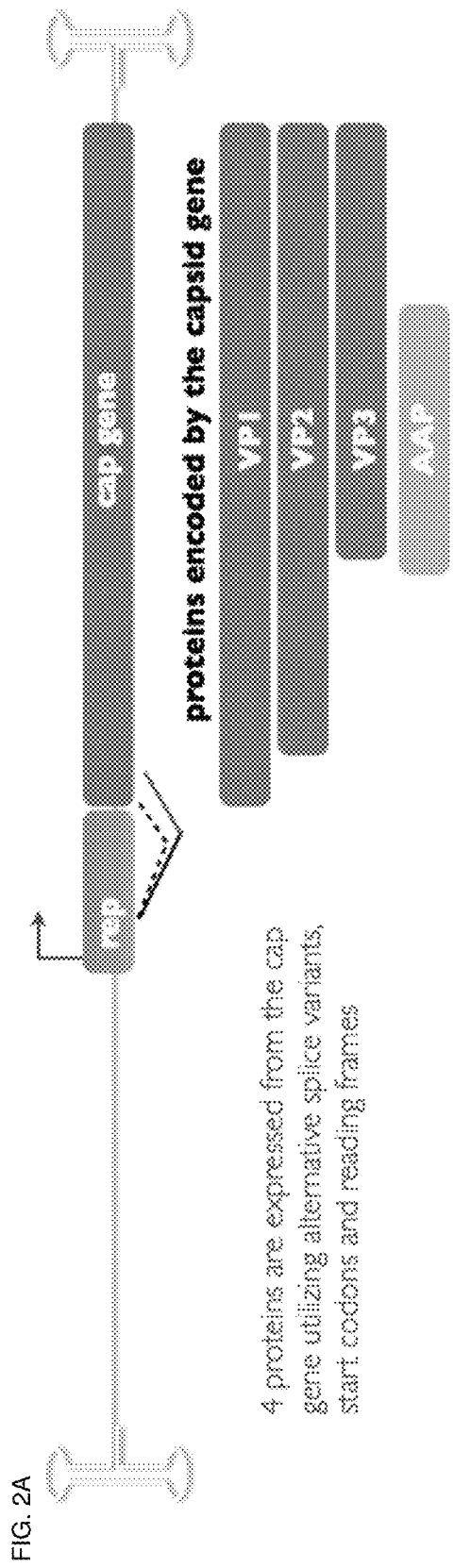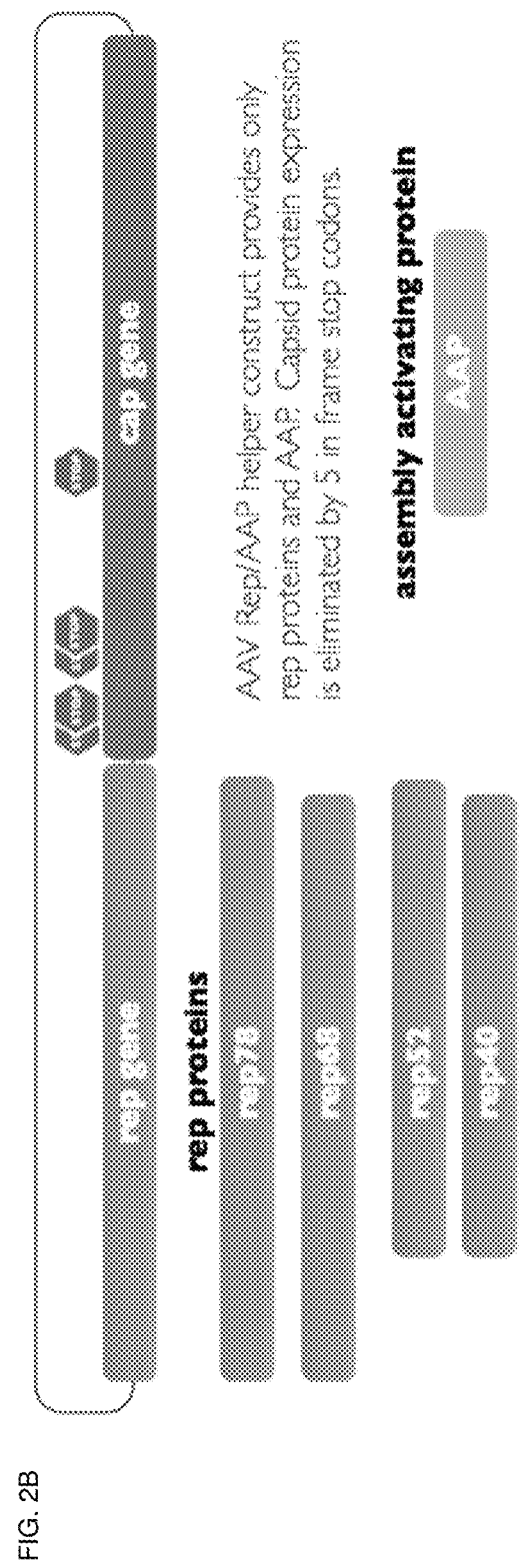
FIG. 2A
FIG. 2B

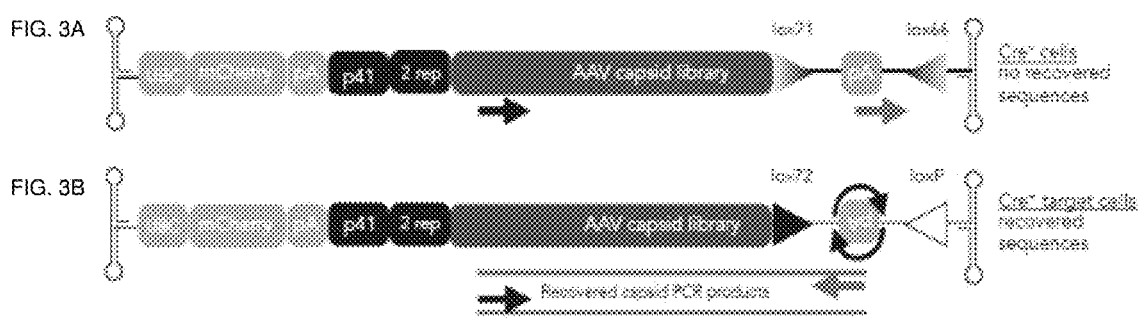

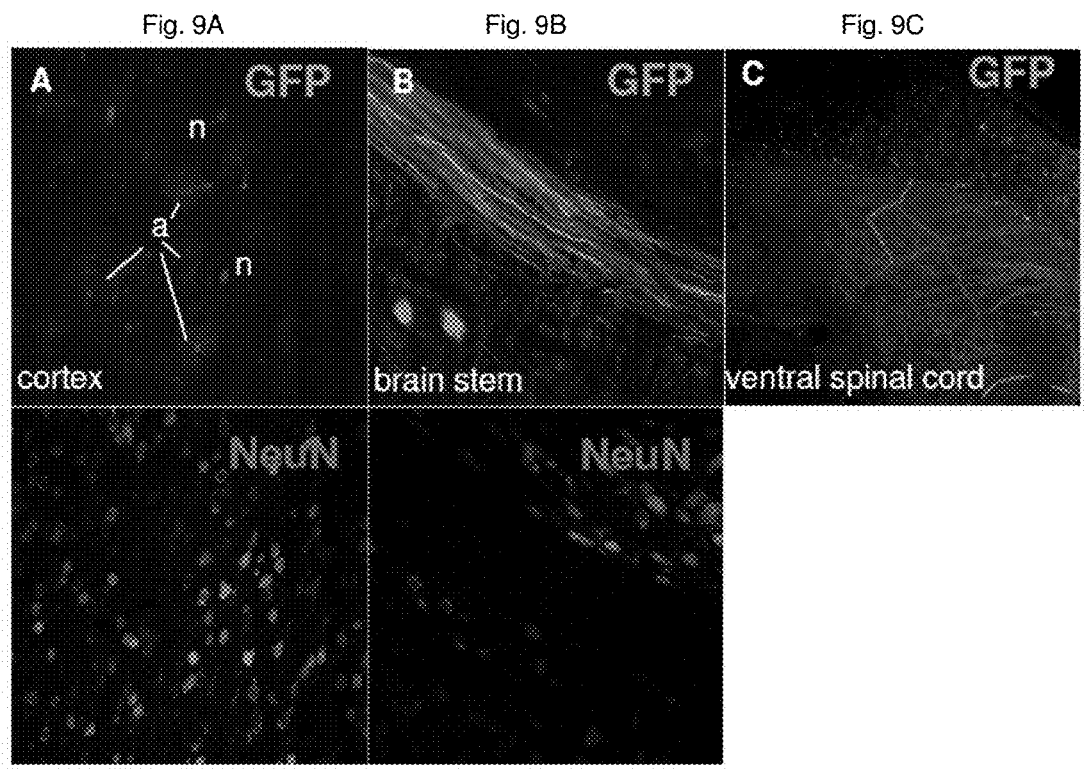

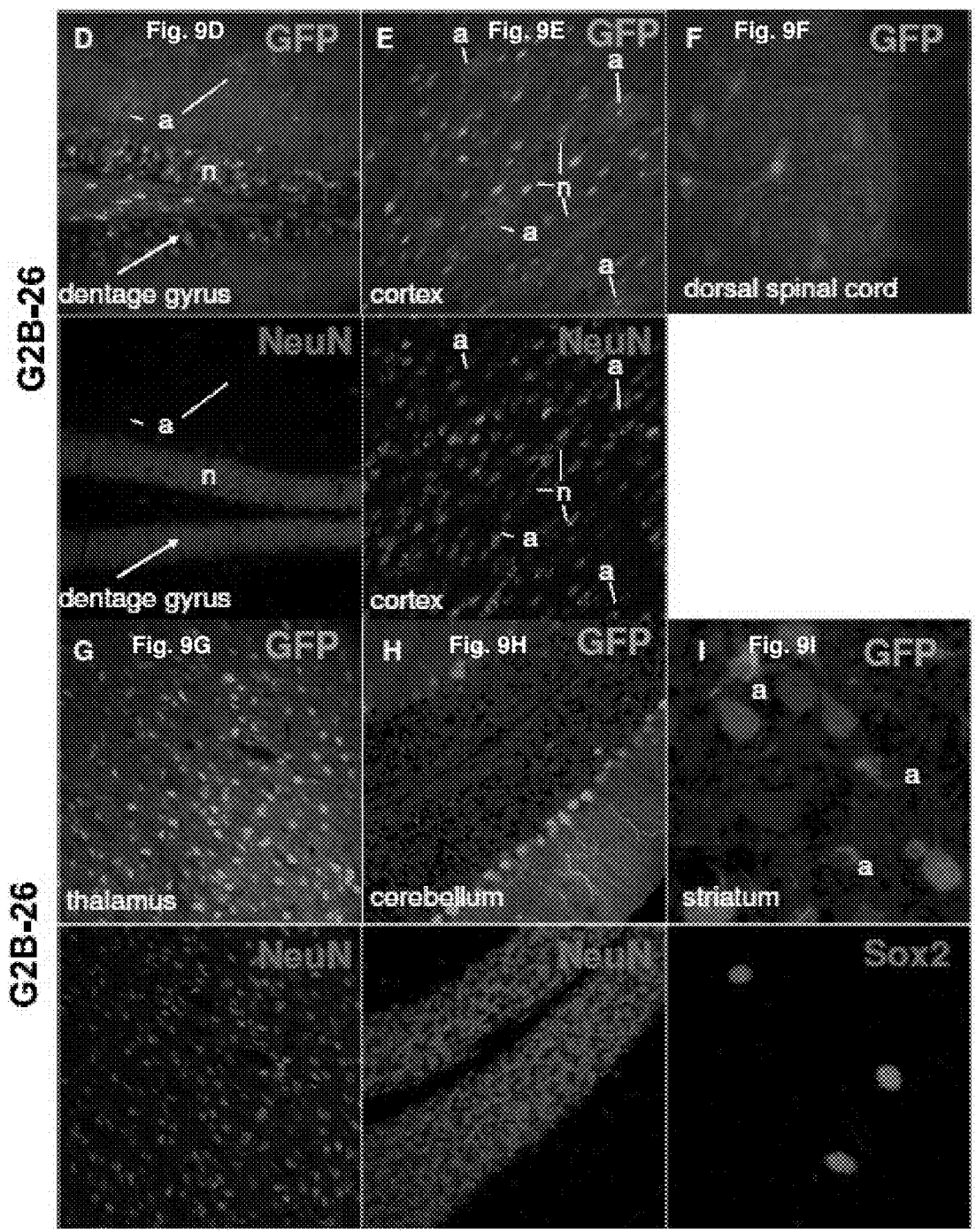

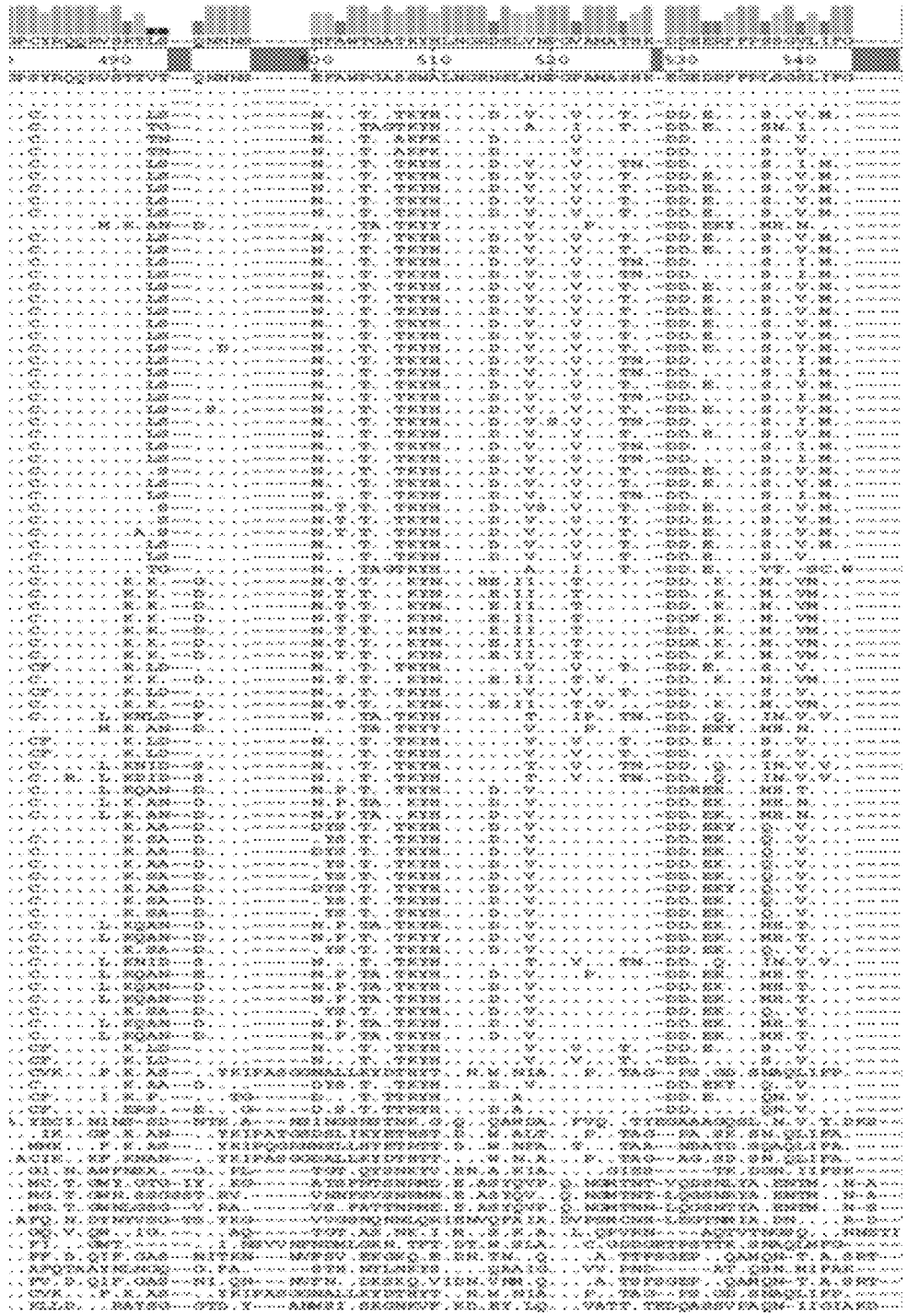
Fig. 13, con't.

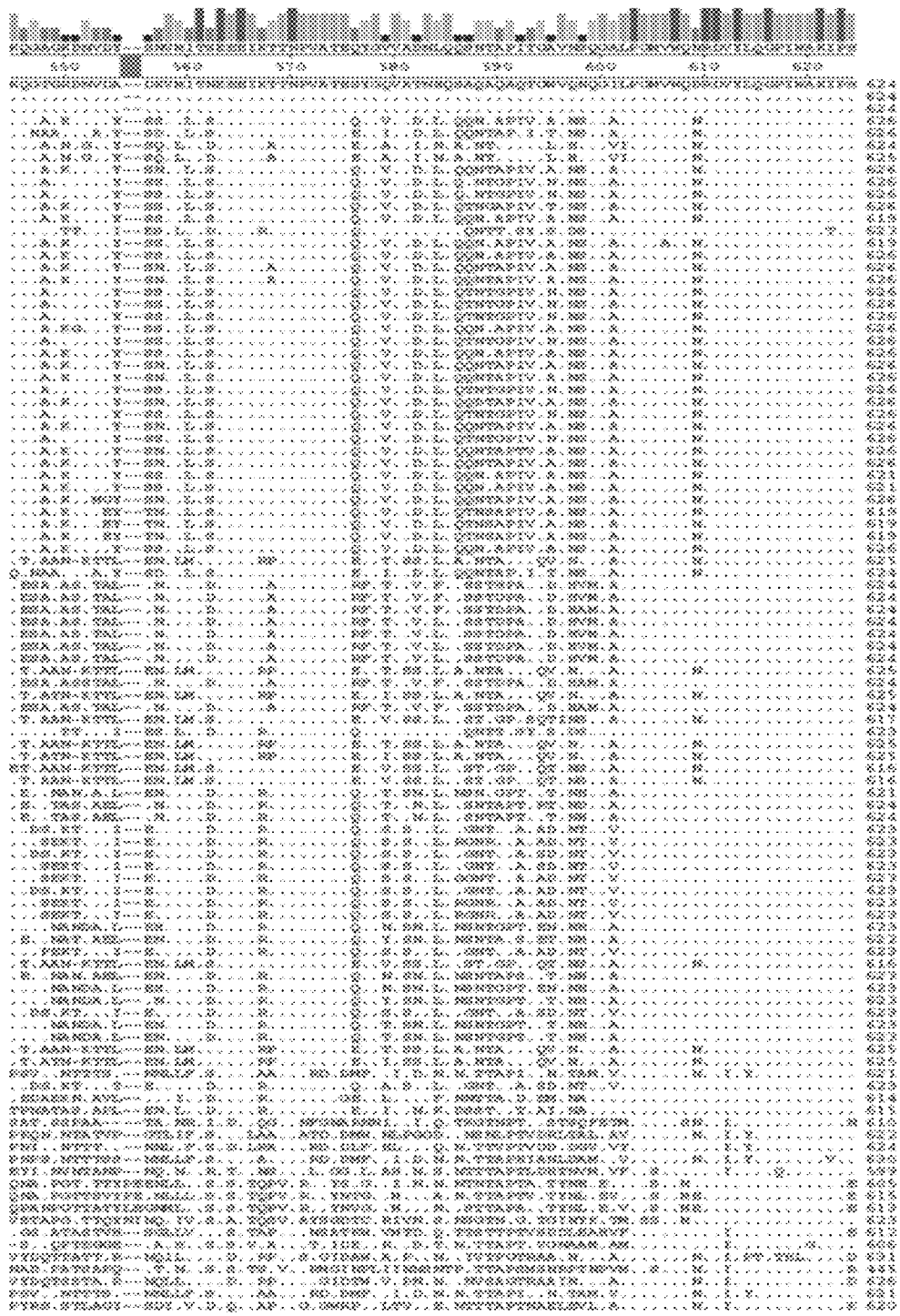
Fig. 13, con't.

FIG. 15

SEQ ID NO: 4

TTGGCCACTCCCTCTCTGCGCGCTCGCTCGCTCACTGAGGCCGGGCGACCAAAGGTCGCCCGACGCCCGGGC
TTTGCCCGGGCGGCCTCAGTGAGCGAGCGAGCGCGCAGAGAGGGAGTGGCCAACTCCATCACTAGGGGTTCC
TACTAGTGGCCTCCGCGCCGGGTTTTGGCGCGTCCCGCGGGCGCCCCCCTCCTCACGGCGAGCGCTGCCACG
TCAGACGAAGGGCGCAGCGAGCGTCCTGATCCTTCCGCCCGGACGCTCAGGACAGCGGCCCGCTGCTCATAA
GACTCGGCCTTAGAACCCCAGTATCAGCAGAAGGACATTTTAGGACGGGACTTGGGTGACTCTAGGGCACTGGT
TTTCTTTCCAGAGAGCGGAACAGGCGAGGAAAAGTAGTCCCTTCTCGGCGATTCTGCGGAGGGATCTCCGTGG
GGCGGTGAACGCCGATGATTATATAAGGACGCGCCGGGTGTGGCACAGCTAGTTCCGTCGCAGCCGGGATTTG
GGTCGCGGTTCTTGTTTGTGGATCGCTGTGATCGTCACTTGGCGGCCGCCATGGTCAGCAAGGGCGAGGAGGA
TAACATGGCCATCATCAAGGAGTTCATGCGCTTCAAGGTGCACATGGAGGGCTCCGTGAACGGCCACGAGTTC
GAGATCGAGGGCGAGGGCGAGGGCCGCCCCTACGAGGGCACCCAGACCGCCAAGCTGAAGGTGACCAAGGG
TGGCCCCCTGCCCTTCGCCTGGGACATCCTGTCCCCTCAATTCATGTATGGCTCCAAGGCCTACGTGAAGCACC
CCGCCGACATCCCCGACTACTTGAAGCTGTCCTTCCCCGAGGGCTTCAAGTGGGAGCGCGTGATGAACTTCGA
GGACGGCGGCGTGGTGACCGTGACCCAGGACTCCTCCTTACAAGACGGCGAGTTCATCTACAAAGTGAAGCTG
CGCGGCACCAACTTCCCCTCCGACGGCCCCGTAATGCAGAAGAAGACCATGGGCTGGGAGGCCTCCTCCGAG
CGGATGTACCCCGAGGACGGCGCCCTGAAGGGCGAGATCAAGCAGAGGCTGAAGCTGAAGGACGGCGGCCAC
TACGACGCTGAGGTCAAGACCACCTACAAGGCCAAGAAGCCCGTGCAGCTGCCCGGCGCCTACAACGTCAACA
TCAAGTTGGACATCACCTCCCACAACGAGGACTACACCATCGTGGAACAGTACGAACGCGCCGAGGGCCGCCA
CTCCACCGGCGGCATGGACGAGCTGTACAAGTAAAGGATCCCCTCCCCCGTGCCTTCCTTGACCCTGGAAGGT
GCCACTCCCACTGTCCTTTCCTCCTCCTAGGAATAAAATATCTTTATTTTCATTACATCTGTGTGTTGGTTTTTTGT
GTAGATCTGTTCAAATTTGAACTGACTAAGCGGCTCCCGCCAGATTTTGGCAAGATTACTAAGCAGGAAGTCAAG
GACTTTTTTGCTTGGGCAAAGGTCAATCAGGTGCCGGTGACTCACGAGTTTAAAGTTCCCAGGGAATTGGCGGG
AACTAAAGGGGCGGGAGAAATCTCTAAAACGCCCACTGGGTGACGTCACCAATACTAGCTATAAAAGTCTGGAGA
AGCGGGCCAGGCTCTCATTTGTTCCCGAGACGCCTCGCAGTTCAGACGTGACTGTTGATCCCGCTCCTCTGCGA
CCGCTAGCTTCGATCAACTACGCGGACAGGTACCAAAACAAATGTTCTCGTCACGTGGGCATGAATCTGATGCT
GTTTCCCTGCAGACAATGCGAGAGACTGAATCAGAATTCAAATATCTGCTTCACTCACGGTGTCAAAGACTGTTT
AGAGTGCTTTCCCGTGTCAGAATCTCAACCCGTTTCTGTCGTCAAAAAGGCGTATCAGAAACTGTGCTACATTCA
TCACATCATGGGAAAGGTGCCAGACGCTTGCACTGCTTGCGACCTGGTCAATGTGGACTTGGATGACTGTGT
TTCTGAACAATAAATGACTTAAACCAGGTATGGCTGCCGATGGTTATCTTCCAGATTGGCTCGAGGACAACCTTA
GTGAAGGAATTCGCGAGTGGTGGGCTTTGAAACCTGGAGCCCCTCAACCCAAGGCAAATCAACAACATCAAGAC
AACGCTCGAGGTCTTGTGCTTCCGGGTTACAAATACCTTGGACCCGGCAACGGACTCGACAAGGGGGAGCCGG
TCAACGCAGCAGACGCGGCGGCCCTCGAGCACGACAAGGCCTACGACCAGCAGCTCAAGGCCGGAGACAACC
CGTACCTCAAGTACAACCACGCCGACGCCGAGTTCCAGGAGCGGCTCAAAGAAGATACGTCTTTTGGGGGCAA
CCTCGGGCGAGCAGTCTTCCAGGCCAAAAAGAGGCTTCTTGAACCTCTTGGTCTGGTTGAGGAAGCGGCTAAG
ACGGCTCCTGGAAAGAAGAGGCCTGTAGAGCAGTCTCCTCAGGAACCGGACTCCTCCGCGGGTATTGGCAAAT
CGGGTGCACAGCCCGCTAAAAAGAGACTCAATTTCGGTCAGACTGGCGACACAGAGTCAGTCCCAGACCCTCA
ACCAATCGGAGAACCTCCCGCAGCCCCTCAGGTGTGGGATCTCTTACAATGGCTTCAGGTGGTGGCGCACCA
GTGGCAGACAATAACGAAGGTGCCGATGGAGTGGGTAGTTCCTCGGGAAATTGGCATTGCGATTCCCAATGGCT
GGGGGACAGAGTCATCACCACCAGCACCCGAACCTGGGCCCTGCCCACCTACAACAATCACCTCTACAAGCAA
ATCTCCAACAGCACATCTGGAGGATCTTCAAATGACAACGCCTACTTCGGCTACAGCACCCCCTGGGGGTATTTT
GACTTCAACAGATTCCACTGCCACTTCTCACCACGTGACTGGCAGCGACTCATCAACAACAACTGGGGATTCCG
GCCTAAGCGACTCAACTTCAAGCTCTTCAACATTCAGGTCAAAGAGGTTACGGACAACAATGGAGTCAAGACCAT
CGCCAATAACCTTACCAGCACGGTCCAGGTCTTCACGGACTCAGACTATCAGCTCCCGTACGTGCTCGGGTCGG
CTCACGAGGGCTGCCTCCCGCCGTTCCCAGCGGACGTTTTCATGATTCCTCAGTACGGGTATCTGACGCTTAAT
GATGGAAGCCAGGCCGTGGGTCGTTCGTCCTTTTACTGCCTGGAATATTTCCCGTCGCAAATGCTAAGAACGGG
TAACAACTTCCAGTTCAGCTACGAGTTTGAGAACGTACCTTTCCATAGCAGCTACGCTCACAGCCAAAGCCTGGA
CCGACTAATGAATCCACTCATCGACCAATACTTGTACTATCTCTAGAACTATTAACGGTTCTGGACAGAATCAA
CAAACGCTAAAATTCAGTGTGGCCGGACCCAGCAACATGGCTGTCCAGGGAAGAAACTACATACCTGGACCCAG
CTACCGACAACAACGTGTCTCAACCACTGTGACTCAAAACAACAACAGCGAATTTGCTTGGCCTGGAGCTTCTTC
TTGGGCTCTCAATGGACGTAATAGCTTGATGAATCCTGGACCTGCTATGGCCAGCCACAAAGAAGGAGAGGACC
GTTTCTTTCCTTTGTCTGGATCTTTAATTTTTGGCAAACAAGGAACTGGAAGAGACAACGTGGATGCGGACAAAG
TCATGATAACCAACGAAGAAGAAATTAAAACTACTAACCCGGTAGCAACGGAGTCCTATGGACAAGTGGCCACAA
ACCACCAGAGTGCCCAAGCACAGGCGCAGACCGGTTGGGTTCAAAACCAAGGAATACTTCCGGGTATGGTTTG
GCAGGACAGAGATGTGTACCTGCAAGGACCCATTTGGGCCAAAATTCCTCACACGGACGGCAACTTTCACCCTT
CTCCGCTGATGGGAGGGTTTGGAATGAAGCACCCGCCTCCTCAGATCCTCATCAAAAACACACCTGTACCTGCG
GATCCTCCAACGGCCTTCAACAAGGACAAGCTGAACTCTTTCATCACCCAGTATTCTACTGGCCAAGTCAGCGTG
GAGATCGAGTGGGAGCTGCAGAAGGAAAACAGCAAGCGCTGGAACCCGGAGATCCAGTACACTTCCAACTATT
ACAAGTCTAATAATGTTGAATTTGCTGTTAATACTGAAGGTGTATATAGTGAACCCCGCCCCATTGGCACCAGATA
CCTGACTCGTAATCTGTAAGTCGACTACCGTTCGTATAGCATACATTATACGAAGTTATCATATGTTCGAGCAGAC
ATGATAAGATACATTGATGAGTTTGGACAAACCACAACTAGAATGCAGTGAAAAAAATGCTTTATTTGTGAAATTT
GTGATGCTATTGCTTTATTTGTAACCATTATAAGCTGCAATAAACAAGTTAACAACAACAATTGCATTCATTTTATG
TTTCAGGTTCAGGGGGAGATGTGGGAGGTTTTTTAAAGCAAGTAAAACCTCTACAAATGTGGTAAAATCGAGCTC
TACCGTTCGTATAATGTATGCTATACGAAGTTATGATATCAAGCTTAGGAACCCCTAGTGATGGAGTTGGCCACT
CCCTCTCTGCGCGCTCGCTCGCTCACTGAGGCCGGGCGACCAAAGGTCGCCCGACGCCCGGGCTTT

```
GCCCGGGCGGCCTCAGTGAGCGAGCGAGCGCGCAGAGAGGGAGTGGCCAAGCTAGCGGGCGATTAAGGAAA
GGGCTAGATCATTCTTGAAGACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTTGTTTATTTTTCTAAATACATT
CAAATATGTATCCGCTCATGAGACAATAACCCTGATAAATGCTTCAATAATATTGAAAAAGGAAGAGTATGAGTAT
TCAACATTTCCGTGTCGCCCTTATTCCCTTTTTTGCGGCATTTTGCCTTCCTGTTTTTGCTCACCCAGAAACGCTG
GTGAAAGTAAAAGATGCTGAAGATCAGTTGGGTGCACGAGTGGGTTACATCGAACTGGATCTCAACAGCGGTAA
GATCCTTGAGAGTTTTCGCCCCGAAGAACGTTTTCCAATGATGAGCACTTTTAAAGTTCTGCTATGTGGCGCGGT
ATTATCCCGTGTTGACGCCGGGCAAGAGCAACTCGGTCGCCGCATACACTATTCTCAGAATGACTTGGTTGAGT
ACTCACCAGTCACAGAAAAGCATCTTACGGATGGCATGACAGTAAGAGAATTATGCAGTGCTGCCATAACCATGA
GTGATAACACTGCGGCCAACTTACTTCTGACAACGATCGGAGGACCGAAGGAGCTAACCGCTTTTTTGCACAAC
ATGGGGGATCATGTAACTCGCCTTGATCGTTGGGAACCGGAGCTGAATGAAGCCATACCAAACGACGAGCGTG
ACACCACGATGCCTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCATATATACTTTAGATTGATT
TAAAACTTCATTTTTAATTTAAAAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAGCTACCAACT
CTTTTTCCGAAGGTAACTGGCTTCAGCAGAGCGCAGATACCAAATACTGTTCTTCTAGTGTAGCCGTAGTTAGGC
CACCACTTCAAGAACTCTGTAGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAGGCGCAGCGGTCGGGCTGAA
CGGGGGGTTCGTGCACACAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTCCTGTCGGGTTTCGCCACCTCTGA
CTTGAGCGTCGATTTTTGTGATGCTCGTCAGGGGGCGGAGCCTATGGAAAAACGCCAGCAACGCGGCCTTTTT
ACGGTTCCTGGCCTTTTGCTGGCCTTTTGCTCACATGTAATAAACACACACACACCAACAACCGTGGTTGGTTGT
TGTGTTGGTTTATTCTCGAG
```

SEQ ID NO:4

SEQ ID NO: 5

```
GTCGACGGTATCGGGGGAGCTCGCAGGGTCTCCATTTTGAAGCGGGAGGTTTGAACGCGCAGCCGCCATGCC
GGGGTTTTACGAGATTGTGATTAAGGTCCCCAGCGACCTTGACGAGCATCTGCCCGGCATTTCTGACAGCTTTG
TGAACTGGGTGGCCGAGAAGGAATGGGAGTTGCCGCCAGATTCTGACATGGATCTGAATCTGATTGAGCAGGC
ACCCCTGACCGTGGCCGAGAAGCTGCAGCGCGACTTTCTGACGGAATGGCGCCGTGTGAGTAAGGCCCCGGA
GGCTCTTTTCTTTGTGCAATTTGAGAAGGGAGAGAGCTACTTCCACATGCACGTGCTCGTGGAAACCACCGGGG
TGAAATCCATGGTTTTGGGACGTTTCCTGAGTCAGATTCGCGAAAAACTGATTCAGAGAATTTACCGCGGGATCG
AGCCGACTTTGCCAAACTGGTTCGCGGTCACAAAGACCAGAAATGGCGCCGGAGGCGGGAACAAGGTGGTGGA
TGAGTGCTACATCCCCAATTACTTGCTCCCCAAAACCCAGCCTGAGCTCCAGTGGGCGTGGACTAATATGGAAC
AGTATTTAAGCGCCTGTTTGAATCTCACGGAGCGTAAACGGTTGGTGGCGCAGCATCTGACGCACGTGTCGCAG
ACGCAGGAGCAGAACAAAGAGAATCAGAATCCCAATTCTGATGCGCCGGTGATCAGATCAAAAACTTCAGCCAG
GTACATGGAGCTGGTCGGGTGGCTCGTGGACAAGGGGATTACCTCGGAGAAGCAGTGGATCCAGGAGGACCA
GGCCTCATACATCTCCTTCAATGCGGCCTCCAACTCGCGGTCCCAAATCAAGGCTGCCTTGGACAATGCGGGAA
AGATTATGAGCCTGACTAAAACCGCCCCGACTACCTGGTGGGCCAGCAGCCCGTGGAGGACATTTCCAGCAA
TCGGATTTATAAAATTTTGGAACTAAACGGGTACGATCCCCAATATGCGGCTTCCGTCTTTCTGGGATGGGCCAC
GAAAAAGTTCGGCAAGAGGAACACCATCTGGCTGTTTGGGCCTGCAACTACCGGGAAGACCAACATCGCGGAG
GCCATAGCCCACACTGTGCCCTTCTACGGGTGCGTAAACTGGACCAATGAGAACTTTCCCTTCAACGACTGTGT
CGACAAGATGGTGATCTGGTGGGAGGAGGGGAAGATGACCGCCAAGGTCGTGGAGTCGGCCAAAGCCATTCTC
GGAGGAAGCAAGGTGCGCGTGGACCAGAAATGCAAGTCCTCGGCCCAGATAGACCCGACTCCCGTGATCGTCA
CCTCCAACACCAACATGTGCGCCGTGATTGACGGGAACTCAACGACCTTCGAACACCAGCAGCCGTTGCAAGAC
CGGATGTTCAAATTTGAACTCACCCGCCGTCTGGATCATGACTTTGGGAAGGTCACCAAGCAGGAAGTCAAAGA
CTTTTTCCGGTGGGCAAAGGATCACGTGGTTGAGGTGGAGCATGAATTCTACGTCAAAAAGGGTGGAGCCAAGA
AAAGACCCGCCCCCAGTGACGCAGATATAAGTGAGCCCAAACGGGTGCGCGAGTCAGTTGCGCAGCCATCGAC
GTCAGACGCGGAAGCTTCGATCAACTACGCGGACAGGTACCAAAACAAATGTTCTCGTCACGTGGGCATGAATC
TGATGCTGTTTCCCTGCAGACAATGCGAGAGACTGAATCAGAATTCAAATATCTGCTTCACTCACGGTGTCAAAG
ACTGTTTAGAGTGCTTTCCCGTGTCAGAATCTCAACCCGTTTCTGTCGTCAAAAAGGCGTATCAGAAACTGTGCT
ACATTCATCACATCATGGGAAAGGTGCCAGACGCTTGCACTGTTGCGACCTGGTCAATGTGGACTTGGATGAC
TGTGTTTCTGAACAATAAATGACTTAAACCAGGTATGGCTGCCGATGGTTAACTTCCAGATTGACTCGAGGACAA
CCTTAGTGAAGGAATTCGCGAGTGGTGGGCTTTGAAACCTGGAGCCCCTCAACCCAAGGCAAATCAACAACATC
AAGACAACGCTCGAGGTCTTGTGCTTCCGGGTTACAAATACCTTGGACCCGGCAACGGACTCGACAAGGGGGA
GCCGGTCAACGCAGCAGACGCGGCGGCCCTCGAGCACGACAAGGCCTACGACCAGCAGCTCAAGGCCGGAGA
CAACCCGTACCTCAAGTACAACCACGCCGACGCCGAGTTCCAGGAGCGGCTCAAAGAAGATACGTCTTTTGGG
GGCAACCTCGGGCGAGCAGTCTTCCAGGCCAAAAAGAGGCTTCTTGAACCTCTTGGTCTGGTTGAGGAAGCGG
CTAAGACGGCTCTGGATAGAAGAGGCCTGTAGATAGTCTCCTCAGGAACCGGACTCCTCCGCGGGTATTGG
CAAATCGGGTGCACAGCCCGCTAAAAAGAGACTCAATTTCGGTCAGACTGGCGACACAGAGTCAGTCCCAGACC
CTCAACCAATCGGAGAACCTCCCGCAGCCCCCTCAGGTGTGGGATCTCTTACAATGGCTTCAGGTGGTGGCGC
ACCAGTGGCAGACAATAACTAAGGTGCCGATGGAGTGGGTAGTTCCTCGGGAAATTGGCATTGCGATTCCCAAT
GGCTGGGGGACAGAGTCATCACCACCAGCACCCGAACCTGGGCCCTGCCCACCTACAACAATCACCTCTACAA
GCAAATCTCCAACAGCACATCTGGAGGATCTTCAAATGACAACGCCTACTTCGGCTACAGCACCCCCTGGGGGT
ATTTTGACTTCAACAGATTCCACTGCCACTTCTCACCACGTGACTGGCAGCGACTCATCAACAACAACTGGGGAT
TCCGGCCTAAGCGACTCAACTTCAAGCTCTTCAACATTCAGGTCAAAGAGGTTACGGACAACAATGGAGTCAAG
ACCATCGCCAATAACCTTACCAGCACGGTCCAGGTCTTCACGGACTCAGACTATCAGCTCCCGTACGTGCTCGG
GTCGGCTCACGAGGGCTGCCTCCCGCGTTCCCAGCGGACGTTTTCATGATTCCTCAGTACGGGTATCTGACG
CTTAATGATGGAAGCCAGGCCGTGGGTCGTTCGTCCTTTTACTGCCTGGAATATTTCCCGTCGCAAATGCTAAGA
ACGGGTAACAACTTCCAGTTCAGCTACGAGTTTGAGAACGTACCTTTCCATAGCAGCTACGCTCACAGCCAAAG
CCTGGACCGACTAATGAATCCACTCATCGACCAATACTTGTACTATCTCTCAAAGACTATTAACGGTTCTGGACA
GAATCAACAAACGCTAAAATTCAGTGTGGCCGGACCCAGCAACATGGCTGTCCAGGGAAGAAACTACATACCTG
GACCCAGCTACCGACAACAACGTGTCTCAACCACTGTGACTCAAAACAACAACAGCGAATTTGCTTGGCCTGGA
GCTTCTTCTTGGGCTCTCAATGGACGTAATAGCTTGATGAATCCTGGACCTGCTATGGCCAGCCACAAAGAAGG
AGAGGACCGTTTCTTTCCTTTGTCTGGATCTTTAATTTTTTGGCAAACAAGGAACTGGAAGAGACAACGTGGATG
CGGACAAAGTCATGATAACCAACGAAGAAGAAATTAAAACTACTAACCCGTAGCAACGGAGTCCTATGGACAA
GTGGCCACAAACCACCAGAGTGCCCAAGCACAGGCGCAGACCGGCTGGGTTCAAAACCAAGGAATACTTCCGG
GTATGGTTTGGCAGGACAGAGATGTGTACCTGCAAGGACCCATTTGGGCCAAAATTCCTCACACGGACGGCAAC
TTTCACCCTTCTCCGCTGATGGGAGGGTTTGGAATGAAGCACCCGCCTCCTCAGATCCTCATCAAAAACACACCT
GTACCTGCGGATCCTCCAACGGCCTTCAACAAGGACAAGCTGAACTCTTTCATCACCCAGTATTCTACTGGCCAA
GTCAGCGTGGAGATCGAGTGGGAGCTGCAGAAGGAAAACAGCAAGCGCTGGAACCCGGAGATCCAGTACACTT
CCAACTATTACAAGTCTAATAATGTTGAATTTGCTGTTAATACTGAAGGTGTATATAGTGAACCCGCCCCATTGG
CACCAGATACCTGACTCGTAATCTGTAATTGCTTGTTAATCAATAAACCGTTTAATTCGTTTCAGTTGAACTTTGGT
CTCTGCGAAGGGCGAATTCGTTTAAACCTGCAGGACTAGAGGTCCTGTATTAGAGGTCACGTGAGTGTTTTGCG
ACATTTTGCGACACCATGTGGTCACGCTGGGTATTTAAGCCCGAGTGAGCACGCAGGGTCTCCATTTTGAAGCG
GGAGGTTTGAACGCGCAGCCGCCAAGCCGAATTCTGCAGATATCCATCACACTGGCGGCCGCTCGACTAGAGC
GGCCGCCACCGCGGTGGAGCTCCAGCTTTTGTTCCCTTTAGTGAGGGTTAATTGCGCGCTTGGCGTAATCATGG
TCATAGCTGTTTCCTGTGTGAAATTGTTATCCGCTCACAATTCCACACAACATACGAGCCGGAAGCATAAAGTGT
AAAGCCTGGGGTGCCTAATGAGTGAGCTAACTCACATTAATTGCGTTGCGCTCACTGCCCGCTTTCCAGTCGGG
AAACCTGTCGTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGCTCACTCAAAGG
```

```
CGGTAATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCATCACAAAAATC
GACGCTCAAGTCAGAGGTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGGTAAGACACGACT
TATCGCCACTGGCAGCAGCCACTGGTAACAGGATTAGCAGAGCGAGGTATGTAGGCGGTGCTACAGAGTTCTT
GAAGTGGTGGCCTAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGATCCTTTTAAATTAAAA
ATGAAGTTTTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAACTACGATACGG
GAGGGCTTACCATCTGGCCCCAGTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTGCTCTTGCCCGGCGTCAATAC
GGGATAATACCGCGCCACATAGCAGAACTTTAAAAGTGCTCATCATTGGAAAACGTTCTTCGGGGCGAAAACTCT
CAAGGATCTTACCGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAAGTGCCACCTAAATT
GTAAGCGTTAATATTTTGTTAAAATTCGCGTTAAATTTTTGTTAAATCAGCTCATTTTTTAACCAATAGGCCGAAAT
CGGCAAAATCCCTTATAAATCAAAAGAATAGACCGAGATAGGGTTGAGTGTTGTTCCAGTTTGGAACAAGAGTCC
ACTATTAAAGAACGTGGACTCCAACGTCAAAGGGCGAAAAACCGTCTATCAGGGCGATGGCCCACTACGTGAAC
CATCACCCTAATCAAGTTTTTTGGGGTCGAGGTGCCGTAAAGCACTAAATCGGAACCCTAAAGGGAGCCCCCGA
TTTAGAGCTTGACGGGGAAAGCCGGCGAACGTGGCGAGAAAGGAAGGGAAGAAAGCGAAAGGAGCGGGCGCT
AGGGCGCTGGCAAGTGTAGCGGTCACGCTGCGCGTAACCACCACACCCGCCGCGCTTAATGCGCCGCTACAG
GGCGCGTCCCATTCGCCATTCAGGCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACGCCAGGGTTTTCCCAGTCACGACG
TTGTAAAACGACGGCCAGTGAGCGCGCGTAATACGACTCACTATAGGGCGAATTGGGTACCGGGCCCCCCCTC
GATCGAG
```

SEQ ID NO: 5

SEQ ID NO: 6

```
AGCGCCCAATACGCAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGCACCCCAGGCTTTAC
ACTTTATGCTTCCGGCTCGTATGTTGTGTGGAATTGTGAGCGGATAACAATTTCACACAGGAAACAGCTATGACC
ATGATTACGCCAAGCTATTTAGGTGACACTATAGAATACTCAAGCTATGCATCAAGCTTGGTACCGAGCTCGGAT
CCACTAGTAACGGCCGCCAGTGTGCTGGAATTCGCCCTTACTCATCGACCAATACTTGTACTATCTCTCTAGAAC
TATTAACGGTTCTGGACAGAATCAACAAACGCTAAAATTCAGTGTGGCCGGACCCAGCAACATGGCTGTCCAGG
GAAGAAACTACATACCTGGACCCAGCTACCGACAACAACGTGTCTCAACCACTGTGACTCAAAACAACAACAGC
GAATTTGCTTGGCCTGGAGCTTCTTCTTGGGCTCTCAATGGACGTAATAGCTTGATGAATCCTGGACCTGCTATG
GCCAGCCACAAAGAAGGAGAGGACCGTTTCTTTCCTTTGTCTGGATCTTTAATTTTTGGCAAACAAGGTACCGGC
AGAGACAACGTGGATGCGGACAAAGTCATGATAACCAACGAAGAAGAAATTAAAACTACTAACCCGGTAGCAAC
GGAGTCCTATGGACAAGTGGCCACAAACCACCAGAGTGCCCAAGCACAGGCGCAGACCGGTTGGGTTCAAAAC
CAAGGAATACTTCCAAGGGCGAATTCTGCAGATATCCATCACACTGGCGGCCGCTCGAGCATGCATCTAGAGGG
CCCAATTCGCCCTATAGTGAGTCGTATTACAATTCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGCGAAGAGGCCCGCAC
CGATCGCCCTTCCCAACAGTTGCGCAGCCTGAATGGCGAATGGACGCGCCCTGTAGCGGCGCATTAAGCGCGG
CGGGTGTGGTGGTTACGCGCAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGGGCTCCCTTTAGGGTTCCGAT
TTAGTGCTTTACGGCACCTCGACCCCAAAAAACTTGATTAGGGTGATGGTTCACGTAGTGGGCCATCGCCCTGA
TAGACGGTTTTTCGCCCTTTGACGTTGGAGTCCACGTTCTTTAATAGTGGACTCTTGTTCCAAACTGGAACAACA
CTCAACCCTATCTCGGTCTATTCTTTTGATTTATAAGGGATTTTGCCGATTTCGGCCTATTGGTTAAAAAATGAGC
TGATTTAACAAAAATTTAACGCGAATTTTAACAAAATTCAGGGCGCAAGGGCTGCTAAAGGAAGCGGAACACGTA
GAAAGCCAGTCCGCAGAAACGGTGCTGACCCCGGATGAATGTCAGCTACTGGGCTATCTGGACAAGGGAAAAC
GCAAGCGCAAAGAGAAAGCAGGTAGCTTGCAGTGGGCTTACATGGCGATAGCTAGACTGGGCGGTTTTATGGA
CAGCAAGCGAACCGGAATTGCCAGCTGGGGCGCCCTCTGGTAAGGTTGGGAAGCCCTGCAAAGTAAACTGGAT
GGCTTTCTTGCCGCCAAGGATCTGATGGCGCAGGGGATCAAGATCTGATCAAGAGACAGGATGAGGATCGTTTC
GCATGATTGAACAAGATGGATTGCACGCAGGTTCTCCGGCCGCTTGGGTGGAGAGGCTATTCGGCTATGACTG
GGCACAACAGACAATCGGCTGCTCTGATGCCGCCGTGTTCCGGCTGTCAGCGCAGGGGCGCCCGGTTCTTTTT
GTCAAGACCGACCTGTCCGGTGCCCTGAATGAACTGCAGGACGAGGCAGCGCGGCTATCGTGGCTGGCCACG
ACGGGCGTTCCTTGCGCAGCTGTGCTCGACGTTGTCACTGAAGCGGGAAGGGACTGGCTGCTATTGGGCGAAG
TGCCGGGGCAGGATCTCCTGTCATCCCACCTTGCTCCTGCCGAGAAAGTATCCATCATGGCTGATGCAATGCGG
CGGCTGCATACGCTTGATCCGGCTACCTGCCCATTCGACCACCAAGCGAAACATCGCATCGAGCAGCACGTA
CTCGGATGGAAGCCGGTCTTGTCGATCAGGATGATCTGGACGAAGAGCATCAGGGGCTCGCGCCAGCCGAACT
GTTCGCCAGGCTCAAGGCGCGCATGCCCGACGGCGAGGATCTCGTCGTGACCCATGGCGATGCCTGCTTGCC
GAATATCATGGTGGAAAATGGCCGCTTTTCTGGATTCATCGACTGTGGCCGGCTGGGTGTGGCGGACCGCTATC
AGGACATAGCGTTGGCTACCCGTGATATTGCTGAAGAGCTTGGCGGCGAATGGGCTGACCGCTTCCTCGTGCTT
TACGGTATCGCCGCTCCCGATTCGCAGCGCATCGCCTTCTATCGCCTTCTTGACGAGTTCTTCTGAATTGAAAAA
GGAAGAGTATGAGTATTCAACATTTCCGTGTCGCCCTTATTCCCTTTTTTGCGGCATTTTGCCTTCCTGTTTTTGC
TCACCCAGAAACGCTGGTGAAAGTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCAATGATGAGCACTTTTAAAGTTC
TGCTATGTGGCGCGGTATTATCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAACTATTAACTGGCGAACTA
CTTACTCTAGCTTCCCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTGATAATCTCATGACC
AAAATCCCTTAACGTGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATACTGTTCTTCTAGTG
TAGCCGTAGTTAGGCCACCACTTCAAGAACTCTGTAGCACCGCCTACATACCTCGCTCTGCTAATCCTGTTACCA
GTGGCTGCTGCCAGTGGCGATAAGTCGTGTCTTACCGGGTTGGACTCAAGACGATAGTTACCGGATAAGGCGC
AGCGGTCGGGCTGAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGCGGAGCCTATGGAAAAACGCCAG
CAACGCGGCCTTTTTACGGTTCCTGGCCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCGCAGCCGAACGACCGAGCGCAGCG
AGTCAGTGAGCGAGGAAGCGGAAG
```

SEQ ID NO: 6

FIG. 18

SEQ ID NO: 7

TTGGCCACTCCCTCTCTGCGCGCTCGCTCGCTCACTGAGGCCGGGCGACCAAAGGTCGCCCGACGCCCGGGC
TTTGCCCGGGCGGCCTCAGTGAGCGAGCGAGCGCGCAGAGAGGGAGTGGCCAACTCCATCACTAGGGGTTCC
TACTAGTGGCCTCCGCGCCGGGTTTTGGCGCCTCCCGCGGGCGCCCCCTCCTCACGGCGAGCGCTGCCACG
TCAGACGAAGGGCGCAGCGAGCGTCCTGATCCTTCCGCCCGGACGCTCAGGACAGCGGCCCGCTGCTCATAA
GACTCGGCCTTAGAACCCCAGTATCAGCAGAAGGACATTTTAGGACGGGACTTGGGTGACTCTAGGGCACTGGT
TTTCTTTCCAGAGAGCGGAACAGGCGAGGAAAAGTAGTCCCTTCTCGGCGATTCTGCGGAGGGATCTCCGTGG
GGCGGTGAACGCCGATGATTATATAAGGACGCGCCGGGTGTGGCACAGCTAGTTCCGTCGCAGCCGGGATTTG
GGTCGCGGTTCTTGTTTGTGGATCGCTGTGATCGTCACTTGGCGGCCGCCATGGTCAGCAAGGGCGAGGAGGA
TAACATGGCCATCATCAAGGAGTTCATGCGCTTCAAGGTGCACATGGAGGGCTCCGTGAACGGCCACGAGTTC
GAGATCGAGGGCGAGGGCGAGGGCCGCCCCTACGAGGGCACCCAGACCGCCAAGCTGAAGGTGACCAAGGG
TGGCCCCCTGCCCTTCGCCTGGGACATCCTGTCCCCTCAATTCATGTATGGCTCCAAGGCCTACGTGAAGCACC
CCGCCGACATCCCCGACTACTTGAAGCTGTCCTTCCCCGAGGGCTTCAAGTGGGAGCGCGTGATGAACTTCGA
GGACGGCGGCGTGGTGACCGTGACCCAGGACTCCTCCTTACAAGACGGCGAGTTCATCTACAAAGTGAAGCTG
CGCGGCACCAACTTCCCCTCCGACGGCCCCGTAATGCAGAAGAAGACCATGGGCTGGGAGGCCTCCTCCGAG
CGGATGTACCCCGAGGACGGCGCCCTGAAGGGCGAGATCAAGCAGAGGCTGAAGCTGAAGGACGGCGGCCAC
TACGACGCTGAGGTCAAGACCACCTACAAGGCCAAGAAGCCCGTGCAGCTGCCCGGCGCCTACAACGTCAACA
TCAAGTTGGACATCACCTCCCACAACGAGGACTACACCATCGTGGAACAGTACGAACGCGCCGAGGGCCGCCA
CTCCACCGGCGGCATGGACGAGCTGTACAAGTAAAGGATCCCCTCCCCCGTGCCTTCCTTGACCCTGGAAGGT
GCCACTCCCACTGTCCTTTCCTCCTCCTAGGAATAAAATATCTTTATTTTCATTACATCTGTGTGTTGGTTTTTTGT
GTAGATCTGTTCAAATTTGAACTGACTAAGCGGCTCCCGCCAGATTTTGGCAAGATTACTAAGCAGGAAGTCAAG
GACTTTTTTGCTTGGGCAAAGGTCAATCAGGTGCCGGTGACTCACGAGTTTAAAGTTCCCAGGGAATTGGCGGG
AACTAAAGGGGCGGAGAAATCTCTAAAACGCCCACTGGGTGACGTCACCAATACTAGCTATAAAAGTCTGGAGA
AGCGGGCCAGGCTCTCATTTGTTCCCGAGACGCCTCGCAGTTCAGACGTGACTGTTGATCCCGCTCCTCTGCGA
CCGCTAGCTTCGATCAACTACGCGGACAGGTACCAAAACAAATGTTCTCGTCACGTGGGCATGAATCTGATGCT
GTTTCCCTGCAGACAATGCGAGAGACTGAATCAGAATTCAAATATCTGCTTCACTCACGGTGTCAAAGACTGTTT
AGAGTGCTTTCCCGTGTCAGAATCTCAACCCGTTTCTGTCGTCAAAAAGGCGTATCAGAAACTGTGCTACATTCA
TCACATCATGGGAAAGGTGCCAGACGCTTGCACTGCTTGCGACCTGGTCAATGTGGACTTGGATGACTGTGTTT
CTGAACAATAAATGACTTAAACCAGGTATGGCTGCCGATGGTTATCTTCCAGATTGGCTCGAGGACAACCTTAGT
GAAGGAATTCGCGAGTGGTGGGCTTTGAAACCTGGAGCCCCTCAACCCAAGGCAAATCAACAACATCAAGACAA
CGCTCGAGGTCTTGTGCTTCCGGGTTACAAATACCTTGGACCCGGCAACGGACTCGACAAGGGGGAGCCGGTC
AACGCAGCAGACGCGGCGGCCCTCGAGCACGACAAGGCCTACGACCAGCAGCTCAAGGCCGGAGACAACCCG
TACCTCAAGTACAACCACGCCGACGCCGAGTTCCAGGAGCGGCTCAAAGAAGATACGTCTTTTGGGGGCAACCT
CGGGCGAGCAGTCTTCCAGGCCAAAAAGAGGCTTCTTGAACCTCTTGGTCTGGTTGAGGAAGCGGCTAAGACG
GCTCCTGGAAAGAAGAGGCCTGTAGAGCAGTCTCCTCAGGAACCGGACTCCTCCGCGGGTATTGGCAAATCGG
GTGCACAGCCCGCTAAAAAGAGACTCAATTTCGGTCAGACTGGCGACACAGAGTCAGTCCCAGACCCTCAACCA
ATCGGAGAACCTCCCGCAGCCCCCTCAGGTGTGGGATCTCTTACAATGGCTTCAGGTGGTGGCGCACCAGTGG
CAGACAATAACGAAGGTGCCGATGGAGTGGGTAGTTCCTCGGGAAATTGGCATTGCGATTCCCAATGGCTGGG
GGACAGAGTCATCACCACCAGCACCCGAACCTGGGCCTGCCCACCTACAACAATCACCTCTACAAGCAAATCT
CCAACAGCACATCTGGAGGATCTTCAAATGACAACGCCTACTTCGGCTACAGCACCCCCTGGGGGTATTTTGAC
TTCAACAGATTCCACTGCCACTTCTCACCACGTGACTGGCAGCGACTCATCAACAACAACTGGGGATTCCGGCC
TAAGCGACTCAACTTCAAGCTCTTCAACATTCAGGTCAAAGAGGTTACGGACAACAATGGAGTCAAGACCATCG
CCAATAACCTTACCAGCACGGTCCAGGTCTTCACGGACTCAGACTATCAGCTCCCGTACGTGCTCGGGTCGGCT
CACGAGGGCTGCCTCCCGCCGTTCCCAGCGGACGTTTTCATGATTCCTCAGTACGGGTATCTGACGCTTAATGA
TGGAAGCCAGGCCGTGGGTCGTTCGTCCTTTTACTGCCTGGAATATTTCCCGTCGCAAATGCTAAGAACGGGTA
ACAACTTCCAGTTCAGCTACGAGTTTGAGAACGTACCTTTCCATAGCAGCTACGCTCACAGCCAAAGCCTGGAC
CGACTAATGAATCCACTCATCGACCAATACTTGTACTATCTCTCTAGAACTATTACCGGTTGGGTTCAAAACCAAG
GAATACTTCCGGGTATGGTTTGGCAGGACAGAGATGTGTACCTGCAAGGACCCATTTGGGCCAAAATTCCTCAC
ACGGACGGCAACTTTCACCCTTCTCCGCTCGATGGGAGGGTTTGGAATGAAGCACCCGCCTCCTCAGATCCTCAT
CAAAAACACACCTGTACCTGCGGATCCTCCAACGGCCTTCAACAAGGACAAGCTGAACTCTTTCATCACCCAGTA
TTCTACTGGCCAAGTCAGCGTGGAGATCGAGTGGGAGCTGCAGAAGGAAAACAGCAAGCGCTGGAACCCGGAG
ATCCAGTACACTTCCAACTATTACAAGTCTAATAATGTTGAATTTGCTGTTAATACTGAAGGTGTATATAGTGAACC
CCGCCCCATTGGCACCAGATACCTGACTCGTAATCTGTAAGTCGACTACCGTTCGTATAGCATACATTATACGAA
GTTATCATATGTTCGAGCAGACATGATAAGATACATTGATGAGTTTGGACAAACCACAACTAGAATGCAGTGAAA
AAAATGCTTTATTTGTGAAATTTGTGATGCTATTGCTTTATTTGTAACCATTATAAGCTGCAATAAACAAGTTAACA
ACAACAATTGCATTCATTTTATGTTTCAGGTTCAGGGGGAGATGTGGAGGTTTTTAAAGCAAGTAAAACCTCTA
CAAATGTGGTAAAATCGAGCTCTACCGTTCGTATAATGTATGCTATACGAAGTTATGATATCAAGCTTAGGAACCC
CTAGTGATGGAGTTGGCCACTCCCTCTCTGCGCGCTCGCTCGCTCACTGAGGCCGGGCGACCAAAGGTCGCCC
GACGCCCGGGCTTTGCCCGGGCGGCCTCAGTGAGCGAGCGAGCGCGCAGAGAGGGAGTGGCCAAGCTAGCG
GGCGATTAAGGAAAGGGCTAGATCATTCTTGAAGACGAAAGGGCCTCGTGATACGCCTATTTTTATAGGTTAATG
TCATGATAATAATGGTTTCTTAGACGTCAGGTGGCACTTTTCGGGGAAATGTGCGCGGAACCCCTATTTGTTTATT
TTTCTAAATACATTCAAATATGTATCCGCTCATGAGACAATAACCCTGATAAATGCTTCAATAATATTGAAAAAGGA
AGAGTATGAGTATTCAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTACATCGAACTGGATC
TCAACAGCGGTAAGATCCTTGAGAGTTTTCGCCCCGAAGAACGTTTTCCAATGATGAGCACTTTTAAAGTTCTGC
TATGTGGCGCGGTATTATCCCGTGTTGACGCCGGGCAAGAGCAACTCGGTCGCCGCATACACTATTCTCAGAAT

```
GACTTGGTTGAGTACTCACCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAATGAAGCCATACCAAA
CGACGAGCGTGACACCACGATGCCTGTAGCAATGGCAACAACGTTGCGCAAACTATTAACTGGCGAACTACTTA
CTCTAGCTTCCCGGCAACAATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAGTTTACTCATATATA
CTTTAGATTGATTTAAAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACTGTTCTTCTAGTGTAG
CCGTAGTTAGGCCACCACTTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTACCGGATAAGGCGCAGC
GGTCGGGCTGAACGGGGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGGCGGAGCCTATGGAAAAACGCCAGCA
ACGCGGCCTTTTTACGGTTCCTGGCCTTTTGCTGGCCTTTTGCTCACATGTAATAAACACACACACACCAACAAC
CGTGGTTGGTTGTTGTGTTGGTTTATTCTCGAG
```

SEQ ID NO: 7

FIG. 18 Cont.

AA sequence of AAV-PHP.B (AAV-G2B26) capsid VP1 protein

SEQ ID NO: 8

MAADGYLPDWLEDNLSEGIREWWALKPGAPQPKANQQHQDNARGLVLPGYKYLGPGNGLDKGEPVNA
ADAAALEHDKAYDQQLKAGDNPYLKYNHADAEFQERLKEDTSFGGNLGRAVFQAKKRLLEPLGLVEEAA
KTAPGKKRPVEQSPQEPDSSAGIGKSGAQPAKKRLNFGQTGDTESVPDPQPIGEPPAAPSGVGSLTMAS
GGGAPVADNNEGADGVGSSSGNWHCDSQWLGDRVITTSTRTWALPTYNNHLYKQISNSTSGGSSNDN
AYFGYSTPWGYFDFNRFHCHFSPRDWQRLINNNWGFRPKRLNFKLFNIQVKEVTDNNGVKTIANNLTST
VQVFTDSDYQLPYVLGSAHEGCLPPFPADVFMIPQYGYLTLNDGSQAVGRSSFYCLEYFPSQMLRTGNN
FQFSYEFENVPFHSSYAHSQSLDRLMNPLIDQYLYYLSRTINGSGQNQQTLKFSVAGPSNMAVQGRNYIP
GPSYRQQRVSTTVTQNNNSEFAWPGASSWALNGRNSLMNPGPAMASHKEGEDRFFPLSGSLIFGKQG
TGRDNVDADKVMITNEEEIKTTNPVATESYGQVATNHQSAQTLAVPFKAQAQTGWVQNQGILPGMVWQ
DRDVYLQGPIWAKIPHTDGNFHPSPLMGGFGMKHPPPQILIKNTPVPADPPTAFNKDKLNSFITQYSTGQ
VSVEIEWELQKENSKRWNPEIQYTSNYYKSNNVEFAVNTEGVYSEPRPIGTRYLTRNL

SEQ ID NO: 8

FIG. 19

SEQ ID NO: 9

ATGGCTGCCGATGGTTATCTTCCAGATTGGCTCGAGGACAACCTTAGTGAAGGAATTCGCGAGTGGT
GGGCTTTGAAACCTGGAGCCCCTCAACCCAAGGCAAATCAACAACATCAAGACAACGCTCGAGGTC
TTGTGCTTCCGGGTTACAAATACCTTGGACCCGGCAACGGACTCGACAAGGGGGAGCCGGTCAACG
CAGCAGACGCGGCGGCCCTCGAGCACGACAAGGCCTACGACCAGCAGCTCAAGGCCGGAGACAAC
CCGTACCTCAAGTACAACCACGCCGACGCCGAGTTCCAGGAGCGGCTCAAAGAAGATACGTCTTTT
GGGGGCAACCTCGGGCGAGCAGTCTTCCAGGCCAAAAAGAGGCTTCTTGAACCTCTTGGTCTGGTT
GAGGAAGCGGCTAAGACGGCTCCTGGAAAGAAGAGGCCTGTAGAGCAGTCTCCTCAGGAACCGGA
CTCCTCCGCGGGTATTGGCAAATCGGGTGCACAGCCCGCTAAAAAGAGACTCAATTTCGGTCAGAC
TGGCGACACAGAGTCAGTCCCAGACCCTCAACCAATCGGAGAACCTCCCGCAGCCCCCTCAGGTGT
GGGATCTCTTACAATGGCTTCAGGTGGTGGCGCACCAGTGGCAGACAATAACGAAGGTGCCGATGG
AGTGGGTAGTTCCTCGGGAAATTGGCATTGCGATTCCCAATGGCTGGGGGACAGAGTCATCACCAC
CAGCACCCGAACCTGGGCCCTGCCCACCTACAACAATCACCTCTACAAGCAAATCTCCAACAGCACA
TCTGGAGGATCTTCAAATGACAACGCCTACTTCGGCTACAGCACCCCCTGGGGGTATTTTGACTTCA
ACAGATTCCACTGCCACTTCTCACCACGTGACTGGCAGCGACTCATCAACAACAACTGGGGATTCCG
GCCTAAGCGACTCAACTTCAAGCTCTTCAACATTCAGGTCAAAGAGGTTACGGACAACAATGGAGTC
AAGACCATCGCCAATAACCTTACCAGCACGGTCCAGGTCTTCACGGACTCAGACTATCAGCTCCCGT
ACGTGCTCGGGTCGGCTCACGAGGGCTGCCTCCCGCCGTTCCCAGCGGACGTTTTCATGATTCCTC
AGTACGGGTATCTGACGCTTAATGATGGAAGCCAGGCCGTGGGTCGTTCGTCCTTTTACTGCCTGGA
ATATTTCCCGTCGCAAATGCTAAGAACGGGTAACAACTTCCAGTTCAGCTACGAGTTTGAGAACGTA
CCTTTCCATAGCAGCTACGCTCACAGCCAAAGCCTGGACCGACTAATGAATCCACTCATCGACCAAT
ACTTGTACTATCTCTC*TAGA*ACTATTAACGGTTCTGGACAGAATCAACAAACGCTAAAATTCAGTGTG
GCCGGACCCAGCAACATGGCTGTCCAGGGAAGAAACTACATACCTGGACCCAGCTACCGACAACAA
CGTGTCTCAACCACTGTGACTCAAAACAACAACAGCGAATTTGCTTGGCCTGGAGCTTCTTCTTGGG
CTCTCAATGGACGTAATAGCTTGATGAATCCTGGACCTGCTATGGCCAGCCACAAAGAAGGAGAGGA
CCGTTTCTTTCCTTTGTCTGGATCTTTAATTTTTGGCAAACAAGG*TAC*C*GG*C*AGAGACAACGTGGATG
CGGACAAAGTCATGATAACCAACGAAGAAGAAATTAAAACTACTAACCCGGTAGCAACGGAGTCCTA
TGGACAAGTGGCCACAAACCACCAGAGTGCCCAAACTTTGGCGGTGCCTTTTAAGGCACAGGCGCA
GACCGG*TT*GGGTTCAAAACCAAGGAATACTTCCGGGTATGGTTTGGCAGGACAGAGATGTGTACCT
GCAAGGACCCATTTGGGCCAAAATTCCTCACACGGACGGCAACTTTCACCCTTCTCCGCTGATGGGA
GGGTTTGGAATGAAGCACCCGCCTCCTCAGATCCTCATCAAAAACACACCTGTACCTGCGGATCCTC
CAACGGCCTTCAACAAGGACAAGCTGAACTCTTTCATCACCCAGTATTCTACTGGCCAAGTCAGCGT
GGAGATCGAGTGGGAGCTGCAGAAGGAAAACAGCAAGCGCTGGAACCCGGAGATCCAGTACACTT
CCAACTATTACAAGTCTAATAATGTTGAATTTGCTGTTAATACTGAAGGTGTATATAGTGAACCCCGC
CCCATTGGCACCAGATACCTGACTCGTAATCTGTAA

SEQ ID NO: 9

SEQ ID NO: 10 gtcgacggtatcgggggagctcgcagggtctccatttgaagcgggaggtttgaacgcgcagccgccatgccggggttttacgagattgtgattaag
gtccccagcgaccttgacgagcatctgcccggcatttctgacagctttgtgaactgggtggccgagaaggaatgggagttgccgccagattctgaca
tggatctgaatctgattgagcaggcacccctgaccgtggccgagaagctgcagcgcgactttctgacggaatggcgccgtgtgagtaaggccccg
gaggctcttttctttgtgcaatttgagaagggagagagctacttccacatgcacgtgctcgtggaaaccaccggggtgaaatccatggttttgggacgtt
tcctgagtcagattcgcgaaaaactgattcagagaatttaccgcgggatcgagccgactttgccaaactggttcgcggtcacaaagaccagaaatg
gcgccggaggcgggaacaaggtggtggatgagtgctacatccccaattacttgctccccaaaacccagcctgagctccagtgggcgtggactaat
atggaacagtatttaagcgcctgtttgaatctcacggagcgtaaacggttggtggcgcagcatctgacgcacgtgtcgcagacgcaggagcagaa
caaagagaatcagaatcccaattctgatgcgccggtgatcagatcaaaaacttcagccaggtacatggagctggtcggtggctcgtggacaagg
ggattacctcggagaagcagtggatccaggaggaccaggcctcatacatctccttcaatgcggcctccaactcgcggtcccaaatcaaggctgcct
tggacaatgcgggaaagattatgagcctgactaaaaccgccccgactacctggtgggccagcagcccgtggaggacatttccagcaatcggatt
tataaaattttggaactaaacgggtacgatcccccaatatgcggcttccgtctttctgggatgggccacgaaaaagttcggcaagaggaacaccatct
ggctgtttgggcctgcaactaccgggaagaccaacatcgcggaggccatagcccacactgtgcccttctacgggtgcgtaaactggaccaatgag
aactttcccttcaacgactgtgtcgacaagatggtgatctggtgggaggaggggaagatgaccgccaaggtcgtggagtcggccaaagccattctc
ggaggaagcaaggtgcgcgtggaccagaaatgcaagtcctcggcccagatagacccgactcccgtgatcgtcacctccaacaccaacatgtgc
gccgtgattgacgggaactcaacgaccttcgaacaccagcagccgttgcaagaccggatgttcaaatttgaactcaccgccgtctggatcatgact
ttgggaaggtcaccaagcaggaagtcaaagactttttccggtggcaaaggatcacgtggttgaggtggagcatgaattctacgtcaaaaagggtg
gagccaagaaaagacccgcccccagtgacgcagatataagtgagcccaaacgggtgcgcgagtcagttgcgcagccatcgacgtcagacgc
ggaagcttcgatcaactacgcggacaggtaccaaaacaaatgttctcgtcacgtgggcatgaatctgatgctgtttccctgcagacaatgcgagag
actgaatcagaattcaaatatctgcttcactcacggtgtcaaagactgtttagagtgctttcccgtgtcagaatctcaacccgtttctgtcgtcaaaaagg
cgtatcagaaactgtgctacattcatcacatcatgggaaaggtgccagacgcttgcactgcttgcgacctggtcaatgtggacttggatgactgtgttc
tgaacaataaatgacttaaaccaggtatgagtcggctggataaatctaaagtcataaacggcgctctggaattactcaatgaagtcggtatcgaagg
cctgacgacaaggaaactcgctcaaaagctgggagttgagcagcctaccctgtactggcacgtgaagaacaagcgggccctgctcgatgccctg
gccatcgagatgctggacaggcatcatacccacttctgcccctggaaggcgagtcatggcaagacttctgcggaacaacgccaagtcattccgc
tgtgctctcctctcacatcgcgacggggctaaagtgcatctcggcacccgcccaacagagaaacagtacgaaaccctggaaaatcagctcgcgtt
cctgtgtcagcaaggcttctccctggagaacgcactgtacgctctgtccgccgtgggccactttacactgggctgcgtattggaggaacaggagcatc
aagtagcaaaagaggaaagagagacacctaccaccgattctatgcccccacttctgagacaagcaattgagctgttcgaccggcagggagccg
aacctgccttccttttcggcctggaactaatcatatgtggcctggagaaacagctaaagtgcgaaagcggcgggccggccgacgcccttgacgattt
tgacttagacatgctcccagccgatgcccttgacgactttgaccttgatatgctgcctgctgacgctcttgacgattttgaccttgacatgctccccgggta
aatgcatgaattcgatctagagggcccctattctatagtgtcacctaaatgctagagctcgctgatcagcctcgactgtgccttctagttgccagccatctg
ttgtttgcccctcccccgtgccttccttgaccctggaaggtgccactcccactgtcctttcctaataaaatgaggaaattgcatcgcattgtctgagtaggt
gtcattctattctgggggtggggtggggcaggacagcaaggggggaggattgggaagacaatagcaggcatgctggggatgcggtgggctctat
ggcttctgaggcggaaagaaccagctggggctcgaatcaagctatcaagtgccacctgacgtctccctatcagtgatagagaagtcgacacgtctc
gagctccctatcagtgatagagaaggtacgtctagaacgtctccctatcagtgatagagaagtcgacacgtctcgagctccctatcagtgatagaga
aggtacgtctagaacgtctccctatcagtgatagagaagtcgacacgtctcgagctccctatcagtgatagagaaggtacgtctagaacgtctccta
tcagtgatagagaagtcgacacgtctcgagctccctatcagtgatagagaaggtaccccctatataagcagagagatcgttcaaatttgaactgact
aagcggctcccgccagatttggcaagattactaagcaggaagtcaaggactttttgcttgggcaaaggtcaatcaggtgccggtgactcacgagtt
taaagttcccagggaattggcgggaactaaagggggcggagaaatctctaaaacgcccactgggtgacgtcaccaatactagctataaaagtctgg
agaagcgggccaggctctcattgttcccgagacgcctcgcagttcagacgtgactgttgatcccgctcctctgcgaccgctagcttcgatcaactac
gcggacaggtaccaaaacaaatgttctcgtcacgtgggcatgaatctgatgctgtttccctgcagacaatgcgagagactgaatcagaattcaaata
tctgcttcactcacggtgtcaaagactgtttagagtgctttcccgtgtcagaatctcaacccgtttctgtcgtcaaaaaggcgtatcagaaactgtgctac
attcatcacatcatgggaaaggtgccagacgcttgcactgcttgcgacctggtcaatgtggacttggatgactgtgttctgaacaataaatgacttaaa
ccaggtatggctgccgatggttatcttccagattggctcgaggacaaccttagtgaaggaattcgcgagtggtgggctttgaaacctggagcccctca
acccaaggcaaatcaacaacatcaagacaacgctcgaggtcttgtgcttccgggttacaaatacctggacccggcaacggactcgacaaggg
gagccggtcaacgcagcagacgcggcgccctcgagcacgacaaggcctacgaccagcagctcaaggccggagacaacccgtacctcaag
tacaaccacgccgacgccgagttcaggagcggctcaaagaagatacgtctttggggcaacctcgggcgagcagtcttccaggccaaaaag
aggcttcttgaacctcttggtctggttgaggaagcggctaagacggctcctggaaagaagaggcctgtagagcagtctcctcaggaaccggactcct
ccgcgggtattggcaaatcgggtgcacagcccgctaaaaagagactcaatttcggtcagactggcgacacagagtcagtcccagaccctcaacc
aatcggagaacctcccgcagcccctcaggtgtgggatctcttacaatggcttcaggtggtggcgcaccagtggcagacaataacgaaggtgccg
atggagtgggtagttcctcgggaaattggcattgcgattcccaatggctgggggacagagtcatcaccaccagcacccgaacctgggcctgccc
acctacaacaatcacctctacaagcaaatcccaacagcacatctggaggatcttcaaatgacaacgcctacttcggctacagcacccctggg
gtatttgacttcaacagattccactgccactctcaccacgtgactggcagcgactcatcaacaacaactggggattccggcctaagcgactcaactt
caagctcttcaacattcaggtcaaagaggttacggacaacaatggagtcaagaccatcgccaataaccttaccagcacggtccaggtcttcacgg
actcagactatcagctcccgtacgtgctcggtcggctcacgagggctgcctcccgccgttcccagcggacgttcatgattcctcagtacgggtatct
gacgcttaatgatggaagccaggccgtgggtcgttcgtccttttactgcctggaatatttcccgtcgcaaatgctaagaacgggtaacaacttccagttc
agctacgagtttgagaacgtaccttccatagcagctacgctcacagccaaagcctggaccgactaatgaatccactcatcgaccaatacttgtacta
tctctcTaGAactattaacgttctggacagaatcaacaaacgctaaaattcagtgtggccggacccagcaacatggctgtccagggaagaaact
acatacctggacccagctaccgacaacaacgtgtctcaaccactgtgactcaaaacaacaacagcgaatttgcttggcctggagcttcttcttgggct ctcaatggacgtaatagcttgatgaatcctggacctgctatggccagccacaaagaaggagaggaccgtttctttcctttgtctggatctttaattttggc
aaacaaggTacCggCagagacaacgtggatgcggacaaagtcatgataaccaacgaagaagaaattaaaactactaacccggtagcaacg
gagtcctatggacaagtggccacaaaccaccagagtgcccaaACTTTGGCGGTGCCTTTTAAGgcacaggcgcagaccggTtgg
gttcaaaaccaaggaatacttccgggtatggtttggcaggacagagatgtgtacctgcaaggacccatttgggccaaaattcctcacacggacggc
aactttcacccttctccgctgatgggagggtttggaatgaagcaccgcctcctcagatcctcatcaaaaacacacctgtacctgcggatcctccaac
ggccttcaacaaggacaagctgaactcttcatcacccagtattctactggccaagtcagcgtggagatcgagtgggagctgcagaaggaaaaca
gcaagcgctggaacccggagatccagtacacttccaactattacaagtctaataatgttgaatttgctgttaatactgaaggtgtatatagtgaacccc
gccccattggcaccagatacctgactcgtaatctgtaattgcttgttaatcaataaaccgtttaattcgtttcagttgaactttggtctctgcgaagggcga
attcgtttaaacctgcaggactagaggtcctgtattagaggtcacgtgagtgttttgcgacattttgcgacaccatgtggtcacgctgggtatttaagccc
gagtgagcacgcagggtctccattttgaagcgggaggtttgaacgcgcagccgccaagccgaattctgcagatatccatcacactggcggccgct
cgactagagcggccgccaccgcggtggagctccagcttttgttccctttagtgaggttaattgcgcgcttggcgtaatcatggtcatagctgtttcctgt
gtgaaattgttatccgctcacaattccacacaacatacgagccggaagcataaagtgtaaagcctggggtgcctaatgagtgagctaactcacatta
attgcgttgcgctcactgcccgctttccagtcgggaaacctgtcgtgccagctgcattaatgaatcggccaacgcgcggggagaggcggtttgcgtat
tgggcgctcttccgcttcctcgctcactgactcgctgcgctcggtcgttcggctgcggcgagcggtatcagctcactcaaaggcggtaatacggttatc
cacagaatcaggggataacgcaggaaagaacatgtgagcaaaaggccagcaaaaggccaggaaccgtaaaaaggccgcgttgctggcgtttt
tccataggctccgcccccctgacgagcatcacaaaaatcgacgctcaagtcagaggtggcgaaacccgacaggactataaagataccaggcgtt
tccccctggaagctccctcgtgcgctctcctgttccgaccctgccgcttaccggatacctgtccgcctttctccctttcgggaagcgtggcgctttctcatag
ctcacgctgtaggtatctcagttcggtgtaggtcgttcgctccaagctgggctgtgtgcacgaaccccccgttcagcccgaccgctgcgccttatccggt
aactatcgtcttgagtccaacccggtaagacacgacttatcgccactggcagcagccactggtaacaggattagcagagcgaggtatgtaggcggt
gctacagagttcttgaagtggtggcctaactacggctacactagaagaacagtatttggtatctgcgctctgctgaagccagttaccttcggaaaaag
agttggtagctcttgatccggcaaacaaaccaccgctggtagcggtggtttttttgtttgcaagcagcagattacgcgcagaaaaaaaggatctcaag
aagatcctttgatcttttctacggggtctgacgctcagtggaacgaaaactcacgttaagggattttggtcatgagattatcaaaaaggatcttcacctag
atccttttaaattaaaaatgaagttttaaatcaatctaaagtatatatgagtaaacttggtctgacagttaccaatgcttaatcagtgaggcacctatctca
gcgatctgtctatttcgttcatccatagttgcctgactccccgtcgtgtagataactacgatacgggagggcttaccatctggccccagtgctgcaatgat
accgcgagacccacgctcaccggctccagatttatcagcaataaaccagccagccggaagggccgagcgcagaagtggtcctgcaactttatcc
gcctccatccagtctattaattgttgccgggaagctagagtaagtagttcgccagttaatagtttgcgcaacgttgttgccattgctacaggcatcgtggt
gtcacgctcgtcgtttggtatggcttcattcagctccggttcccaacgatcaaggcgagttacatgatcccccatgttgtgcaaaaaagcggttagctcc
ttcggtcctccgatcgttgtcagaagtaagttggccgcagtgttatcactcatggttatggcagcactgcataattctcttactgtcatgccatccgtaagat
gcttttctgtgactggtgagtactcaaccaagtcattctgagaatagtgtatgcggcgaccgagttgctcttgcccggcgtcaatacgggataataccgc
gccacatagcagaactttaaaagtgctcatcattggaaaacgttcttcggggcgaaaactctcaaggatcttaccgctgttgagatccagttcgatgta
acccactcgtgcacccaactgatcttcagcatcttttactttcaccagcgtttctgggtgagcaaaaacaggaaggcaaaatgccgcaaaaaaggg
aataagggcgacacggaaatgttgaatactcatactcttcctttttcaatattattgaagcatttatcagggttattgtctcatgagcggatacatatttgaat
gtatttagaaaaataaacaaataggggttccgcgcacatttccccgaaaagtgccacctaaattgtaagcgttaatattttgttaaaattcgcgttaaatt
tttgttaaatcagctcatttttaaccaataggccgaaatcggcaaaatcccttataaatcaaaagaatagaccgagatagggttgagtgttgttccagtt
tggaacaagagtccactattaaagaacgtggactccaacgtcaaagggcgaaaaaccgtctatcagggcgatggcccactacgtgaaccatcac
cctaatcaagttttttggggtcgaggtgccgtaaagcactaaatcggaacctaaagggagcccccgatttagagcttgacggggaaagccggcg
aacgtggcgagaaaggaagggaagaaagcgaaaggagcgggcgctagggcgctggcaagtgtagcggtcacgctgcgcgtaaccaccaca
cccgccgcgcttaatgcgccgctacagggcgcgtcccattcgccattcaggctgcgcaactgttgggaagggcgatcggtgcgggcctcttcgctat
tacgccagctggcgaaaggggggatgtgctgcaaggcgattaagttgggtaacgccagggttttcccagtcacgacgttaaaacgacggccagt
gagcgcgcgtaatacgactcactataggggcgaattgggtaccgggccccccctcgatcgag

SEQ ID NO: 10

FIG. 21 Cont.

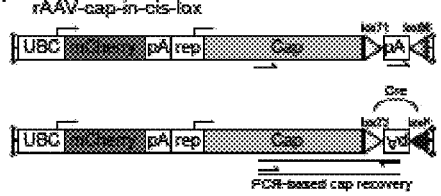
Fig. 22A rAAV-cap-in-cis-lox
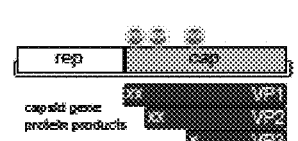
Fig. 22B rep-AAP AAV helper
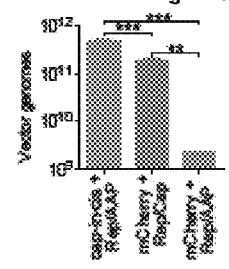
Fig. 22C
Fig. 22D
Fig. 22E rAAV-Δcap-in-cis acceptor
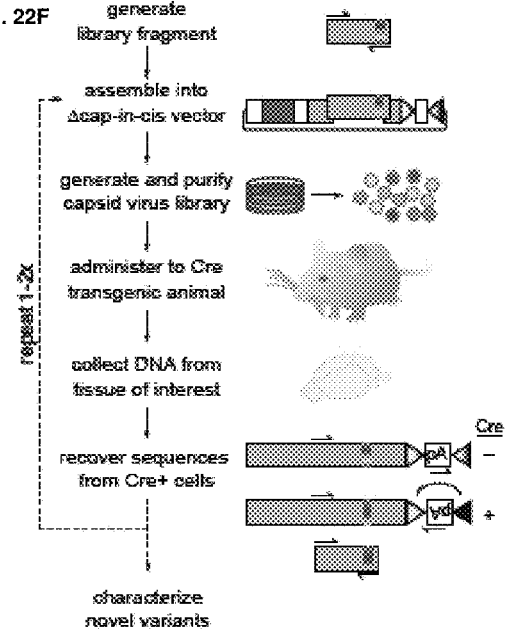
Fig. 22F

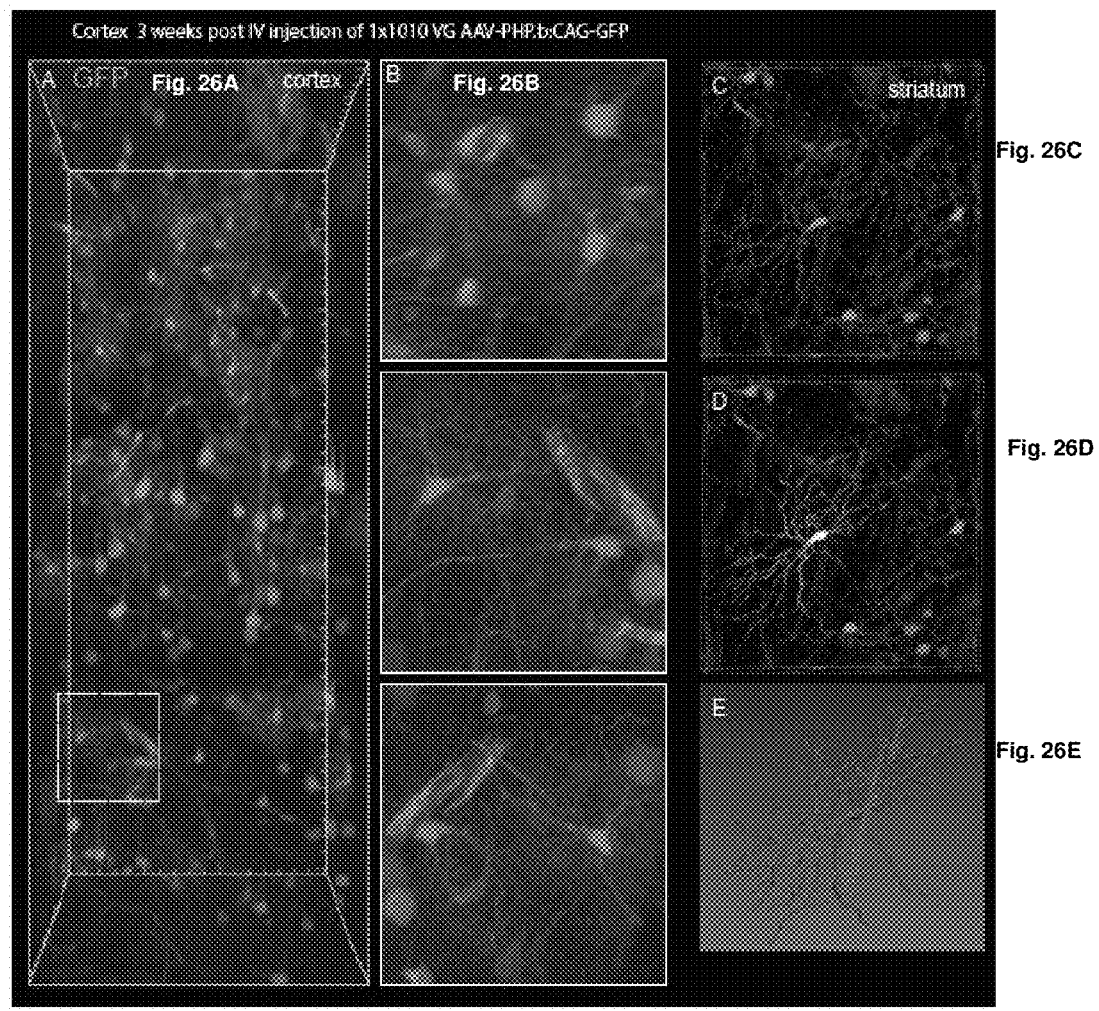

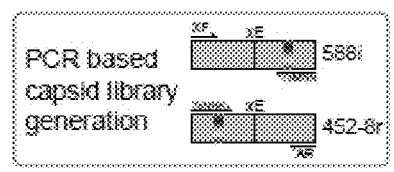

Fig. 27A

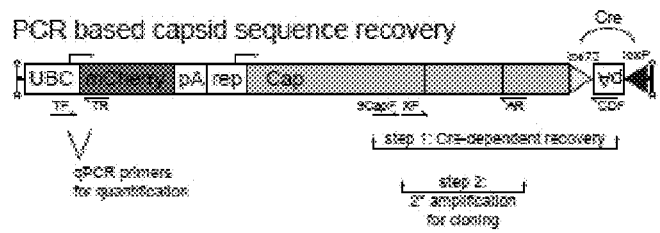

Fig. 27B

| | Primer | Purpose | Sequence |
|---|---|---|---|
| SEQ ID NO: 16 | 9CapF | Step 1: forward | CAGGTCTTCACGGACTCAGACTATCAG |
| SEQ ID NO: 17 | CDF | Step 1: reversed by Cre | CAAGTAAAACCTCTACAAATGTGGTAAAATCG |
| SEQ ID NO: 18 | XF | Step 2 forward | ACTCATCGACCAATACTTGTACTATCTCTCTAGAAC |
| SEQ ID NO: 19 | AR | Step 2 reverse | GGAAGTATTCCTTGGTTTTGAACCCA |
| SEQ ID NO: 20 | TF | qPCR forward | GGTCGCGGTTCTTGTTTGTGGAT |
| SEQ ID NO: 21 | TR | qPCR reverse | GCACCTTGAAGCGCATGAACTCCT |
| SEQ ID NO: 22 | 7xNNK | 452-8r library generation | CATCGACCAATACTTGTACTATCTCTCTAGAACTATTNNKNNK NNKNNKNNKNNKNNKCAAACGCTAAAATTCAGTGTGGCCGGA |
| SEQ ID NO: 23 | 7xMNN | 588i library generation | GTATTCCTTGGTTTTGAACCCAACCGGTCTGCGCCTGTGCMNN MNNMNNMNNMNNMNNMNNTTGGGCACTCTGGTGGTTTGTG |

Fig. 27C

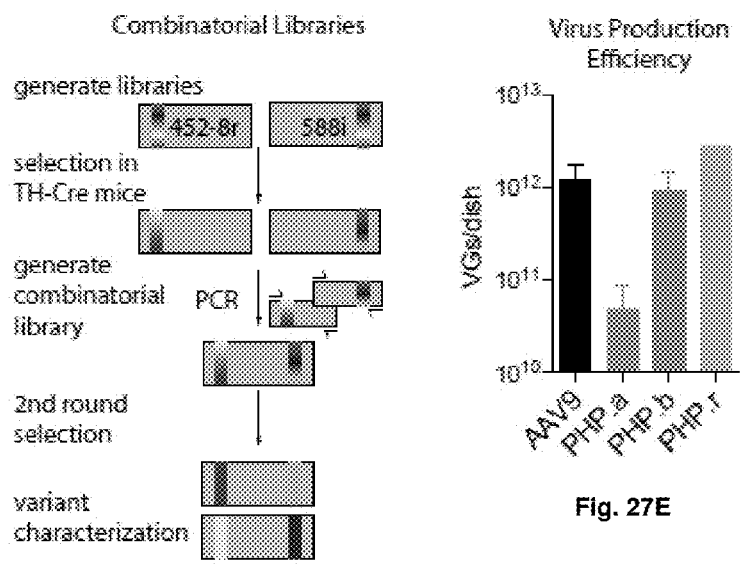

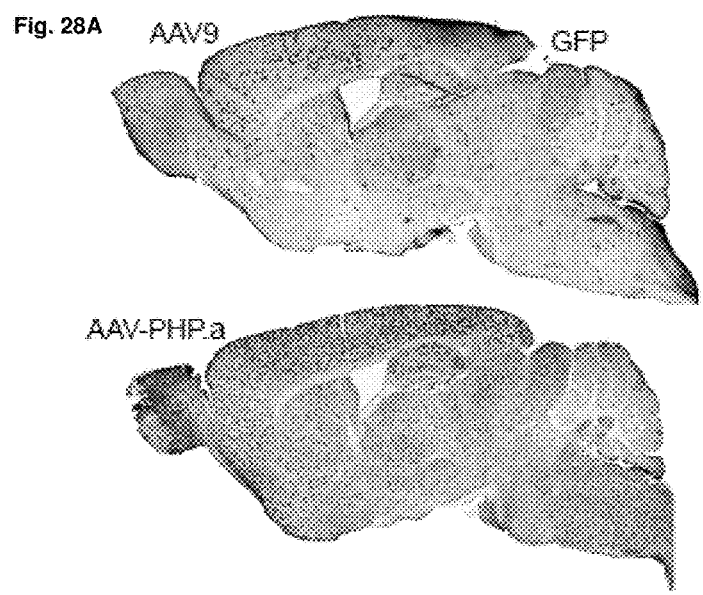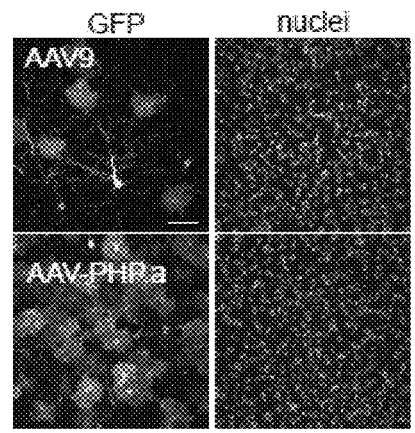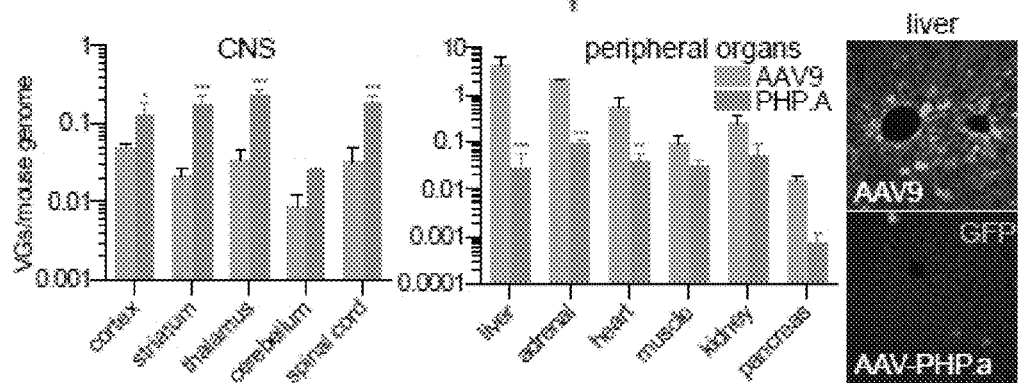
Fig. 28A
Fig. 28B
Fig. 28C
Fig. 28D
Fig. 28E AAV9 VP1 amino acid sequence.

SEQ ID NO: 2

MAADGYLPDWLEDNLSEGIREWWALKPGAPQPKANQQHQDNARGLVLPGYKYLGPGNGLDKGEPVNA
ADAAALEHDKAYDQQLKAGDNPYLKYNHADAEFQERLKEDTSFGGNLGRAVFQAKKRLLEPLGLVEEAA
KTAPGKKRPVEQSPQEPDSSAGIGKSGAQPAKKRLNFGQTGDTESVPDPQPIGEPPAAPSGVGSLTMAS
GGGAPVADNNEGADGVGSSSGNWHCDSQWLGDRVITTSTRTWALPTYNNHLYKQISNSTSGGSSNDN
AYFGYSTPWGYFDFNRFHCHFSPRDWQRLINNNWGFRPKRLNFKLFNIQVKEVTDNNGVKTIANNLTST
VQVFTDSDYQLPYVLGSAHEGCLPPFPADVFMIPQYGYLTLNDGSQAVGRSSFYCLEYFPSQMLRTGNN
FQFSYEFENVPFHSSYAHSQSLDRLMNPLIDQYLYYLSKTINGSGQNQQTLKFSVAGPSNMAVQGRNYIP
GPSYRQQRVSTTVTQNNNSEFAWPGASSWALNGRNSLMNPGPAMASHKEGEDRFFPLSGSLIFGKQG
TGRDNVDADKVMITNEEEIKTTNPVATESYGQVATNHQSAQAQAQTGWVQNQGILPGMVWQDRDVYLQ
GPIWAKIPHTDGNFHPSPLMGGFGMKHPPPQILIKNTPVPADPPTAFNKDKLNSFITQYSTGQVSVEIEWE
LQKENSKRWNPEIQYTSNYYKSNNVEFAVNTEGVYSEPRPIGTRYLTRNL

SEQ ID NO: 2

AAV9 VP1 nucleic acid sequence

SEQ ID NO. 11 atggctgccgatggttatcttccagattggctcgaggacaaccttagtgaaggaattcgcgagtggtgggctttgaaacctggagcccctcaacccaa
ggcaaatcaacaacatcaagacaacgctcgaggtcttgtgcttccgggttacaaatacctggacccggcaacggactcgacaaggggggagccg
gtcaacgcagcagacgcggcggccctcgagcacgacaaggcctacgaccagcagctcaaggccggagacaacccgtacctcaagtacaacc
acgccgacgccgagttccaggagcggctcaaagaagatacgtcttttgggggcaacctcggcgagcagtcttccaggccaaaaagaggcttctt
gaacctcttggtctggttgaggaagcggctaagacggctcctggaaagaagaggcctgtagagcagtctcctcaggaaccggactcctcgcggg
tattggcaaatcgggtgcacagcccgctaaaaagagactcaatttcggtcagactggcgacacagagtcagtcccagaccctcaaccaatcgga
gaacctcccgcagcccctcaggtgtgggatcttctacaatggcttcaggtggtggcgcaccagtggcagacaataacgaaggtgccgatggagt
gggtagttcctcgggaaattggcattgcgattcccaatggctgggggacagagtcatcaccaccagcacccgaacctgggccctgcccacctaca
acaatcacctctacaagcaaatctccaacagcacatctggaggatcttcaaatgacaacgcctacttcggctacagcacccccctggggtatttga
cttcaacagattccactgccactctcaccacgtgactggcagcgactcatcaacaacaactgggattccggcctaagcgactcaacttcaagctct
tcaacattcaggtcaaagaggttacggacaacaatggagtcaagaccatcgccaataaccttaccagcacggtccaggtcttcacggactcagac
tatcagctcccgtacgtgctcgggtcggctcacgagggctgcctcccgccgttccagcggacgtttcatgattcctcagtacgggtatctgacgctta
atgatggaagccaggccgtgggtcgttcgtccttttactgcctggaatatttcccgtcgcaaatgctaagaacgggtaacaactccagttcagctacg
agtttgagaacgtaccttccatagcagctacgctcacagccaaagcctggaccgactaatgaatccactcatcgaccaatacttgtactatctctcaa
agactattaacggttctggacagaatcaacaaacgctaaaattcagtgtggccggacccagcaacatggctgtccagggaagaaactacatacct
ggacccagctaccgacaacaacgtgtctcaaccactgtgactcaaaacaacaacagcgaatttgcttggcctggagcttcttcttgggctctcaatgg
acgtaatagcttgatgaatcctggacctgctatggccagccacaaagaaggagaggaccgtttctttcctttgtctggatctttaatttttggcaaacaag
gaactggaagagacaacgtggatgcggacaaagtcatgataaccaacgaagaagaaattaaaactactaacccggtagcaacggagtcctat
ggacaagtggccacaaaccaccagagtgcccaagcacaggcgcagaccggctgggttcaaaaccaaggaatacttccgggtatggtttggcag
gacagagatgtgtacctgcaaggacccatttgggccaaaattcctcacacgacggcaactttcaccttctccgctgatgggagggtttggaatga
agcacccgcctcctcagatcctcatcaaaaacacacctgtacctgcggatcctccaacgccttcaacaaggacaagctgaactctttcatcaccc
agtattctactggccaagtcagcgtggagatcgagtgggagctgcagaaggaaaacagcaagcgctggaacccgagatccagtacacttcca
actattacaagtctaataatgttgaatttgctgttaatactgaaggtgtatatagtgaaccccgccccattggcaccagatacctgactcgtaatctgtaa

SEQ ID NO: 11

FIG. 31

| Sequence ID | Nucleic acid sequence | AA sequence | Percent of total clones |
|---|---|---|---|
| SEQ ID NO:24 | ACTTTGGCGGTGCCTTTTAAG | TLAVPFK (SEQ ID NO: 1) | 25% (20/80) |
| SEQ ID NO:25 | AGTGTGAGTAAGCCTTTTTTG | SVSKPFL (SEQ ID NO: 28) | 10% (8/80) |
| SEQ ID NO:26 | TTTACGTTGACGACGCCTAAG | FTLTTPK (SEQ ID NO: 29) | 7.5% (6/80) |
| SEQ ID NO:27 | ATGAATGCTACGAAGAATGTG | MNATKNV (SEQ ID NO: 30) | 5% (4/80) |

SELECTIVE RECOVERY

RELATED APPLICATIONS

The present application is a divisional of U.S. application Ser. No. 14/485,024, filed Sep. 12, 2014, which claims priority to U.S. Provisional Application No. 61/877,506, filed Sep. 13, 2013, U.S. Provisional Application No. 61/983,624, filed Apr. 24, 2014, U.S. Provisional Application No. 62/020,658, filed Jul. 3, 2014, and U.S. Provisional Application No. 62/034,060, filed Aug. 6, 2014, each of which is hereby incorporated by reference in its entirety.

STATEMENT REGARDING FEDERALLY SPONSORED R & D

This invention was made with government support under Grant No. MH100556, Grant No. MH086383, Grant No. AG047664 and Grant No. OD017782 awarded by the National Institutes of Health. The government has certain rights in the invention.

SEQUENCE LISTING IN ELECTRONIC FORMAT

The present application is being filed along with a Sequence Listing in electronic format. The Sequence Listing is provided as a file entitled SEQUENCELISTING_CALTE103D1.TXT, created on Oct. 21, 2014, last modified on Feb. 1, 2017, which is 98,622 bytes in size. The information in the electronic format of the Sequence Listing is incorporated herein by reference in its entirety.

FIELD OF THE INVENTION

The present invention relates to methods of selective recovery and targeting proteins and/or methods.

BACKGROUND

Recombinant adeno-associated viruses (rAAV) are vectors for in vivo gene transfer applications. Several rAAV-based gene therapies are proving to be efficacious, most notably for the treatment of Leber's congenital amaurosis, hemophilia associated with factor IX deficiency and lipoprotein lipase deficiency (Simonelli et al 2010; Nathwani et al 2011; Gaudet et al. 2010). Recently, the first rAAV-based gene therapy, Glybera, was approved by the European Medicines Agency for the treatment of lipoprotein lipase deficiency. rAAVs have also shown success in preclinical models of a large variety of diseases, including Rett syndrome, congenital ALS, Parkinson's, Huntington's disease, Spinal Muscular Atrophy, among others and for the prophylactic delivery of broad neutralizing antibodies against infectious diseases such as HIV and influenza (Garg et al 2013; Valori et al. 2010; Foust et al. 2010; Foust et al 2013; Southwell et al 2009; Balazs et al 2011; and Balazs et al 2013). In addition, rAAVs are also popular vectors for in vivo delivery of transgenes for non-therapeutic scientific studies, such as optogenics.

SUMMARY OF THE INVENTION

In some embodiments, an AAV vector is provided that comprises an amino acid sequence that comprises at least 4 contiguous amino acids from the sequence TLAVPFK (SEQ ID NO: 1) or KFPVALT (SEQ ID NO: 3).

In some embodiments, a central nervous system targeting peptide is provided that comprises an amino acid sequence of SEQ ID NO: 1 (or any of the amino acid sequences in FIG. 31).

In some embodiments, a nucleic acid sequence encoding any four contiguous amino acids in TLAVPFK (SEQ ID NO: 1) or in KFPVALT (SEQ ID NO: 3) is provided (or for any of the sequences from FIG. 31).

In some embodiments, a method of delivering a nucleic acid sequence to a nervous system is provided. The method can comprise providing a protein comprising TLAVPFK (SEQ ID NO: 1) (or any of the other targeting sequences provided herein, for example, in FIG. 31), wherein the protein is part of a capsid of an AAV, and wherein the AAV comprises a nucleic acid sequence to be delivered to a nervous system; and administering the AAV to the subject.

In some embodiments, an rAAV genome is provided that comprises at least one inverted terminal repeat configured to allow packaging into a vector and a cap gene.

In some embodiments a plasmid system is provided that comprises a first plasmid comprising a modified AAV2/9 rep-cap helper plasmid configured such that it eliminates at least one of VP1, VP2, or VP3 expression and a second plasmid comprising a rAAV-cap-in-cis plasmid.

In some embodiments, a method of developing a capsid with a desired characteristic is provided. The method can comprise providing a population of rAAV genomes (of any provided herein), selecting the population by a specific set of criteria, and selecting the rAAV genome that meets the screening criteria.

In some embodiments, a capsid protein is provided that comprises an amino acid sequence that comprises at least 4 contiguous amino acids from the sequence TLAVPFK (SEQ ID NO: 1) or KFPVALT (SEQ ID NO: 3) (or from any of the sequences in FIG. 31).

In some embodiments, a library of nucleic acid sequences is provided. The library can comprise a selectable element and one or more recombinase recognition sequences.

In some embodiments, a method of developing a capsid with a desired characteristic is provided. The method comprises providing a library of plasmids that comprise a capsid gene, and at least one recombinase recognition sequence, configured such that it allows a recombinase-dependent change in a sequence of a plasmid of the library that comprises the capsid gene that is a detectable change. The method can further comprise selecting the population by a specific set of criteria and selecting the rAAV genome that meets the screening criteria.

BRIEF DESCRIPTION OF THE DRAWINGS

FIG. 1A depicts various embodiments for aspects of various targeting proteins (in this case, examples of AAV capsid proteins), including G2B-13, G2B-26, TH1.1-32 and TH1.1-35.

FIG. 2A depicts some embodiments of AAV genome manipulation.

FIG. 2B depicts some embodiments of capsid gene manipulation.

FIGS. 3A and 3B. A strategy for recombinase-dependent recovery of sequences from transduced target cells. (FIG. 3A) The schematic shows the cap-in-cis rAAV genome. A ubiquitin C promoter fragment can be used to drive expression of an mCherry reporter followed by a synthetic polyA sequence. An AAV capsid gene, controlled by rep regulatory sequences, is followed by a lox71- and lox66-flanked SV40 late polyA signal. The lox66 site is inverted relative to lox71. In this configuration, Cre mediates the inversion (FIG. 3B) of the sequence flanked by the mutant lox sites. After the inversion, incompatible, double mutant lox72 and a loxP site are generated, reducing the efficiency of inversion back to the original state. Using PCR primers represented by the arrows in the schematic, cap sequences can be recovered selectively from genomes that have undergone a Cre-dependent inversion.

(FIG. 4A) Single inverted loxP or lox71 and lox66 sites can be replaced by double loxP (white triangle) and lox2272 (black triangle) for irreversible recombination. (FIG. 4B) loxP sites or similar sites (lox2272 or other variants) inserted in the same orientation to mediate a deletion also allow selective recombination-dependent amplification. Recombination specific recovery can be achieved by performing the PCR-based recovery with three primers: one 5' of the randomized sequence (black arrow), one reverse primer downstream of the 3' loxP sequence (dark gray arrow) and a second forward primer that binds specifically within the deleted sequence (light gray arrow). This primer out competes the 5' (black) forward primer during amplification, reducing amplification of cap sequences from non-recombined sequences. Recovery of non-recombined sequences can also be reduced by digestion with an enzyme that recognizes a site within the sequence deleted by the recombinase. Alternatively, Cre-dependent and -independent products can be separated by size by gel electrophoresis. (FIGS. 4C & 4D) Inverted loxP, lox71 and lox66 (shown), or DIO, FLEX sites can be placed in alternative configurations. (FIG. 4C) shows lox sites in an inverted orientation surrounding the rep and cap sequences, which can be inverted in the presence of Cre. (FIG. 4D) Schematic shows the option of flanking the reporter with lox sites. In this embodiment, the reporter is inverted and can be expressed after recombination.

(FIG. 5A) DNase-resistant AAV genome copies (GCs) produced with the split AAV2/9 rep-AAP and AAV9 cap-in-cis genome (left), the AAV2/9 rep-AAP and a mCherry expressing rAAV genome (no cap-middle) or a control AAV2/9 rep/cap helper with the same AAV2:mCherry genome (right). (FIG. 5B) DNase-resistant viral GCs obtained from larger scale (7-10 150 mm plate) preps of libraries with randomized 7-mer sequences replacing AAV9 capsid amino acids 452-8 (left) or inserted after amino acid 588 (right) (n=4/per library±SEM). (FIG. 5C) The PCR fragments containing the capsid sequence variation (black, 452-8 or light gray, 588) libraries are generated and cloned into a rAAV9R-delta-X/Acap-in-cis vector that has been modified to insert unique restriction sites XbaI (X) and AgeI (A) flanking the region to be modified.

(FIG. 6A) The schematic shows an overview of the selection process. In example 3, GFAP-Cre+ mice were injected with AAV virus containing AAV9-cap-in-cis, or the cap libraries with random 7mers at amino acids 452-8 or 588, and PCR products were recovered using primers that selectively amplify sequences from cap-in-cis genomes that have undergone Cre-mediated inversion of the sequence 3' to the cap gene. (FIG. 6B) The image shows an ethidium bromide-stained agarose gel of the PCR products recovered after the second PCR step using primers 1331 and 1312. (FIG. 6C) Recovered PCR products are then cloned into the rAAV9R-delta-X/A-cap-in-cis vector as a first step to generate the next round of capsid virus libraries.

(FIG. 8A) Panels show native eGFP fluorescence in whole brain. (FIG. 8B) Immunostaining for eGFP expression in the sectioned brains of mice injected with the indicated virus show efficient transduction of multiple cell types including neurons (n) and astrocytes (a). (FIG. 8C) Panels show native eGFP fluorescence in the livers of mice injected with the indicated virus.

FIGS. 9A-9I. G2B13 and G2B26 variants mediate enhanced transduction of CNS neurons and glia after IV administration as compared to AAV9. A rAAV-CAG-eGFP-2A-ffLUC-WPRE-SV40-pA vector was packaged into G2B13 (FIG. 9A-9C) or G2B26 (FIG. 9D-9I) and 1e12 GC of the indicated virus was injected IV into individual 5-week old female wt C57Bl/6 mice. (FIG. 9A-9B, FIG. 9D-9I) Panels show immunostaining for eGFP in the sectioned brains of mice 6 days after they were injected IV with G2B13:CAG-GFP2A-Luc (FIG. 9A-9B) or G2B26:CAG-GFP2A-Luc (FIG. 9D, FIG. 9E, FIG. 9G-9I). Both vectors show transduction of several cell types including neurons (n) and astrocytes (a). (FIG. 9A-9B, FIG. 9D-9E, FIG. 9G-9H) Panels show eGFP immunostaining (upper panels) and NeuN immunostaining (lower panels) from paired image fields. (FIG. 9C and FIG. 9F) Panels show native eGFP fluorescence in the spinal cords of mice injected with G2B13

(FIG. 9C) or G2B26 (FIG. 9F). (FIG. 9I) Panel shows eGFP immunostaining in (upper panels) co-localized (arrows) with the glial marker Sox2 (lower panels) from the same image field.

(FIG. 11A) The Brain Explorer 2 (Allen Brain Atlas) schematic shows an overview of the selection process. Capsid virus libraries were injected bilaterally into the strait of TH-Cre+ mice (asterisks show approximate injection sites), and capsid sequences were recovered from the substantia nigra (highlighted with a white square). (FIG. 11B) The image shows native mCherry fluorescence from 1 mm slices through the forebrain containing the striatal injection sites. (FIG. 11C) mCherry+ fibers from striatal neurons can be seen in slices from the SNr. The SNr and SNc located dorsal to the SNr were collected for capsid sequence recovery. (FIG. 11D) Panels show ethidium bromide stained PCR products recovered from TH-Cre+ cells of mice injected with AAV virus containing the libraries with random 7mers at amino acids 452-8 or 588 (round 1). (FIG. 11E) Cap-in-cis genomes were recovered by a Cre-independent PCR strategy from Cre+ and Cre− mice demonstrating the presence of virus in all samples.

(FIG. 12A) GFP expression within the striatum surrounding the injection site of the TH1.1-35 variant. (FIG. 12B-E) Panels show GFP immunostaining (FIG. 12B and FIG. 12D) and TH immunostaining (FIG. 12C and FIG. 12E) within the same image field within the SN. Co-localization of GFP and TH+ immunostaining within the same cell is noted with arrows. GFP expression is evident in the SNr and a subpopulation of TH+ neurons in the SNc of a mouse injected with TH1.1-35 (FIG. 12B-C) or TH1.1-32 (FIG. 12D-E). (FIG. 12F) GFP immunostaining in the frontal cortex of a mouse injected with the TH1.1-35 variant. GFP immunostaining in the thalamus (FIG. 12G) and amygdala (FIG. 12H) of a mouse injected with the TH1.1-32 variant.

FIG. 14 depicts a structural model of some embodiments of a capsid protein showing the loop regions where targeting sequences can be added or substituted in.

FIG. 15 depicts some embodiments of the rAAV9R-delta-X/A-cap-in-cis vector.

FIG. 16 depicts some embodiments of an AAV rep/cap helper plasmid that was modified by inserting a total of 5 stop codons within the cap gene within the VP1, 2 and 3 reading frame (1 stop codon disrupts VP3, 3 disrupt VP2 and all 5 disrupt VP1—FIG. 2F, SEQ ID NO: 5).

FIG. 17 depicts some embodiments of a template DNA (pCRII-9R-X/A EK plasmid, SEQ ID NO: 6.)

FIG. 18 depicts AAV9R-delta-X/A-cap-in-cis, SEQ ID NO: 7, in which the coding region between the XbaI and AgeI sites was eliminated to prevent "wt" AAV9R X/A capsid protein production from any undigested vector during library virus production.

FIG. 19 depicts some embodiments of a sequence of an AAV-PHP.B (AAV-G2B26) capsid VP1 protein.

FIG. 20 depicts some embodiments of a nucleic acid sequence for an AAV-PHP.B (AAV-G2B26) capsid gene coding sequence.

FIG. 21 depicts some embodiments in which a nucleic acid sequence for a targeting protein is cloned into an AAV Rep-Cap helper plasmid.

FIGS. 22A-22F. Recombinase-dependent recovery of AAV capsid sequences from transduced target cells. FIG. 22A is a schematic showing the rAAV-cap-in-cis rAAV genome used for capsid library generation. Cre mediates the inversion of the sequence flanked by the mutant lox sites and PCR primers, represented by half arrows in the schematic, are used to selectively amplify the recombined sequences. (FIG. 22B) The schematic shows the AAV components of the Rep-AAP helper plasmid. Stop codons inserted in the VP reading frame eliminate VP1, VP2 and VP3. (FIG. 22C) DNase-resistant AAV genome copies (GCs) produced with the split AAV2/9 rep-AAP and AAV9 cap-in-cis genome (left) as compared to a control AAV2/9 rep/cap helper with a control AAV-UBC-mCherry genome (middle) or the AAV2/9 rep-AAP and control AAV-UBC-mCherry genome (no cap—right). (FIG. 22D) Representative PCR products showing Cre dependent (top) and Cre independent (bottom) amplification of recovered capsid library sequences from TH-Cre positive or Cre negative mice. (FIG. 22E) The capsid sequence variation libraries at AA452-8 or after AA588 of AAV9 (vertical gradient) are generated by PCR and cloned into a rAAV-Δcap-in-cis vector that has been modified to insert unique restriction sites XbaI (x) and AgeI (a) flanking the variable region(s). (FIG. 22F) The schematic shows an overview of some embodiments of the selection process.

(FIG. 23A) Capsid libraries were injected into the striatum (left) and tissue from the substantia nigra was collected for capsid sequence recovery 10 days later. (FIG. 23A) Images show native mCherry fluorescence expressed from the cap-in-cis library genomes surrounding the injection sites (left) and mCherry positive axons from striatal neurons in the SNr (right). (FIG. 23B-FIG. 23H) The recovered AAV variant PHP.R2 was used to package ssAAV-CAG-GFP and $7 \times 10^9$ VG was injected into the striatum. Seven days later, the mice were assessed for GFP expression by immunostaining. The images show GFP positive cells at the striatal injection site (FIG. 23B) or at the indicated brain regions that contain GFP+ cell bodies (FIG. 23C, FIG. 23E-I). (FIG. 23D) shows immunostaining for TH in the SNc. (FIG. 23E) shows GFP immunostaining from the same field shown in FIG. 23D. Co-localization of GFP and TH immunostaining within the same cell is noted with arrows. Scale bars are 100 um in C, E-H and 20 um in 23D.

(FIG. 24A) Images show GFP immunostaining in sagittal brain sections from mice given AAV9 (left), an equivalent dose of AAV-PHP.B (middle) or 1×10$^{11}$ VG of AAV-PHP.B (right). (FIG. 24B) Representative cortical (left) or striatal (right) 50 um maximum confocal projection images of native eGFP fluorescence from the brains of mice treated as in 24A. (FIG. 24C) Nearly all Calbindin$^+$ Purkinje cells (bottom) are GFP$^+$ (top) 3 weeks after IV injection of 1×10$^{12}$ VG of AAV-PHP.B (FIG. 24D) Representative image of native GFP fluorescence from the lumbar spinal cord. The inset shows an enlargement of the boxed ventral spinal cord area. (FIG. 24E) Confocal maximum projection image of GFP fluorescence from a whole mount retina. (FIG. 24F) Cross section of the retina. (FIG. 24G) CLARITY images of GFP fluorescence from the cortex (left), striatum (right) and ventral spinal cord of a mouse transduced with 1×10$^{12}$ VG of AAV-PHP.B. AAV biodistribution in the brain (FIG. 24H) and peripheral organs (FIG. 24I) 25 days after injection of 1×10$^{11}$ VG IV into adult mice. N=3 for AAV-PHP.B and N=4 for AAV9; error bars show standard deviation (s.d.); *p<0.05, ***p<0.001, one-way ANOVA and Bonferroni's multiple comparison test. Scale bars are 1 mm in FIG. 24A and FIG. 24D, 50 um in 24B, and 200 μm in FIG. 24C. Major tick marks in FIG. 24G are 100 um.

FIG. 26. Systemic, low-dose AAV-PHP.B reporter vector labeling can be used together with CLARITY for single cell morphological phenotyping. (FIG. 26A) A tiled image of the cortex shows sparse labeling of cells with GFP after IV administration of 1×10$^{10}$ VG of rAAV-PHP.B:CAG-GFP. The region highlighted by the box is shown magnified in 3 different orientations (FIG. 26B). Two astrocytes can be seen making contact with a blood vessel containing an endothelial cell with a GFP+ nucleus. The astrocyte endfeet can be seen spiraling around the blood vessel. In some embodiments, this can be used to label individual cells, assess the morphology of the cells and see the material's impact on the cells. (FIG. 26C) An image of the striatum shows sparse labeling of cells with GFP after IV administration of 1×10$^{10}$ VG of rAAV-PHP.B:CAG-GFP. (FIG. 26D) An individual medium spiny neuron is highlighted using an semi-automated filament tracing method (Imaris, Bitplane software). (FIG. 26E) The same medium spiny neuron highlighted in FIG. 26D is shown isolated along with several closely associated neural processes. In some embodiments, this can be used to sparsely label cells and assess the association of the labeled cells.

FIGS. 27A-27C Primers used for generating capsid library fragments and Cre-dependent capsid sequence recovery. (FIG. 27A) Schematic shows PCR products as the right hand shaded section with 7AA of randomized sequence (represented by vertical multishaded bars) inserted after amino acid 588 (588i library) or replacing AA452-8 (452-8r library). The primers used to generate these libraries are indicted by name and half arrow. For the generation of the second library, the template was modified to eliminate a naturally occurring EarI restriction site within the capsid gene fragment (xE). In this way, any contamination from amplified wt AAV capsid sequence could be eliminated by digesting the recovered libraries with EarI. (FIG. 27B) Schematic shows the rAAV-Cap-in-cis vector and the primers used to quantify vector genomes (left) and recover sequences that have transduced Cre expressing cells (left). (FIG. 27C) The figure provides the sequences for the primers shown in FIG. 27A and FIG. 27B. Table 0.1 also provides a listing of the sequences:

TABLE 0.1

| Primer | Purpose | Sequence |
|---|---|---|
| 9CapF | Step 1: forward | CAGGTCTTCACGGACTCAGACTATCAG SEQ ID NO: 16 |
| CDF | Step 1: reversed by Cre | CAAGTAAAACCTCTACAAATGTGGTAAAATCG SEQ ID NO: 17 |
| XE | Step 2 forward | ACTCATCGACCAATACTTGTACTATCTCTCTAGAAC SEQ ID NO: 18 |
| AR | Step 2 reverse | GGAAGTATTCCTTGGTTTTGAACCCA SEQ ID NO: 19 |
| TF | qPCR forward | GGTCGCGGTTCTTGTTTGTGGAT SEQ ID NO: 20 |
| TR | qPCR reverse | GCACCTTGAAGCGCATGAACTCCT SEQ ID NO: 21 |
| 7xNNK | 452-8r library generation | CATCGACCAATACTTGTACTATCTCTCTAGAACTATTNNKNNK NNKNNKNNKNNKNNKNNKCAAACGCTAAAATTCAGTGTGGCCGGA SEQ ID NO: 22 |
| 7xMNN | 588i library generation | GTATTCCTTGGTTTTGAACCCAACCGGTCTGCGCCTGTGCMNN MNNMNNMNNMNNMNNMNNTTGGGCACTCTGGTGGTTTGTG SEQ ID NO: 23 |

FIG. 27D The schematic shows an overview of some embodiments of a process used to introduce 2-site randomization after the first round of selection (combinatorial libraries). This process was used to develop AAV-PHP.R2. Both libraries (452-8r and 588i) were generated by PCR, cloned into the rAAV-Cap-in-cis vector and capsid selection was performed in TH-Cre mice. Sequences from both libraries were recovered and were combined using an overlapping PCR strategy to generate a new library that should contain all possible combinations of the 7mer sequences recovered from the 452-8r library with all of the 7mer sequences recovered at the 588i in one library. This library was subjected to a second round of selection in TH-Cre mice and recovered variants that showed signs of enrichment were characterized individually.

FIG. 27E DNase-resistant vector genomes (VGs) obtained from preps of individual variants recovered from GFAP-Cre and TH-Cre selections. Yields are given as vector genome copies per 150 mm dish of producer cells. Error bars show s.d. N=3 for AAV9, PHP.A and PHP.B. N=1 for PHP.r. One way analysis of variance (ANOVA).

FIG. 28A-28E AAV-PHP.A more efficiently and selectively transduces CNS astrocytes. (FIG. 28A) Representative images of GFP immunostaining of brain sections from mice injected as adults with $3 \times 10^{11}$ VG of a ssAAV-CAG-eGFP expressing vector packaged into AAV9 or PHP.A as indicated. (FIG. 28B) Panels show GFP immunostaining (left) and cell nuclei (right) in the cortex of mice that received AAV9 or PHP.A as indicated. AAV biodistribution in the brain (FIG. 28C) and peripheral organs (FIG. 28D) 25 days after injection of $1 \times 10^{11}$ VG IV into adult mice. N=4; error bars show standard deviation (s.d.); *p<0.05, p<0.01, *p<0.001, one-way ANOVA and Bonferroni's multiple comparison test. (FIG. 28E) Representative images of GFP immunostaining of liver sections from mice injected as adults with $3 \times 10^{11}$ VG of a ssAAV-CAG-eGFP expressing vector packaged into AAV9 or PHP.A as indicated. Scale bar is 50 µm in 28B.

Figure 29:
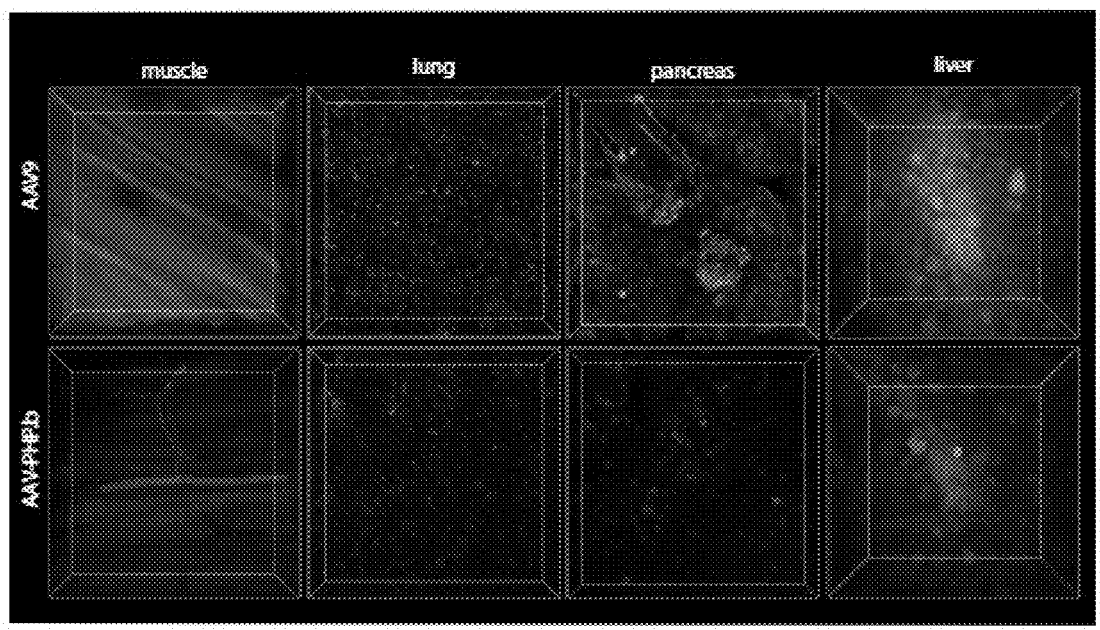

FIG. 29. Rapid cellular level tropism characterization with whole animal tissue clearing. Images show native GFP fluorescence in the indicated organs of mice 3 weeks after IV injection of $1 \times 10^{12}$ AAV9 or AAV-PHP.B as indicated. The indicated organs were rendered optically transparent using the PARS-based CLARITY (a whole body tissue clearing method—Yang et al. 2014). Confocal Z-stack images were reconstructed into three-dimensional images using Imaris software (Bitplane).

FIG. 30 depicts a set of embodiments for amino acid and nucleic acid of AAV9.

FIG. 31 Depicts a set of embodiments for additional targeting proteins. Any of the targeting protein embodiments provided in FIG. 31 can be swapped out for any of the embodiments involving any other particular targeting protein embodiment described herein. Similarly, any of the nucleic acids provided in FIG. 31 can similarly be swapped out for any of the particular nucleic acids provided herein. The figure depicts the most highly enriched sequences recovered from the second round of selection for AAV variants that transduce GFAP-Cre+ astrocytes following intravenous administration.

DETAILED DESCRIPTION OF EMBODIMENTS rAAVs have reinvigorated the field of gene therapy and facilitate the gene transfer critical for a wide variety of basic science studies. Several characteristics make rAAVs attractive as gene delivery vehicles: (i) they provide long-term transgene expression, (ii) they are not associated with any known human disease, (iii) they elicit relatively weak immune responses, (iv) they are capable of transducing a variety of dividing and non-dividing cell types and (v) the rAAV genome can be packaged into a variety of capsids, or protein coat of the virus, which have different transduction characteristics and tissue tropisms. Despite these advantages, the use of AAV for many applications is limited by the lack of capsid serotypes that can efficiently transduce certain difficult cell types and by the lack of serotypes that can efficiently and selectively target a desired cell type/organ after systemic delivery.

Using Directed Evolution to Improve AAV Capsid Characteristics.

One approach that has been used to develop rAAVs with improved tissue/cell type targeting is to perform directed evolution on the AAV capsid gene. Typically this is done by making a library of replication competent AAVs that are modified to introduce random mutations into the AAV cap gene, which codes for the capsid proteins that determines the tissue tropism. The AAV capsid virus library is then injected in an animal or delivered to cells in culture. After a certain time, capsid sequences that are present in the cells/tissue of interest are recovered. These recovered sequences are then used to generate a new pool of viruses and then the process is repeated. Through repeated rounds of selection/sequence recovery, sequences that generate capsids that function better (i.e., those repeatedly pass the selection process) will be enriched. The capsids that exhibit an improved ability to transduce the target can then be recovered and assessed as individual clones or mutated further and subjected to additional rounds of selection.

Directed evolution has been used to generate AAVs that evade neutralizing antibodies (Maheshri et al 2006) and better target glioma cells (McGuire et al. 2010), airway epithelium (Excoffon et al. 2009) and photoreceptors in the retina after intravitreal injection (Dalkara et al 2013). In addition, using a human/mouse chimeric liver model, Lisowski et al. developed a rAAV that specifically and efficiently targeted the human hepatocytes (2013).

Some of the embodiments herein described provide methods for the enrichment and selective recovery of sequences with desirable traits from libraries of sequence variants using a recombination-dependent recovery strategy. This method is widely applicable for the selective enrichment of sequences from randomized libraries that mediate an increased contact between the nucleic acid containing the randomized sequence and a recombinase that recognizes a specific sequence or sequences present on the same nucleic acid as the randomized sequence. The recombinase can be expressed in response to desired stimuli, in a desired subcellular compartment or expressed in a specific target population of cells in vitro or in vivo.

As an example of the use of some embodiments, an option for selectively recovering adeno-associated virus (AAV) capsid sequences that encode capsid proteins that more efficiently and/or selectively transduce specific Cre recombinase (Cre) expressing target cell populations has been provided herein. Cre recognition sites (loxP or variants of loxP sites) can be inserted into an rAAV genome adjacent or flanking to the capsid gene. In this way, when the capsid gene enters the nucleus of a Cre expressing cell and is converted to dsDNA, Cre can induce a recombination event between the lox sites within the rAAV genome resulting on an inversion or deletion (depending on their relative orientations) of the sequence flanked by the lox sites. Using a recovery strategy that is dependent on the recombination event, capsid sequences that encode capsids that direct the rAAV genome to the nucleus of Cre+ cells can be enriched through one or more rounds of selection. Capsid gene directed evolution is only one example application of this technology. In some embodiments, the method can be adapted for the selection of any other coding or non-coding sequences with desirable traits within an AAV genome or any sequences within other viruses or non-viral nucleic acids that alter the interaction with the recombinase.

The following sections provide a brief set of definitions for the various terms and then various embodiments that have been produced through these screening methods. Following this, detailed variants and embodiments of the screening method are provided, as well as examples thereof.

Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

A "plasmid" is as a nucleic acid that can be used to replicate recombinant DNA sequences within a host organism. The sequence can be preferably double stranded DNA.

The term "recombinase recognition sequence" or "recombinase recognition site" refers to a sequence of nucleic acid that is recognizable by a recombinase and can serve as the substrate for a recombination event catalyzed by said recombinase. The sequence can be double stranded DNA.

The term "virus genome" refers to a nucleic acid sequence that is flanked by cis acting nucleic acid sequences that mediate the packaging of the nucleic acid into a viral capsid. For AAVs and parvoviruses, for example it is known that the "inverted terminal repeats" (ITRs) that are located at the 5' and 3' end of the viral genome have this function and that the ITRs can mediate the packaging of heterologous, for example, non-wt virus genomes, into a viral capsid.

The term "element" refers to a separate or distinct part of something, for example, a nucleic acid sequence with a separate function within a longer nucleic acid sequence.

The term "rAAV" refers to a "recombinant AAV". Recombinant AAV refers to an AAV genome in which part or all of the rep and cap genes have been replaced with heterologous sequences.

The term "AAV" or "adeno-associated virus" refers to a *Dependoparvovirus* within the Parvoviridae genus of viruses. Herein, AAV can refer to an AAV derived from a naturally occurring "wild-type" virus, an AAV derived from a rAAV genome packaged into a capsid derived from capsid proteins encoded by a naturally occurring cap gene and/or a rAAV genome packaged into a capsid derived from capsid proteins encoded by a non-natural capsid cap gene, for example, AAV-PHP.B.

The term "rep-cap helper plasmid" refers to a plasmid that provides the viral rep and cap gene functions. This plasmid can be useful for the production of AAVs from rAAV genomes lacking functional rep and/or the capsid gene sequences.

The term "vector" is defined as a vehicle for carrying or transferring a nucleic acid. Examples of vectors include plasmids and viruses.

The term "cap gene" refers to the nucleic acid sequences that encode capsid proteins that form, or contribute to the formation of, the capsid, or protein shell, of the virus. In the case of AAV, the capsid protein may be VP1, VP2, or VP3. For other parvoviruses, the names and numbers of the capsid proteins can differ.

The term "rep gene" refers to the nucleic acid sequences that encode the non-structural proteins (rep78, rep68, rep52 and rep40) required for the replication and production of virus.

A "library" may be in the form of a multiplicity of linear nucleic acids, plasmids, viral particles or viral vectors. A library will include at least two linear nucleic acids.

When the inserted nucleic acid sequences are randomly generated, N=A,C,G or T; K=G or T; M=A or C.

Unless specified otherwise, the left-hand end of any single-stranded polynucleotide sequence discussed herein is the 5' end; the left-hand direction of double-stranded polynucleotide sequences is referred to as the 5' direction.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "naturally occurring" as used herein refers to materials which are found in nature or a form of the materials that is found in nature.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients As described herein, SEQ ID NO:4—rAAV-cap-in-cis plasmid may also be referred to as: AAV-cap-in-cis, rAAV-Cap-in-cis vector, rAAV-CAP-in-cis genome, rAAV-Cap-in-cis construct, rAAV9-cap-in-cis, rAAV9R-X/A-cap-in-cis, or cap-in-cis, rAAV mCherry-cap-lox71/66 genome, rAAV-CAP-in-cis-lox, AAV9 cap-in-cis genome, rAAV-cap-in-cis rAAV genome, or the cap-in-cis rAAV genome.

As described herein, SEQ ID NO:7 (for example)—rAAV-delta-cap-in-cis may also be referred to as: rAAV9R-delta-X/A-cap-in-cis, rAAV9R-delta-X/A-cap-in-cis vector, rAAV-Δcap-in-cis vector, rAAV-cap-in-cis acceptor vector, cap-in-cis acceptor construct, rAAV9R-delta-X/A-cap-in-cis acceptor construct, rAAV-cap-in-cis library acceptor, or AAV9R-delta-X/A-cap-in-cis.

As described herein, SEQ ID NO:5 (for example)—AAV Rep-AAP helper may also be referred to as the Rep-AAP, rep-AAP helper and REP-AAP helper, AAV REP-AAP helper, AAV2/9 rep-AAP, or AAV2/9 REP-AAP helper plasmid.

As described herein, SEQ ID NO:6 (for example)—pCRII-9R-X/A EK plasmid or pCRII-9Cap-xE are interchangeable terms.

As described herein, AAV-PHP.B denotes the same thing as AAV-PHP.b, which denotes the same things as AAV-G2B26.

As described herein, AAV-PHP.A denotes the same things as AAV-PHP.a.

As described herein, AAV-PHP.R2 denotes the same thing as AAV-PHP.r, which denotes the same thing as AAV-TH1.1-35.

As described herein, 1253 is also referred to as 9CapF; 1316 is also referred to as CDF; 1331 is also referred to as XF; 1312 is also referred to as AR; 1287 is also referred to as 7xNNK; and 1286 is also referred to as 7xMNN.

The term "central nervous system" or "CNS" as used herein refers to the art recognized use of the term. The CNS includes the brain, optic nerves, cranial nerves, and spinal cord. The CNS also includes the cerebrospinal fluid, which fills the ventricles of the brain and the central canal of the spinal cord.

Systemic administration of vectors including a capsid protein that includes a targeting protein of SEQ ID NO:1 of the are particularly suitable for delivering exogenous DNA sequences encoding polypeptides, proteins, or non-coding DNA, RNA, or oligonucleotides to, for example, cells of the CNS of subjects afflicted by a CNS disease.

Targeting Sequence:

In some embodiments, a central nervous system targeting peptide is provided. In some embodiments, the peptide comprises an amino acid sequence of SEQ ID NO: 1. In some embodiments, the peptide is further conjugated to a nanoparticle, a second molecule, a viral capsid protein, or inserted between amino acids 588 and 589 of AAV9 (SEQ ID NO: 2, FIG. 30).

In some embodiments, the central nervous system targeting peptide includes 4 or more amino acids of residues that overlap with residues 585 to 595 within SEQ ID NO: 8.

In some embodiments, the central nervous system targeting peptide includes 4 or more contiguous amino acids of SEQ ID NO: 1 (or any of the sequences in FIG. 31). In some embodiments, the central nervous system targeting peptide comprises 4-7 amino acids of SEQ ID NO: 1 (or any of the sequences in FIG. 31). In some embodiments, the central nervous system targeting peptide comprises 4-6 amino acids of SEQ ID NO: 1 (or any of the sequences in FIG. 31). In some embodiments, the central nervous system targeting peptide includes one or more of the following options: TLAVPFK (SEQ ID NO: 1); LAVPFK (SEQ ID NO: 31); AVPFK (SEQ ID NO: 32); VPFK (SEQ ID NO: 33); TLAVPF (SEQ ID NO: 34); TLAVP (SEQ ID NO: 35); or TLAV (SEQ ID NO: 36). In some embodiments, the targeting peptide can consist of, consist essentially of, or comprise one or more of the sequences in FIG. 31. In some embodiments, 2 or fewer amino acids can be altered within TLAVPFK (or for any of the sequences within FIG. 31). In some embodiments, one amino acid can be altered within TLAVPFK (or for any of the sequences within FIG. 31). In some embodiments, the alteration is a conservative alteration (within any of the targeting peptides provided herein). In some embodiments, the alteration is a deletion or insertion of one or two amino acids (within any of the targeting peptides provided herein). In some embodiments, the amino acid can include a non-natural amino acid. In some embodiments, the central nervous system targeting peptide sequence can be one or more of: SQTLA, QTLAV, TLAVP, LAVPK, AVPKA, VPKAQ. In some embodiments, the targeting peptide can be at least 75% identical to one or more of the above sequences, for example, at least 80% identical.

In some embodiments, the central nervous system targeting peptide sequence can be inverted, such as in KFPVALT (SEQ ID NO: 3) (similarly, any of the sequences in FIG. 31 can also be inverted). In such embodiments, 4 or more contiguous amino acids can be employed. For example, the sequence can comprise and/or consist of KFPV, FPVA, PVAL, VALT, etc. In some embodiments, the targeting peptide can be at least 75% identical to one or more of the above sequences, for example, at least 80%.

In some embodiments, the central nervous system targeting peptide comprises an amino acid sequence that comprises at least 4 contiguous amino acids from the sequence TLAVPFK (SEQ ID NO: 1) or KFPVALT (SEQ ID NO: 3) or any of the sequences in FIG. 31. In some embodiments, the amino acid sequence results in an increase in CNS cell transduction by the AAV. In some embodiments, the amino acid sequence is part of a capsid protein of the AAV vector. In some embodiments, the sequence TLAVPFK (SEQ ID NO: 1; (or any of the sequences in FIG. 31)) is inserted between AA588-589 of an AAV sequence of the vector (SEQ ID NO: 2). In some embodiments, the sequence TLAVPFK (SEQ ID NO: 1; or any of the sequences in FIG. 31) is inserted between AA586-592 of an AAV sequence of the vector (SEQ ID NO: 2). In some embodiments, the sequence TLAVPFK (SEQ ID NO: 1; or any of the sequences in FIG. 31) further comprises at least two of amino acids 587, 588, 589, or 590 of SEQ ID NO: 2. In some embodiments, the targeting peptide can be at least 75% identical to one or more of the above sequences.

In some embodiments, the central nervous system targeting peptide comprises, consists, or consists essentially of any one or more of the above sequences. In some embodiments, the central nervous system targeting peptide is inserted into a longer peptide, as described herein.

In some embodiments, the targeting peptide is part of an AAV, as described herein. In some embodiments, the targeting peptide is part of an AAV9. In some embodiments, the targeting peptide can be linked to any molecule that should be targeted as desired. In some embodiments, the targeting peptide can be linked, without limitation, to a recombinant protein, antibody, a cell, a diagnostic, a therapeutic, a nanomolecule, etc.

In some embodiments, the targeting sequence is an amino acid sequence. In some embodiments, the targeting sequence is a nucleic acid sequence. In some embodiments, the targeting sequence is a capsid protein comprising an amino acid sequence that comprises at least 4 contiguous amino acids from the sequence TLAVPFK (SEQ ID NO: 1) and/or KFPVALT (SEQ ID NO: 3) and/or any of the sequences in FIG. 31.

Some embodiments of options of targeting sequences, as outlined in the examples below, are provided in FIG. 1A, which includes G2B-13, G2B-26, TH1.1-32, and TH1.1-35, by way of example.

In some embodiments, the targeting protein can be inserted into any desired section of a protein. In some embodiments, the targeting protein can be inserted into a capsid protein. In some embodiments, the targeting protein is inserted on a surface of the desired protein. In some embodiments, the targeting protein is inserted into the primary sequence of the protein. In some embodiments, the targeting protein is linked to the protein. In some embodiments, the targeting protein is covalently linked to the protein. In some embodiments, the targeting protein is inserted into an unstructured loop of the desired protein. In some embodiments, the unstructured loop can be one identified via a structural model of the protein.

Figure 13:
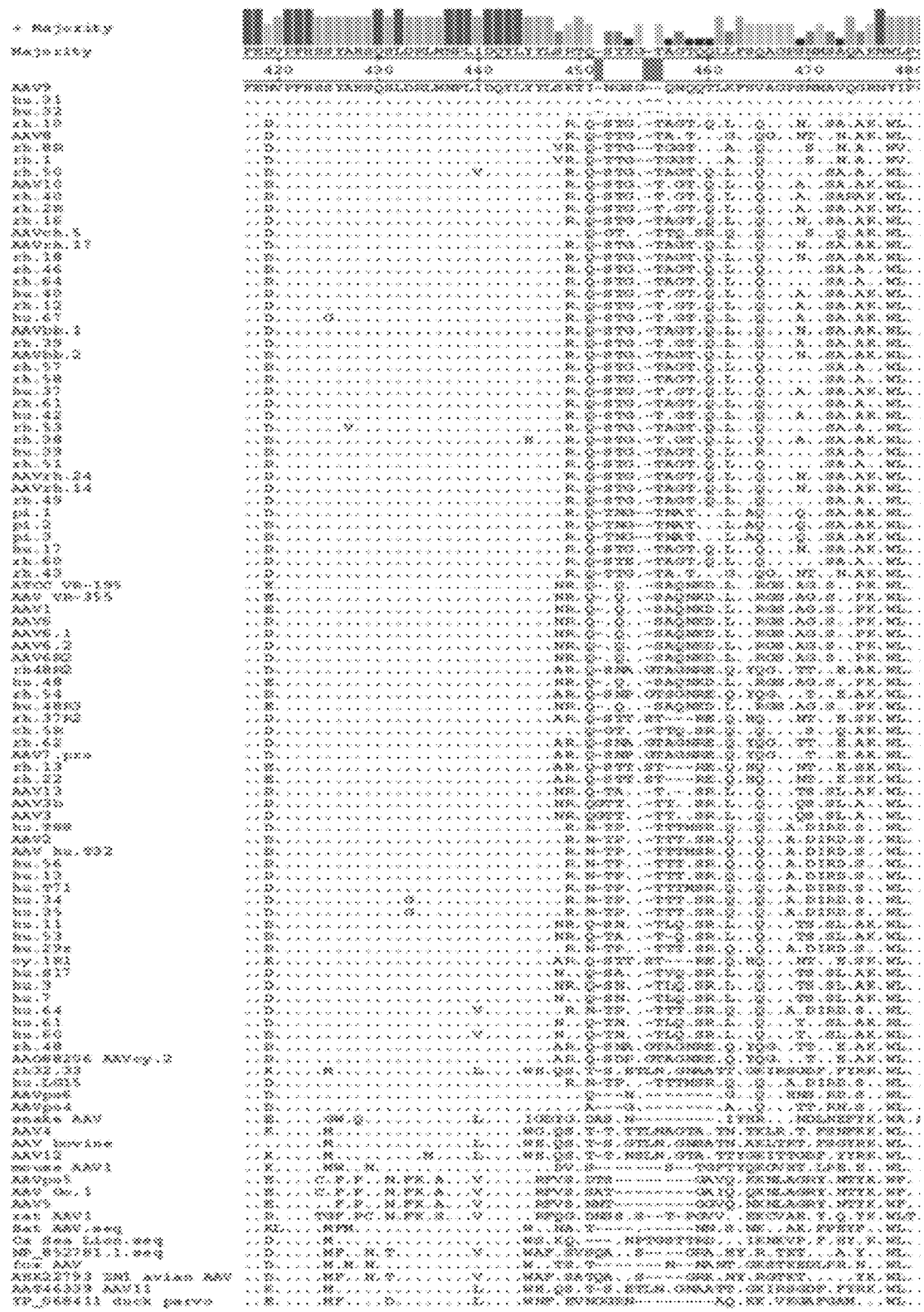
FIG. 13 depicts a sequence alignment of AAVs and related parvoviruses showing diversity at 7mer insertion/replacement sites. The figure is split into three parts, with the first sheet representing the left-hand side of the figure, the second sheet representing the middle part of the figure, and the third sheet of FIG. 13 representing the right-hand side of the sheet. That is, the names for each of the rows in the first sheet are intended to carry across to the other two sheets (in each row).

In some embodiments, the unstructured loop can be one identified by sequence comparisons, such as shown in FIG. 13. FIG. 13 shows an alignment of VP1 capsid amino sequence from AAV and related parvoviruses aligned to AAV9. Sequence identity is shown as a dot. The AAs that differ from AAV9 are indicated. The numbering is based on AAV9 VP1. Only AA 418-624 are shown, although such an alignment can be done by one of skill in the art for any desired section of protein. Shaded vertical bars of different length represent the relative conservation at each AA. Longer bars indicate greater conservation. Horizontal shaded bars indicate sites of the unstructured loops into which the targeting protein can be inserted.

Figure 14:
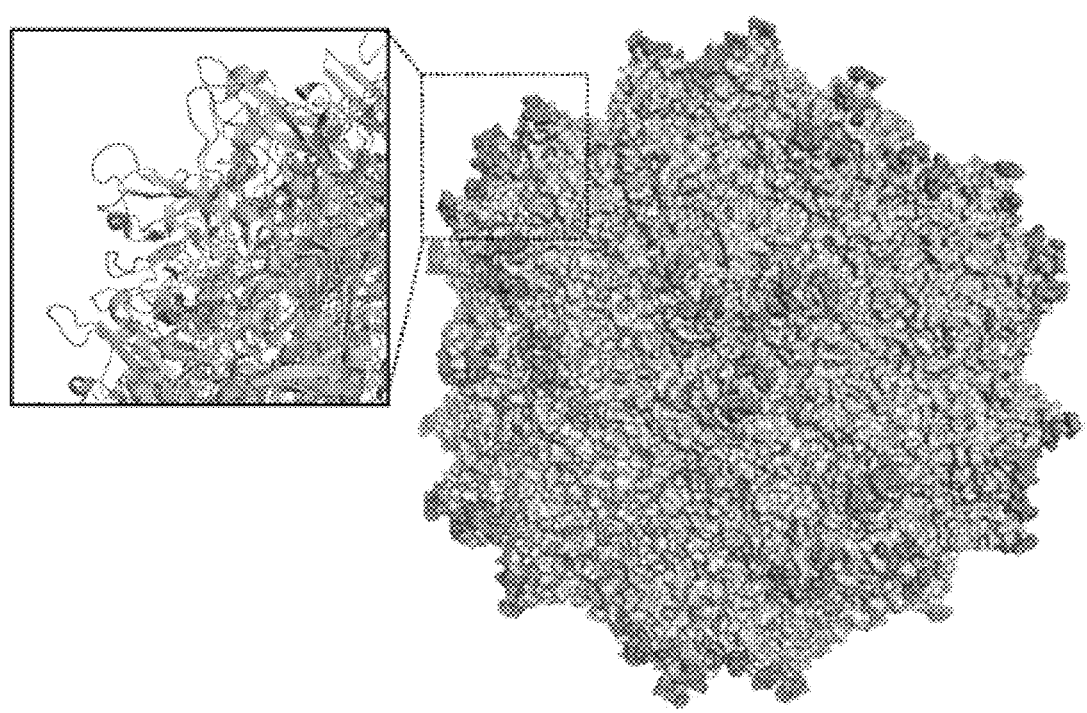

In some embodiments, the location of insertion of the targeting protein into the desired protein can be achieved by a structural model. An example of such a structural model is shown in FIG. 14. FIG. 14 depicts a structural model highlighting surface loops randomized by targeted sequence insertion. The insert (which is a blow up) depicts a ribbon diagram of AAV9 surface model constructed in PyMol from the AAV9 Protein Data Bank file 3ux1.pdb. The capsid surface is shown in gray and the loop regions chosen for sequence insertion are highlighted by shading (AA586-592) and (AA452-458). Other regions of sequence insertion or replacement can be identified from within regions that are not highly conserved. Additional examples include the regions of AAV9 between AA262-269, AA464-473, AA491-495, AA546-557 and AA659-668 or the homologous regions of other the capsid proteins from other AAVs or parvoviruses.

In some embodiments, the capsid protein can comprise or consist of the sequence shown in FIG. 19, SEQ ID NO: 8. The underlined amino acid is a K to R mutation that was made to provide a unique XbaI restriction site, this can be optional. For references, SEQ ID NO: 1 (TLAVPFK) is in bold text. Any of the other targeting peptides provided herein (for example, in FIG. 31) can also be inserted in place of SEQ ID NO: 1. FIG. 20 depicts some embodiments of a nucleic acid sequence for an AAV-PHP.B (AAV-G2B26) capsid gene coding sequence). The recovered nucleic acid sequence encoding SEQ ID NO: 1 (TLAVPFK) is in bold and underlined text. The mutations introduced to insert or remove restriction sites are highlighted with double underlined italicized text.

Vectors

In some embodiments, a viral vector can include one or more of the noted targeting sequences (for example, any of the central nervous system targeting peptides noted herein or any peptide provided by the screening methods provided herein). In some embodiments, an AAV vector can be provided that comprises a sequence TLAVPFK (SEQ ID NO: 1) (or any of the other targeting proteins provided herein, including those in FIG. 31).

In some embodiments, one or more targeting sequences can be employed in a single system. For example one can employ one or more targeting sequences and also modify other sites to reduce the recognition of the AAVs by the pre-existing antibodies present in the host, such as a human. In some embodiments, the AAV vector can include a capsid, which influences the tropism/targeting, speed of expression and possible immune response. The vector can also include the rAAV, which genome carries the transgene/therapeutic aspects (e.g., sequences) along with regulatory sequences. In some embodiments, the vector can include the targeting sequence within/on a substrate that is or transports the desired molecule (therapeutic molecule, diagnostic molecule, etc.).

In some embodiments, any one or more of the targeting sequences provided herein can be incorporated into a vector.

In some embodiments, the sequence TLAVPFK (SEQ ID NO: 1) (or any of the other targeting proteins provided herein, including those in FIG. 31) results in an increase in CNS cell transduction from a virus containing the vector. In some embodiments, the increase is at least 2, 10, 20, 30, 40, 50, 60, 70, 80, 90, or at least 100 fold more than transduction without the targeting sequence. In some embodiments, there is a 40-90 fold increase in transduction of the CNS, as compared with AAV9 transduction.

In some embodiments, the sequence TLAVPFK (SEQ ID NO: 1) (or any of the other targeting proteins provided herein, including those in FIG. 31) is part of a capsid protein of the AAV vector. In some embodiments, the sequence TLAVPFK (SEQ ID NO: 1) (or any of the other targeting proteins provided herein, including those in FIG. 31) is inserted between AA588-589 of an AAV sequence of the vector (SEQ ID NO: 2). In some embodiments, the sequence TLAVPFK (SEQ ID NO:1) (or any of the other targeting proteins provided herein, including those in FIG. 31) is inserted within AA452-458 of an AAV sequence of the vector (SEQ ID NO: 2). In some embodiments, the sequence TLAVPFK (SEQ ID NO:1) (or any of the other targeting proteins provided herein, including those in FIG. 31) is inserted within AA491-495 of an AAV sequence of the vector (SEQ ID NO: 2). In some embodiments, the sequence TLAVPFK (SEQ ID NO:1) (or any of the other targeting proteins provided herein, including those in FIG. 31) is inserted within AA546-557 of an AAV sequence of the vector (SEQ ID NO: 2). In some embodiments, any of the targeting sequences (or combination thereof) in FIG. 31 can be used and/or substituted for any of the embodiments provided herein regarding SEQ ID NO: 1. Thus, for example, one or more of the sequences within FIG. 31 can be inserted between AA588-589 of an AAV sequence of the vector (SEQ ID NO: 2). In some embodiments, the targeting sequence can be one or more of: SVSKPFL (SEQ ID NO: 28); FTLTTPK (SEQ ID NO: 29); or MNATKNV (SEQ ID NO: 30). FIG. 31 depicts some of the most highly enriched sequences recovered from the second round of selection for AAV variants that transduce GFAP-Cre+ astrocytes following intravenous administration.

In some embodiments, the targeting sequence that is part of the vector can comprise any four contiguous AAs within AAV9 VP1 AA585-598 of SEQ ID NO: 8.

While the numbering is not identical between serotypes, the exact insertion site is not critical. In some embodiments, the targeting sequence is inserted within the unstructured (see FIG. 14) and poorly conserved (see alignment, FIG. 13) surface exposed loops. In some embodiments, the insertion of the targeting sequence can be achieved within other AAV capsids by inserting the targeting sequence within the homologous unstructured loops of other AAV sequences.

In some embodiments, an rAAV genome is provided. The genome can comprise at least one inverted terminal repeat configured to allow packaging into a vector and a cap gene. In some embodiments, it can further include a sequence within a rep gene required for expression and splicing of the cap gene. In some embodiments, the genome can further include a sequence capable of expressing VP3.

In some embodiments, the only protein that is expressed is VP3 (the smallest of the capsid structural proteins that makes up most of the assembled capsid—the assembled capsid is composed of 60 units of VP proteins, ~50 of which are VP3). In some embodiments, VP3 expression alone is adequate to allow the method of screening to be adequate.

In some embodiments, the system for screening involves placing the selectable element, (which in some embodiments can be the AAV cap gene into the AAV genome) together with one or more recombinase recognition sites (loxP or mutant loxP sites are preferred, but others could be used). In some embodiments, the AAV genome can be defined by a nucleic acid comprising at least one inverted terminal repeat.

In some embodiments, the rAAV genome further comprises a mCherry reporter cassette comprising a ubiquitin C gene, a mCherry cDNA, and a minimal synthetic polyA sequence.

In some embodiments, the genome further comprises cre-dependent switch comprising: a polyA sequence and a pair of inverted loxP sites flanking the polyA sequence. In some embodiments, the polyA sequence is downstream of the cap gene. In some embodiments, the pair of inverted loxP sites comprises lox71 and lox66. In some embodiments, the genome contains only those sequences within the rep gene required for expression and splicing of the cap gene product.

In some embodiments, AAV-PHP.B delivers genes efficiently to one or more organs including, but not limited to the central nervous system, liver, muscle, heart, lungs, stomach, adrenal gland, adipose and intestine.

In some embodiments, a capsid library is provided that comprises AAV genomes that contain both the full rep and cap sequence that have been modified so as to not prevent the replication of the virus under conditions in which it could normally replicate (co-infection of a mammalian cell along with a helper virus such as adenovirus). A pseudo wt genome can be one that has an engineered cap gene within a "wt" AAV genome.

In some embodiments, the capsid library is made within a "pseudo-wild type" AAV genome containing the viral replication gene (rep) and capsid gene (cap) flanked by inverted terminal repeats (ITRs). In some embodiments, the capsid library is not made within a "pseudo-wild type" AAV genome containing the viral replication gene (rep) and capsid gene (cap) flanked by inverted terminal repeats (ITRs).

In some embodiments, the rAAV genome contains the cap gene and only those sequences within the rep gene required for the expression and splicing of the cap gene products (FIG. 22B).

In some embodiments, a capsid gene recombinase recognition sequence is provided with inverted terminal repeats flanking these sequences.

In some embodiments, the system could be used to develop capsids that exhibit enhanced targeting of specific cells/organs, select for capsids that evade immunity, select for genomes that are more at homologous recombination, select for genome elements that increase the efficiency of conversion of the single stranded AAV genome to a double stranded DNA genome within a cell and/or select for genome elements that increase the conversion of AAV genome to a persistent, circularized form within the cell.

Nucleic Acid Sequences

In some embodiments, a nucleic acid sequence encoding any of the targeting sequences provided herein is provided. In some embodiments, the nucleic acid sequence is AAGTTTCCTGTGGCGTTGACT FOR SEQ ID NO 3). ACT TTG GCG GTG CCT TTT AAG (SEQ ID NO:49) for a sequence encoding the AA sequence of SEQ ID NO: 1. In some embodiments, the nucleic acid sequence is one that will hybridize to this sequence under stringent conditions. In some embodiments, the nucleic acid sequence includes a nucleic acid sequence that encodes for SEQ ID NOS: 1 and/or 3 and the sequence is part of a larger nucleic acid sequence. In some embodiments, any one or more of the sequences from FIG. 31 can provide the noted nucleic acid sequence (that is, any nucleic acid sequence that encodes for any of these sequences can be provided). In some embodiments, the nucleic acid sequence is one that will hybridize to any of the sequences within FIG. 31 (or the sequences that encode the amino acid sequences) under stringent conditions. In some embodiments, the nucleic acid sequence includes a nucleic acid sequence that encodes for any of the sequences within FIG. 31 and the sequence is part of a larger nucleic acid sequence. In some embodiments, the nucleic acid sequence is one or more of: AGTGTGAGTAAGC-CTTTTTTG (SEQ ID NO: 24); TTTACGTTGACGACGC-CTAAG (SEQ ID NO: 26); or ATGAATGCTAC-GAAGAATGTG (SEQ ID NO: 27).

In some embodiments, the nucleic acid sequence that encodes for SEQ ID NO: 1 is inserted between a sequence encoding for amino acids 588 and 589 of AAV9 (SEQ ID NO: 2).

In some embodiments, a nucleic acid sequence encoding any four contiguous amino acids in TLAVPFK (SEQ ID NO: 1) or in KFPVALT (SEQ ID NO: 3) is provided. In some embodiments, a nucleic acid sequence encoding any five contiguous amino acids in TLAVPFK (SEQ ID NO: 1) or in KFPVALT (SEQ ID NO: 3) is provided. In some embodiments, a nucleic acid sequence encoding any six contiguous amino acids in TLAVPFK (SEQ ID NO: 1) or in KFPVALT (SEQ ID NO: 3) (or any of the other targeting proteins provided herein, including those in FIG. 31) is provided.

In some embodiments, the nucleic acid sequence is inserted between a sequence encoding for amino acids 588 and 589 of AAV9 (SEQ ID NO: 2).

In some embodiments, a plasmid system is provided. The plasmid can include a first plasmid comprising a modified AAV2/9 rep-cap helper plasmid comprising at least one in frame stop codon within its VP1, VP2 and VP3 reading frame. The stop codon is positioned to disrupt VP expression without altering the amino acid sequence of the assembly activating protein. The plasmid system can further include a second plasmid comprising a rAAV-cap-in-cis plasmid.

In some embodiments, the method does not involve expressing single VP proteins from heterologous plasmids to generate "mosaic" capsids made from VP proteins encoded by different plasmids.

In some embodiments, a library of nucleic acid sequences is provided. The library can comprise a selectable element and one or more recombinase recognition sequences. In some embodiments, the nucleic acid sequences and one or more recombinase recognition sequences are incorporated within a virus genome. In some embodiments, the viral genome is an AAV genome. In some embodiments, the selectable element encodes an AAV capsid. In some embodiments, the selectable element is a genetic element that increases conversion to dsDNA. In some embodiments, the selectable element increases the efficiency of homologous recombination between the element and the endogenous genome. In some embodiments, the recombinase recognition sequences are comprised of one or more loxP sites. In some embodiments, the loxP site is a lox71 site and an inverted lox66 site.

In some embodiments, the gene encoding the targeting protein and/or the capsid can be cloned into an AAV Rep-Cap helper plasmid in place of the existing capsid gene. When introduced together into producer cells, this plasmid can be used to package an rAAV genome into the targeting protein and/or capsid. Producer cells can be any cell type possessing the genes necessary to promote AAV genome replication, capsid assembly and packaging. Preferred producer cells are 293 cells, or derivatives, HELA cells or insect cells together with helper virus or a second plasmid encoding the helper virus genes known to promote rAAV genome replication. In some embodiments, an AAV rep-cap helper sequence can be modified to introduce a tetracycline-inducible expression system in between the rep and the cap gene to increase capsid expression and virus production. In some embodiments, a tetracycline transactivator cDNA, poly adenylation sequence, tetracycline responsive element and AAV5 p41 promoter and AAV2 splicing regulatory elements contained within the AAV2 rep gene are inserted between the rep gene and the gene encoding the capsid or targeting protein. Use of this inducible rep-cap plasmid when making rAAV provides 1.5-2-fold more virus than the AAV2/9 rep-cap plasmid. Some embodiments of such a nucleic acid cloned into a plasmid are depicted in FIG. 21, SEQ ID NO: 10. The cap gene sequence is underlined in FIG. 21. Uppercase letters indicate sites where the capsid sequence differs from AAV9.

Methods of Use

In some embodiments, a method of delivering a nucleic acid sequence to a nervous system (or other desired system) is provided. The method can include providing a protein comprising any one or more of the targeting sequences provided herein. The protein can be part of a capsid of an AAV. The AAV can comprise a nucleic acid sequence to be delivered to a nervous system. One can then administer the AAV to the subject.

In some embodiments, the nucleic acid sequence to be delivered to a nervous system comprises one or more sequences that would be of some use or benefit to the nervous system and/or the local of delivery or surrounding tissue or environment. In some embodiments, it can be a nucleic acid that encodes a trophic factor, a growth factor, or other soluble factors that might be released from the transduced cells and affect the survival or function of that cell and/or surrounding cells. In some embodiments, it can be a cDNA that restores protein function to humans or animals harboring a genetic mutation(s) in that gene. In some embodiments, it can be a cDNA that encodes a protein that can be used to control or alter the activity or state of a cell. In some embodiments, it can be a cDNA that encodes a protein or a nucleic acid used for assessing the state of a cell. In some embodiments, it can be a cDNA and/or associated RNA for performing genomic engineering. In some embodiments, it can be a sequence for genome editing via homologous recombination. In some embodiments, it can be a DNA sequence encoding a therapeutic RNA. In some embodiments, it can be a shRNA or an artificial miRNA delivery system. In some embodiments, it can be a DNA sequence that influences the splicing of an endogenous gene.

In some embodiments, the resulting targeting molecules can be employed in methods and/or therapies relating to in vivo gene transfer applications to long-lived cell populations. In some embodiments, these can be applied to any rAAV-based gene therapy, including, for example: spinal muscular atrophy (SMA), amyotrophic lateral sclerosis (ALS), Parkinson's disease, Pompe disease, Huntington's disease, Alzheimer's disease, Battens disease, lysosomal storage disorders, glioblastoma multiforme, Rett syndrome, Leber's congenital amaurosis, chronic pain, stroke, spinal cord injury, traumatic brain injury and lysosomal storage disorders. In addition, rAAVs can also be employed for in vivo delivery of transgenes for non-therapeutic scientific studies such as optogenetics, gene overexpression, gene knock-down with shRNA or miRNAs, modulation of endogenous miRNAs using miRNA sponges or decoys, recombinase delivery for conditional gene deletion, conditional (recombinase-dependent) expression, or gene editing with CRISPRs, TALENs, and zinc finger nucleases.

Provided herein are methods for treating and/or preventing Huntington's disease using the methods and compositions described herein. The method of treating and/or preventing Huntington's disease can include identifying the subject(s), providing a vector for delivery of a polynucleotide to the nervous system of the subject as provided herein, administering the vector in an effective dose to the subject thereby treating and/or preventing Huntington's disease in the subject. In some embodiments, the methods for treating a subject with Huntington's disease involve compositions where the vector delivers the polynucleotide composition comprising a Zinc finger protein (ZFP) engineered to represses the transcription of the Huntington (HTT) gene. In some embodiments, the ZFP selectively represses the transcription of the HTT gene allele responsible for causing the Huntington's disease in the subject by binding to the CAG repeat region of the HTT gene in a CAG repeat length-dependent manner. In some embodiments, the ZNFTR selectively represses transcription of both alleles of the HTT gene.

In some embodiments, the therapeutic item to be administered to the subject comprises a short hairpin RNA (shRNA) or microRNA (miRNA) that knocks down Huntingtin expression by inducing the selective degradation of, or inhibiting translation from, RNA molecules transcribed from the disease causing HTT allele by binding to the CAG repeat. In some embodiments, the therapeutic item to be administered to the subject comprises a short hairpin RNA (shRNA) or microRNA (miRNA) that knocks down Huntingtin expression by inducing the degradation of, or inhibiting translation from, RNA molecules transcribed from one or both alleles of the HTT gene. In some embodiments, the therapeutic item to be administered to the subject comprises a short hairpin RNA (shRNA) or microRNA (miRNA) that knocks down Huntingtin expression by inducing the selective degradation of, or inhibiting translation from, RNA molecules transcribed from the disease causing HTT allele through the selective recognition of one or more nucleotide polymorphisms present within the disease causing allele. The nucleotide polymorphisms can be used by one skilled in the art to differentiate between the normal and disease causing allele.

In some embodiments, the therapeutic item to be administered to the subject comprises a polynucleotide that encodes an RNA or protein that alters the splicing or production of the HTT RNA. In some embodiments, the therapeutic item to be administered to the subject comprises a polynucleotide that encodes one or more polypeptides and/or RNAs for genome editing using a Transcription activator-like effector nuclease (TALEN), zinc finger nuclease or clustered regularly interspaced short palindromic repeats—cas9 gene (CRISPR/Cap9) system engineered by one skilled in the art to induce a DNA nick or double-stranded DNA break within or adjacent to the HTT gene to cause an alteration in the HTT gene sequence. In some embodiments, the therapeutic item to be administered to the subject comprises a polynucleotide encoding a polypeptide that binds to a polypeptide from the HTT gene, alters the conformation of a polypeptide from the HTT gene or alters the assembly of a polypeptide from the HTT gene into aggregates or alters the half-life of a polypeptide from the HTT gene. In some embodiments, the therapeutic item to be administered to the subject comprises a polynucleotide that encodes a RNA or polypeptide that causes or prevents a post-transcriptional modification of a polypeptide from the HTT gene. In some embodiments, the therapeutic item to be administered to the subject comprises a polynucleotide that encodes a polypeptide from a chaperone protein known to those skilled in the art to influence the conformation and/or stability of a polypeptide from the HTT gene.

In some embodiments, the therapeutic item to be administered to the subject comprises regulatory elements known to one skilled in the art to influence the expression of the RNA and/or protein products encoded by the polynucleotide within desired cells of the subject.

In some embodiments, the therapeutic item to be administered to the subject comprises a therapeutic item applicable for any disease or disorder of choice. In some embodiments, this can include compositions for treating and/or preventing Alzheimers disease using the methods and compositions described herein, for example, ApoE2 or ApoE3 for Alzheimer's disease; SMN for the treatment of SMA; frataxin delivery for the treatment of Friedreich's ataxia; and/or shRNA or miRNA for the treatment of ALS.

In some embodiments, the therapeutic item for delivery is a protein (encodes a protein) or RNA based strategy for reducing synuclein aggregation for the treatment of Parkinson's. For example delivering a polynucleotide that encodes a synuclein variant that is resistant to aggregation and thus disrupts the aggregation of the endogenous synuclein.

In some embodiments, a transgene encoding a trophic factor for the treatment of AD, PD, ALS, SMA, HD can be the therapeutic item involved. In some embodiments, a trophic factor can be employed and can include, for example, BDNF, GDNF, NGF, LIF, and/or CNTF.

Dosages of a viral vector can depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1\times10^9$ to $1\times10^{16}$ genomes virus vector. A preferred human dosage can be about $1\times10^{13}$ to $1\times10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting from the vector of the invention.

In some embodiments, the polynucleotides vector also includes regulatory control elements known to one skilled in the art to influence the expression of the RNA and/or protein products encoded by the polynucleotide within desired cells of the subject.

In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an intron and the splice donor and splice acceptor sequences that regulate the splicing of said intron. Another example of a regulatory element is a transcription termination signal and/or a polyadenylation sequences.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide in response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

Any one or more of the above aspects can be included within any of the vectors provided herein, in combination with any targeting protein.

Method of Selection

Current directed evolution protocols used to enhance AAV capsids have several shortcomings. The first is that it is difficult to design an in vivo screen that specifically recovers sequences from the target cell of interest when that target cell is one of many cell types in a complex organ. Typically, after the virus is administered in vivo, the tissue of interest is collected, and virus DNA is recovered from the DNA of the entire tissue, or region of tissue. Recently, Dalkara et al. reported the use of FACS sorting the target cells (photoreceptors) as a means to selectively recover capsid sequences present in those cells. But this method is labor intensive and costly, especially for sorting from large volumes of dissociated tissues. In addition, this additional sorting effort does not overcome the other major limitation of selecting for AAV capsid sequences: all capsid sequences present within the cell/tissue are recovered regardless of whether or not these viruses functionally transduced any cells. In other words, sequences from viruses stuck on the cell surface or viruses that entered the cell bound to a receptor that trafficked to an intracellular compartment not compatible with AAV unpackaging and transduction are recovered by these screens along with sequences that encoded capsids that successfully induced transgene expression in the target cell population. Therefore, non-functional capsids are also enriched by typical selection methods. Finally, most current methods also require the use of libraries made from replication competent AAV, which is a potential biosafety concern, especially if the virus will be introduced in animal facilities where there are primates since these viruses could replicate in animals carrying helper viruses. Herein is described an AAV capsid library screening platform that overcomes one or more of each of these limitations.

Successful production of an AAV capsid variant library depends upon each variant cap gene being packaged by the particular capsid proteins it encodes. Therefore, it is useful that the cap gene is present in cis (within the AAV genome). However, it is not essential that the non-structural rep genes be present in cis. Herein is disclosed a replication incompetent rAAV genome expressing the cap gene and in place of much of the rep sequence, several recombinant elements have been added that provide a way to selectively recover only those capsid sequences that have functionally transduced the target cell population of interest without the need for target cell isolation.

Selective Recovery of AAV Capsid Sequences from Specific Cre+ Cell Populations

Figure 1B:
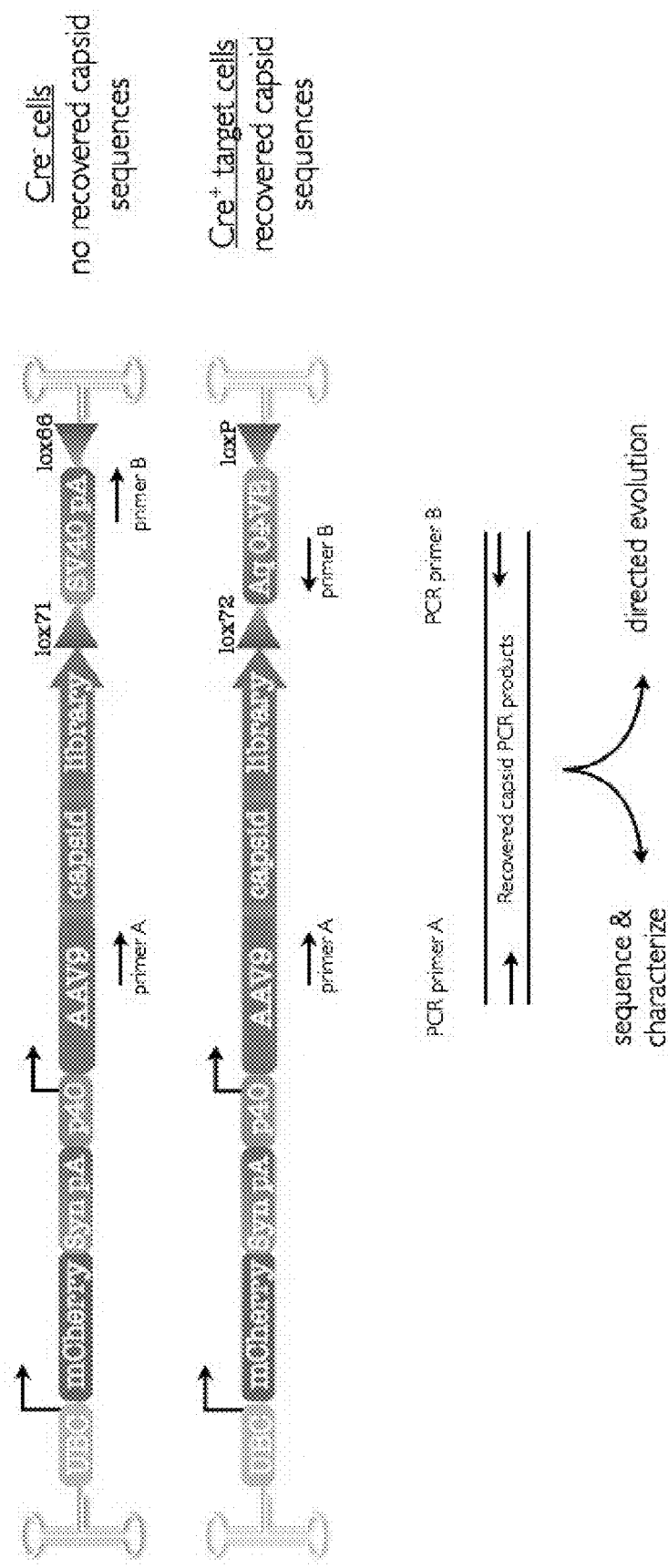
FIG. 1B depicts some embodiments of selective recovery of capsid proteins.

In some embodiments, the approach incorporates a Cre recombinase-dependent switch that uses PCR (polymerase chain reaction) to selectively recover capsid sequences that have transduced Cre+ target cells. This can be accomplished by inserting mutant Cre recognition sites (lox66 and lox71 in a head-to-head orientation) into the rAAV genome around a sequence adjacent to the cap gene (FIG. 1B). Cre recombination results in an inversion of the sequence flanked by the lox66 and lox71 sites, and one can then use a PCR recovery strategy that only amplifies the cap gene sequence from rAAV genomes after Cre-mediated inversion of the cap gene adjacent sequence (one PCR primer binds the invertible sequence and one binds the cap gene). Mutant loxP sites (lox66 and lox71) can be chosen so that the inversion would be less reversible (Alberts et al. 1995). FIG. 1B shows an embodiments of a rAAV plasmid that has been developed.

In some embodiments, the method takes advantage of the large number of Cre transgenic mice that have been (and can be) developed. These lines express Cre under the control of cell specific promoters such that Cre is present only in a subpopulation of cells within a given organ. Hundreds of Cre transgenic lines are available from commercial vendors and academic sources, and custom lines can be generated.

In some embodiments, one can apply this for developing capsids that more efficiently transduce astrocytes in the central nervous system after IV virus administration. Transgenic mGFAP-Cre mice are available that express Cre specifically within astrocytes and neural stem cells (NSCs) in the adult brain and spinal cord. Using the Cre-dependent sequence recovery strategy, one can deliver rAAV capsid libraries in vivo, collect DNA from the entire brain and spinal cord and recover rAAV capsid sequences specifically from astrocytes and NSCs.

Another advantage of some embodiments of this approach is that this Cre dependent strategy only recovers those sequences that have transduced the target cell. AAV is a single stranded DNA virus, and its genome must enter the nucleus and be converted to double stranded DNA (dsDNA) for functional transduction. Since Cre only recombines dsDNA, only those capsid sequences that have trafficked properly to the cell nucleus and have been converted to dsDNA will be recovered.

Inclusion of a Reporter Gene Cassette to Facilitate Cell Sorting

For cases where Cre+ transgenics are not available, one can also incorporate a reporter cassette driven by a ubiquitous promoter/enhancer to facilitate sorting of transduced/transgene expressing cells from within a mixed population. This second option is more labor intensive than the Cre-based strategy as it requires generating single cell suspensions and FACS or magnetic bead/antibody-based sorting. But the reporter method is also powerful in that it can be combined with sorting for specific target cell populations using antibodies to known surface markers or with GFP transgenics to limit recovery to a particular population. And like the Cre strategy above, it will only lead to the recovery of sequences that are present in transduced cells. The reporter also facilitates following the transduction characteristics of the pooled library during screening (useful for both the Cre- and reporter-dependent methods).

The technology described herein can be used in conjunction with any transgenic line expressing Cre in the target cell type of interest to develop AAV capsids that more efficiently transduce that target cell population. Applications include, but are not limited to, developing capsids that are more efficient at transducing specific cell types in any organ after IV AAV administration, targeting specific populations of neurons, improving interneuronal transport, targeting tumor cells, hematopoetic stem cells, insulin producing beta cells, lung epithelium, etc. The method is not limited to any one virus delivery method. The vector may be delivered via any route including, but not limited to, oral, intravenous, intraarticular, intracardiac, intramuscular, intradermal, topical, intranasal, intraparitoneal, rectal, sublingual, subcutaneous, epidural, intracerebral, intracerebroventricular, intrathecal, intravitreal or subretinal administrations. The system can also be used to develop viruses that better cross specific barriers (blood brain barrier, gut epithelium, placenta, etc.). The method can also be used in vitro to develop capsids that are better at achieving nuclear entry and second strand synthesis (conversion to dsDNA).

In addition, this system is not limited to AAV9. Any starting AAV capsid (naturally occurring or modified variants) can be incorporated into this rAAV-cap vector, mutagenized by standard methods to create the capsid library and then screened with this Cre-dependent recovery strategy. Preferred AAV capsids include AAV1, AAV2, AAV3, AAV3b, AAV4, AAV5, AAV6, AAV7, AAV8, AAV9, AAV10, human isolates (for example, hu.31 and hu.32), rhesus isolates (for example, rh.8 and rh.10), AAVs or related parvoviruses from other primates, mammals and non-mammalian species. Furthermore, this method is not limited to any one commonly used capsid mutagenesis strategy. Any method can be used to generate the library diversity, including but not limited to capsid domain shuffling, random sequence insertion and random mutagenesis by error prone PCR. Finally, the vector has been designed to be modular making it simple to replace various elements such as the reporter cassette or capsid sequence to further customize the screening options.

To make this system possible, an option for incorporating the AAV capsid gene within the rAAV genome while providing the other non-structural AAV gene products in trans from a helper plasmid was developed. This was not necessarily straightforward since the cap gene codes for 4 proteins (the capsid proteins VP1, VP2, VP3 and the assembly activating protein (AAP)) using a combination of alternative splicing, alternative start codons and alternative reading frames. Maintaining proper regulation of the expression of these proteins is relevant for efficient virus production. It was found that the capsid proteins could be expressed from a rAAV genome when a fragment of the 3' end of the rep gene, which contains critical promoter/enhancer and splicing signals, is included (FIG. 2A). Retaining only the 3' end of the rep gene together with the capsid gene left enough space within the rAAV genome to incorporate the Cre invertible polyA sequence downstream of the cap gene as well as an mCherry (red fluorescent protein) reporter cassette.

To insure that the capsid is made entirely from the capsid gene encoded within the rAAA capsid library genome, an AAV helper plasmid that would provide the AAV non-structural proteins but not any capsid protein expression (typically rAAV are produced by supplying both rep and cap genes in trans from the AAV helper plasmid) was developed. Using a AAV2/9 RepCap plasmid vector core as a starting point, 5 stop codons were inserted within the cap gene near the translation initiation sites for the three capsid proteins VP1, VP2 and VP3 (FIG. 2B). This effectively eliminated rAAV production unless the VP1-3 capsid proteins are provided elsewhere (such as in cis on the AAV genome cap library construct described above).

In some embodiments, a method of developing a capsid with a desired characteristic is provided. The method can comprise providing a population of rAAV genomes provided herein. The method can further involve screening the population by a specific set of criteria. The method can further involve selecting the rAVV genome that meets the screening criteria.

In some embodiments, some of the methods of screening provided herein provide at least one of the following advantages. First, in some embodiments, the method makes use of the growing library of Cre-transgenics to provide selective pressure for capsids that more efficiently transduce genetically defined cell populations (for example, see cre.jax, gensat, creportal, connectivity.brain-map (MGI) (all ".org"). Second, in some embodiments, since Cre only recombines double stranded DNA (dsDNA) and the AAV genome is single stranded, only those capsid sequences that mediate the proper intracellular trafficking and conversion of the packaged genome to a persistent dsDNA form will be recovered. Therefore, such an approach can provide additional selective pressure for functional capsids.

Figure 2C:
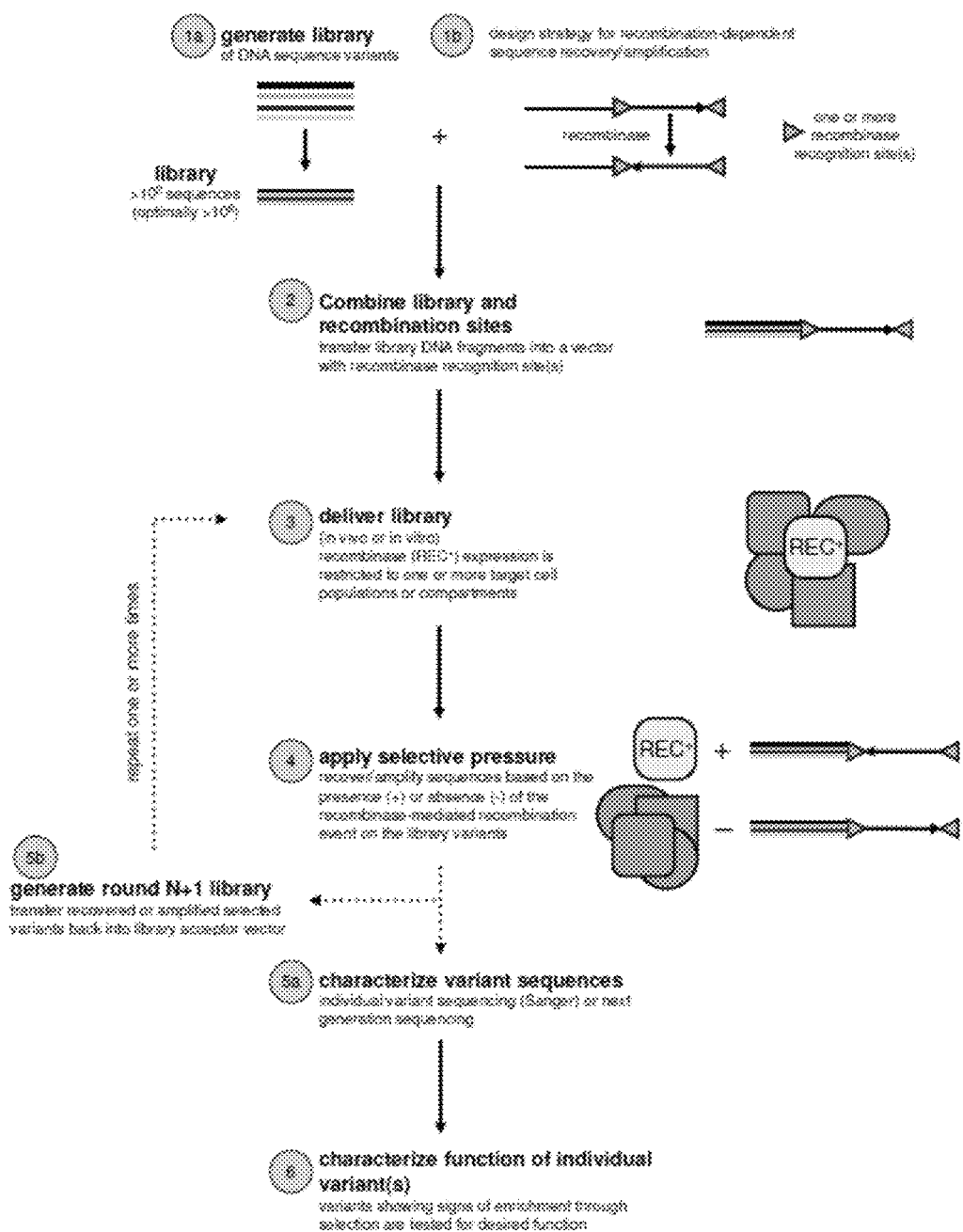
FIG. 2C depicts a flow chart for some embodiments of selective recovery embodiments.

As depicted in FIG. 2C, additional sequence variants can be selected based on their ability to mediated an increased association of the nucleic acid carrying the sequence library and recombinase site with the recombinase for similar or different desired applications. In some embodiments, the process can start by generating a library of DNA sequence variants (1A). In some embodiments, this can include $10^2$ if not more sequences (for example $10^6$ or more). Within the same nucleic acid, one can also incorporate one or more recombinase recognition sequences (1B). A strategy is then designed for recombination-dependent sequence recovery/amplification of the sequence variants. (1B). This can involve one or more recombinase recognition sites. One can then combine the library and recombination sites to transfer library DNA fragments into a vector with recombinase recognition sites (2). One can then deliver the library (for example, in vivo and/or in vitro). The recombinase (REC+) expression is restricted to one or more target cell populations or compartments (3). One can then apply a selected selective pressure to the system such that one can recover/amplify sequences based on the presence or absence of the recombinase-mediated recombination events on the nucleic acids comprising the library variants (4). This process can be repeated if necessary, transferring the recovered or amplified selected variants back into the library acceptor vector (5B) for 1 to 5, or more rounds of selection. One can then obtain and characterize the variant sequences (5A) by various methods, such as Sanger sequencing or next generation sequencing. Finally, one can then characterize the function of any or all of the individual variants.

A Method for Selectively Recovering Capsid Sequences That Have Transduced Specific Target Cell Populations Within Complex Tissue Samples.

Figure 2D:
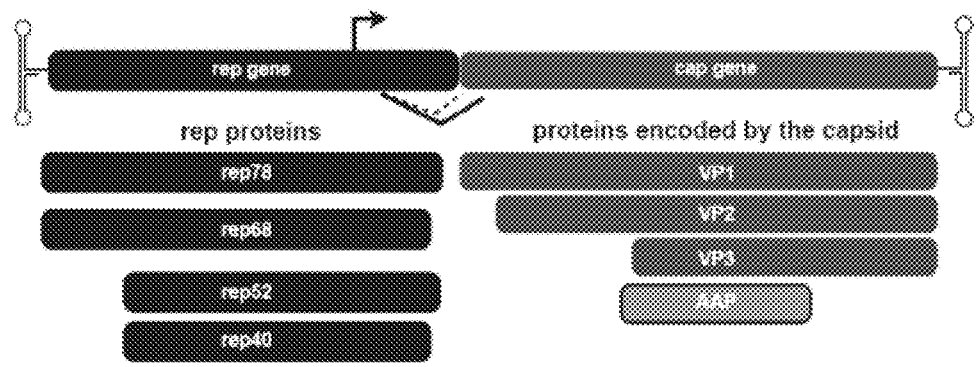
FIG. 2D depicts a schematic of AAV genes and their known products. The AAV rep gene makes four protein products shown in black. The cap gene makes three structural capsid proteins (VP1-3) from one reading frame by a combination of alternative splicing and alternative initiator codons. In addition, the capsid gene also encodes an additional protein, assembly-activating protein (AAP), which is expressed from an alternative reading frame.
Figure 2E:
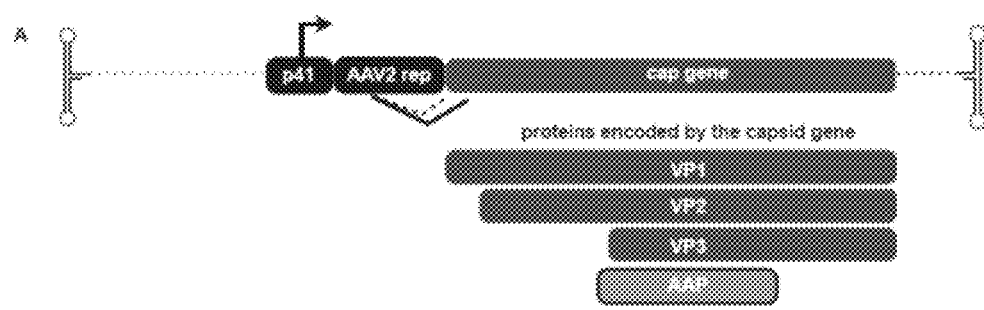
FIG. 2E is a schematic for the design of constructs used for some embodiments of the rAAV-based capsid library selection method. A capsid gene is inserted within a recombinant AAV genome flanked by ITRs. The expression and splicing of the AAV capsid gene products is controlled by the AAV5 p41 promoter upstream of the AAV2 rep sequences that contain the splice donor and intron sequences for the capsid gene products. By eliminating most of the rep gene, space (represented by the dotted lines) is available within the rAAV cap-in-cis genome for the insertion of additional elements.
Figure 2F:
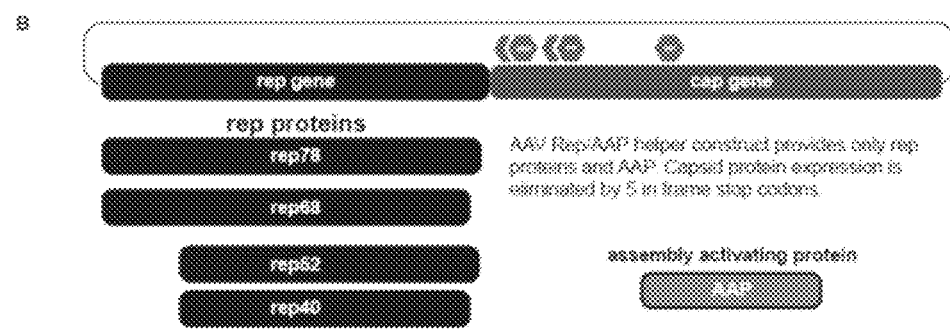
FIG. 2F is a schematic showing the AAV components of the rep-AAP helper plasmid. Five stop codons were inserted within the capsid VP reading frame to ensure that VP1, VP2 and VP3 expression is eliminated from the rep-AAP helper.
Figure 4A:
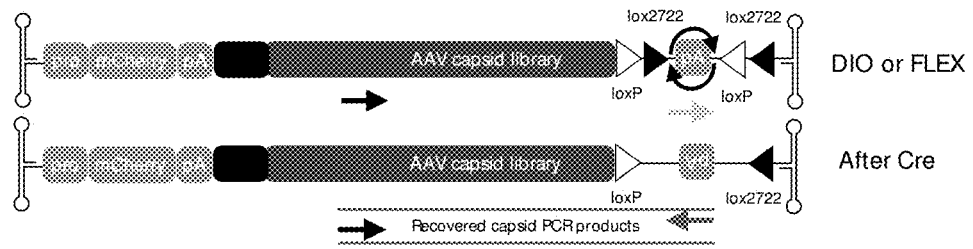
FIGS. 4A-4D. Alternative lox strategies for recombinase dependent recovery.
Figure 4B:
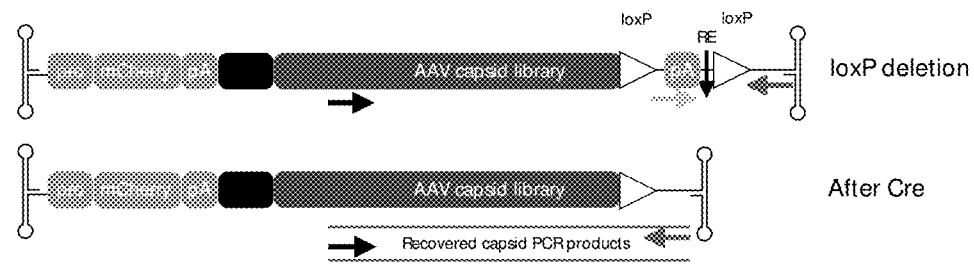
Figure 4C:
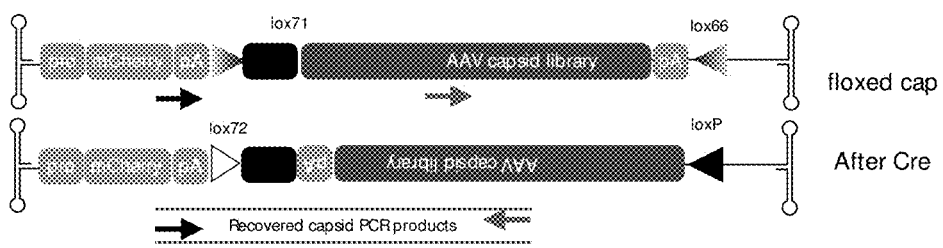
Figure 4D:
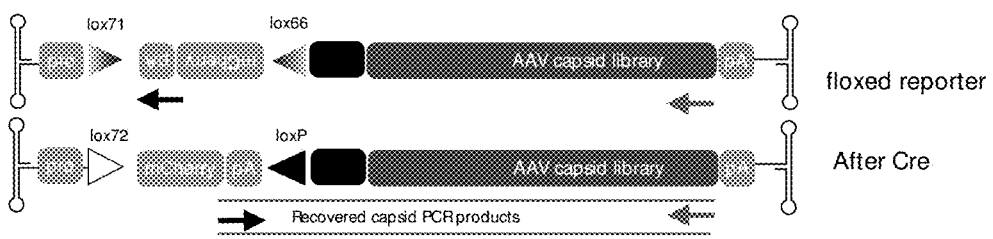

The AAV genome has two genes—rep, which encodes 4 nonstructural proteins relevant for replication (rep78, rep68, rep52 and rep40) and cap, which encodes three proteins (VP1, VP2, and VP3) that form the shell, or capsid, of the virus (FIG. 2D). In addition, the cap gene also encodes an accessory protein Assembly-activating protein (AAP) that is required for capsid assembly. Capsid directed evolution methods make use of replication competent AAV so that the capsid gene is present in cis (that is, within the viral genome). However, successful production of an AAV capsid variant library depends only upon each variant cap gene being packaged by the particular capsid proteins it encodes. Therefore, while it is useful that the cap gene is present in cis, it is not essential that the nonstructural replication (rep) genes be present in cis. With this in mind, a replication-incompetent, rAAV genome expressing the cap gene and only those regions of the rep gene necessary for expression and splicing of the capsid gene (FIG. 2D) has been developed. In place of the remaining rep sequences, several recombinant elements that provide a means to selectively recover only those capsid sequences that have functionally transduced the target cell population of interest without the need for target cell isolation have been incorporated (FIG. 3A). To ensure that the proteins encoded by the cap are properly expressed, the splicing donor and acceptor sequences (and all intervening sequences) present within the AAV2 rep gene upstream of the AAV cap gene within the recombinant genome (FIG. 2E) were incorporated. A p41 promoter fragment from AAV5 was used to drive translation from the capsid gene (SEQ ID NO: 4, FIG. 15, depicting the entire plasmid: the plasmid backbone, AAV ITRs, UBC-mCherry-syn-pA, AAV5 p41 promoter-AAV2 rep splicing seq, AAV9 cap, lox71-SV40 polyA-lox66-ITR). To provide rep and AAP helper function, an AAV rep/cap helper plasmid was modified by inserting a total of 5 stop codons within the cap gene within the VP1, 2 and 3 reading frame (1 stop codon disrupts VP3, 3 disrupt VP2 and all 5 disrupt VP1—FIG. 2F, SEQ ID NO: 5, FIG. 16). These stop codons were designed such that they did not disrupt the coding sequence of the AAP protein, which is encoded within an alternative reading frame.

Selective Recovery of AAV Capsid Sequences from Specific Cre+ Cell Populations.

To facilitate selective recovery of only those capsid sequences that encode the capsid protein that mediate transduction of a specific target cell population, a system was designed to take advantage of the large number of Cre transgenic mice, rats or other Cre transgenic organisms that have been (and can be) developed. These lines express Cre under the control of cell-specific promoters such that Cre is present only in a subpopulation of cells within a given organ. This approach incorporates a Cre recombinase-dependent "switch" that provides a means to selectively recover capsid sequences that have transduced Cre+ target cells. Cre recombination results in an inversion or deletion (depending on the configuration the lox sites used—see FIGS. 3 and 4) of a sequence within the AAV genome, and a PCR-based recovery strategy was used that only amplifies the cap gene sequence from rAAV genomes that have undergone a Cre-mediated inversion event. This strategy can also be adapted to select for AAV capsids that target cells that had previously been made to express Cre through non transgenic means (e.g., prior transduction with a Cre expressing virus), which could be useful for selection in larger species where Cre transgenes are not available.

An advantage of some of these embodiments is that this recombinase-dependent strategy only recovers those sequences that have transduced the target cell. AAV is a single stranded DNA virus, and its genome must be converted to double-stranded DNA (dsDNA) for functional transduction. Since Cre only recombines dsDNA, only those capsid sequences that have trafficked properly and have been converted to dsDNA will be recovered. This increases the selective pressure applied, which we anticipate will reduce the number of selection rounds that are necessary to develop viruses with improved properties.

This application is not limited to using Cre-lox as a recombinase/target site system. Other embodiments can include recombinases/integrases including, for example, Flp, phiC31 or Bxb1. The method can also be adapted for use with recombination-dependent, non-PCR-based recovery strategies. Furthermore, a recombinant AAV genome lacking most of the rep sequences was used to provide space for the lox switch and a reporter cassette, a cre-dependent switch could alternatively be inserted within a "replication competent" AAV genome in such a manner that it did not disrupt virus gene expression and packaging.

Recent efforts to use rAAV as a vehicle for gene therapy hold promise for its applicability as a treatment for human diseases based on genetic defects. rAAV vectors provide long-term expression of introduced genes from an episomal genome, although integration of the rAAV genome into the host chromosomes has been noted (Kaeppel 2013). An additional advantage of rAAV is its ability to perform this function in both dividing and non-dividing cell types including hepatocytes, neurons and skeletal myocytes. rAAV has been used successfully as a gene therapy vehicle to enable expression of erythropoietin in skeletal muscle of mice (Kessler et al., 1996), tyrosine hydroxylase and aromatic amino acid decarboxylase in the CNS in monkey models of Parkinson disease (Kaplitt et al., 1994) and Factor IX in skeletal muscle and liver in animal models of hemophilia. At the clinical level, the rAAV vector has been used in human clinical trials to deliver the cftr gene to cystic fibrosis patients, the Factor IX gene to hemophilia patients (Flotte, et al., 1998, Wagner et al, 1998).

Recombinant AAV is produced in vitro by introduction of gene constructs into cells known as producer cells. Some systems for production of rAAV employ three fundamental elements: 1) a gene cassette containing the gene of interest, 2) a gene cassette containing AAV rep and cap genes and 3) a source of "helper" virus genes.

The first gene cassette is constructed with the gene of interest flanked by inverted terminal repeats (ITRs) from AAV. ITRs function to direct the packaging of the gene of interest into the AAV virion. The second gene cassette contains rep and cap, AAV genes encoding proteins needed for replication and packaging of rAAV. The rep gene encodes four proteins (Rep 78, 68, 52 and 40) required for DNA replication. The cap genes encode three structural proteins (VP1, VP2, and VP3) that make up the virus capsid.

The third element is relevant because AAV-2 does not replicate on its own. Helper functions are protein products from helper DNA viruses that create a cellular environment conducive to efficient replication and packaging of rAAV. Adenovirus (Ad) has been used almost exclusively to provide helper functions for rAAV. The gene products provided by Ad are encoded by the genes E1a, E1b, E2a, E4orf6, and Va.

Production of rAAV vectors for gene therapy can be carried out in vitro, using suitable producer cell lines such as 293 and HeLa. One strategy for delivering all of the required elements for rAAV production utilizes two plasmids and a helper virus. This method relies on transfection of the producer cells with plasmids containing gene cassettes encoding the necessary gene products, as well as infection of the cells with Ad to provide the helper functions. This system employs plasmids with two different gene cassettes. The first is a proviral plasmid encoding the recombinant DNA to be packaged as rAAV. The second is a plasmid encoding the rep and cap genes. To introduce these various elements into the cells, the cells are infected with Ad as well as transfected with the two plasmids. Alternatively, in more recent protocols, the Ad infection step can be replaced by transfection with an adenovirus "helper plasmid" containing the VA, E2A and E4 genes. As provided herein, the rep and cap arrangements can be in trans for the screening aspects.

While Ad has been used conventionally as the helper virus for rAAV production, it is known that other DNA viruses, such as Herpes simplex virus type 1 (HSV-1) can be used as well. The minimal set of HSV-1 genes required for AAV-2 replication and packaging has been identified, and includes the early genes UL5, UL8, UL52 and UL29. These genes encode components of the HSV-1 core replication machinery, i.e., the helicase, primase, primase accessory proteins, and the single-stranded DNA binding protein. This rAAV helper property of HSV-1 has been utilized in the design and construction of a recombinant Herpes virus vector capable of providing helper virus gene products needed for rAAV production.

The following examples are presented as exemplary embodiments only, and are not intended to be limiting on the scope of the claims. In addition, there are further sections of various embodiments provided between some of the various examples below, as appropriate, and as indicated by the text and spacing of the document.

Example 1

The Split Rep-AAP and rAAV-Cap-In-Cis Constructs Generate High Titer rAAV.

Figure 5A:
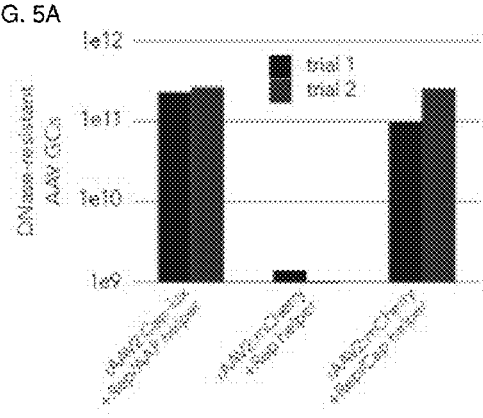
FIGS. 5A-5C. A split Rep/AAP helper and rAAV-Cap-lox vector produces high titer virus.
Figure 5B:
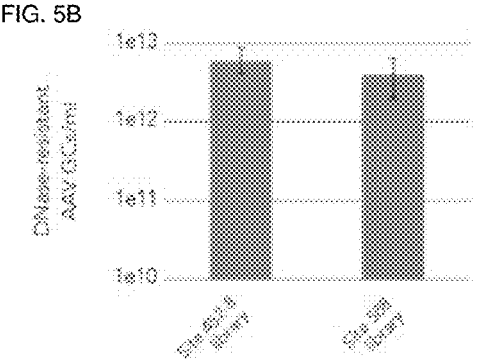

To test whether the split rep-AAP helper and rAAV-cap-in-cis system generates rAAV virus, a triple transfection of 293T (ATCC) cells was performed with the rep-AAP helper, rAAV mCherry-cap-lox71/66 genome and the adenoviral helper construct pHelper. Plasmids were transfected at a ratio of 2:1:4 (0.263 ug total DNA/cm2 of plated cell surface area), respectively using linear polyethylenimine (PEI) as the transfection reagent with a N:P ratio of 25. With these constructs, one was able to generate recombinant virus with an efficiency that was equivalent to that observed with the standard AAV2/9 rep/cap helper, a rAAV2 genome expressing mCherry only and pHelper (FIG. 5A). In contrast, when the rep-AAP helper and pHelper were used together with an rAAV genome encoding mCherry, but not an AAV cap, little to no virus was generated. This confirms that capsid expression in cis was required for rAAV production.

Generating the Capsid Libraries: Introducing Short Randomized Sequences into Surface Loops of AAV9.

Several strategies can be used to introduce sequence diversity into the cap gene. Examples include, but are not limited to (i) error prone PCR, which introduces mutations at a controllable rate throughout a region of the cap gene amplified by PCR, (ii) capsid domain shuffling, where libraries are generated through recombination events between fragmented capsid sequences generated from a panel of different capsid serotypes and (iii) targeted sequence modification at specific sites using primers with mixed bases, which generates stretches of randomized sequences at specific sites within the capsid. Each of these methods has advantages and disadvantages. In some embodiments, one can use targeted sequence modification strategy to replace or insert random sequences of seven amino acids (21 nucleotides) into two different surface loops.

Example 2

To generate libraries of AAV capsid variants, seven amino acids of randomized sequence was introduced into the AAV9 capsid. In one library, (452-8r) AA452-8, (VP1 counting) was replaced by randomized sequence. In a second library, (588i) seven AA of randomized sequence was inserted after AA588 in the AAV9 capsid. Using this targeted randomization strategy the sites can be randomized together in the same library or randomized sequentially after selection at an individual site.

The library fragments were generated by PCR. AA452-458 of AAV9 were replaced with 7 random amino acids through the use of a primer containing a stretch of 21 hand-mixed bases (7×NNK, Primer 1287). Primer 1312 was used as a reverse primer. For the 588i library, a stretch of 7AA was inserted after AA588 using a primer containing a stretch of 21 hand-mixed bases (7×MNN, primer 1286). Primer 1331 was used as a forward primer. The PCR conditions reactions were performed using 200 nM of each primer, 0.1-0.5 ng of template DNA (pCRII-9R-X/A EK plasmid, SEQ ID NO: 6, FIG. 17), 200 um dNTPs, 0.5 ul Q5 Hot Start, High-Fidelity DNA Polymerase (NEB), 10 ul 5× buffer and 10 ul GC enhancer provided by the manufacturer. The template plasmid contained a fragment of the AAV9 capsid gene that has been modified to have two unique restriction sites (XbaI and AgeI) flanking the region that was varied (this region creates an overlap with the rAAV9R-X/A-cap-in-cis acceptor plasmid cut with the same enzymes, see FIG. 5C). In addition, the PCR template fragment was further modified to eliminate a naturally occurring EarI restriction site within the capsid gene fragment and insert a KpnI site. The modification to remove the EarI restriction site provides a way to eliminate any "wild-type" AAV capsid vector sequence contamination from the libraries that might arise during cloning by digesting the libraries with the EarI enzyme. The EarI digestion step may not be necessary if care is taken to eliminate the possibility of wt AAV capsid sequence carry over/amplification. The insertion of the XbaI site caused a K449R mutation, but the other mutations introduced into the AAV9 sequence are silent.

Figure 5C:
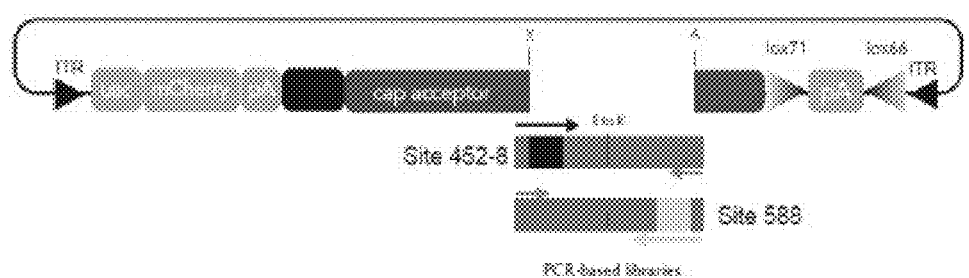

To facilitate cloning of the PCR fragments comprising the capsid library sequences into a recombinant AAV genome, the rAAV-cap-in-cis plasmid was modified to introduce the same two unique restriction sites, XbaI and AgeI, within the capsid sequence flanking the region that will be replaced by the PCR-based libraries (FIG. 5C). In addition, the coding region between the XbaI and AgeI sites was eliminated to prevent "wt" AAV9R X/A capsid protein production from any undigested vector during library virus production (AAV9R-delta-X/A-cap-in-cis, SEQ ID NO: 7, FIG. 18).

To assemble the PCR library products into the acceptor vector, the PCR products can be digested with XbaI and AgeI restriction enzymes and then ligated into the cap-in-cis acceptor construct cut with the same enzymes. Alternatively, the PCR products and the rAAV-cap-in-cis acceptor vector can be assembled using the Gibson Assembly method (Gibson et al., 2009). Enzymatic assembly of DNA molecules up to several hundred kilobases. *Nature Methods*, 6(5), 343-345. doi:10.1038/nmeth.1318). In the examples presented here, the Gibson Assembly method was used to consistently assemble over 100 ng of Plasmid Safe DNase-resistant circular DNA from an assembly reaction made from 400 ng of XbaI and AgeI digested, alkaline phosphatase treated AAV9R-delta-X/A-cap-in-cis vector and 67 ng of library PCR product with 30 ul of 2× Gibson Assembly Master Mix (NEB) in a total volume of 60 ul. The reactions were run at 50 C for 120 minutes.

Following Gibson assembly, reaction products were digested with a Plasmid Safe (PS) DNase as directed (Epicenter), which digests linearized but not circularized DNA molecules. The assembly reactions were incubated with 1 ul (10 U) of PS DNase in a reaction containing 2 ul ATP and 7 ul of the reaction buffer supplied by the manufacturer (Epicentre) at 37 C for 20 minutes followed by a heat inactivation step at 70 C for 30 minutes. This reaction typically yielded over 100 ng of assembled plasmid (as defined by the measured amount of product remaining after the PS DNase reaction (measured by Qubit dsDNA Broad Range kit from Invitrogen). 100 ng is sufficient to transfect 10 150 mm dishes at 10 ng/dish. It was useful to transfect this amount of the rAAV-cap-in-cis library plasmid to minimize number of packaging cells that were transfected with multiple copies of the rAAV-cap-in-cis plasmid, which could cause the generation of mosaic capsids. Mosaic capsids (those having a capsid shell composed of more than one capsid protein variant) would only carry one capsid variant genome. Therefore, not all of the amino acids within the capsids would be encoded by the capsid gene within the packaged genome By directly transfecting the assembled DNA, rather than first transforming it into competent cells and amplifying it in bacteria, it was possible to transfect the packaging cells with a maximally diverse library (theoretically >1e10 unique sequences).

Transfection of 293 Cells for Capsid Library Virus Production.

7-10 150 mm dishes of near confluent 293T cells that had been seeded 16-30 hour prior to transfection were typically transfected. In addition to the 10 ng of rAAV-cap-in-cis library vector, 5.7 ug of puc18, 11.4 ug of Rep-AAP helper and 22.82 ug of pHelper (per dish) were co-transfected using PEI at a N:P ratio of 25 (see Grieger et al 2006). The transfection mix was made in phosphate buffered saline (PBS) and was incubated at room temperature for 10 minutes and then added drop wise into the media. 12-18 hours after transfection, the media on the transfected cells was exchanged for fresh DMEM supplemented with 5% FBS, 1× Pen/Strep and 1× non-essential amino acid mix (Invitrogen). This media was then collected 48 hours after transfection, and replaced with fresh media. At 60 hours post transfection the media and cells were collected. Virus present in the media was concentrated by precipitation by adding poly (ethylene glycol) and sodium chloride to 8% and 0.5M, respectively. The cell pellets were resuspended in 10 mM Tris, 2 mM $MgCl_2$ and the viruses were released from the cells by 3 freeze-thaw cycles (alternating between a bath made from 100% ethanol and dry ice and a 37 C water bath. After the final thaw at 37 C, the lysates were treated with 50 U of Benzonase for 1 hour at 37 C. The virus precipitated from the media was then collected by centrifugation at 4000×g for 30 minutes at 4 C. The pelleted virus from the media was resuspended in the same Tris-$MgCl_2$ buffer as above and then combined with the cell lysate viral stock. At this time, deoxycholine (DOC) was added to 0.5% and the virus stock was incubated at 37 C for an additional 30 minutes. The virus stock was then adjusted to 500 mM NaCl and incubated for a further 30 minutes before the lysate was cleared by spinning at 4000×g for 15 minutes at 25 C. After spinning, the cleared viral stock lysates were purified over iodixanol (Optiprep, Sigma) step gradients (15%, 25%, 40% and 60% as described by Ayuso et al 2010). Viruses were then sterile filtered and dialyzed with Amicon Ultra 100K Centrifugal filters as directed (Invitrogen) and concentrated in PBS. Virus titers were determined by measuring the number of DNaseI-resistant genome copies (GCs) using qPCR and a linearized plasmid as a control (Gray et al 2011).

The virus production was halted at 60 hours post-transfection to reduce the likelihood of secondary transduction of the producer cells by the rAAV-cap-in-cis virus that is released into the medium.

Secondary transduction of cells that were successfully transfected with all of the plasmids necessary for virus production may lead to the generation of viruses from more than one capsid sequence (i.e., mosaics). Effort can be taken to minimize mosaic virus production to ensure that each capsid gene is packaged only into the physical capsid variant that it encodes.

Discussion of Additional Embodiments and Further Examples

Based on the results from the initial examples presented below, it is expected that this system can be used in conjunction with any transgenic line expressing a recombinase in the target cell type of interest to develop AAV capsids that more efficiently transduce that target cell population. Applications include, but are not limited to, developing capsids that are more efficient at transducing specific cell types in any organ after IV AAV administration, targeting specific populations of neurons after intraparenchymal brain injections, improving neuronal transport (anterograde or retrograde), targeting tumor cells, hematopoetic stem cells, insulin producing beta cells, lung epithelium, skeletal or cardiac muscle. Thus, the selection methods provided herein can be applied for one or more these aspects.

In addition, the approach can be used to select for viruses that target human cells in human/mouse chimeric animals (the human cells would be made to express Cre prior to in vivo delivery). This last example can be useful in the successful development of efficient vectors for gene therapy applications as there is evidence that the AAV serotypes that function best in animal models may not always function with the same efficiencies in humans (Lisowski et al 2013). Therefore, it can be advantageous to select for viruses that most efficiently transduce the target human cell population in the in vivo context of an animal model.

In addition, the method can be used in conjunction with any virus delivery method (e.g., intravenously, SC, IP, intramuscular, intranasal, i.c.v, intrathecal, oral or intracranial/intraparenchymal brain injection). In some embodiments, the vector can be delivered via any route including, but not limited to: oral, intravenous, intraarticular, intracardiac, intramuscular, intradermal, topical, intranasal, intraparitoneal, rectal, sublingual, subcutaneous, epidural, intracerebral, intracerebroventricular, intrathecal, intravitreal or subretinal administrations.

Although the examples herein have used AAV9 as a starting point, any naturally occurring or previously engineered AAV capsid could also be used as a starting point for selection using this approach. Furthermore, this method could also be useful for identifying other coding or non-coding sequences within an AAV or other viral genome that influenced transduction of recombinase expressing cells. Preferred examples include selecting for sequences within the AAV genome that increase conversion of the viral genome to dsDNA, increase the persistence of viral genomes by facilitating recombination or circularization, increase the efficiency of integration of the viral genome into a favored site(s) in the cellular genome or sequences that influence gene expression in the target cell population.

In some embodiments, provided herein is the use of CREATE (Cre Recombinase-based AAV Targeted Evolution), a novel platform for the selective recovery of capsid sequences that transduce $Cre^+$ target cell populations. Using CREATE, it was possible to develop several new AAV capsid variants with useful properties, including one, AAV-PHP.R2, that mediates efficient retrograde transduction within the brain as early as seven days post administration, and a second variant, AAV-PHP.B that crosses the adult mouse blood brain barrier (BBB) and transduces a variety of CNS neural cell types with an efficiency that is at least 40-fold greater than AAV9, the current standard for systemic delivery. In addition, whole animal tissue clearing using PARS-based CLARITY (Yang et al., 2014b) as a more rapid method for assessing serotype tropism at the cellular level and as a method to study individual cell morphology in the brain when combined with low-dose systemic AAV-PHP.B delivery is provided. Used together, transduction mapping in intact tissues and the Cre-based capsid selection method presented provide a novel platform that should facilitate further custom virus development.

Example 3

In Vivo Selection Using GFAP-Cre Transgenic Animals

Figure 6A:
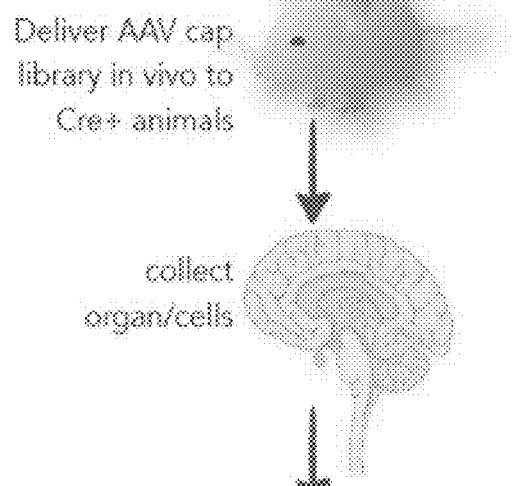
FIGS. 6A-6C. Cre-dependent sequence recovery after selection in Cre transgenics or Cre+ cells.
Figure 6B:
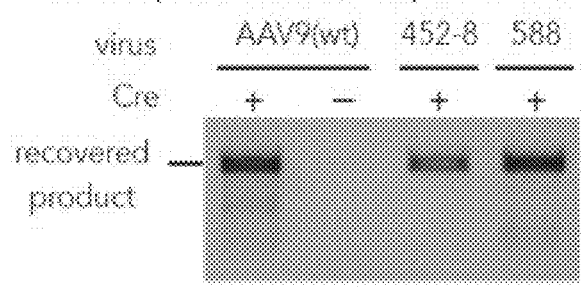
Figure 6C:

AAV capsids were developed that more efficiently transduce cells within the CNS of adult mice after IV injection. For this purpose, transgenic mGFAP-Cre mice were used that express Cre specifically within astrocytes and neural stem cells (NSCs) in the adult brain and spinal cord. The capsid libraries (1.2e11 GC) were delivered intravenously (IV) to mice through the retro-orbital sinus. 7-8 days later, the DNA was collected from the entire brain and spinal cord and recovered rAAV capsid sequences from GFAP-Cre+ cells (FIG. 6). Vector DNA was recovered from one hemisphere of the brain and half of the spinal cord using 4 ml of Trizol (Invitrogen). The manufacture's protocol was followed, and the aqueous, RNA-containing fraction was precipitated with isopropanol and subjected to three washes in 70% ethanol made with water (all water used for PCR recovery of capsid sequences in this protocol is treated with UV using a UV light box for 10-15 minutes prior to use). The precipitated material was then resuspended in 10 mM Tris pH8.0. In addition to RNA, this fraction also contains a significant fraction of the viral genome as well as some mitochondrial DNA. To eliminate the RNA, which reduced the efficiency of the PCR-based recovery of capsid sequences, the samples were treated with 1 ul of RNase (Qiagen) overnight. Alternative strategies for selective recovery of viral genomes away from the animal's genomic DNA could also be used, e.g., the HIRT extraction protocol (Hirt 1967), sized-based gel-purification, sequences specific capture/hybridization methods or selective digestion of the mouse genomic DNA by PS DNase following digestion with a restriction enzyme that does not cut the rAAV-cap-in-cis genome.

Capsid sequence recovery was performed in a Cre-dependent manner using primers 1253+1316. PCR conditions were 20-28 cycles with 95 C 20 sec/60 C for 20 sec/72 C for 30 sec using Q5 Hot Start High-fidelity DNA Polymerase. The PCR product was then diluted 1:10 and then used as a template for a second, PCR reaction that generated the X to A fragment (using primers 1331+1312) that was cloned back into the rAAV9R-deltaX/A-cap-in-cis acceptor construct to generate the next round of library virus using the same methods describe above. 1 ul of the Gibson Assembly reactions was then diluted 1:10 and transformed into Sure2 competent cells (Agilent) as directed by the manufacturer. At least 10 colonies/library were picked 12-16 hours later, DNA was isolated by miniprep kit (Qiagen) and the clones were sequenced. Alternatively, DNA from the clones can be amplified by PCR using primers 1253 and 1312 and sequenced directly, eliminating the need to perform mini plasmid DNA preps.

After the first round of selection all of the clones sequenced for both libraries were unique. Therefore, a second selection round was performed to further enrich for the most potent sequences. The assembled rAAV-cap-in-cis library regenerated after the first round of selection was used to generate a second round of virus which was then injected into a second batch of GFAP-Cre+ mice as described above. After the second round, two sequences, G2B13 and G2B26 showed evidence of enrichment (Table 2).

TABLE 2

Enriched Sequences from GFAP-Cre in vivo selection

| Variant | Mouse line | Delivery | Selection rounds | site | 7 mer DBA sequence(s) | 7 mer AA sequence(s) | % of total clones |
|---|---|---|---|---|---|---|---|
| G2B-13 | GFAP-Cre | IV | 2 | 452-8 | CAGTCGTCGCAGACGCC TAGG (SEQ ID NO: 48) | QSSQTPR (SEQ ID NO: 54) | 18% |
| G2B-26 | GFAP-Cre | IV | 2 | 588 | ACTTTGGCGGTGCCTTTT AAG (SEQ ID NO: 49) | TLAVPFK (SEQ ID NO: 1) | 27% |
| TH1.1-32 | TH-Cre | intracrainial (striatum) | 1 + 1 | 452-8 + 588 | ATTCTGGGGACTGGTACT TCG (SEQ ID NO: 50) ACGCGGACTAATCCTGA GCCT (SEQ ID NO: 51) | ILGTGTS (452-8) (SEQ ID NO: 55) TRTNPEA (588) (SEQ ID NO: 56) | 18% 9% |
| TH1.1-35 | TH-Cre | intracrainial (striatum) | 1 + 1 | 452-8 + 588 | ATTCTGGGGACTGGTACT TCG (SEQ ID NO: 52) AATGGGGGACTAGTAC TTCT (SEQ ID NO: 53) | ILGTGTS (452-8) (SEQ ID NO: 57) NGGTSSS (588) (SEQ ID NO: 58) | 18% 36% |

To test the variants recovered, the sequences were cut with BsiWI and AgeI and ligated into an AAV2/9R-X/A rep/cap helper (AAV2/9 rep/cap helper modified with the AAV9R-X/A capsid sequence from rAAV-cap-in-cis plasmid) also cut with BsiWI and AgeI and transformed into DH5alpha competent cells (NEB). Plasmid DNA was purified using an Endofree Plasmid Maxi Kit (Qiagen). The resulting rep/cap plasmids carrying the novel variant sequences, or AAV2/9 rep/cap as a control, were then used to package a rAAV genome containing a dual eGFP-2A-luciferase reporter cassette driven by a ubiquitous CAG promoter (rAAV-CAG-eGFP-2A-Luc-WPRE-SV40pA).

Figure 7:
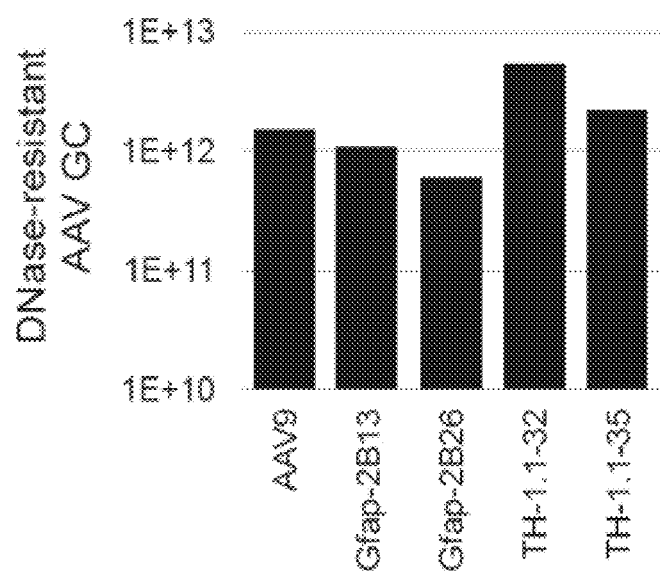
FIG. 7. The novel AAV variants generate virus with efficiencies similar to AAV9. The graph shows the DNase-resistant viral GCs generated per 150 mm dish of near confluent 293 producer cells for AAV9 and the four novel AAV serotypes.

The novel capsids packaged the genome with efficiencies comparable with AAV9 (FIG. 7). 1e12 GC of each vector was injected IV into individual adult female C57Bl/6 mice. Six days later, the mice were perfused with 4% paraformaldehyde in 100 mM phosphate buffer and the brains were examined for eGFP fluorescence.

Figure 8A:
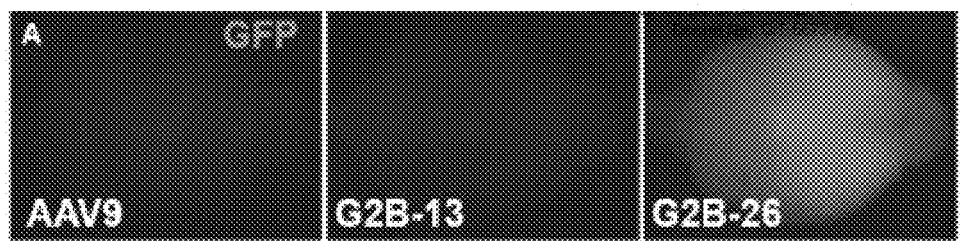
FIGS. 8A-8C. G2B13 and G2B26 variants mediate enhanced transduction of the brain and spinal cord after IV administration as compared to AAV9. An AAV-CAG-eGFP-2A-ffLUC-WPRE-SV40 pA vector was packaged into AAV9 (left) or the novel variants G2B13 (middle) or G2B26 (right). 1e12 GC of each virus was injected IV into individual 5-week old female wt C57Bl/6 mice and the brains of the mice were assessed for GFP expression 6 days later.
Figure 8B:
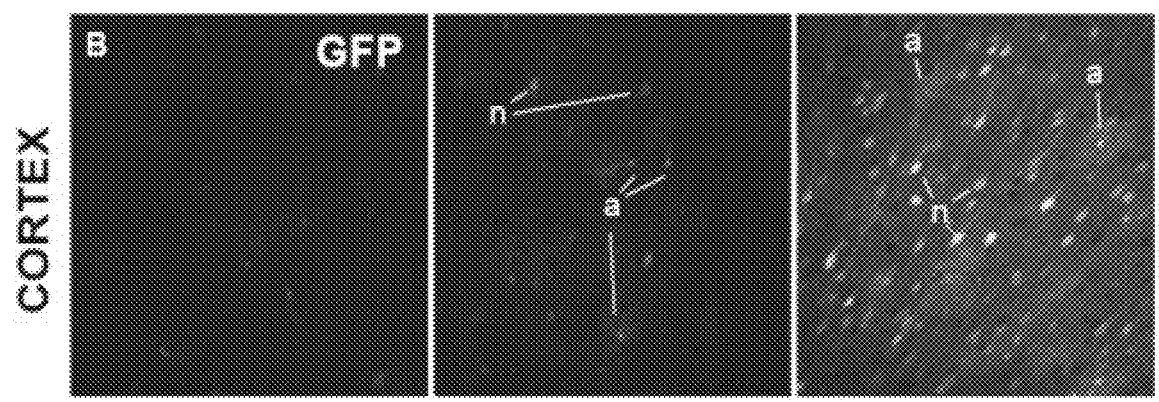
Figure 8B:
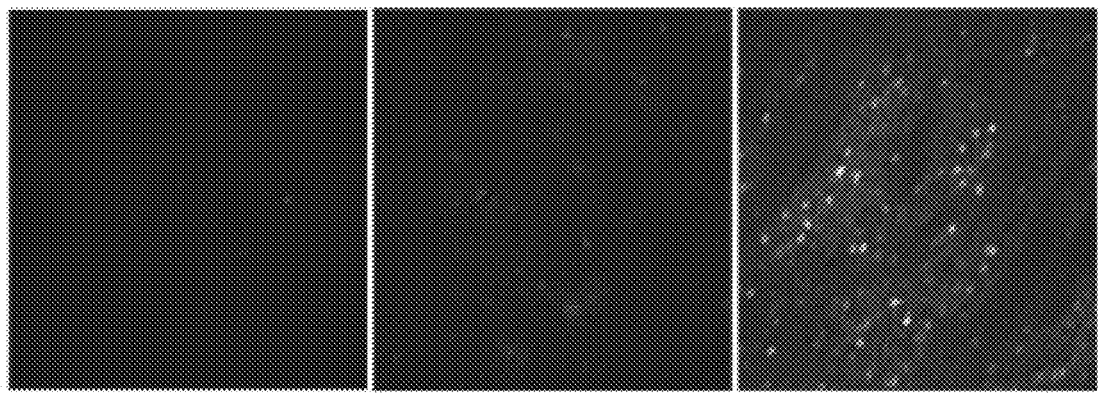
Figure 8B:
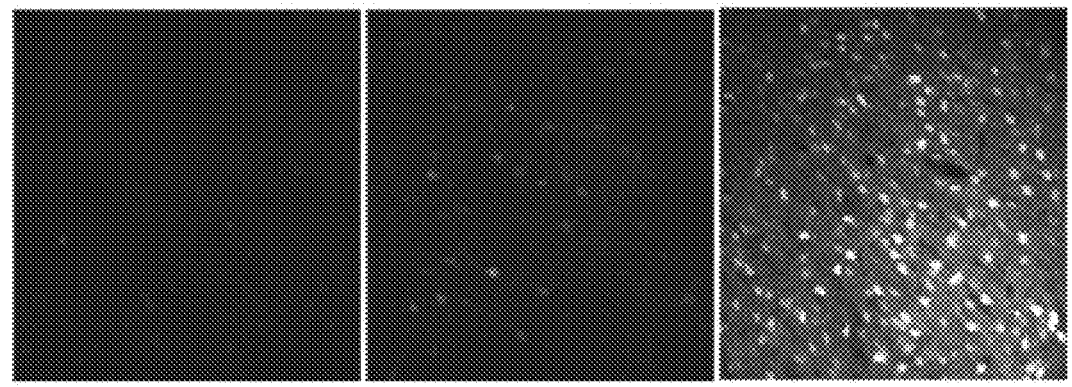
Figure 8C:
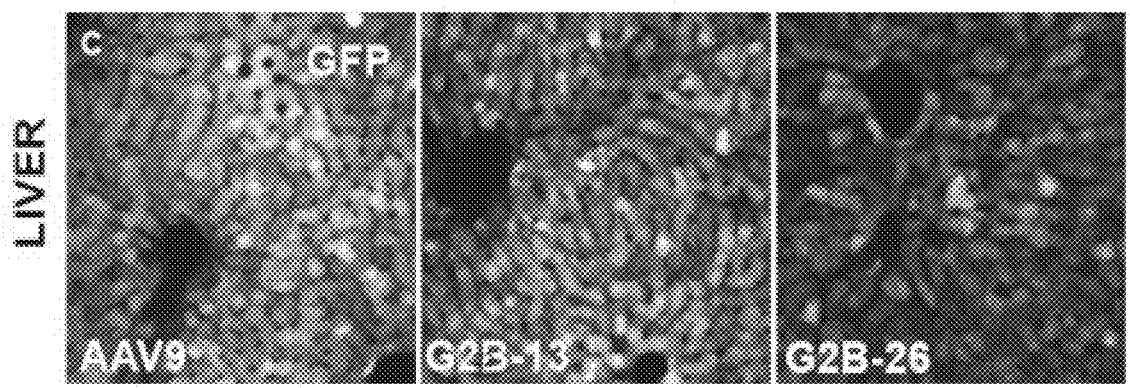

Remarkably, transduction by the G2B26 variant was efficient enough that the native eGFP fluorescence throughout the intact brain could be seen with a 1× objective on an epifluorescence microscope (FIG. 8A). At this same exposure setting, little to no eGFP fluorescence is evident in the brain from the mouse injected with AAV9. In sections prepared from a brain from a mouse injected with G2B26, transduction of neurons and glia in all regions examined in the brain and spinal cord were seen (FIGS. 8 and 9). In certain thalamic nuclei, over 90% of the NeuN+ cell bodies expressed GFP (FIG. 9G). Transduction of motor neurons in the ventral spinal cord was also robust (FIG. 9F). Numerous Sox2+ glia expressed GFP (FIG. 9I). The G2B13 variant also transduced astrocytes and neurons more efficiently than AAV9, but the effect was not as dramatic as compared to the transduction by G2B26 (FIGS. 8 and 9A-C). The G2B13 variant showed strong transduction of fiber tracts in the dorsal brain stem (FIG. 9B) and spinal cord (FIG. 9C) as well as robust liver transduction (FIG. 8C). It also appears that the G2B26 variant provides more rapid onset of expression in the CNS than AAV9. Transduction by AAV9 transduction at six days post-injection was weak. Stronger expression was observed per cell and more eGFP expressing cells with the same dose of AAV9 at 21 days post injection.

Since rapid unpackaging has been proposed to be an important component of transduction efficiency and viral genome persistence (Wang et al. 2007), recovering capsid sequences soon after injection (in this case 7-8 days) may be an important component of a successful selection.

In the example above, the number of cycles can be determined empirically with the optimal number of cycles being within a range that yields more product from samples taken from Cre+ cells/animals than from samples lacking Cre+ cells. If the PCR reaction is allowed to continue past this optimal range by performing too many cycles, products may be recovered even from Cre negative samples. It can be desirable to avoid doing too many cycles.

Example 4

In Vivo Selection for Improved Retrograde Transduction Using TH-CRE Animals

In a second test of the Cre-dependent selection platform, it was asked whether one could generate novel AAV serotypes that lead to more efficient transduction of TH+ neurons in the substantia nigra (SN) compact part after virus injection into the striatum, a structure that receives axons from TH neurons. This selection scheme is designed to develop AAVs that are capable of rapid retrograde transport and transduction of TH+ and non-TH+ cells.

Figure 10:
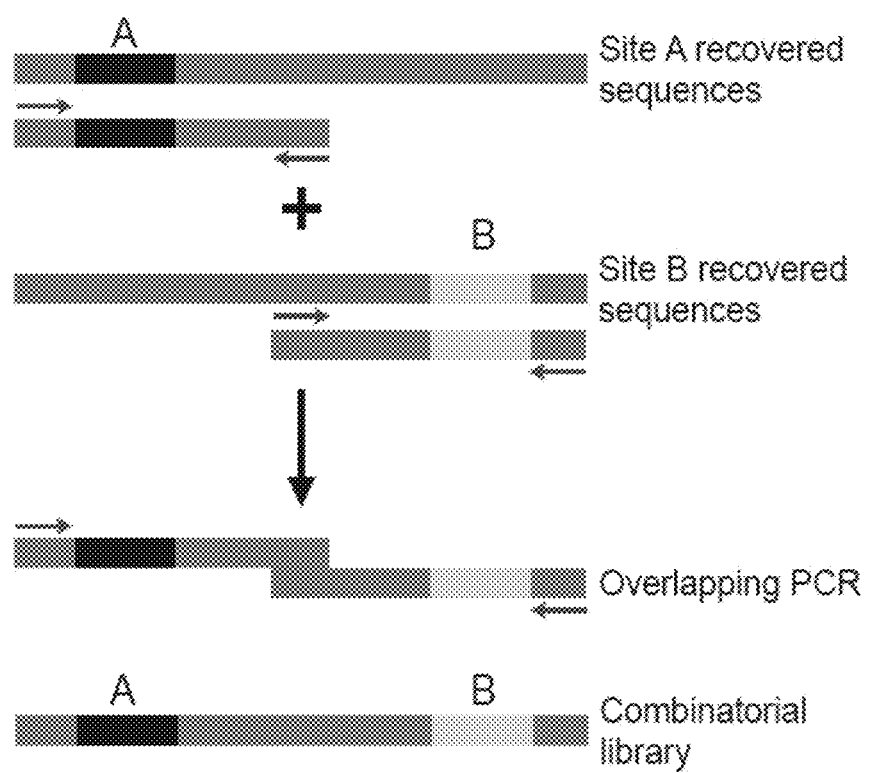
FIG. 10. Strategy for generating further diversity by combining sequences recovered at multiple sites. Following one or more rounds of selection for novel cap variants at two different sites, the pools of selected variants can be mixed to generate libraries that combine the randomized sequences at two or more sites by overlapping PCR. Using the same strategy, individual clones with novel sequences at 2 more sites can also be combined to generate clones with multiple modifications.
Figure 11A:
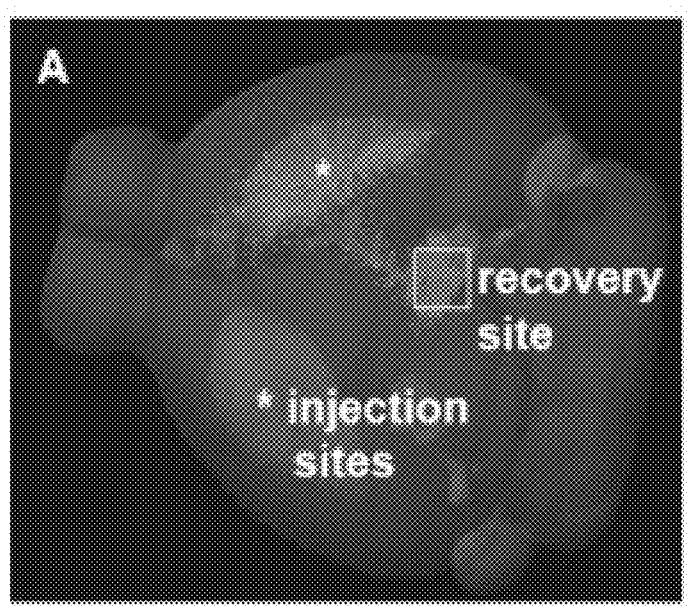
FIGS. 11A-11E. Cre-dependent sequence recovery after in vivo selection.
Figure 11B:
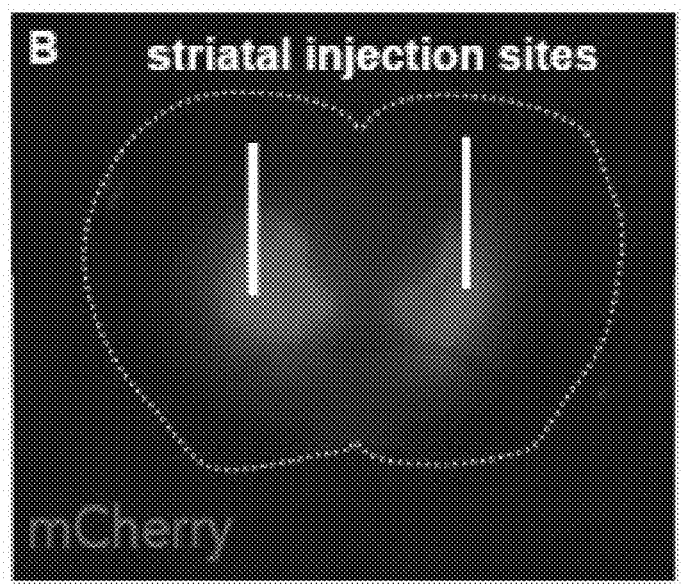
Figure 11C:
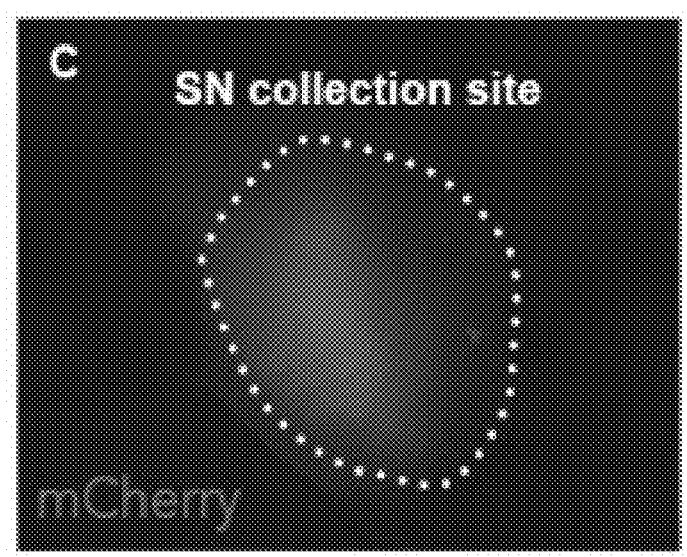
Figure 11D:
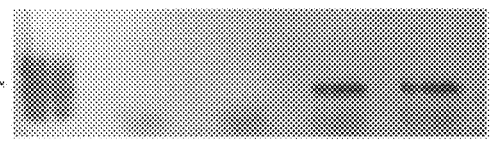
Figure 11E:
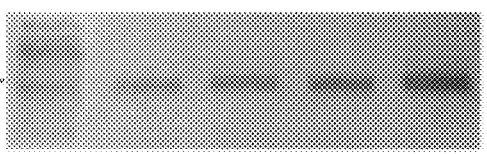

The same libraries were used as initially generated for the Example 3 selection and injected 0.6 ul of the virus bilaterally into the striata of adult TH-Cre+ male mice using the stereotaxic coordinates 0.7 mm rostral, 2.0 mm lateral and 3.0 mm ventral from Bregma. 10 days later, the region containing the SN was collected and isolated virus DNA from the tissue as described above. For these dissections, the mCherry reporter expressed from the rAAV-cap-in-cis genome aided in the identification of the SN (FIG. 10C) and the confirmation that the virus libraries injections had targeted the desired areas (FIG. 10B). Virus DNA was obtained from the SN-containing tissue sample using Trizol (Invitrogen) as described above and the same Cre-dependent PCR strategy was used to selectively recover those capsid sequences that led to the transduction of TH+ neurons (FIG. 10D). Using primers that amplify capsid sequences from all genomes regardless of recombination status (1253+1267) demonstrate that the viral sequences were also present in the Cre− controls (FIG. 10D, lower panel). Sequences recovered through the Cre-recombination dependent strategy were cloned back into the rAAV-cap-in-cis library acceptor as described above in Example 3.

Colonies were picked for sequencing. After the first round of selection, all of the tested sequences were unique, so a second round of selection was performed as described above. In addition to continuing with the libraries modified at the two individual sites, combinatorial libraries were also made by mixing all of the sequences recovered at the 452-8 replacement site with the sequences recovered at the 588 insertion site using the PCR strategy outlined in FIG. 10. Capsid virus libraries from the recovered sequences were prepared, selected again in TH-Cre mice and recovered as described above.

Figure 12A:
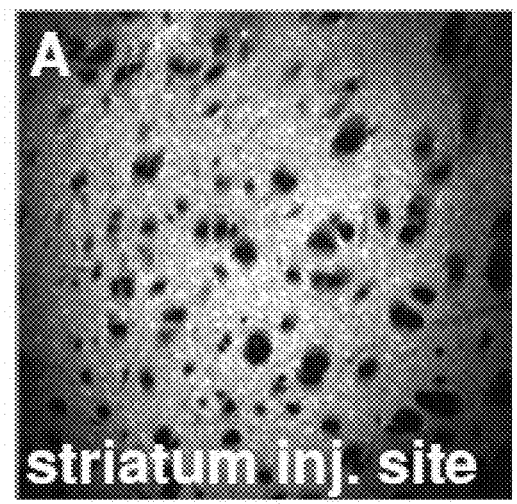
FIGS. 12A-12H. TH1.1-32 and -35 variants exhibit rapid and efficient retrograde transduction of TH+ SNc neurons as well as neurons in additional regions known to project to the striatum. AAV-TH1.1-32:CAG-GFP or AAVTH1.1-35:CAG-GFP were injected into the striatum of adult mice and mice were killed 7 days later for GFP expression analysis. Panels show immunostaining for eGFP (FIG. 12A-B, FIG. 12D and FIG. 12F-H) or TH (FIG. 12C and FIG. 12E).
Figure 12B:
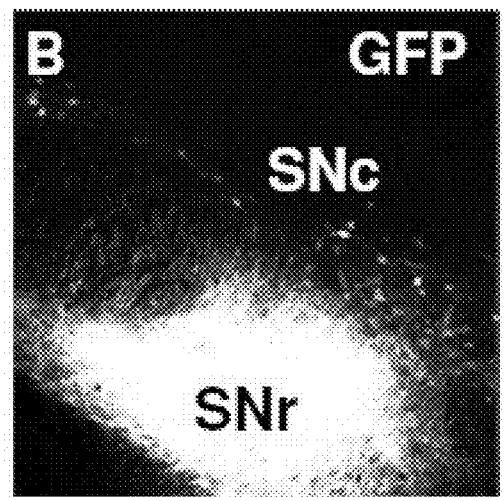
Figure 12C:
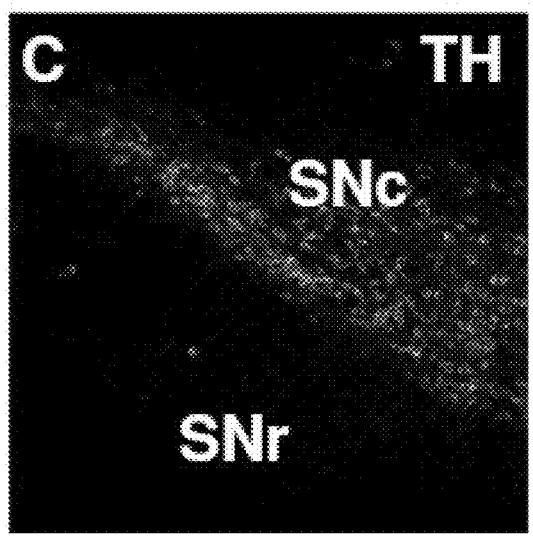
Figure 12D:
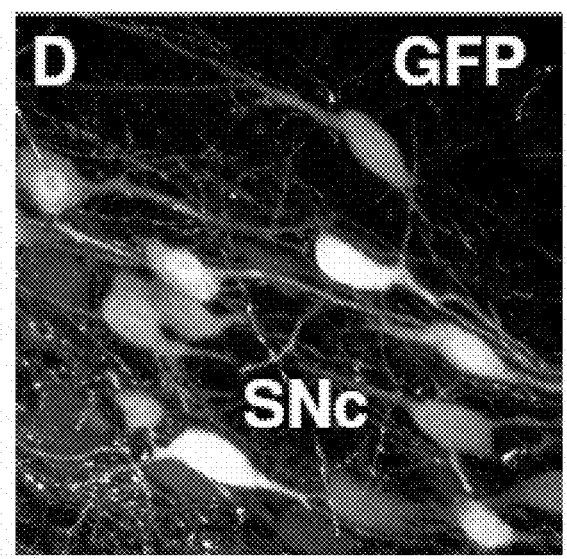
Figure 12E:
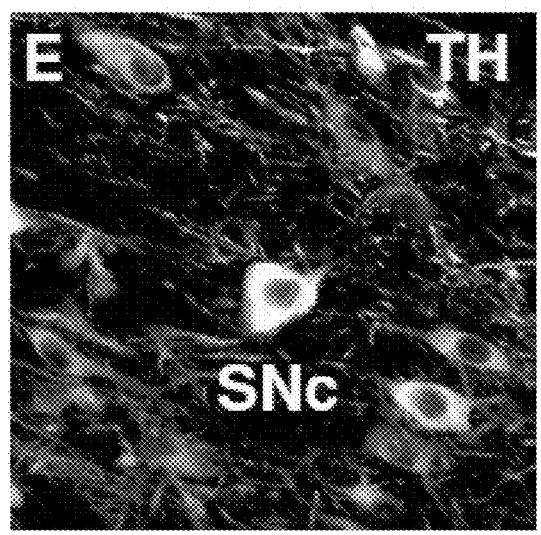
Figure 12F:
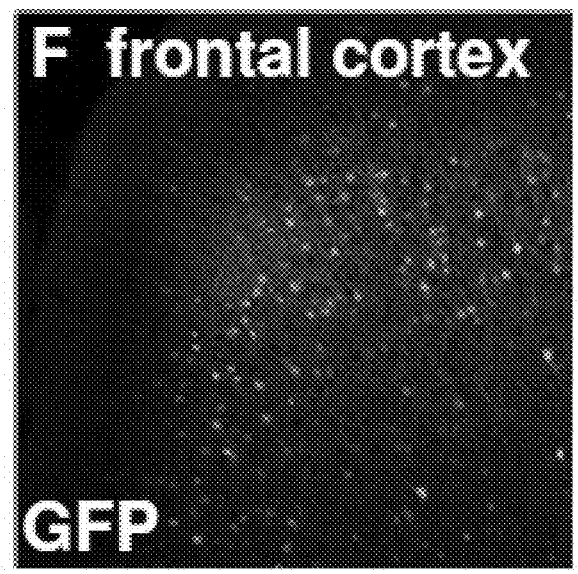
Figure 12G:
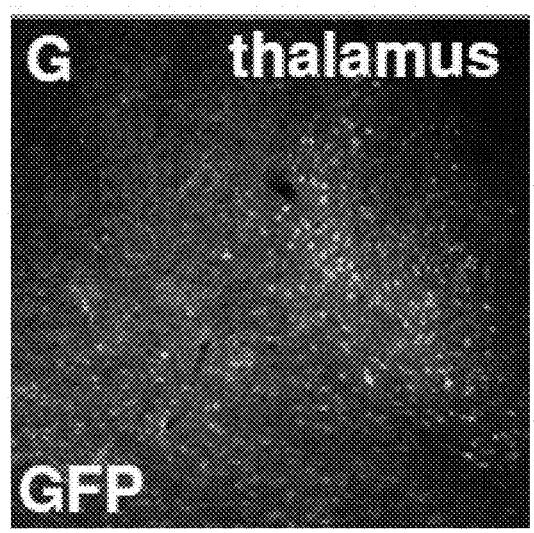
Figure 12H:
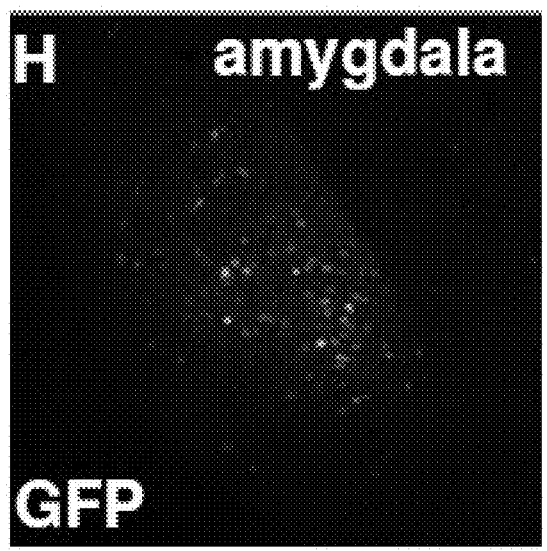
Figures 23A, 23B:
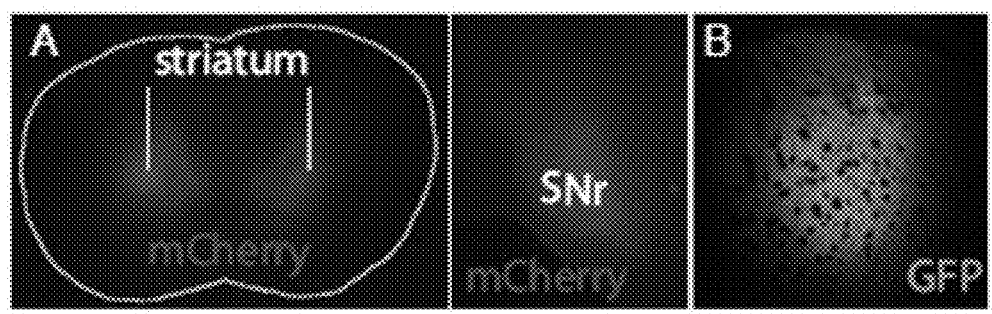
FIGS. 23A-23I. AAV-PHP.R2 mediates rapid and efficient retrograde transduction.
Figure 23C:
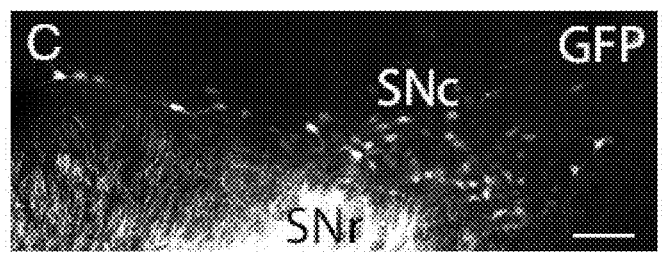
Figure 23D:

After the second selection round in the combinatorial library, several sequences at both randomization sites showed evidence of enrichment. Several novel capsid sequences were selected to test as individual variants. The sequences were cloned into an AAV2/9R-X/A rep/cap helper using unique BsiWI and AgeI sites present in both vectors. The resulting rep/cap plasmids carrying the novel variant sequences, or AAV2/9 rep/cap as a control, were then used to package a single stranded (ss) rAAV-CAG-GFP-W-pA genome. The novel capsids packaged the genome with efficiencies comparable with AAV9 (FIG. 7). 7e9 VGs (in 0.5 ul) of each virus was injected individually, and bilaterally, into adult C57Bl/6 mice using the same stereotaxic coordinates described above. 7 days later, mice were given an overdose of Euthasol and killed by cardiac perfusion with 4% PFA as described above. At this time, there were few if any GFP+/TH+ neurons in the SNc of mice that received an injection of the control virus, AAV9:CAG-GFP-W-SV40pA. In contrast, there were numerous GFP+/TH+ neurons present in the mice given injections of the same rAAV genome packaged into the novel clones TH1.1-32 (FIG. 12D) or TH1.1-35 (FIG. 23D)

A listing of the primers used in examples 3 and 4 is provided in Table 1 below:

TABLE 1

| Primer | Purpose | Sequence |
|---|---|---|
| 1253 | Cre-dependent amplification, forward | CAGGTCTTCACGGACTCAGACTATCAG (SEQ ID NO: 16) |
| 1254 | 9R-X/A delta, reverse | CAACCGGTAATAGTTCTAGAGAGATAGTACAAGTATTGGTCGATGAGTG (SEQ ID NO: 37) |

TABLE 1-continued

| Primer | Purpose | Sequence |
|---|---|---|
| 1255 | 9R-X/A delta, forward | CTCTCTAGAACTATTACCGGTTGGGTTCAAAACCAAGGAATACTTC (SEQ ID NO: 38) |
| 1267 | Library recovery, non-recombined, reverse | GTCCAAACTCATCAATGTATCTTATCATGTCTG (SEQ ID NO: 39) |
| 1280 | VP1 stop, reverse | GAGTCAATCTGGAAGTTAACCATCGGCA (SEQ ID NO: 40) |
| 1281 | VP1 stop, forward | GATGGTTAACTTCCAGATTGACTCG (SEQ ID NO: 41) |
| 1283 | VP2 stop, reverse | GACTACTCTACAGGCCTCTTCTATCCAG (SEQ ID NO: 42) |
| 1284 | VP2 stop, forward | GATAGAAGAGGCCTGTAGAGTAGTCTCC (SEQ ID NO: 43) |
| 1285 | VP3 stop, reverse | CATCGGCACCTTAGTTATTGTCTG (SEQ ID NO: 44) |
| 1286 | VP3 stop, forward | GACAATAACTAAGGTGCCGATGGAGTGG (SEQ ID NO: 45) |
| 1286 | Site 588 randomization, reverse | GTATTCCTTGGTTTTGAACCCAACCGGTCTGCGCCTGTGCMNNMNNMN NMNNMNNMNNMNNTTGGGCACTCTGGTGGTTTGTG (SEQ ID NO: 23) |
| 1287 | Site 452-8 randomization, forward | CATCGACCAATACTTGTACTATCTCTCTAGAACTATTNNKNNKNNKNNKN NKNNKNNKCAAACGCTAAAATTCAGTGTGGCCGGA (SEQ ID NO: 22) |
| 1312 | Site 452-8, reverse and X/A fragment generation, reverse | GGAAGTATTCCTTGGTTTTGAACCCA (SEQ ID NO: 19) |
| 1316 | Library recovery, Cre-dependent, forward (reversed by recombination) | CAAGTAAAACCTCTACAAATGTGGTAAAATCG (SEQ ID NO: 17) |
| 1331 | Site 588, forward and X/A fragment generation, forward | ACTCATCGACCAATACTTGTACTATCTCTCTAGAAC (SEQ ID NO: 18) |
| 1352 | Combinatorial library generation, EarI to KpnI mutation insertion, Rev | GTCTCTGCCGGTACCTTGTTTGCCAAAAATTAAAGATCCA (SEQ ID NO: 46) |
| 1353 | Combinatorial library generation, EarI to KpnI mutation insertion, For | GCAAACAAGGTACCGGCAGAGACAACGTGGATGCGGACA (SEQ ID NO: 47) |

By using the platform for selection provided herein, it was possible to developed several capsids that provide enhanced, widespread gene expression in the CNS.

Notably, one capsid (AAV-PHP.R2) was capable of rapid, retrograde transport within CNS neurons after intracerebral injection, while another capsid (AAV-PHP.B) transduced cells throughout central nervous systems with 40-90-fold greater efficiency than AAV9 when delivered systemically. AAV-PHP.B transduces both neurons and glia and is therefore well suited for gene transfer to global CNS neural cell types including neurons, astrocytes and oligodendrocytes.

Given the large collection of cell type-specific Cre transgenic lines, the present capsid-selection platform is a valuable resource for customizing gene delivery vectors for biomedical applications.

Example 5

Within the rAAV cap-in-cis recombinant genome, two elements were introduced to facilitate the selection. The first is an mCherry reporter cassette, having a 398 base pair promoter fragment from the ubiquitin C gene (UBC), the 711 bp mCherry cDNA, and a 118 bp 3' untranslated region containing a 51 bp synthetic poly adenylation (polyA) sequence (Levitt et al., 1989). The second, and more relevant element is a Cre-dependent "switch", having a pair of inverted, modified loxP sites (lox71 and lox66) (Araki et al., 1997) flanking a SV40 polyA sequence downstream of the cap gene. This floxed element created a Cre-invertible sequence that allows for the selective PCR amplification and recovery of only those cap sequences contained within the AAV genomes that have transduced Cre+ cells (FIG. 22A).

To provide rep, but not cap, gene function in trans, an AAV2/9 REP-CAP helper plasmid was modified by inserting five in frame stop codons within the reading frame for the capsid proteins, VP1, VP2 and VP3. These stop codons were designed to disrupt capsid protein expression, but not alter the amino acid sequence of the assembly activating protein (AAP), which is expressed from an alternative reading frame within the cap gene (FIG. 22B) (Sonntag et al., 2010). In this way, the modified REP-AAP helper plasmid continues to provide all of the AAV gene products in trans, save for capsid protein expression. To test whether this split rAAV-CAP-in-cis-lox and REP-AAP helper system efficiently generates rAAV, a triple transfection of HEK 293T cells was performed with the rAAV-CAP-in-cis genome, the REP-AAP helper, and the adenoviral helper plasmid, pHelper. Importantly, with these plasmids, it was possible to generate recombinant virus with an efficiency that was equivalent, if not greater than, that observed when an AAV2/9 REP-CAP helper was used to package a rAAV genome encoding mCherry (AAV-UBC-mCherry) (FIG. 22C).

In contrast, when the AAV REP-AAP helper was used to package AAV-UBC-mCherry, lacking the cap gene in cis, little to no virus was generated, confirming that capsid protein expression from the rAAV-CAP-in-cis-lox vector was required for rAAV production. Used together, the rAAV-CAP-in-cis-lox and AAV REP-AAP helper provided a novel platform, which is here below termed CREATE, for selective capsid sequence recovery from genetically defined populations of cells within complex tissue samples.

Example 6

Two AAV9-based capsid libraries were generated by PCR using a mixed base randomization strategy. One library was made by inserting 7 amino acids of randomized sequence between AA588-9 (VP1 position) of the AAV9 capsid and another with 7 amino acids of randomized sequence replacing AA452-8 of AAV9. The cloning strategy was designed such that the recoverable PCR product would contain only the stretch of amino acids spanning the variable regions (sequences between AA450 and AA592), which encompasses a significant portion of the surface exposed amino acids, while the rest of the capsid sequence within the backbone vector remains unmodified. Library fragments were then cloned into the rAAV-delta-cap-in-cis vector and assembled products were directly transfected into packaging cells to produce virus, bypassing the primary bottleneck of library diversification, bacterial transformation. With this approach, the library diversity is limited by the number of transfected cells, rather than the number of bacterial transformants resulting in an estimated diversity of $1 \times 10^7$-$1 \times 10^8$ unique sequences. Using this approach, it was possible to achieve yields of 5-$10 \times 10^{11}$ VGs.

Vectors that mediate efficient retrograde transduction of neurons, i.e., the uptake of vector by axons and transport back to the nucleus, are desired for neuronal circuit tracing and intersectional approaches for circuit-specific gene expression, and may also have uses for clinical gene delivery. While viruses such as recombinant rabies and herpes simplex virus (HSV), exhibit highly efficient retrograde transduction and are useful for short-term circuit tracing studies, their long-term toxicity precludes their use for longitudinal experiments or experiments where their impact on cellular health would cofound (e.g. optogenetics, aging, neurodegeneration studies). For long-lasting gene expression, AAVs capable of efficient retrograde transduction would be highly valuable as they would allow the extensive tool-set available in the rAAV genome format to be applied to applications requiring retrograde transduction (NIH Brain Initative Working Group, 2013).

Example 7

In Vivo Selection for AAV Variants with Enhanced Retrograde Transduction in the Rodent CNS Several AAV serotypes have been shown to mediate retrograde transduction of neurons in the CNS with varying efficiencies (Aschauer et al., 2013; Castle et al., 2014a; Castle et al., 2014b; Cearley and Wolfe, 2007; Hutson et al., 2012; Löw et al., 2013; Salegio et al., 2013; Samaranch et al., 2012). To develop AAV capsids with improved retrograde transduction, an in vivo selection for capsids that transduced TH$^+$ dopaminergic neurons in the substantia nigra via retrograde transport from their axons within striatum (Smith and Bolam, 1990) was set up. The AAV-CAP-in-cis-lox 452-8r and 588i libraries were separately injected into the striata of adult TH-Cre$^+$ mice. 10 days later the tissue surrounding the substantia nigra (SN) (FIG. 23A) was dissected and isolated viral DNA. For these dissections, the mCherry reporter expressed from the AAV-cap-in-cis library vectors aided in the identification of the SN as the SN pars reticulata (SNr) was easily identified from the mCherry$^+$ axons that project to the SNr from the striatum. mCherry expression in the striatum confirmed that the virus library injections had been properly targeted (FIG. 23A). After the first round of selection, 10 clones from each library were sequenced and it was found that all of the tested sequences were unique, so a second round of selection was performed. To further diversify the libraries after the initial round of enrichment, combinatorial libraries were made by mixing all of the sequences recovered from the 452-8r library with all of the sequences recovered from the 588i library by PCR (see FIG. 27D). Viral capsid libraries from the combinatorial library were prepared and selected again in TH-Cre mice as described above. After the second selection round, several sequences at both randomization sites showed evidence of enrichment.

The most highly enriched variant, PHP.R2, was further characterized by testing it individually (see Table 3 for sequence information and enrichment data).

TABLE 3

| Variant | Selection | Route | Rounds | Site(s) | 7 mer DNA sequence | AA seq. | % |
|---|---|---|---|---|---|---|---|
| PHP.R2 | TH | i.c. | 1 + 1 | 452-8r | ATTCTGGGGACTGGTACTTCG (SEQ ID NO: 50) | ILGTGTS (SEQ ID NO: 55) | 18% |
|  |  |  |  | 588i | AATGGGGGACTAGTAGTTCT (SEQ ID NO: 53) | NGGTSSS (SEQ ID NO: 58) | 36% |
| PHP.A | GFAP | i.v. | 2 | 588i | TATACTTTGTCGCAGGGTTGG (SEQ ID NO: 59) | YTLSQGW (SEQ ID NO: 60) | 40% |
| PHP.B | GFAP | i.v. | 2 | 588i | ACTTTGGCGGTGCCTTTTAAG (SEQ ID NO: 49) | TLAVPFK (SEQ ID NO: 1) | 27% |

Table 3 lists the AAV-PHP variants, the Cre transgenic line used to perform the library selection, the route of administration and the number of selection rounds used to enrich for the improved variants. 1+1 refers to one round of selection of the two separate libraries and then an additional round of selection of the combinatorial library. The site within AAV9 that was modified in each recovered variant is listed as is the 7mer DNA sequence(s) and amino acid sequence(s) (AA seq.) that are modified in each capsid variant. The number of occurrences of the enriched sequence as a percentage of the total number of clones sequenced is also given.

Figure 23E:
Figures 23F, 23G:
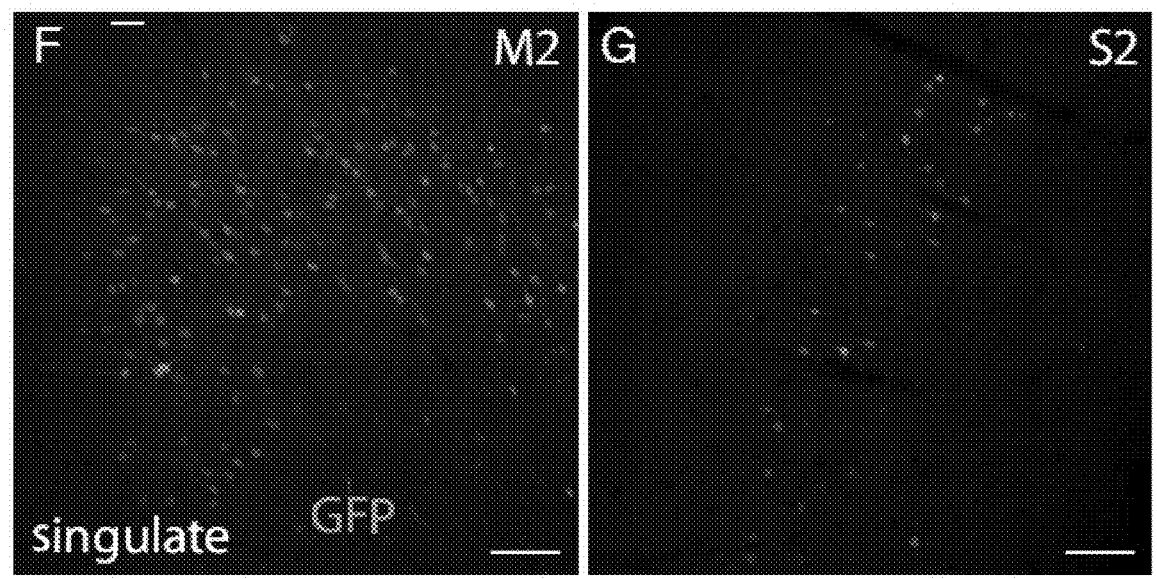
Figure 23H:
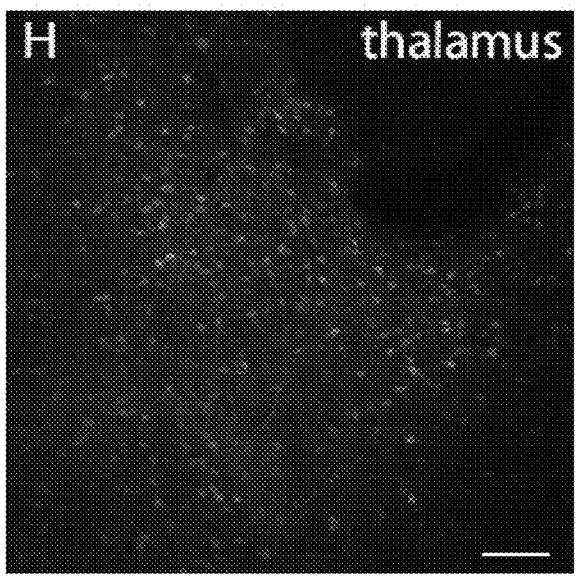
Figure 23I:
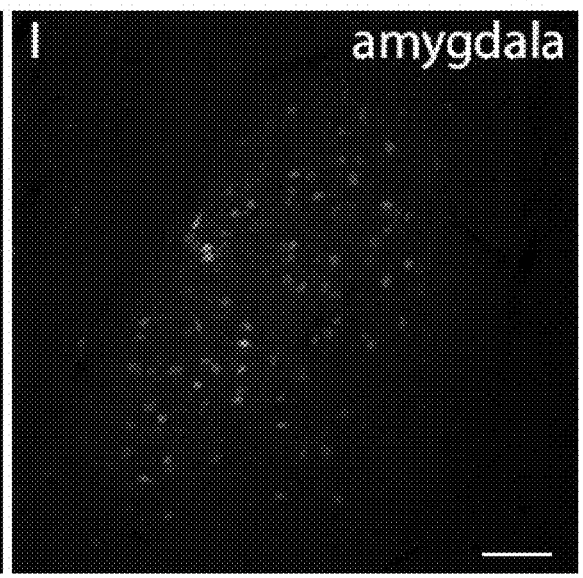

AAV-PHP.R2 was used to package a single stranded (ss) AAV-CAG-GFP genome and injected it into the striatum of adult mice. Notably, after only 7 days, robust GFP expression was observed at the striatal injection site (FIG. 23B) as well as at sites distant to the injection that are known to send projections to the striatum including the SNc (FIGS. 23C and 23D), the cortex (FIGS. 23E and 23F), the thalamus (FIG. 23G) and the amygdala (FIG. 23H). These results demonstrate that AAV-PHP.R2 can provide rapid retrograde transduction of several distributed neuronal populations.

Example 8

In Vivo Selection for AAV Variants Capable of Widespread CNS Transduction Following Systemic Administration The present example examines the development of AAV capsids that more efficiently transduce cells throughout the CNS. Several AAVs, most notably AAV9, rh.10 and rh.8, transduce CNS neurons and glia after neonatal or adult systemic, intravenous delivery (Duque et al., 2009; Foust et al., 2009; Gray et al., 2011; Samaranch et al., 2011; Yang et al., 2014a). While systemic rAAV administration with these serotypes is capable of widespread CNS delivery, the transduction efficiency is significantly reduced compared to that achievable in other organs such as liver, heart or skeletal muscle (Pulicherla et al., 2011). The present example demonstrates the use of the CREATE platform to develop capsids that more efficiently transduce the CNS globally. This was done given the important roles astrocytes play in the pathogenesis of neurodegenerative disease, together with the baseline tropism of AAV9 for astrocytes.

The AA452-8r and AA588i capsid libraries described above were delivered into transgenic mGFAP-Cre mice that express Cre from the mouse GFAP promoter, which is expressed within astrocytes and neural stem cells (NSCs) in the adult brain and spinal cord (Garcia et al., 2004). $1 \times 10^{11}$ VG of each capsid library were injected into separate adult GFAP-Cre positive mice and GFAP-Cre negative mice as controls. Seven days later, virus DNA from the brains and spinal cords and recovered capsid sequences from viral genomes that had undergone Cre-mediated recombination by PCR were isolated. The recovered fragments were cloned back into the rAAV-CAP-in-cis-lox acceptor vector, and clones from each library were picked at random for sequencing. As observed in the first round of the TH-Cre selection, all of the tested sequences recovered from both libraries after the first round were unique. After the second round, a single sequence, designate as AAV-PHP.B, was identified from the 588i library and showed signs of enrichment.

Figures 24A, 24B:
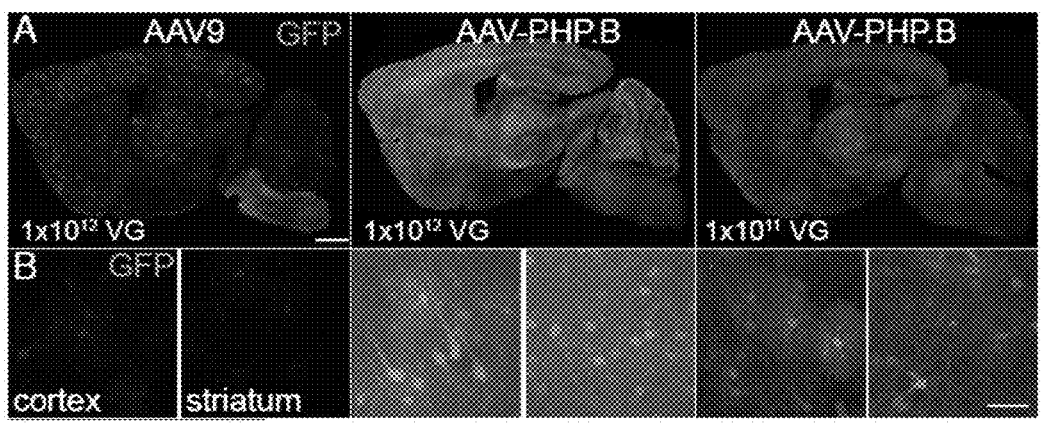
FIGS. 24A-24I. AAV-PHP.B mediates robust transduction of the entire CNS after IV administration. Representative images from mice transduced with b 1×10$^{12}$ VG of ssAAV-CAG-GFP-2A-Luc packaged in AAV9 or AAV-PHP.B. GFP expression was assessed 3 weeks later by immunostaining (FIG. 24A and FIG. 24C) or native GFP fluorescence (FIG. 24B, FIG. 24D-24G).
Figure 24C:
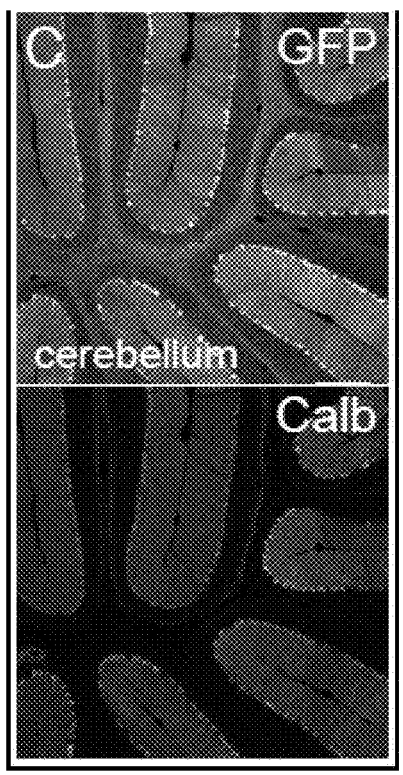
Figures 24D, 24E, 24F:
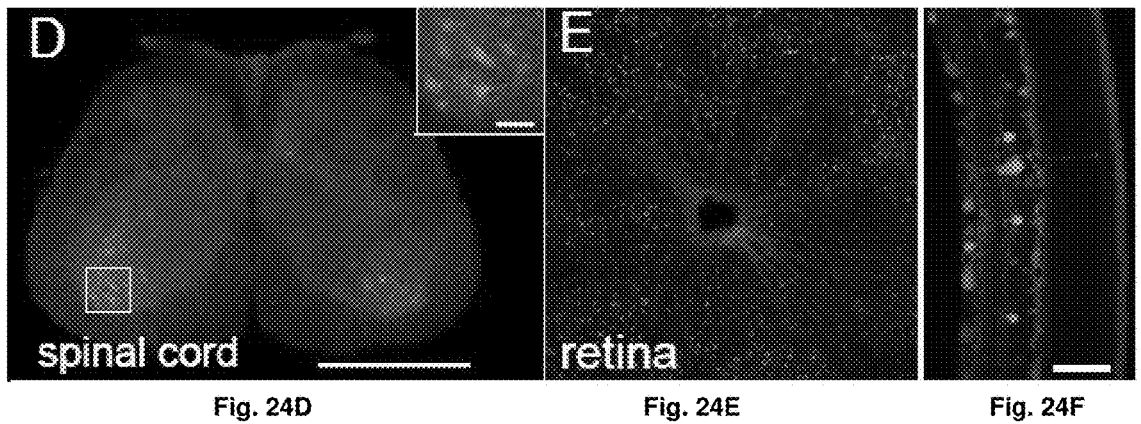
Figure 24G:
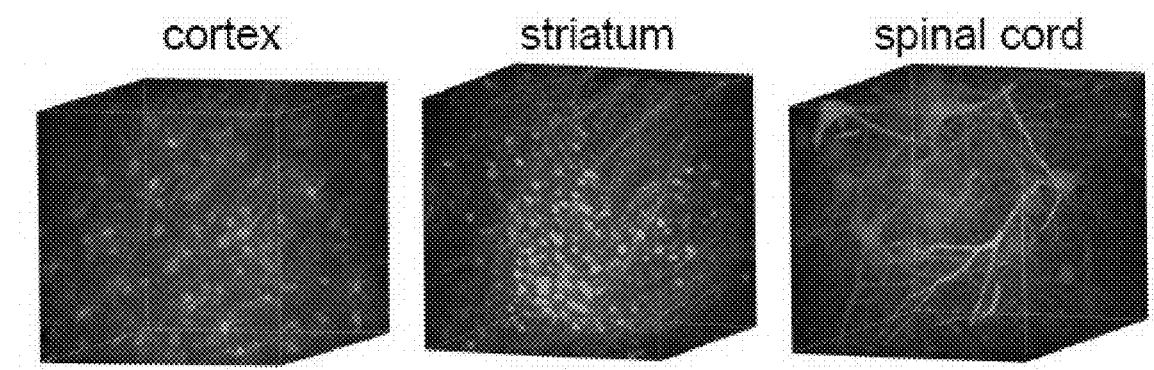
Figures 25A, 25B:
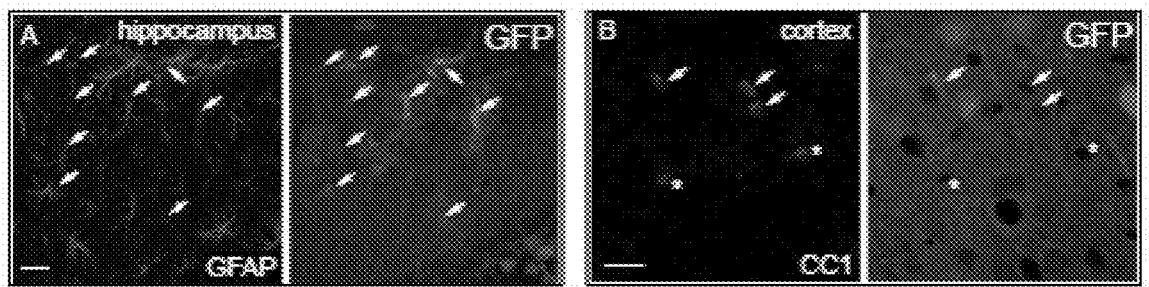
FIGS. 25A-25J. AAV-PHP.b transduces many CNS neuronal and glial cell types. Representative images show immunostaining for GFP (FIG. 25A-25D, FIG. 25G-25I) or native GFP fluorescence (FIG. 25E, FIG. 25F, and FIG. 25J). Images are of the brain regions indicated in the panel or striatum (FIG. 25E) or hippocampus (FIG. 25H). For FIGS. 25A-25F, the left image shows the antigen immunostaining, while the right image in each pair shows GFP expression. For FIGS. 25G-25J, the top image shows the indicated antigen immunostaining, the middle images show GFP expression and the lower paired images show a higher magnification views of the indicated boxed areas. Mice received 1×10$^{11}$ VG (FIG. 25A) or 1×10$^{12}$ VG (FIG. 25B-25J) at 5-6 weeks of age and were assessed for eGFP expression 3 weeks later. Scale bars are 50 μm in FIG. 25A, and 20 μm in FIG. 25B-25J. In all panels, arrows indicate colocalization and asterisks indicate cells that are positive for the indicated antigen but negative for GFP.

To assess the AAV-PHP.B variant individually, this capsid or AAV9 was used to package a dual-GFP and firefly Luciferase reporter vector, ssAAV-CAG-GFP-2A-Luc. AAV-PHP.B packaged the recombinant genome with an efficiency similar to AAV9 (FIGS. 27A-27E). Next, $1 \times 10^{12}$ VG of ssAAV-CAG-GFP-2A-Luc packaged into AAV-PHP.B or AAV9 was delivered into adult mice by IV injection and assessed transduction by GFP expression three weeks later. Remarkably, this variant transduced the entire CNS with high efficiency as indicated by immunostaining for GFP (FIGS. 24A and 24C) and analysis of native eGFP fluorescence in several brain regions (FIGS. 24B, 24D, and 24G), the spinal cord (FIGS. 24D and 24G) and retina (FIG. 24E-24F). Native GFP fluorescence remained dramatically increased over AAV9 even when 10-fold less AAV-PHP.B was delivered (FIG. 25A—right and 25D). In stark contrast with AAV9, which sparsely labels neurons and glia, individual transduced astrocytes were difficult to discern in mice that received $1 \times 10^{12}$ VG AAV-PHP.B, but could be seen in animals that received 10-fold less virus (FIGS. 24A-24B and FIG. 25A). AAV-PHP.B also transduced cerebellar Purkinje cells with strikingly high efficiency as demonstrated by co-localization of GFP and Calbindin immunostaining (FIG. 24C). Taking advantage of recent advances in CLARITY-based tissue clearing (Yang et al., 2014b), the native eGFP fluorescence was imaged through several hundred micron thick sections of tissue from the cortex, striatum and ventral spinal cord. These 3D renderings further demonstrate the efficiency of transduction by the AAV-PHP.B variant and confirm tissue clearing (Chung and Deisseroth, 2013; Tomer et al., 2014; Yang et al., 2014b) as a means of assessing the three-dimensional distribution of transduced cells within the brain (FIG. 24G).

Figure 24H:
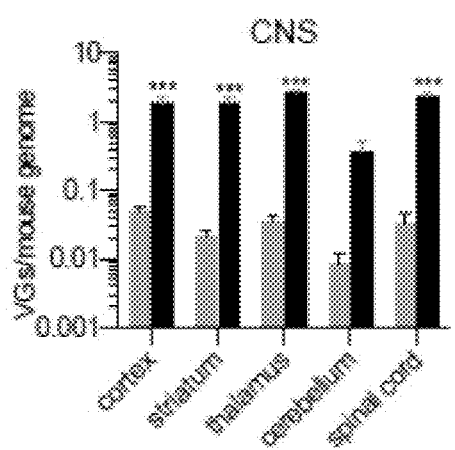
Figure 24I:
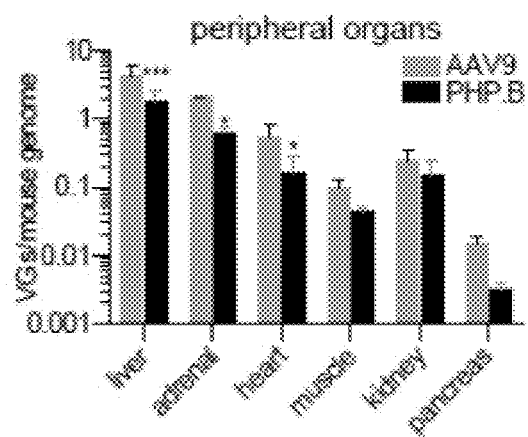

To quantify CNS transduction by this variant as compared to AAV9, the number of viral genomes present in several brain regions 25 days post injection were measured. Brain and spinal cord transduction by AAV-PHP.B was between 40 and 92-fold more efficient than AAV9, depending on the region examined (FIG. 24H), while outside of the CNS, the AAV-PHP.B vector transduced several peripheral organs less efficiently than AAV9 (FIG. 24I). Remarkably, in all regions other than the cerebellum, the number of viral genomes detected in the CNS in mice treated with AAV-PHP.B was similar that observed in the liver and greater than that seen in the other peripheral organs examined. In stark contrast, after AAV9 transduction, the number of AAV genomes detected within any of the CNS regions examined was at least 120-fold less than the number found in the liver. Therefore, while the tropism of AAV-PHP.B was not CNS specific, the enhanced transduction exhibited by this vector was CNS specific. In an initial selection using CREATE in GFAP-Cre mice an AAV9-based variant, AAV-PHP.A, was identified that exhibited both more efficient astrocyte transduction as well as reduced tropism for several peripheral organs (FIG. 28A-28E). Based on these results, AAV-PHP.B appears applicable for non-invasive, CNS-wide gene transfer in the adult.

Figure 25C:
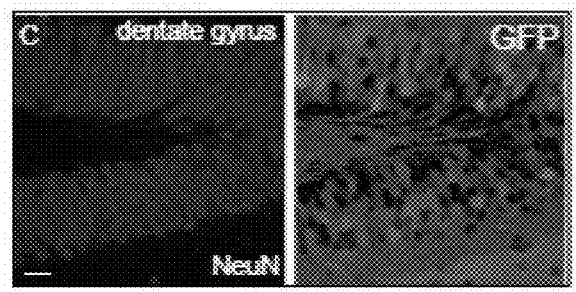

AAV9 preferentially transduces astrocytes when delivered systemically to adult animals, but it also transduces neurons in several regions (FIG. 24A and FIG. 25A, Foust et al 2009, and Yang et al 2014). To examine the cell types transduced by AAV-PHP.B, the colocalization of GFP expression with proteins expressed in specific cell populations was analyzed. AAV-PHP.B transduced GFAP$^+$ astrocytes (FIG. 25A), CC1$^+$ oligodendrocytes (FIG. 25B), NeuN$^+$ neurons (FIG. 25C and FIG. 25D) but not IBA1$^+$ microglia (FIG. 25E).

Figure 25D:
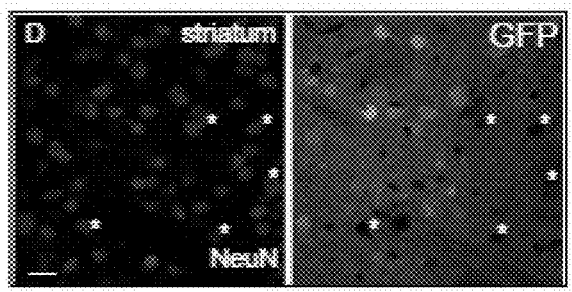
Figure 25E:
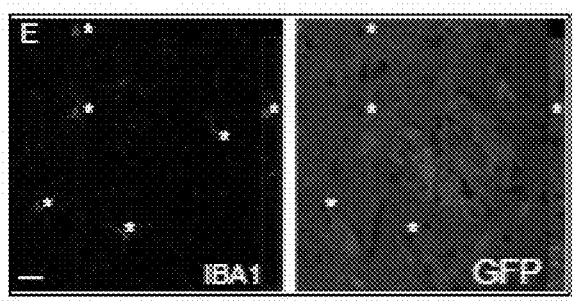
Figure 25F:
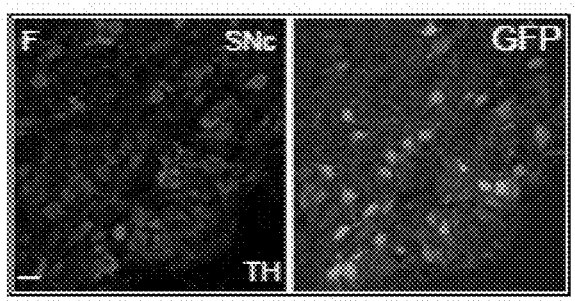
Figure 25G:
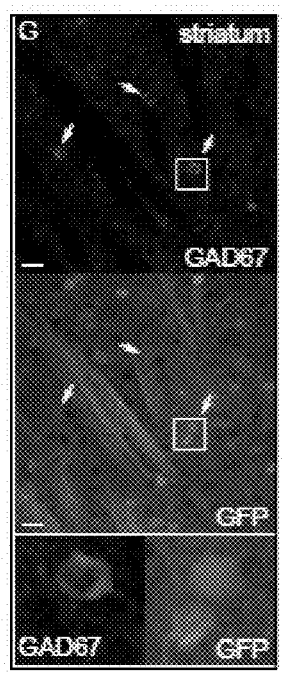
Figure 25H:
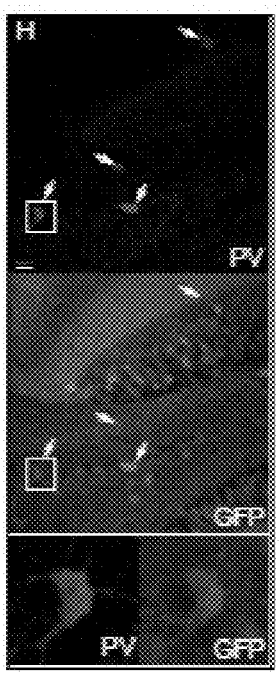
Figure 25I:
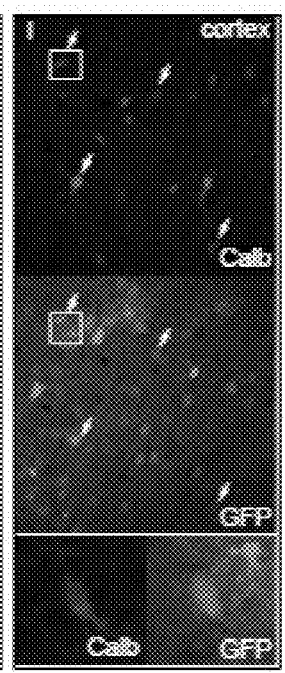
Figure 25J:
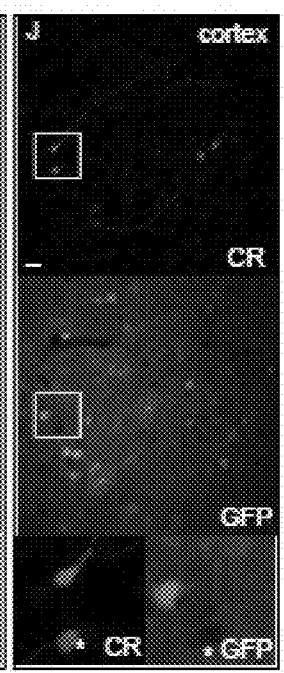

Several cell types of clinical importance are also targeted with high efficiency including TH$^+$ dopaminergic neurons in the SNc (FIG. 25F), spinal motor neurons (FIG. 34D and FIG. 24H) and striatal medium spiny neurons (FIG. 25D). In addition, several interneuron populations were also transduced (FIG. 25G-25J), although strong eGFP fluorescence was rarely found to colocalize with cells with Calretinin staining (FIG. 25J).

In sum, adult IV administration of AAV-PHP.B can be used to target, with high efficiency, numerous CNS cell types of scientific and clinical interest.

Tissue Clearing for Serotype Tropism Characterization and 3D Cell Phenotyping

Because CLARITY allows for the 3D imaging of cells in thick sections or intact tissue (Chung et al 2013; Yang et al. 2014) and AAV-PHP.B transduces numerous glial and neuronal cell types in the brain, whether CLARITY could be used together with a low dose of AAV-PHP.B to provide random, Golgi-like labeling of neural cells in the CNS was examined. To evaluate this approach, $1\times10^{10}$ VG of AAV-PHP.B expressing GFP was delivered into adult mice by IV injection. These mice were perfusion cleared and native GFP fluorescence in the brains of the mice was imaged. Individual neurons, astrocytes and endothelial cells were visible and could be imaged through at least 400 um of cleared tissue (FIG. 26D).

This approach can be useful for studying the morphology of individual cells in normal and diseased states. This approach can be used to co-express a reporter along with any of the following examples of genetic elements to investigate the effects of said genetic element on cell morphology or connectivity in vivo: a gene encoding a protein of interest; Cre, or another recombinase, for conditional gene modification in transgenic animals harboring a floxed target allele(s); conditional, floxed, alleles to transgenic animals made to express Cre in a defined target cell population; a gene knockdown cassettes containing a suitable promoter and shRNA or miRNA, or an endogenous miRNA sponge or decoy. Given the ease of adjusting the labeling/gene modification frequency by modulating the amount of virus administered, this vector could also be used to address questions related to cell autonomy by generating genetic mosaics.

Whole animal tissue clearing using PARS-based CLARITY may also be useful for the assessment of AAV tropism at a cellular level. This is typically a labor-intensive process that requires processing, mounting and imaging individual thin (1-100 micron) sections of tissue from each organ. The potential whole animal tissue clearing to reduce this burden was explored. $1\times10^{12}$ VG of ssAAV-CAG-GFP-2A-Luc packaged into AAV-PHP.B or AAV9 was delivered into adult mice by IV injection. Three weeks later, all of the tissue in the mice was cleared using the PARS-based CLARITY method described in Yang et al. (2014) and used confocal imaging and 3D image reconstruction (Imaris software, Bitplane) to assess native GFP expression as a reporter of vector transduction. In several organs, including skeletal muscle, lung, pancreas, and the liver, the mice that received AAV-PHP.B showed a reduction in the expression of GFP as compared to the mice that received an equivalent dose of AAV9 (FIG. 29). The reduced GFP expression in several peripheral organs observed with AAV-PHP.B as compared with AAV9 appears consistent with the number of VGs detected for each vector in these same peripheral organs (FIG. 24I). Note the GFP positive nerve fibers present in the muscle and pancreas of mice injected with AAV9 and AAV-PHP.B.

rAAV labeling combined with CLARITY will be a useful approach for studying the 3D morphologies of peripheral nerves.

The following aspects apply to the experiments outlined in Examples 7 and 8 above:

Mice 5-week-old female C57Bl/6 mice were purchased from the Jackson Labs (Maine). GFAP-Cre mice expressing Cre under the control of the mouse GFAP promoter (Garcia et al., 2004) and TH-Cre mice (Savitt et al., 2005) were from the Jackson Labs. In vivo selection was performed in adult mice of either sex.

Plasmids

The rAAV-cap-in-cis-lox plasmid contains the following elements cloned into a vector containing AAV2 ITRs (Balazs et al. 2011). An mCherry expression cassette (398 bp fragment of the human UBC gene upstream of the mCherry reporter followed by a 48 bp synthetic polyA sequence—(Levitt et al., 1989) followed by the AAV9 capsid cassette. Expression of the AAV9 capsid gene was placed under the control of the p41 promoter sequence from AAV5 (1680-1974 of GenBank AF085716.1; Qiu, Nayak Pintel 2002 and Farris and Pintel 2008) and splicing sequences taken from the rep gene from the AAV9 packaging plasmid (U. Penn). A SV40 polyA sequence flanked by inverted lox71 and lox66 sites was placed downstream of the AAV9 capsid. The rAAV-cap-in-cis-lox plasmid was modified to introduce two unique restriction sites, XbaI and AgeI, within the capsid sequence flanking the region that was replaced by the PCR fragment. The insertion of the XbaI site caused a K449R mutation and the mutations required to insert the AgeI site were silent.

In the second iteration of the library construction (used in the second GFAP-Cre capsid selection that yielded PHP.B), two modifications were made to reduce contamination of the libraries by AAV9 or the starting AAV9R X/A capsid. First, the coding region between the XbaI and AgeI sites was eliminated in the plasmid used for the capsid library cloning (rAAV-Δcap-in-cis acceptor) to eliminate any potential carryover of undigested plasmid. Second, the PCR fragment covering the capsid library variable region between the XbaI and AgeI sites was modified to remove a unique EarI restriction site (xE) within this region of AAV9 and insert a unique KpnI site. The modified xE fragment was TA cloned into pCRII to generate pCRII-9Cap-xE, which served as the template for our later library PCR fragments Eliminating the EarI site provided a secondary precaution allowing for the digestion of any contaminating AAV9 sequences recovered by PCR. It was not necessary to use this digestion step as taking standard PCR precautions including UV treating reagents and pipettors and using the rAAV-ΔCap-in-cis acceptor for cloning the libraries was sufficient to prevent contamination from AAV9 or AAV9R X/A.

The AAV2/9 REP-AAP helper plasmid was constructed by introducing 5 stop codons into the coding sequence of the VP reading frame of the AAV9 gene at AAs 6, 10, 142, 148, 216 (VP1 numbering). The stop codon at AA216 was designed such that it did not disrupt the coding sequence of the AAP protein, which is encoded within an alternative reading frame.

Library Generation

The 452-8r and 588i library fragments were generated by PCR using Q5 Hot Start, High-Fidelity DNA Polymerase (NEB). A schematic showing the approximate primer binding sites and the primer sequences are given in FIGS. 27A and 27C, respectively. To facilitate cloning of the PCR fragments comprising the capsid library sequences into a rAAV genome, the rAAV-cap-in-cis plasmid was modified to introduce two unique restriction sites, XbaI and AgeI, within the capsid sequence flanking the region that was replaced by the PCR fragment. The insertion of the XbaI site caused a K449R mutation and the mutations required to insert the AgeI site were silent. To prevent contamination of the libraries by "wild type" AAV9R X/A capsid, the coding region between the XbaI and AgeI sites was eliminated from the rAAV-cap-in-cis plasmid to create rAAV-Cap-in-cis.

To generate the rAAV based library, the PCR products containing the library and the XbaI and AgeI digested cap-in-cis acceptor vector were assembled using Gibson Assembly. The reaction products were then treated with PS DNase (Epicentre) to eliminate any unassembled fragments. This reaction typically yielded over 100 ng of assembled plasmid (as defined by the amount of DNA remaining after a PS DNase digestion step). 100 ng is sufficient to transfect 10 150 mm dishes at 10 ng/dish.

Virus Production And Purification

Recombinant AAVs were generated by triple transfection of 293T cells using PEI. Viral particles were harvested from the media at 72 h post transfection and from the cells and media at 120 h. Virus present in the media was concentrated by precipitation with 8% poly(ethylene glycol) and 500 mM sodium chloride (Ayuso et al 2010) and then the precipitated virus was added to the lysates prepared from the collected cells. The viruses were purified over iodixanol (Optiprep, Sigma) step gradients (15%, 25%, 40% and 60% as described by Zolotukhin et al 1999). Viruses were concentrated and formulated in PBS. Virus titers were determined by measuring the number of DNaseI-resistant vector genome copies (VGs) using qPCR and the linearized genome plasmid as a control (Gray et al 2011).

For capsid library virus generation, two modifications were made to the virus production protocol to reduce the production of mosaic capsids that could arise from the presence of multiple capsid sequences in the same cell. First, only 10 ng per dish of AAV-Cap9-in-cis library vector per dish was transfected to insure that the vast majority of transfected cells only received one capsid variant sequence. Second, the virus was collected earlier (48 h and 60 hours, instead of 72 h and 120 h as above) to minimize the secondary transduction of the producer cells with the rAAV library virus released into the medium.

In Vivo Selection

For the selections in GFAP-Cre mice, $1\times10^{11}$ vg of the capsid libraries were injected IV (retro-orbital route) into adult Cre+ mice. Seven or eight days post-injection, mice were euthanized and the brain and spinal cord were collected. Vector DNA was recovered from one hemisphere of the brain and half of the spinal cord using 4-5 ml of Trizol (Invitrogen). For the selections in TH-Cre mice, $8\times10^{9}$ vg of each capsid was injected by intracranially using the stereotaxic coordinates 0.7 mm rostral, 2.0 mm lateral and 3.0 mm ventral from bregma. 10 days later, the region containing the substantia nigra was collected and the tissue was homogenized in 1 ml of Trizol. For virus DNA isolation, the manufacture's RNA extraction protocol was followed (the upper aqueous, RNA-containing fraction collected). In addition to RNA, it was found that this fraction also contains a significant portion of the viral genome as well as some mitochondrial DNA. RNA was eliminated by treating the samples with 1 ul of RNase (Qiagen) at 37 C overnight. The Cre recombination-dependent PCR strategy involved a two-step amplification strategy (FIG. 27A-27E). Sequence recovery was first performed in a Cre-dependent manner using the primers 9CAPF and CDF (FIG. 27A-27E). PCR was performed for 20-26 cycles of 95 C for 20 sec, 60 C for 20 sec and 72 C for 30 sec using Q5 Hot Start High-fidelity DNA Polymerase. The PCR product was then diluted 1:10-1:100 and then used as a template for a second, PCR reaction using primer XF and AR that generated a shorter fragment that was cloned back into the rAAV-delta-cap-in-cis acceptor construct as described above. 1 ul of the Gibson Assembly reactions was then diluted 1:10 and transformed into Sure2 competent cells (Agilent) as directed by the manufacturer to generate individual clones for sequencing.

Clones that showed evidence of enrichment were cut with BsiWI and AgeI and ligated into a custom 2/9R-X/A rep/cap helper also cut with BsiWI and AgeI and then transformed into DH5alpha competent cells (NEB). The resulting rep/cap plasmids carrying the novel variant sequences, or AAV2/9 rep/cap as a control, were then used to package a rAAV genome containing a dual eGFP-2A-luciferase reporter cassette driven by a ubiquitous CAG promoter (rAAV-CAG-eGFP-2A-Luc-WPRE-SV40pA) for the IV injected variants (AAV-PHP.A and AAV-PHP.B) or a similar vector lacking the Luc gene (rAAV-CAG-eGFP-WPRE-SV40pA) for the intracranial injections (AAV-PHP.R2).

Tissue Preparation And Immunostaining

Mice were anesthetized with Nembutal and transcardially perfused first with 0.1 M phosphate buffer (PB), pH 7.4 and then with freshly prepared 4% paraformaldehyde in PB. Brains were postfixed overnight and then sectioned by vibratome or cryoprotected and sectioned by cryostat. Immunostaining was performed on the floating sections by diluting primary and secondary antibodies in PBS containing 10% goat or donkey serum 0.5% Triton X-100 or no detergent (GAD67 staining). Primary antibodies used were rabbit anti-GFP (1:1000; Invitrogen), chicken anti-GFP (1:1000; Abcam), mouse anti-CC1 (1:200; Calbiochem), rabbit anti-GFAP (1:1000; Dako), mouse anti-NeuN (1:500; Millipore), rabbit anti IbaI (1:500; Biocare Medical), mouse anti-Calbindin (1:200; Sigma), rabbit anti-Calretinin (1:1000; Chemicon), mouse anti-GAD67 (1:1000; Millipore), mouse anti-Parvalbumin (1:1000). Primary antibodies incubations were performed for 16-24 hours at room temperature. The sections washed and incubated with secondary antibodies conjugated to Alexa 568 (1:1000; Invitrogen) for 2-16 hours.

Tissue Clearing

Mice were perfused via peristaltic pump through the left ventricle with phosphate buffer (PB) followed by an initial perfusion with 60-80 mL of 4% PFA in PB at a flow rate of 14 mL per minute. The flow rate was then reduced to 2-3 mL per minute and continued for 2 hours at room temperature. The mice were then placed in individual custom-built perfusion chambers and perfused with 200 mL of recycling 4% acrylamide in PB at the same flow rate at room temperature overnight followed by a 2-hour perfusion flush with PB to remove residual polymers/monomers in the vasculature. The polymerization process was initiated placing the chambers in a 42° C. water bath and delivering, by perfusion at the same flow rate, 200 mL of recycling, degassed 0.25% VA-044 initiator in PB. After polymerization was complete, the mice were perfused with a clearing solution of 8% SDS in 0.1M PB, pH 7.5 for 7 days. The SDS containing solution was changed two times and then flushed by the perfusion of roughly 2 L of nonrecirculating PB overnight. Tissue samples cleared of lipids were incubated in RIMS solution (Yang et al. 2014) until imaging (at least one week for optimal transparency of unsectioned mouse brain tissue). The samples were then mounted in RIMS and enclosed with a coverglass on a slide using an appropriate thickness spacer (iSpacer, SunJin Lab Co.). Images were taken with a Zeiss LSM 780 single-photon microscope. 3 dimensional image reconstructions were performed using Imaris imaging software (Bitplane).

Vector Biodistribution

Mice were injected IV with $1\times10^{11}$ VG of a rAAV-CAG-GFP2A-Luc-WPRE-SV40-pA vector packaged into the indicated capsids. 25 days later, the mice were euthanized and tissues and indicated brain regions were collected and frozen at −80 C. DNA was isolated using Qiagen DNeasy Blood and Tissue kit. Vector genomes were detected using PCR primers that bind to the WPRE element and were normalized to mouse genomes using primers specific to the mouse glucagon gene. Absolute quantification was performed by comparing unknown samples to serial dilutions of standards of known concentration.

Example 9

Method of Treatment Employing Targeting Proteins

A subject having a disorder that can be treated by the application of a nucleic acid to be expressed within a subject is identified. The subject is then administered a first amount of a vector that includes the polynucleotide to be expressed. The polynucleotide encodes for a therapeutic protein. The vector will include a capsid protein that includes a targeting protein section that is SEQ ID NO: 1, so as to allow proper targeting of the protein to be expressed to the appropriate system within the subject. If needed, the subject is administered a second or third dose of the vector, until a therapeutically effective amount of the protein to be expressed is expressed within the subject in the appropriate system.

Example 10

Method of Treatment of Huntington's Disease

A subject having Huntington's disease is identified. The subject is then administered a first amount of a vector that includes the polynucleotide to be expressed. The polynucleotide encodes for a therapeutic protein. The vector will include a capsid protein that includes a targeting protein section that is SEQ ID NO: 1, so as to allow proper targeting of the protein to be expressed to the nervous system within the subject. If needed, the subject is administered a second or third dose of the vector, until a therapeutically effective amount of the protein to be expressed is expressed within the subject in the nervous system.

Example 11

Method of Treatment of Huntington'Disease

A subject having Huntington's disease is identified. The subject is then administered a first amount of a vector that includes a polynucleotide that encodes for a small non-coding RNA (small hairpin RNA (shRNA) or microRNA (miRNA)) configured to reduce expression of the Huntingtin protein by its sequence). The vector will include a capsid protein that includes a targeting protein of SEQ ID NO: 1, so as to allow proper targeting of the said polynucleotide to the nervous system. If needed, the subject is administered a second or third dose of the vector, until a therapeutically effective amount of the small non-coding RNA is expressed the subject in the nervous system.

Example 12

Method of Treatment

A subject having Huntington's disease is identified. The subject is then systemically administered a first amount of a vector that includes a polynucleotide that encodes for a Zinc finger protein (ZFP) engineered to represses the transcription of the Huntingtin (HTT) gene. The vector will include a capsid protein that includes a targeting protein of SEQ ID NO: 1 or any of the targeting proteins in FIG. 31, so as to allow proper targeting of the ZFP to the nervous system, among other organs. If needed, the subject is administered a second or third dose of the vector, until a therapeutically effective amount of the ZFP is expressed the subject in the nervous system.

Example 13

Method of Treatment

A subject having Huntington's disease is identified. The subject is then systemically administered a first amount of a vector that includes a polynucleotide that encodes for a small non-coding RNA (small hairpin RNA (shRNA) or microRNA (miRNA)) designed by one skilled in the art to reduce expression of the Huntingtin protein. The vector will include a capsid protein that includes a targeting protein of SEQ ID NO: 1 or any of the targeting proteins in FIG. 31, so as to allow proper targeting of the polynucleotide to the nervous system, among other organs. If needed, the subject is administered a second or third dose of the vector, until a therapeutically effective amount of the small non-coding RNA is expressed the subject in the nervous system.

Example 14

Method of Treatment

A subject having Alzheimer's disease is identified. The subject is then administered a first amount of a vector that includes a polynucleotide that encodes for an anti-Abeta antibodies or antibody fragments. The vector will include a capsid protein that includes a targeting protein of SEQ ID NO: 1 or any of the targeting proteins in FIG. 31, so as to allow proper targeting of the antibody or antibody fragment to be expressed to the nervous system. If needed, the subject is administered a second or third dose of the vector, until a therapeutically effective amount of the antibody or antibody fragment is expressed the subject in the nervous system.

Example 15

Method of Treatment

A subject having Alzheimer's disease is identified. The subject is then administered a first amount of a vector that includes a polynucleotide that encodes for an apolipoprotein E (ApoE) protein, preferably the human apoE polypeptide apoE2 or modified variant of apoE2. The vector will include a capsid protein that includes a targeting protein of SEQ ID NO: 1 or any of the targeting proteins in FIG. 31, so as to allow proper targeting of the antibody or antibody fragment to be expressed to the nervous system. If needed, the subject is administered a second or third dose of the vector, until a therapeutically effective amount of the ApoE protein is expressed the subject in the nervous system.

Example 16

Method of Treatment

A subject having spinal muscular atrophy (SMA) is identified. The subject is then administered a first amount of a vector that includes a polynucleotide that encodes for a survival motor neuron 1 (SMN1) polypeptide. The vector will include a capsid protein that includes a targeting protein of SEQ ID NO: 1 or any of the targeting proteins in FIG. 31, so as to allow proper targeting of the SMN protein to be expressed to the nervous system. If needed, the subject is administered a second or third dose of the vector, until a therapeutically effective amount of the SMN protein is expressed the subject in the nervous system.

Example 17

Method of Treatment

A subject having Friedreich's ataxia is identified. The subject is then systemically administered a first amount of a vector that includes a polynucleotide that encodes for a frataxin protein. The vector will include a capsid protein that includes a targeting protein of SEQ ID NO: 1 or any of the targeting proteins in FIG. 31, so as to allow proper targeting of the frataxin protein to be expressed to the nervous system and heart, among other organs. If needed, the subject is administered a second or third dose of the vector, until a therapeutically effective amount of the frataxin protein is expressed the subject in the nervous system and heart.

Example 18

Method of Treatment

A subject having Pompe disease is identified. The subject is then systemically administered a first amount of a vector that includes a polynucleotide that encodes for an acid alpha-glucosidase (GAA) protein. The vector will include a capsid protein that includes a targeting protein of SEQ ID NO: 1 or any of the targeting proteins in FIG. 31, so as to allow proper targeting of the GAA protein to be expressed to the nervous system and heart, among other organs. If needed, the subject is administered a second or third dose of the vector, until a therapeutically effective amount of the GAA protein is expressed the subject in the nervous system and heart.

Example 19

Method of Treatment

A subject having Late Infantile neuronal ceroid lipofuscinosis (LINCL) is identified. The subject is then systemically administered a first amount of a vector that includes a CLN2 polynucleotide that encodes for the tripeptidyl peptidase 1 protein. The vector will include a capsid protein that includes a targeting protein of SEQ ID NO: 1 or any of the targeting proteins in FIG. 31, so as to allow proper targeting of the tripeptidyl peptidase 1 protein to be expressed to the nervous system. If needed, the subject is administered a second or third dose of the vector, until a therapeutically effective amount of the tripeptidyl peptidase 1 protein is expressed the subject in the nervous system.

Example 20

Method of Treatment

A subject having the Juvenile NCL form of Batten disease is identified. The subject is then systemically administered a first amount of a vector that includes a CLN3 polynucleotide that encodes for the battenin protein. The vector will include a capsid protein that includes a targeting protein of SEQ ID NO: 1 or any of the targeting proteins in FIG. 31, so as to allow proper targeting of the battenin protein to be expressed to the nervous system. If needed, the subject is administered a second or third dose of the vector, until a therapeutically effective amount of the battenin protein is expressed the subject in the nervous system.

Example 21

Method of Treatment

A subject having Canavan disease is identified. The subject is then systemically administered a first amount of a vector that includes an ASPA polynucleotide that encodes for the aspartoacylase protein. The vector will include a capsid protein that includes a targeting protein of SEQ ID NO: 1 or any of the targeting proteins in FIG. 31, so as to allow proper targeting of the aspartoacylase protein to be expressed to the nervous system. If needed, the subject is administered a second or third dose of the vector, until a therapeutically effective amount of the aspartoacylase protein is expressed the subject in the nervous system.

Example 22

Method of Treatment

A subject having Parkinson's disease is identified. The subject is then systemically administered a first amount of one or more vectors that each includes one or more polynucleotide(s) that encode an enzyme(s) necessary for the increased production of dopamine from non-dopaminergic cells. The vector will include a capsid protein that includes a targeting protein of SEQ ID NO: 1 or any of the targeting proteins in FIG. 31, so as to allow proper targeting of said enzyme(s) to be expressed to the nervous system. If needed, the subject is administered a second or third dose of the vector, until a therapeutically effective amount of the enzyme(s) is expressed the subject in the nervous system.

Example 23

Method of Treatment

A subject having Parkinson's disease is identified. The subject is then systemically administered a first amount of a vector that includes a polynucleotide that encode a modified, aggregation-resistant form of alpha-synuclein protein that reduces the aggregation of endogenous alpha-synuclein. The vector will include a capsid protein that includes a targeting protein of SEQ ID NO: 1 or any of the targeting proteins in FIG. 31, so as to allow proper targeting of the aggregation-resistant alpha-synuclein protein to be expressed to the nervous system. If needed, the subject is administered a second or third dose of the vector, until a therapeutically effective amount of the protein is expressed the subject in the nervous system.

Example 24

Method of Treatment

A subject having amyotrophic lateral sclerosis or frontal dementia caused by a mutation in C9ORF72 is identified. The subject is then administered a first amount of a vector that includes a polynucleotide that encodes a non-coding RNA(s) that reduce nuclear RNA foci caused by the hexanucleotide expansion (GGGGCC) in the subjects cells. The vector will include a capsid protein that includes a targeting protein of SEQ ID NO: 1 or any of the targeting proteins in FIG. 31, so as to allow proper targeting of the RNA(s) to be expressed to the nervous system. If needed, the subject is administered a second or third dose of the vector, until a therapeutically effective amount of the RNA(s) is expressed the subject in the nervous system.

Example 25

Method of Treatment

A subject having multiple sclerosis is identified. The subject is then systemically administered a first amount of a vector that includes a polynucleotide that encode a trophic or immunomodulatory factor, for example leukemia inhibitory factor (LIF) or ciliary eurotrophic factor (CNTF). The vector will include a capsid protein that includes a targeting protein of SEQ ID NO: 1 or any of the targeting proteins in FIG. 31, so as to allow proper targeting of the said factor to be expressed to the nervous system. If needed, the subject is administered a second or third dose of the vector, until a therapeutically effective amount of the factor is expressed the subject in the nervous system.

Example 26

Method of Treatment

A subject having amyotrophic lateral sclerosis caused by SOD1 mutation is identified. The subject is then administered a first amount of a vector that includes a polynucleotide that encodes for a small non-coding RNA (small hairpin RNA (shRNA) or microRNA (miRNA)) designed by one skilled in the art to reduce expression of mutant SOD1 protein. The vector will include a capsid protein that includes a targeting protein of SEQ ID NO: 1 or any of the targeting proteins in FIG. 31, so as to allow proper targeting of the small non-coding RNA to be expressed to the nervous system. If needed, the subject is administered a second or third dose of the vector, until a therapeutically effective amount of the small non-coding RNA is expressed the subject in the nervous system.

ADDITIONAL EMBODIMENTS

In some embodiments, provided herein is a CREATE—Cre Recombinase-based AAV Targeted Evolution platform.

In some embodiments, provided herein is an AAV-PHP.B, which allows Broad gene delivery to CNS neurons and glia via the vasculature.

In some embodiments, provided herein is an AAV-PHP.R2, which allows Rapid Retrograde transduction in the CNS.

INCORPORATION BY REFERENCE

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of generating an AAV with a desired tropism, the method comprising:
   providing a population of rAAV genomes, wherein each of the rAAV genomes comprises:
   an AAV capsid gene, and
   one or more recognition sequences for a Cre recombinase, wherein the one or more recognition sequences are configured to allow generation of a recombinase-dependent change that is detectable, and wherein the one or more recombinase recognition sequences comprises two Cre-recognition sites;
   transfecting a target cell expressing the Cre recombinase with the population of rAAV genomes, whereby the Cre recombinase induces a recombination event to generate a recombinase-dependent change in at least one of the rAAV genomes of the population, and wherein the recombinase-dependent change comprises an inversion of the sequences that are flanked by the Cre-recognition sites;
   detecting at least one recombinase-dependent change; and
   identifying an rAAV genome generated by the at least one recombinase-dependent change, wherein said identified rAAV genome comprises the inversion, and wherein said identified rAAV genome encodes an AAV capsid with the desired tropism.

2. The method of claim 1, wherein the target cell is present in a tissue, an organ, an organism, or a combination thereof.

3. The method of claim 1, wherein the capsid genes of the population of rAAV genomes encode mutant capsid proteins.

4. The method of claim 1, wherein the two Cre-recombinase recognition sites are two loxP or variants of loxP sites in a head-to-head orientation.

5. The method of claim 1, wherein the target cell is a neuronal cell, a neural stem cell, an astrocytes, a tumor cell, a hematopoetic stem cell, an insulin producing beta cell, a lung epithelium, a skeletal cell, or a cardiac muscle cell.

6. The method of claim 1, wherein the target cell is located in a brain or spinal cord.

7. The method of claim 1, further comprising recovering the rAAV that is identified to have a capsid with the desired tropism.

8. A method of generating an AAV with a desired tropism, the method comprising:
   providing a population of rAAV genomes, wherein each of the rAAV genomes comprises:
   an AAV capsid gene, and
   one or more recognition sequences for a recombinase, wherein the one or more recognition sequences are configured to allow generation of a recombinase-dependent change that is detectable;
   transfecting a target cell expressing the recombinase with the population of rAAV genomes, wherein the target cell is in a Cre-transgenic mouse, and whereby the recombinase induces a recombination event to generate a recombinase-dependent change in at least one of the rAAV genomes of the population;
   detecting at least one recombinase-dependent change; and
   identifying an rAAV genome generated by the at least one recombinase-dependent change wherein said identified rAAV genome encodes an AAV capsid with the desired tropism.

9. The method of claim 8, wherein the target cell is present in a tissue, an organ, an organism, or a combination thereof.

10. The method of claim 8, wherein the capsid genes of the population of rAAV genomes encode mutant capsid proteins.

11. The method of claim 8, wherein the recombinase is Cre recombinase.

12. The method of claim 11, wherein the one or more recombinase recognition sequences comprise two Cre-recognition sites.

13. The method of claim 11, wherein the recombinase-dependent change comprises an inversion of the sequences that are flanked by the Cre-recognition sites; and wherein the method comprises identifying the rAAV genomes that comprise the inversion.

14. The method of claim 11, wherein the two Cre-recombinase recognition sites are two loxP or variants of loxP sites in a head-to-head orientation.

15. The method of claim 8, wherein the target cell is a neuronal cell, a neural stem cell, an astrocytes, a tumor cell, a hematopoetic stem cell, an insulin producing beta cell, a lung epithelium, a skeletal cell, or a cardiac muscle cell.

16. The method of claim 8, wherein the target cell is located in a brain or spinal cord.

17. The method of claim 8, further comprising recovering the rAAV that is identified to have a capsid with the desired tropism.

* * * * *

SEQUENCE LISTING

```
<160> NUMBER OF SEQ ID NOS: 60

<210> SEQ ID NO 1
<211> LENGTH: 7
<212> TYPE: PRT
<213> ORGANISM: Artificial Sequence
<220> FEATURE:
<223> OTHER INFORMATION: Adeno-associated virus capsid protein

<400> SEQUENCE: 1

Thr Leu Ala Val Pro Phe Lys
1               5

<210> SEQ ID NO 2
<211> LENGTH: 736
<212> TYPE: PRT
<213> ORGANISM: Artificial Sequence
<220> FEATURE:
<223> OTHER INFORMATION: Adeno-associated viruS

<400> SEQUENCE: 2

Met Ala Ala Asp Gly Tyr Leu Pro Asp Trp Leu Glu Asp Asn Leu Ser
1               5                   10                  15
```

-continued

Glu Gly Ile Arg Glu Trp Trp Ala Leu Lys Pro Gly Ala Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser

```
                435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 3
<211> LENGTH: 7
<212> TYPE: PRT
<213> ORGANISM: Artificial Sequence
<220> FEATURE:
<223> OTHER INFORMATION: Adeno-associated virus capsid protein

<400> SEQUENCE: 3

Lys Phe Pro Val Ala Leu Thr
1               5

<210> SEQ ID NO 4
<211> LENGTH: 6672
<212> TYPE: DNA
<213> ORGANISM: Artificial Sequence
<220> FEATURE:
<223> OTHER INFORMATION: Plasmid

<400> SEQUENCE: 4
```

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctactag tggcctccgc gccgggtttt ggcgcctccc     180
gcgggcgccc ccctcctcac ggcgagcgct gccacgtcag acgaagggcg cagcgagcgt     240
cctgatcctt ccgcccggac gctcaggaca gcggcccgct gctcataaga ctcggcctta     300
gaacccagt atcagcagaa ggacatttta ggacgggact tgggtgactc tagggcactg      360
gttttctttc cagagagcgg aacaggcgag gaaaagtagt cccttctcgg cgattctgcg     420
gagggatctc cgtggggcgg tgaacgccga tgattatata aggacgcgcc gggtgtggca     480
cagctagttc cgtcgcagcc gggatttggg tcgcggttct tgtttgtgga tcgctgtgat     540
cgtcacttgg cggccgccat ggtcagcaag ggcgaggagg ataacatggc catcatcaag     600
gagttcatgc gcttcaaggt gcacatggag ggctccgtga acggccacga gttcgagatc     660
gagggcgagg gcgagggccg cccctacgag ggcacccaga ccgccaagct gaaggtgacc     720
aagggtggcc cctgcccctt cgcctgggac atcctgtccc ctcaattcat gtatggctcc     780
aaggcctacg tgaagcaccc cgccgacatc cccgactact tgaagctgtc cttccccgag     840
ggcttcaagt gggagcgcgt gatgaacttc gaggacggcg gcgtggtgac cgtgacccag     900
gactcctcct acaagacgg cgagttcatc tacaaagtga agctgcgcgg caccaacttc      960
ccctccgacg gccccgtaat gcagaagaag accatgggct gggaggcctc ctccgagcgg    1020
atgtaccccg aggacggcgc cctgaagggc gagatcaagc agaggctgaa gctgaaggac    1080
ggcggccact acgacgctga ggtcaagacc acctacaagg ccaagaagcc cgtgcagctg    1140
cccggcgcct acaacgtcaa catcaagttg gacatcacct cccacaacga ggactacacc    1200
atcgtggaac agtacgaacg cgccgagggc cgccactcca ccggcggcat ggacgagctg    1260
tacaagtaaa ggatcccctc ccccgtgcct tccttgaccc tggaaggtgc cactcccact    1320
gtcctttcct cctcctagga ataaaatatc tttattttca ttacatctgt gtgttggttt    1380
tttgtgtaga tctgttcaaa tttgaactga ctaagcggct cccgccagat tttggcaaga    1440
ttactaagca ggaagtcaag gacttttttg cttgggcaaa ggtcaatcag gtgccggtga    1500
ctcacgagtt taaagttccc agggaattgg cgggaactaa aggggcggag aaatctctaa    1560
aacgcccact gggtgacgtc accaatacta gctataaaag tctggagaag cgggccaggc    1620
tctcatttgt tcccgagacg cctcgcagtt cagacgtgac tgttgatccc gctcctctgc    1680
gaccgctagc ttcgatcaac tacgcggaca ggtaccaaaa caaatgttct cgtcacgtgg    1740
gcatgaatct gatgctgttt ccctgcagac aatgcgagag actgaatcag aattcaaata    1800
tctgcttcac tcacggtgtc aaagactgtt tagagtgctt tcccgtgtca gaatctcaac    1860
ccgtttctgt cgtcaaaaag gcgtatcaga aactgtgcta cattcatcac atcatgggaa    1920
aggtgccaga cgcttgcact gcttgcgacc tggtcaatgt ggactggat gactgtgttt     1980
ctgaacaata aatgacttaa accaggtatg gctgccgatg gttatcttcc agattggctc    2040
gaggacaacc ttagtgaagg aattcgcgag tggtgggctt tgaaacctgg agcccctcaa    2100
cccaaggcaa atcaacaaca tcaagacaac gctcgaggtc ttgtgcttcc gggttacaaa    2160
taccttggac ccggcaacgg actcgacaag ggggagccgg tcaacgcagc agacgcggcg    2220
gccctcgagc acgacaaggc ctacgaccag cagctcaagg ccggagacaa cccgtacctc    2280
aagtacaacc acgccgacgc cgagttccag gagcggctca agaagatac gtcttttggg    2340
ggcaacctcg ggcgagcagt cttccaggcc aaaaagaggc ttcttgaacc tcttggtctg    2400
```

```
gttgaggaag cggctaagac ggctcctgga aagaagaggc ctgtagagca gtctcctcag    2460
gaaccggact cctccgcggg tattggcaaa tcgggtgcac agcccgctaa aaagagactc    2520
aatttcggtc agactggcga cacagagtca gtcccagacc ctcaaccaat cggagaacct    2580
cccgcagccc cctcaggtgt gggatctctt acaatggctt caggtggtgg cgcaccagtg    2640
gcagacaata acgaaggtgc cgatggagtg ggtagttcct cgggaaattg cattgcgat     2700 tcccaatggc tgggggacag agtcatcacc accagcaccc gaacctgggc cctgcccacc    2760
tacaacaatc acctctacaa gcaaatctcc aacagcacat ctggaggatc ttcaaatgac    2820
aacgcctact tcggctacag caccccctgg gggtattttg acttcaacag attccactgc    2880
cacttctcac cacgtgactg gcagcgactc atcaacaaca actggggatt ccggcctaag    2940
cgactcaact tcaagctctt caacattcag gtcaaagagg ttacggacaa caatggagtc    3000
aagaccatcg ccaataacct taccagcacg gtccaggtct tcacggactc agactatcag    3060
ctcccgtacg tgctcgggtc ggctcacgag ggctgcctcc cgccgttccc agcggacgtt    3120
ttcatgattc ctcagtacgg gtatctgacg cttaatgatg gaagccaggc cgtgggtcgt    3180
tcgtcctttt actgcctgga atatttcccg tcgcaaatgc taagaacggg taacaacttc    3240
cagttcagct acgagtttga gaacgtacct ttccatagca gctacgctca cagccaaagc    3300
ctggaccgac taatgaatcc actcatcgac caatacttgt actatctctc tagaactatt    3360
aacggttctg gacagaatca acaaacgcta aaattcagtg tggccggacc cagcaacatg    3420
gctgtccagg gaagaaacta catacctgga cccagctacc gacaacaacg tgtctcaacc    3480
actgtgactc aaaacaacaa cagcgaattt gcttggcctg gagcttcttc ttgggctctc    3540
aatggacgta atagcttgat gaatcctgga cctgctatgg ccagccacaa agaaggagag    3600
gaccgttctc ttcctttgtc tggatctttta attttggca aacaaggaac tggaagagac    3660
aacgtggatg cggacaaagt catgataacc aacgaagaag aaattaaaac tactaacccg    3720
gtagcaacgg agtcctatgg acaagtggcc acaaaccacc agagtgccca agcacaggcg    3780
cagaccggtt gggttcaaaa ccaaggaata cttccgggta tggtttggca ggacagagat    3840
gtgtacctgc aaggacccat ttgggccaaa attcctcaca cggacggcaa ctttcaccct    3900
tctccgctga tgggagggtt tggaatgaag caccgcctc ctcagatcct catcaaaaac    3960
acacctgtac ctgcggatcc tccaacggcc ttcaacaagg acaagctgaa ctctttcatc    4020
acccagtatt ctactggcca agtcagcgtg gagatcgagt gggagctgca gaaggaaaac    4080
agcaagcgct ggaaccccga gatccagtac acttccaact attacaagtc taataatgtt    4140
gaatttgctg ttaatactga aggtgtatat agtgaacccc gccccattgg caccagatac    4200
ctgactcgta atctgtaagt cgactaccgt tcgtatagca tacattatac gaagttatca    4260
tatgttcgag cagacatgat aagatacatt gatgagtttg gacaaaccac aactagaatg    4320
cagtgaaaaa aatgctttat ttgtgaaatt tgtgatgcta ttgctttatt tgtaaccatt    4380
ataagctgca ataaacaagt taacaacaac aattgcattc attttatgtt tcaggttcag    4440
ggggagatgt gggaggtttt ttaaagcaag taaaacctct acaaatgtgg taaaatcgag    4500
ctctaccgtt cgtataatgt atgctatacg aagttatgat atcaagctta ggaacccta    4560 gtgatggagt tggccactcc ctctctgcgc gctcgctcgc tcactgaggc cgggcgacca    4620
aaggtcgccc gacgcccggg ctttgcccgg cggcctcag tgagcgagcg agcgcgcaga    4680
gagggagtgg ccaagctagc gggcgattaa ggaaagggct agatcattct tgaagacgaa    4740
```

```
agggcctcgt gatacgccta tttttatagg ttaatgtcat gataataatg gtttcttaga    4800
cgtcaggtgg cacttttcgg ggaaatgtgc gcggaacccc tatttgttta tttttctaaa    4860
tacattcaaa tatgtatccg ctcatgagac aataaccctg ataaatgctt caataatatt    4920
gaaaaaggaa gagtatgagt attcaacatt tccgtgtcgc ccttattccc ttttttgcgg    4980
cattttgcct tcctgttttt gctcacccag aaacgctggt gaaagtaaaa gatgctgaag    5040
atcagttggg tgcacgagtg ggttacatcg aactggatct caacagcggt aagatccttg    5100
agagttttcg ccccgaagaa cgttttccaa tgatgagcac ttttaaagtt ctgctatgtg    5160
gcgcggtatt atcccgtgtt gacgccgggc aagagcaact cggtcgccgc atacactatt    5220
ctcagaatga cttggttgag tactcaccag tcacagaaaa gcatcttacg gatggcatga    5280
cagtaagaga attatgcagt gctgccataa ccatgagtga taacactgcg gccaacttac    5340
ttctgacaac gatcggagga ccgaaggagc taaccgcttt tttgcacaac atgggggatc    5400
atgtaactcg ccttgatcgt tgggaaccgg agctgaatga agccatacca aacgacgagc    5460
gtgacaccac gatgcctgta gcaatggcaa caacgttgcg caaactatta actggcgaac    5520
tacttactct agcttcccgg caacaattaa tagactggat ggaggcggat aaagttgcag    5580
gaccacttct gcgctcggcc cttccggctg gctggtttat tgctgataaa tctggagccg    5640
gtgagcgtgg gtctcgcggt atcattgcag cactggggcc agatggtaag ccctcccgta    5700
tcgtagttat ctacacgacg gggagtcagg caactatgga tgaacgaaat agacagatcg    5760
ctgagatagg tgcctcactg attaagcatt ggtaactgtc agaccaagtt tactcatata    5820
tactttagat tgatttaaaa cttcattttt aatttaaaag gatctaggtg aagatccttt    5880
ttgataatct catgaccaaa atcccttaac gtgagttttc gttccactga gcgtcagacc    5940
ccgtagaaaa gatcaaagga tcttcttgag atcctttttt tctgcgcgta atctgctgct    6000
tgcaaacaaa aaaaccaccg ctaccagcgg tggtttgttt gccggatcaa gagctaccaa    6060 ctcttttttcc gaaggtaact ggcttcagca gagcgcagat accaaatact gttcttctag    6120
tgtagccgta gttaggccac cacttcaaga actctgtagc accgcctaca tacctcgctc    6180
tgctaatcct gttaccagtg gctgctgcca gtggcgataa gtcgtgtctt accgggttgg    6240
actcaagacg atagttaccg gataaggcgc agcggtcggg ctgaacgggg ggttcgtgca    6300
cacagcccag cttggagcga acgacctaca ccgaactgag atacctacag cgtgagctat    6360
gagaaagcgc cacgcttccc gaagggagaa aggcggacag gtatccggta agcggcaggg    6420
tcggaacagg agagcgcacg agggagcttc caggggggaaa cgcctggtat ctttatagtc    6480
ctgtcgggtt tcgccacctc tgacttgagc gtcgattttt gtgatgctcg tcaggggggc    6540
ggagcctatg gaaaaacgcc agcaacgcgg cctttttacg gttcctggcc ttttgctggc    6600
cttttgctca catgtaataa acacacacac accaacaacc gtggttggtt gttgtgttgg    6660
tttattctcg ag                                                      6672

<210> SEQ ID NO 5
<211> LENGTH: 7330
<212> TYPE: DNA
<213> ORGANISM: Artificial Sequence
<220> FEATURE:
<223> OTHER INFORMATION: Plasmid

<400> SEQUENCE: 5
gtcgacggta tcgggggagc tcgcagggtc tccattttga agcgggaggt ttgaacgcgc      60
agccgccatg ccgggggtttt acgagattgt gattaaggtc cccagcgacc ttgacgagca    120
```

```
tctgcccggc atttctgaca gctttgtgaa ctgggtggcc gagaaggaat gggagttgcc      180
gccagattct gacatggatc tgaatctgat tgagcaggca ccctgaccg tggccgagaa       240 gctgcagcgc gactttctga cggaatggcg ccgtgtgagt aaggcccgg aggctctttt       300 ctttgtgcaa tttgagaagg gagagagcta cttccacatg cacgtgctcg tggaaaccac      360
cggggtgaaa tccatggttt tgggacgttt cctgagtcag attcgcgaaa aactgattca      420
gagaatttac cgcgggatcg agccgacttt gccaaactgg ttcgcggtca caagaccag      480 aaatggcgcc ggaggcggga caaggtggt ggatgagtgc tacatcccca attacttgct      540
ccccaaaacc cagcctgagc tccagtgggc gtggactaat atggaacagt atttaagcgc     600
ctgtttgaat ctcacggagc gtaaacggtt ggtggcgcag catctgacgc acgtgtcgca     660
gacgcaggag cagaacaaag agaatcagaa tcccaattct gatgcgccgg tgatcagatc    720
aaaaacttca gccaggtaca tggagctggt cgggtggctc gtggacaagg ggattaccct    780
ggagaagcag tggatccagg aggaccagcc ctcatacatc tccttcaatg cggcctccaa    840
ctcgcggtcc caaatcaagg ctgccttgga caatgcggga aagattatga gcctgactaa    900
aaccgccccc gactacctgg tgggccagca gcccgtggag gacatttcca gcaatcggat    960
ttataaaatt ttggaactaa acgggtacga tccccaatat gcggcttccg tctttctggg    1020
atgggccacg aaaaagttcg gcaagaggaa caccatctgg ctgtttgggc ctgcaactac    1080
cgggaagacc aacatcgcgg aggccatagc ccacactgtg cccttctacg ggtgcgtaaa    1140
ctggaccaat gagaactttc ccttcaacga ctgtgtcgac aagatggtga tctggtggga    1200 ggagggaag atgaccgcca aggtcgtgga gtcggccaaa gccattctcg aggaagcaa     1260 ggtgcgcgtg gaccagaaat gcaagtcctc ggcccagata gacccgactc ccgtgatcgt    1320
cacctccaac accaacatgt gcgccgtgat tgacgggaac tcaacgacct cgaacacca    1380 gcagccgttg caagaccgga tgttcaaatt tgaactcacc cgccgtctgg atcatgactt    1440
tgggaaggtc accaagcagg aagtcaaaga cttttttccgg tgggcaaagg atcacgtggt    1500
tgaggtggag catgaattct acgtcaaaaa gggtggagcc aagaaaagac ccgcccccag    1560
tgacgcagat ataagtgagc ccaaacgggt gcgcgagtca gttgcgcagc catcgacgtc    1620
agacgcggaa gcttcgatca actacgcgga caggtaccaa aacaaatgtt ctcgtcacgt    1680
gggcatgaat ctgatgctgt ttccctgcag acaatgcgag agactgaatc agaattcaaa    1740
tatctgcttc actcacggtg tcaaagactg tttagagtgc tttcccgtgt cagaatctca    1800 acccgttttct gtcgtcaaaa aggcgtatca gaaactgtgc tacattcatc acatcatggg    1860
aaaggtgcca gacgcttgca ctgcttgcga cctggtcaat gtggacttgg atgactgtgt    1920
ttctgaacaa taaatgactt aaaccaggta tggctgccga tggttaactt ccagattgac    1980
tcgaggacaa ccttagtgaa ggaattcgcg agtggtgggc tttgaaacct ggagcccctc    2040
aacccaaggc aaatcaacaa catcaagaca acgctcgagg tcttgtgctt ccgggttaca    2100
aataccttgg acccggcaac ggactcgaca aggggagcc ggtcaacgca gcagacgcgg     2160
cggccctcga gcacgacaag gcctacgacc agcagctcaa ggccggagac aacccgtacc    2220
tcaagtacaa ccacgccgac gccgagttcc aggagcggct caaagaagat acgtcttttg    2280
ggggcaacct cggcgagca gtcttccagg ccaaaaagag gcttcttgaa cctcttggtc     2340
tggttgagga gcggctaag acggctcctg gatagaagag gcctgtagag tagtctcctc     2400
aggaaccgga ctcctccgcg ggtattggca atcgggtgc acagcccgct aaaaagagac      2460
```

```
tcaatttcgg tcagactggc gacacagagt cagtcccaga ccctcaacca atcggagaac    2520
ctcccgcagc cccctcaggt gtgggatctc ttacaatggc ttcaggtggt ggcgcaccag    2580
tggcagacaa taactaaggt gccgatggag tgggtagttc ctcgggaaat tggcattgcg    2640
attcccaatg gctggggggac agagtcatca ccaccagcac ccgaacctgg gccctgccca    2700
cctacaacaa tcacctctac aagcaaatct ccaacagcac atctggagga tcttcaaatg    2760
acaacgccta cttcggctac agcaccccct gggggtattt tgacttcaac agattccact    2820
gccacttctc accacgtgac tggcagcgac tcatcaacaa caactgggga ttccggccta    2880
agcgactcaa cttcaagctc ttcaacattc aggtcaaaga ggttacggac aacaatggag    2940
tcaagaccat cgccaataac cttaccagca cggtccaggt cttcacggac tcagactatc    3000
agctcccgta cgtgctcggg tcggctcacg agggctgcct cccgccgttc ccagcggacg    3060
tttttcatgat tcctcagtac gggtatctga cgcttaatga tggaagccag gccgtgggtc    3120
gttcgtcctt ttactgcctg gaatatttcc cgtcgcaaat gctaagaacg ggtaacaact    3180
tccagttcag ctacgagttt gagaacgtac ctttccatag cagctacgct cacagccaaa    3240
gcctggaccg actaatgaat ccactcatcg accaatactt gtactatctc tcaaagacta    3300
ttaacggttc tggacagaat caacaaacgc taaaattcag tgtggccgga cccagcaaca    3360
tggctgtcca gggaagaaac tacatacctg acccagcta ccgacaacaa cgtgtctcaa    3420
ccactgtgac tcaaaacaac aacagcgaat ttgcttggcc tggagcttct tcttgggctc    3480
tcaatggacg taatagcttg atgaatcctg gacctgctat ggccagccac aaagaaggag    3540
aggaccgttt ctttccttg tctggatctt aattttttgg caaacaagga actggaagag    3600
acaacgtgga tgcggacaaa gtcatgataa ccaacgaaga agaaattaaa actactaacc    3660
cggtagcaac ggagtcctat ggacaagtgg ccacaaacca ccagagtgcc caagcacagg    3720
cgcagaccgg ctgggttcaa aaccaaggaa tacttccggg tatggtttgg caggacagag    3780
atgtgtacct gcaaggaccc atttgggcca aaattcctca cacggacggc aactttcacc    3840
cttctccgct gatgggaggg tttggaatga agcacccgcc tcctcagatc ctcatcaaaa    3900
acacacctgt acctgcggat cctccaacgg ccttcaacaa ggacaagctg aactctttca    3960
tcacccagta ttctactggc caagtcagcg tggagatcga gtgggagctg cagaaggaaa    4020
acagcaagcg ctggaacccg gagatccagt acacttccaa ctattacaag tctaataatg    4080
ttgaatttgc tgttaatact gaaggtgtat atagtgaacc cgccccatt ggcaccagat    4140
acctgactcg taatctgtaa ttgcttgtta atcaataaac cgtttaattc gtttcagttg    4200
aactttggtc tctgcgaagg gcgaattcgt ttaaacctgc aggactagag gtcctgtatt    4260
agaggtcacg tgagtgtttt gcgacatttt gcgacaccat gtggtcacgc tgggtattta    4320
agcccgagtg agcacgcagg gtctccattt tgaagcggga ggtttgaacg cgcagccgcc    4380
aagccgaatt ctgcagatat ccatcacact ggcggccgct cgactagagc ggcgccacc    4440
gcggtggagc tccagctttt gttcccttta gtgagggtta attgcgcgct tggcgtaatc    4500
atggtcatag ctgtttcctg tgtgaaattg ttatccgctc acaattccac acaacatacg    4560
agccggaagc ataaagtgta aagcctgggg tgcctaatga gtgagctaac tcacattaat    4620
tgcgttgcgc tcactgcccg ctttccagtc gggaaacctg tcgtgccagc tgcattaatg    4680
aatcggccaa cgcgcgggga gaggcggttt gcgtattggg cgctcttccg cttcctcgct    4740
cactgactcg ctgcgctcgg tcgttcggct gcggcgagcg gtatcagctc actcaaaggc    4800
ggtaatacgg ttatccacag aatcagggga taacgcagga agaacatgt gagcaaaagg    4860
```

```
ccagcaaaag gccaggaacc gtaaaaaggc cgcgttgctg gcgttttcc ataggctccg    4920
cccccctgac gagcatcaca aaaatcgacg ctcaagtcag aggtggcgaa acccgacagg    4980
actataaaga taccaggcgt ttccccctgg aagctccctc gtgcgctctc ctgttccgac    5040
cctgccgctt accggatacc tgtccgcctt tctcccttcg ggaagcgtgg cgctttctca    5100
tagctcacgc tgtaggtatc tcagttcggt gtaggtcgtt cgctccaagc tgggctgtgt    5160
gcacgaaccc cccgttcagc ccgaccgctg cgccttatcc ggtaactatc gtcttgagtc    5220
caacccggta agacacgact tatcgccact ggcagcagcc actggtaaca ggattagcag    5280
agcgaggtat gtaggcggtg ctacagagtt cttgaagtgg tggcctaact acggctacac    5340
tagaagaaca gtatttggta tctgcgctct gctgaagcca gttaccttcg gaaaaagagt    5400
tggtagctct tgatccggca aacaaaccac cgctggtagc ggtggttttt tgtttgcaa    5460
gcagcagatt acgcgcagaa aaaaggatc tcaagaagat cctttgatct tttctacggg    5520
gtctgacgct cagtggaacg aaaactcacg ttaagggatt ttggtcatga gattatcaaa    5580
aaggatcttc acctagatcc ttttaaatta aaatgaagt tttaaatcaa tctaaagtat    5640
atatgagtaa acttggtctg acagttacca atgcttaatc agtgaggcac ctatctcagc    5700
gatctgtcta tttcgttcat ccatagttgc ctgactcccc gtcgtgtaga taactacgat    5760
acggagggc ttaccatctg gccccagtgc tgcaatgata ccgcgagacc cacgctcacc    5820
ggctccagat ttatcagcaa taaaccagcc agccggaagg gccgagcgca gaagtggtcc    5880
tgcaacttta tccgcctcca tccagtctat taattgttgc cgggaagcta gagtaagtag    5940
ttcgccagtt aatagtttgc gcaacgttgt tgccattgct acaggcatcg tggtgtcacg    6000
ctcgtcgttt ggtatggctt cattcagctc cggttcccaa cgatcaaggc gagttacatg    6060
atcccccatg ttgtgcaaaa aagcggttag ctccttcggt cctccgatcg ttgtcagaag    6120
taagttggcc gcagtgttat cactcatggt tatggcagca ctgcataatt ctcttactgt    6180
catgccatcc gtaagatgct tttctgtgac tggtgagtac tcaaccaagt cattctgaga    6240
atagtgtatg cggcgaccga gttgctcttg cccggcgtca atacgggata ataccgcgcc    6300
acatagcaga actttaaaag tgctcatcat tggaaaacgt tcttcgggc gaaaactctc    6360
aaggatctta ccgctgttga tccagttc gatgtaaccc actcgtgcac ccaactgatc    6420
ttcagcatct tttactttca ccagcgtttc tgggtgagca aaaacaggaa ggcaaaatgc    6480
cgcaaaaaag ggaataaggg cgacacggaa atgttgaata ctcatactct tccttttttca    6540
atattattga agcatttatc agggttattg tctcatgagc ggatacatat ttgaatgtat    6600
ttagaaaaat aaacaaatag gggttccgcg cacatttccc cgaaaagtgc cacctaaatt    6660
gtaagcgtta atattttgtt aaaattcgcg ttaaattttt gttaaatcag ctcatttttt    6720
aaccaatagg ccgaaatcgg caaaatccct tataaatcaa agaatagac cgagataggg    6780
ttgagtgttg ttccagtttg gaacaagagt ccactattaa agaacgtgga ctccaacgtc    6840
aaagggcgaa aaaccgtcta tcagggcgat ggcccactac gtgaaccatc accctaatca    6900
agttttttgg ggtcgaggtg ccgtaaagca ctaaatcgga acctaaaagg agcccccga    6960
tttagagctt gacggggaaa gccggcgaac gtggcgagaa aggaagggaa gaaagcgaaa    7020
ggagcgggcg ctagggcgct ggcaagtgta gcggtcacgc tgcgcgtaac caccacaccc    7080
gccgcgctta atgcgccgct acagggcgcg tcccattcgc cattcaggct gcgcaactgt    7140
tgggaagggc gatcggtgcg ggcctcttcg ctattacgcc agctggcgaa aggggatgt     7200
```

```
gctgcaaggc gattaagttg ggtaacgcca gggttttccc agtcacgacg ttgtaaaacg    7260
acggccagtg agcgcgcgta atacgactca ctatagggcg aattgggtac cgggccccc     7320 ctcgatcgag                                                            7330

<210> SEQ ID NO 6
<211> LENGTH: 4468
<212> TYPE: DNA
<213> ORGANISM: Artificial Sequence
<220> FEATURE:
<223> OTHER INFORMATION: Plasmid

<400> SEQUENCE: 6
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaacgg ccgccagtgt gctggaattc gcccttactc atcgaccaat acttgtacta     360
tctctctaga actattaacg gttctggaca gaatcaacaa cgctaaaat tcagtgtggc      420 cggacccagc aacatggctg tccagggaag aaactacata cctggaccca gctaccgaca     480
acaacgtgtc tcaaccactg tgactcaaaa caacaacagc gaatttgctt ggcctggagc     540
ttcttcttgg gctctcaatg gacgtaatag cttgatgaat cctggacctg ctatggccag     600
ccacaaagaa ggagaggacc gtttctttcc tttgtctgga tctttaattt ttggcaaaca     660
aggtaccggc agagacaacg tggatgcgga caaagtcatg ataaccaacg aagaagaaat     720
taaaactact aacccggtag caacggagtc ctatggacaa gtggccacaa accaccagag     780
tgcccaagca caggcgcaga ccggttgggt tcaaaaccaa ggaatacttc aagggcgaa      840 ttctgcagat atccatcaca ctggcggccg ctcgagcatg catctagagg gcccaattcg     900
ccctatagtg agtcgtatta caattcactg gccgtcgttt tacaacgtcg tgactgggaa     960
aaccctggcg ttacccaact taatcgcctt gcagcacatc ccccttcgc cagctggcgt    1020 aatagcgaag aggcccgcac cgatcgccct tcccaacagt tgcgcagcct gaatggcgaa    1080
tggacgcgcc ctgtagcggc gcattaagcg cggcggtgt ggtggttacg cgcagcgtga    1140
ccgctacact tgccagcgcc ctagcgcccg ctcctttcgc tttcttccct cctttctcg     1200 ccacgttcgc cggctttccc cgtcaagctc taaatcgggg gctcccttta gggttccgat    1260
ttagtgcttt acggcacctc gaccccaaaa aacttgatta gggtgatggt tcacgtagtg    1320
ggccatcgcc ctgatagacg gttttcgcc cttgacgtt ggagtccacg ttctttaata     1380
gtggactctt gttccaaact ggaacaacac tcaaccctat ctcggtctat cttttgatt     1440 tataagggat tttgccgatt tcggcctatt ggttaaaaaa tgagctgatt taacaaaaat    1500
ttaacgcgaa ttttaacaaa attcaggcg caagggctgc taaaggaagc ggaacacgta     1560
gaaagccagt ccgcagaaac ggtgctgacc ccggatgaat gtcagctact gggctatctg    1620
gacaagggaa aacgcaagcg caaagagaaa gcaggtagct tgcagtgggc ttacatggcg    1680
atagctagac tgggcggttt tatggacagc aagcgaaccg gaattgccag ctggggcgcc    1740
ctctggtaag gttgggaagc cctgcaaagt aaactggatg gctttcttgc cgccaaggat    1800 ctgatgcgc aggggatcaa gatctgatca agagacagga tgaggatcgt ttcgcatgat    1860
tgaacaagat ggattgcacg caggttctcc ggccgcttgg gtggagaggc tattcggcta    1920
```

```
tgactgggca acagacaa tcggctgctc tgatgccgcc gtgttccggc tgtcagcgca    1980
ggggcgcccg gttcttttg tcaagaccga cctgtccggt gccctgaatg aactgcagga    2040
cgaggcagcg cggctatcgt ggctggccac gacgggcgtt ccttgcgcag ctgtgctcga    2100
cgttgtcact gaagcgggaa gggactggct gctattgggc gaagtgccgg ggcaggatct    2160
cctgtcatcc caccttgctc ctgccgagaa agtatccatc atggctgatg caatgcggcg    2220
gctgcatacg cttgatccgg ctacctgccc attcgaccac caagcgaaac atcgcatcga    2280
gcgagcacgt actcggatgg aagccggtct tgtcgatcag gatgatctgg acgaagagca    2340 tcagggctc cgccagccg aactgttcgc caggctcaag gcgcgcatgc ccgacgcgca    2400
ggatctcgtc gtgacccatg gcgatgcctg cttgccgaat atcatggtgg aaaatggccg    2460 ctttctgga ttcatcgact gtggccggct gggtgtggcg gaccgctatc aggacatagc    2520
gttggctacc cgtgatattg ctgaagagct tggcggcgaa tgggctgacc gcttcctcgt    2580
gctttacggt atcgccgctc ccgattcgca gcgcatcgcc ttctatcgcc ttcttgacga    2640
gttcttctga attgaaaaag gaagagtatg agtattcaac atttccgtgt cgcccttatt    2700
cccttttttg cggcattttg ccttcctgtt tttgctcacc cagaaacgct ggtgaaagta    2760
aaagatgctg aagatcagtt gggtgcacga gtgggttaca tcgaactgga tctcaacagc    2820
ggtaagatcc ttgagagttt cgccccgaa gaacgttttc aatgatgag cacttttaaa    2880 gttctgctat gtggcgcggt attatcccgt attgacgccg ggcaagagca actcggtcgc    2940
cgcatacact attctcagaa tgacttggtt gagtactcac cagtcacaga aaagcatctt    3000
acggatggca tgacagtaag agaattatgc agtgctgcca taaccatgag tgataacact    3060
gcggccaact tacttctgac aacgatcgga ggaccgaagg agctaaccgc ttttttgcac    3120
aacatggggg atcatgtaac tcgccttgat cgttgggaac cggagctgaa tgaagccata    3180
ccaaacgacg agcgtgacac cacgatgcct gtagcaatgg caacaacgtt gcgcaaacta    3240
ttaactggcg aactacttac tctagcttcc cggcaacaat taatagactg gatggaggcg    3300
gataaagttg caggaccact tctgcgctcg gcccttccgg ctggctggtt tattgctgat    3360
aaatctggag ccggtgagcg tgggtctcgc ggtatcattg cagcactggg gccagatggt    3420
aagccctccc gtatcgtagt tatctacacg acggggagtc aggcaactat ggatgaacga    3480
aatagacaga tcgctgagat aggtgcctca ctgattaagc attggtaact gtcagaccaa    3540
gtttactcat atatacttta gattgattta aacttcatt tttaatttaa aaggatctag    3600
gtgaagatcc tttttgataa tctcatgacc aaaatccctt aacgtgagtt tcgttccac    3660 tgagcgtcag accccgtaga aaagatcaaa ggatcttctt gagatccttt ttttctgcgc    3720
gtaatctgct gcttgcaaac aaaaaaacca ccgctaccag cggtggtttg tttgccggat    3780
caagagctac caactctttt tccgaaggta actggcttca gcagagcgca gataccaaat    3840
actgttcttc tagtgtagcc gtagttaggc caccacttca agaactctgt agcaccgcct    3900
acatacctcg ctctgctaat cctgttacca gtggctgctg ccagtggcga taagtcgtgt    3960
cttaccgggt tggactcaag acgatagtta ccggataagg cgcagcggtc gggctgaacg    4020
gggggttcgt gcacacagcc cagcttggag cgaacgacct acaccgaact gagataccta    4080
cagcgtgagc tatgagaaag cgccacgctt cccgaaggga gaaaggcgga caggtatccg    4140
gtaagcggca gggtcggaac aggagagcgc acgagggagc ttccagggg aaacgcctgg    4200 tatctttata gtcctgtcgg gtttcgccac ctctgacttg agcgtcgatt tttgtgatgc    4260
```

| | |
|---|---:|
| tcgtcagggg ggcggagcct atggaaaaac gccagcaacg cggccttttt acggttcctg | 4320 |
| gccttttgct ggccttttgc tcacatgttc tttcctgcgt tatccoctga ttctgtggat | 4380 |
| aaccgtatta ccgcctttga gtgagctgat accgctcgcc gcagccgaac gaccgagcgc | 4440 |
| agcgagtcag tgagcgagga agcggaag | 4468 |

<210> SEQ ID NO 7
<211> LENGTH: 6249
<212> TYPE: DNA
<213> ORGANISM: Artificial Sequence
<220> FEATURE:
<223> OTHER INFORMATION: Plasmid

<400> SEQUENCE: 7

| | |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctactag tggcctccgc gccgggtttt ggcgcctccc | 180 |
| gcgggcgccc cctcctcac ggcgagcgct gccacgtcag acgaagggcg cagcgagcgt | 240 |
| cctgatcctt ccgcccggac gctcaggaca gcggcccgct gctcataaga ctcggcctta | 300 |
| gaacccagt atcagcagaa ggacatttta ggacgggact tgggtgactc tagggcactg | 360 |
| gttttctttc cagagagcgg aacaggcgag gaaaagtagt cccttctcgg cgattctgcg | 420 |
| gagggatctc cgtggggcgg tgaacgccga tgattatata aggacgcgcc gggtgtggca | 480 |
| cagctagttc cgtcgcagcc gggatttggg tcgcggttct tgtttgtgga tcgctgtgat | 540 |
| cgtcacttgg cggccgccat ggtcagcaag ggcgaggagg ataacatggc catcatcaag | 600 |
| gagttcatgc gcttcaaggt gcacatggag ggctccgtga acggccacga gttcgagatc | 660 |
| gagggcgagg gcgagggccg cccctacgag gcacccaga ccgccaagct gaaggtgacc | 720 |
| aagggtggcc cctgccctt cgcctggac atcctgtccc ctcaattcat gtatggctcc | 780 |
| aaggcctacg tgaagcaccc cgccgacatc ccgactact tgaagctgtc cttccccgag | 840 |
| ggcttcaagt gggagcgcgt gatgaacttc gaggacggcg gcgtggtgac cgtgacccag | 900 |
| gactcctcct acaagacgg cgagttcatc tacaaagtga agctgcgcgg caccaacttc | 960 |
| ccctccgacg gccccgtaat gcagaagaag accatgggct gggaggcctc ctccgagcgg | 1020 |
| atgtacoccg aggacggcgc cctgaagggc gagatcaagc agaggctgaa gctgaaggac | 1080 |
| ggcggccact acgacgctga ggtcaagacc acctacaagg ccaagaagcc cgtgcagctg | 1140 |
| cccggcgcct acaacgtcaa catcaagttg gacatcacct ccacaacga ggactacacc | 1200 |
| atcgtggaac agtacgaacg cgccgagggc cgccactcca ccggcggcat ggacgagctg | 1260 |
| tacaagtaaa ggatcccctc ccccgtgcct tccttgaccc tggaaggtgc cactcccact | 1320 |
| gtccttttcct cctcctagga ataaaatatc tttattttca ttacatctgt gtgttggttt | 1380 |
| tttgtgtaga tctgttcaaa tttgaactga ctaagcggct cccgccagat tttggcaaga | 1440 |
| ttactaagca ggaagtcaag gacttttttg cttgggcaaa ggtcaatcag gtgccggtga | 1500 |
| ctcacgagtt taagttccc agggaattgg cgggaactaa aggggcggag aaatctctaa | 1560 |
| aacgcccact gggtgacgtc accaatacta gctataaaag tctggagaag cgggccaggc | 1620 |
| tctcatttgt tcccgagacg cctcgcagtt cagacgtgac tgttgatccc gctcctctgc | 1680 |
| gaccgctagc ttcgatcaac tacgcggaca ggtaccaaaa caaatgttct cgtcacgtgg | 1740 |
| gcatgaatct gatgctgttt ccctgcagac aatgcgagag actgaatcag aattcaaata | 1800 |
| tctgcttcac tcacggtgtc aaagactgtt tagagtgctt tcccgtgtca gaatctcaac | 1860 |

```
ccgtttctgt cgtcaaaaag gcgtatcaga aactgtgcta cattcatcac atcatgggaa    1920
aggtgccaga cgcttgcact gcttgcgacc tggtcaatgt ggacttggat gactgtgttt    1980
ctgaacaata aatgacttaa accaggtatg gctgccgatg gttatcttcc agattggctc    2040
gaggacaacc ttagtgaagg aattcgcgag tggtgggctt tgaaacctgg agcccctcaa    2100
cccaaggcaa atcaacaaca tcaagacaac gctcgaggtc ttgtgcttcc gggttacaaa    2160
taccttggac ccggcaacgg actcgacaag ggggagccgg tcaacgcagc agacgcggcg    2220
gccctcgagc acgacaaggc ctacgaccag cagctcaagg ccggagacaa cccgtacctc    2280
aagtacaacc acgccgacgc cgagttccag gagcggctca agaagatacg tcttttgggg    2340
ggcaacctcg gcgagcagt cttccaggcc aaaagagggc ttcttgaacc tcttggtctg    2400
gttgaggaag cggctaagac ggctcctgga agaagagggc tgtagagca gtctcctcag    2460 gaaccggact cctccgcggg tattggcaaa tcgggtgcac agcccgctaa aaagagactc    2520
aatttcggtc agactggcga cacagagtca gtcccagacc ctcaaccaat cggagaacct    2580
cccgcagccc cctcaggtgt gggatctctt acaatggctt caggtggtgg cgcaccagtg    2640
gcagacaata acgaaggtgc cgatggagtg ggtagttcct cgggaaattg gcattgcgat    2700
tcccaatggc tgggggacag agtcatcacc accagcaccc gaacctgggc cctgcccacc    2760
tacaacaatc acctctacaa gcaaatctcc aacagcacat ctggaggatc ttcaaatgac    2820
aacgcctact tcggctacag cacccctggg gggtattttg acttcaacag attccactgc    2880
cacttctcac cacgtgactg gcagcgactc atcaacaaca actggggatt ccggcctaag    2940
cgactcaact tcaagctctt caacattcag gtcaaagagg ttacggacaa caatggagtc    3000
aagaccatcg ccaataacct taccagcacg gtccaggtct tcacggactc agactatcag    3060
ctcccgtacg tgctcgggtc ggctcacgag ggctgcctcc cgccgttccc agcggacgtt    3120
ttcatgattc ctcagtacgg gtatctgacg cttaatgatg gaagccaggc cgtgggtcgt    3180
tcgtcctttt actgcctgga atatttcccg tcgcaaatgc taagaacggg taacaacttc    3240
cagttcagct acgagtttga gaacgtacct ttccatagca gctacgctca cagccaaagc    3300
ctggaccgac taatgaatcc actcatcgac caatacttgt actatctctc tagaactatt    3360
accggttggg ttcaaaacca aggaatactt ccgggtatgg tttggcagga cagagatgtg    3420
tacctgcaag gacccatttg ggccaaaatt cctcacacgg acggcaactt tcacccttct    3480
ccgctgatgg agggtttgg aatgaagcac ccgcctcctc agatcctcat caaaaacaca    3540
cctgtacctg cggatcctcc aacggccttc aacaaggaca gctgaactc tttcatcacc    3600 cagtattcta ctggccaagt cagcgtggag atcgagtggg agctgcagaa ggaaaacagc    3660
aagcgctgga acccggagat ccagtacact tccaactatt acaagtctaa taatgttgaa    3720
tttgctgtta atactgaagg tgtatatagt gaaccccgcc ccattggcac cagatacctg    3780
actcgtaatc tgtaagtcga ctaccgttcg tatagcatac attatacgaa gttatcatat    3840
gttcgagcag acatgataag atacattgat gagtttggac aaaccacaac tagaatgcag    3900
tgaaaaaaat gctttatttg tgaaatttgt gatgctattg ctttatttgt aaccattata    3960
agctgcaata aacaagttaa caacaacaat tgcattcatt ttatgtttca ggttcagggg    4020
gagatgtggg aggttttta aagcaagtaa aacctctaca aatgtggtaa aatcgagctc    4080
taccgttcgt ataatgtatg ctatacgaag ttatgtatc aagcttagga accctagtg    4140 atggagttgg ccactccctc tctgcgcgct cgctcgctca ctgaggccgg gcgaccaaag    4200
```

```
gtcgcccgac gcccgggctt tgcccgggcg gcctcagtga gcgagcgagc gcgcagagag     4260
ggagtggcca agctagcggg cgattaagga aagggctaga tcattcttga agacgaaagg     4320
gcctcgtgat acgcctattt ttataggtta atgtcatgat aataatggtt tcttagacgt     4380
caggtggcac ttttcgggga aatgtgcgcg gaacccctat ttgtttattt ttctaaatac     4440
attcaaatat gtatccgctc atgagacaat aaccctgata aatgcttcaa taatattgaa     4500
aaaggaagag tatgagtatt caacatttcc gtgtcgccct tattccctt tttgcggcat      4560 tttgccttcc tgttttgct cacccagaaa cgctggtgaa agtaaaagat gctgaagatc      4620
agttgggtgc acgagtgggt tacatcgaac tggatctcaa cagcggtaag atccttgaga     4680
gttttcgccc cgaagaacgt tttccaatga tgagcacttt taaagttctg ctatgtggcg     4740
cggtattatc ccgtgttgac gccgggcaag agcaactcgg tcgccgcata cactattctc     4800
agaatgactt ggttgagtac tcaccagtca cagaaaagca tcttacggat ggcatgacag     4860
taagagaatt atgcagtgct gccataacca tgagtgataa cactgcgcc aacttacttc      4920 tgacaacgat cggaggaccg aaggagctaa ccgcttttt gcacaacatg ggggatcatg      4980
taactcgcct tgatcgttgg gaaccggagc tgaatgaagc cataccaaac gacgagcgtg     5040
acaccacgat gcctgtagca atggcaacaa cgttgcgcaa actattaact ggcgaactac     5100
ttactctagc ttcccggcaa caattaatag actggatgga ggcggataaa gttgcaggac     5160
cacttctgcg ctcggccctt ccggctggct ggtttattgc tgataaatct ggagccggtg     5220
agcgtgggtc tcgcggtatc attgcagcac tggggccaga tggtaagccc tcccgtatcg     5280
tagttatcta cacgacgggg agtcaggcaa ctatggatga acgaaataga cagatcgctg     5340
agataggtgc ctcactgatt aagcattggt aactgtcaga ccaagtttac tcatatatac     5400
tttagattga tttaaaactt cattttaat ttaaaaggat ctaggtgaag atccttttg       5460 ataatctcat gaccaaaatc ccttaacgtg agttttcgtt ccactgagcg tcagaccccg     5520
tagaaaagat caaaggatct tcttgagatc cttttttct gcgcgtaatc tgctgcttgc      5580
aaacaaaaaa accaccgcta ccagcggtgg tttgtttgcc ggatcaagag ctaccaactc     5640 ttttccgaa ggtaactggc ttcagcagag cgcagatacc aaatactgtt cttctagtgt      5700
agccgtagtt aggccaccac ttcaagaact ctgtagcacc gcctacatac ctcgctctgc     5760
taatcctgtt accagtggct gctgccagtg gcgataagtc gtgtcttacc gggttggact     5820
caagacgata gttaccggat aaggcgcagc ggtcgggctg aacggggggt tcgtgcacac     5880
agcccagctt ggagcgaacg acctacaccg aactgagata cctacagcgt gagctatgag     5940
aaagcgccac gcttcccgaa gggagaaagg cggacaggta tccggtaagc ggcagggtcg     6000
gaacaggaga gcgcacgagg gagcttccag gggaaacgc ctggtatctt tatagtcctg      6060
tcgggtttcg ccacctctga cttgagcgtc gatttttgtg atgctcgtca ggggggcgga     6120
gcctatggaa aaacgccagc aacgcggcct ttttacggtt cctggccttt tgctggcctt     6180
ttgctcacat gtaataaaca cacacacacc aacaaccgtg gttggttgtt gtgttggttt     6240
attctcgag                                                             6249
```

<210> SEQ ID NO 8
<211> LENGTH: 743
<212> TYPE: PRT
<213> ORGANISM: Artificial Sequence
<220> FEATURE:
<223> OTHER INFORMATION: Adeno-associated virus capsid VP1 protein

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415
```

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 9
<211> LENGTH: 2232
<212> TYPE: DNA
<213> ORGANISM: Artificial Sequence
<220> FEATURE:
<223> OTHER INFORMATION: Adeno-associated virus capsid gene

<400> SEQUENCE: 9
atggctgccg atggttatct tccagattgg ctcgaggaca accttagtga aggaattcgc      60
gagtggtggg cttgaaacc tggagcccct caacccaagg caaatcaaca acatcaagac     120
aacgctcgag gtcttgtgct tccgggttac aaataccttg acccggcaa cggactcgac     180

```
aaggggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa dacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg  tgtgggatct    600 cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct cacccgtga ctggcagcga    900 ctcatcaaca acaactgggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctctagaact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct    1620
ttaatttttg gcaaacaagg taccggcaga gacaacgtgg atgcggacaa agtcatgata    1680
accaacgaag aagaaattaa aactactaac ccggtagcaa cggagtccta tggacaagtg    1740
gccacaaacc accagagtgc ccaaactttg gcggtgcctt ttaaggcaca ggcgcagacc    1800
ggttgggttc aaaaccaagg aatacttccg ggtatggttt ggcaggacag agatgtgtac    1860
ctgcaaggac ccatttgggc caaaattcct cacacggacg gcaactttca cccttctccg    1920
ctgatgggag ggtttggaat gaagcacccg cctcctcaga tcctcatcaa aaacacacct    1980
gtacctgcgg atcctccaac ggccttcaac aaggacaagc tgaactcttt catcacccag    2040
tattctactg gccaagtcag cgtggagatc gagtgggagc tgcagaagga aaacagcaag    2100
cgctggaacc cggagatcca gtacacttcc aactattaca gtctaataa  tgttgaattt    2160 gctgttaata ctgaaggtgt atatagtgaa ccccgcccca ttggcaccag ataccctgact    2220 cgtaatctgt aa                                                       2232
```

<210> SEQ ID NO 10
<211> LENGTH: 9378
<212> TYPE: DNA
<213> ORGANISM: Artificial Sequence
<220> FEATURE:
<223> OTHER INFORMATION: Plasmid

<400> SEQUENCE: 10

```
gtcgacggta tcgggggagc tcgcagggtc tccattttga agcgggaggt ttgaacgcgc    60
agccgccatg ccgggttttt acgagattgt gattaaggtc cccagcgacc ttgacgagca   120
tctgcccggc atttctgaca gctttgtgaa ctgggtggcc gagaaggaat gggagttgcc   180
gccagattct gacatggatc tgaatctgat tgagcaggca cccctgaccg tggccgagaa   240
gctgcagcgc gactttctga cggaatggcg ccgtgtgagt aaggcccggg aggctctttt   300
ctttgtgcaa tttgagaagg gagagagcta cttccacatg cacgtgctcg tggaaaccac   360
cggggtgaaa tccatggttt tgggacgttt cctgagtcag attcgcgaaa aactgattca   420
gagaatttac cgcgggatcg agccgacttt gccaaactgg ttcgcggtca caagaccag   480 aaatggcgcc ggaggcggga caaggtggt ggatgagtgc tacatcccca attacttgct   540
ccccaaaacc cagcctgagc tccagtgggc gtggactaat atggaacagt atttaagcgc   600
ctgtttgaat ctcacggagc gtaaacggtt ggtggcgcag catctgacgc acgtgtcgca   660
gacgcaggag cagaacaaag agaatcagaa tcccaattct gatgcgccgg tgatcagatc   720
aaaaacttca gccaggtaca tggagctggt cgggtggctc gtggacaagg ggattacctc   780
ggagaagcag tggatccagg aggaccaggc ctcatacatc tccttcaatg cggcctccaa   840
ctcgcggtcc caaatcaagg ctgccttgga caatgcggga agattatga gcctgactaa   900 aaccgccccc gactacctgg tgggccagca gcccgtggag gacatttcca gcaatcggat   960
ttataaaatt ttggaactaa acgggtacga tccccaatat gcggcttccg tctttctggg  1020
atgggccacg aaaaagttcg gcaagaggaa caccatctgg ctgtttgggc ctgcaactac  1080
cgggaagacc aacatcgcgg aggccatagc ccacactgtg cccttctacg ggtgcgtaaa  1140
ctggaccaat gagaactttc ccttcaacga ctgtgtcgac aagatggtga tctggtggga  1200
ggaggggaag atgaccgcca aggtcgtgga gtcgccaaa gccattctcg aggaagcaa   1260 ggtgcgcgtg gaccagaaat gcaagtcctc ggcccagata gacccgactc ccgtgatcgt  1320
cacctccaac accaacatgt gcgccgtgat tgacgggaac tcaacgacct cgaacacca   1380 gcagccgttg caagaccgga tgttcaaatt tgaactcacc cgccgtctgg atcatgactt  1440
tgggaaggtc accaagcagg aagtcaaaga cttttttccgg tgggcaaagg atcacgtggt  1500
tgaggtggag catgaattct acgtcaaaaa gggtggagcc aagaaaagac ccgccccccag  1560 tgacgcagat ataagtgagc ccaaacgggt gcgcgagtca gttgcgcagc catcgacgtc  1620
agacgcggaa gcttcgatca actacgcgga caggtaccaa aacaaatgtt ctcgtcacgt  1680
gggcatgaat ctgatgctgt ttccctgcag acaatgcgag agactgaatc agaattcaaa  1740
tatctgcttc actcacggtg tcaaagactg tttagagtgc tttccgtgt cagaatctca   1800 acccgtttct gtcgtcaaaa aggcgtatca gaaactgtgc tacattcatc acatcatggg  1860
aaaggtgcca gacgcttgca ctgcttgcga cctggtcaat gtggacttgg atgactgtgt  1920
ttctgaacaa taaatgactt aaaccaggta tgagtcggct ggataaatct aaagtcataa  1980
acggcgctct ggaattactc aatgaagtcg gtatcgaagg cctgacgaca aggaaactcg  2040
ctcaaaagct gggagttgag cagcctaccc tgtactggca cgtgaagaac aagcgggccc  2100
tgctcgatgc cctggccatc gagatgctgg acaggcatca tacccacttc tgcccctgg   2160 aaggcgagtc atggcaagac tttctgcgga caacgccaa gtcattccgc tgtgctctcc  2220
tctcacatcg cgacggggct aaagtgcatc tcggcacccg cccaacagag aaacagtacg  2280
aaaccctgga aaatcagctc gcgttcctgt gtcagcaagg cttctccctg gagaacgcac  2340
```

-continued

```
tgtacgctct gtccgccgtg ggccacttta cactgggctg cgtattggag gaacaggagc    2400
atcaagtagc aaaagaggaa agagagacac ctaccaccga ttctatgccc ccacttctga    2460
gacaagcaat tgagctgttc gaccggcagg gagccgaacc tgccttcctt ttcggcctgg    2520
aactaatcat atgtggcctg gagaaacagc taaagtgcga aagcggcggg ccggccgacg    2580
cccttgacga ttttgactta gacatgctcc cagccgatgc ccttgacgac tttgaccttg    2640
atatgctgcc tgctgacgct cttgacgatt ttgaccttga catgctcccc gggtaaatgc    2700
atgaattcga tctagagggc cctattctat agtgtcacct aaatgctaga gctcgctgat    2760
cagcctcgac tgtgccttct agttgccagc catctgttgt ttgcccctcc cccgtgcctt    2820
ccttgaccct ggaaggtgcc actcccactg tccttteccta ataaaatgag gaaattgcat    2880
cgcattgtct gagtaggtgt cattctattc tggggggtgg ggtggggcag gacagcaagg    2940
gggaggattg ggaagacaat agcaggcatg ctggggatgc ggtgggctct atggcttctg    3000
aggcggaaag aaccagctgg ggctcgaatc aagctatcaa gtgccacctg acgtctccct    3060
atcagtgata gagaagtcga cacgtctcga gctccctatc agtgatagag aaggtacgtc    3120
tagaacgtct ccctatcagt gatagagaag tcgacacgtc tcgagctccc tatcagtgat    3180
agagaaggta cgtctagaac gtctccctat cagtgataga gaagtcgaca cgtctcgagc    3240
tccctatcag tgatagagaa ggtacgtcta gaacgtctcc ctatcagtga tagagaagtc    3300
gacacgtctc gagctcccta tcagtgatag agaaggtacc ccctatataa gcagagagat    3360
ctgttcaaat ttgaactgac taagcggctc ccgccagatt ttggcaagat tactaagcag    3420
gaagtcaagg actttttgc ttgggcaaag gtcaatcagg tgccggtgac tcacgagttt    3480
aaagttccca gggaattggc gggaactaaa ggggcggaga atctctaaa cgcccactg     3540
ggtgacgtca ccaatactag ctataaaagt ctggagaagc gggccaggct ctcatttgtt    3600
cccgagacgc ctcgcagttc agacgtgact gttgatcccg ctcctctgcg accgctagct    3660
tcgatcaact acgcggacag gtaccaaaac aaatgttctc gtcacgtggg catgaatctg    3720
atgctgtttc cctgcagaca atgcgagaga ctgaatcaga attcaaatat ctgcttcact    3780
cacggtgtca aagactgttt agagtgcttt cccgtgtcag aatctcaacc cgtttctgtc    3840
gtcaaaaagg cgtatcagaa actgtgctac attcatcaca tcatgggaaa ggtgccagac    3900
gcttgcactg cttgcgacct ggtcaatgtg gacttggatg actgtgtttc tgaacaataa    3960
atgacttaaa ccaggtatgg ctgccgatgg ttatcttcca gattggctcg aggacaacct    4020
tagtgaagga attcgcgagt ggtgggcttt gaaacctgga gccctcaac ccaaggcaaa     4080
tcaacaacat caagacaacg ctcgaggtct tgtgcttccg ggttacaaat accttggacc    4140
cggcaacgga ctcgacaagg gggagccggt caacgcagca gacgcggcgg ccctcgagca    4200
cgacaaggcc tacgaccagc agctcaaggc cggagacaac ccgtacctca gtacaaccaa    4260
cgccgacgcc gagttccagg agcggctcaa agaagatacg tcttttgggg gcaacctcgg    4320
gcgagcagtc ttccaggcca aaagaggct tcttgaacct cttggtctgg ttgaggaagc    4380
ggctaagacg gctcctggaa agaagaggcc tgtagagcag tctcctcagg aaccggactc    4440
ctccgcgggt attggcaaat cggtgcaca gcccgctaaa aagagactca atttcggtca    4500
gactggcgac acagagtcag tcccagaccc tcaaccaatc ggagaacctc cgcagccccc    4560
ctcaggtgtg ggatctctta caatggcttc aggtggtggc gcaccagtgg cagacaataa    4620
cgaaggtgcc gatggagtgg gtagttcctc gggaaattgg cattgcgatt cccaatggct    4680
gggggacaga gtcatcacca ccagcacccg aacctgggcc ctgcccacct acaacaatca    4740
```

```
cctctacaag caaatctcca acagcacatc tggaggatct tcaaatgaca acgcctactt    4800
cggctacagc acccctggg ggtattttga cttcaacaga ttccactgcc acttctcacc    4860
acgtgactgg cagcgactca tcaacaacaa ctggggattc cggcctaagc gactcaactt    4920
caagctcttc aacattcagg tcaaagaggt tacggacaac aatggagtca agaccatcgc    4980
caataacctt accagcacgg tccaggtctt cacggactca gactatcagc tcccgtacgt    5040
gctcgggtcg gctcacgagg gctgcctccc gccgttccca gcggacgttt tcatgattcc    5100
tcagtacggg tatctgacgc ttaatgatgg aagccaggcc gtgggtcgtt cgtcctttta    5160
ctgcctggaa tatttcccgt cgcaaatgct aagaacgggt aacaacttcc agttcagcta    5220
cgagtttgag aacgtacctt tccatagcag ctacgctcac agccaaagcc tggaccgact    5280
aatgaatcca ctcatcgacc aatacttgta ctatctctct agaactatta acggttctgg    5340
acagaatcaa caaacgctaa aattcagtgt ggccggaccc agcaacatgg ctgtccaggg    5400
aagaaactac atacctggac ccagctaccg acaacaacgt gtctcaacca ctgtgactca    5460
aaacaacaac agcgaatttg cttggcctgg agcttcttct tgggctctca atggacgtaa    5520
tagcttgatg aatcctggac ctgctatggc cagccacaaa gaaggagagg accgtttctt    5580
tcctttgtct ggatctttaa ttttggcaa acaaggtacc ggcagagaca acgtggatgc    5640
ggacaaagtc atgataacca acgaagaaga aattaaaact actaacccgg tagcaacgga    5700
gtcctatgga caagtggcca caaccacca gagtgcccaa actttggcgg tgccttttaa    5760
ggcacaggcg cagaccggtt gggttcaaaa ccaaggaata cttccgggta tggtttggca    5820
ggacagagat gtgtacctgc aaggacccat ttgggccaaa attcctcaca cggacggcaa    5880
ctttcaccct tctccgctga tgggagggtt tggaatgaag cacccgcctc ctcagatcct    5940
catcaaaaac acacctgtac ctgcggatcc tccaacggcc ttcaacaagg acaagctgaa    6000
ctctttcatc acccagtatt ctactggcca agtcagcgtg gagatcgagt gggagctgca    6060
gaaggaaaac agcaagcgct ggaacccgga gatccagtac acttccaact attacaagtc    6120
taataatgtt gaatttgctg ttaatactga aggtgtatat agtgaacccc gccccattgg    6180
caccagatac ctgactcgta atctgtaatt gcttgttaat caataaaccg tttaattcgt    6240
ttcagttgaa ctttggtctc tgcgaagggc gaattcgttt aaacctgcag gactagaggt    6300
cctgtattag aggtcacgtg agtgttttgc gacattttgc gacaccatgt ggtcacgctg    6360
ggtatttaag cccgagtgag cacgcagggt ctccattttg aagcgggagg tttgaacgcg    6420
cagccgccaa gccgaattct gcagatatcc atcacactgg cggccgctcg actagagcgg    6480
ccgccaccgc ggtggagctc cagcttttgt tccctttagt gagggttaat tgcgcgcttg    6540
gcgtaatcat ggtcatagct gtttcctgtg tgaaattgtt atccgctcac aattccacac    6600
aacatacgag ccggaagcat aaagtgtaaa gcctggggtg cctaatgagt gagctaactc    6660
acattaattg cgttgcgctc actgcccgct ttccagtcgg gaaacctgtc gtgccagctg    6720
cattaatgaa tcggccaacg cgcggggaga ggcggtttgc gtattgggcg ctcttccgct    6780
tcctcgctca ctgactcgct gcgctcggtc gttcggctgc ggcgagcggt atcagctcac    6840
tcaaaggcgg taatacggtt atccacagaa tcaggggata acgcaggaaa gaacatgtga    6900
gcaaaaggcc agcaaaaggc caggaaccgt aaaaaggccg cgttgctggc gtttttccat    6960
aggctccgcc cccctgacga gcatcacaaa aatcgacgct caagtcagag gtggcgaaac    7020
ccgacaggac tataaagata ccaggcgttt ccccctggaa gctccctcgt gcgctctcct    7080
```

```
gttccgaccc tgccgcttac cggatacctg tccgcctttc tcccttcggg aagcgtggcg    7140
cttttctcata gctcacgctg taggtatctc agttcggtgt aggtcgttcg ctccaagctg   7200
ggctgtgtgc acgaaccccc cgttcagccc gaccgctgcg ccttatccgg taactatcgt    7260
cttgagtcca acccgtaag acacgactta tcgccactgg cagcagccac tggtaacagg     7320
attagcagag cgaggtatgt aggcggtgct acagagttct tgaagtggtg gcctaactac    7380
ggctacacta aagaacagt atttggtatc tgcgctctgc tgaagccagt taccttcgga    7440
aaaagagttg gtagctcttg atccggcaaa caaaccaccg ctggtagcgg tggttttttt    7500
gtttgcaagc agcagattac gcgcagaaaa aaggatctc aagaagatcc tttgatcttt     7560
tctacggggt ctgacgctca gtggaacgaa aactcacgtt aagggatttt ggtcatgaga    7620
ttatcaaaaa ggatcttcac ctagatcctt ttaaattaaa aatgaagttt taaatcaatc    7680
taaagtatat atgagtaaac ttggtctgac agttaccaat gcttaatcag tgaggcacct   7740
atctcagcga tctgtctatt tcgttcatcc atagttgcct gactccccgt cgtgtagata    7800
actacgatac gggagggctt accatctggc cccagtgctg caatgatacc gcgagaccca    7860
cgctcaccgg ctccagattt atcagcaata accagccag ccggaagggc cgagcgcaga    7920
agtggtcctg caactttatc cgcctccatc cagtctatta attgttgccg ggaagctaga    7980
gtaagtagtt cgccagttaa tagtttgcgc aacgttgttg ccattgctac aggcatcgtg   8040
gtgtcacgct cgtcgtttgg tatggcttca ttcagctccg gttcccaacg atcaaggcga    8100
gttacatgat cccccatgtt gtgcaaaaaa gcggttagct ccttcggtcc tccgatcgtt    8160
gtcagaagta agttggccgc agtgttatca ctcatggtta tggcagcact gcataattct    8220
cttactgtca tgccatccgt aagatgcttt tctgtgactg gtgagtactc aaccaagtca    8280
ttctgagaat agtgtatgcg cgaccgagt tgctcttgcc cggcgtcaat acgggataat     8340
accgcgccac atagcagaac tttaaaagtg ctcatcattg gaaaacgttc ttcggggcga    8400
aaactctcaa ggatcttacc gctgttgaga tccagttcga tgtaacccac tcgtgcaccc    8460
aactgatctt cagcatcttt tactttcacc agcgtttctg ggtgagcaaa aacaggaagg    8520
caaaatgccg caaaaaaggg aataagggcg cacggaaat gttgaatact catactcttc    8580
ctttttcaat attattgaag catttatcag ggttattgtc tcatgagcgg atacatattt    8640
gaatgtattt agaaaaataa acaaataggg gttccgcgca catttccccg aaaagtgcca    8700
cctaaattgt aagcgttaat attttgttaa aattcgcgtt aaattttgt taaatcagct    8760
catttttaa ccaataggcc gaaatcggca aaatccctta taaatcaaaa gaatagaccg    8820
agatagggtt gagtgttgtt ccagtttgga acaagagtcc actattaaag aacgtggact    8880
ccaacgtcaa agggcgaaaa accgtctatc agggcgatgg cccactacgt gaaccatcac    8940
cctaatcaag ttttttgggg tcgaggtgcc gtaaagcact aaatcggaac cctaagggga    9000
gccccgatt tagagcttga cggggaaagc cggcgaacgt ggcgagaaag gaagggaaga    9060
aagcgaaagg agcgggcgct agggcgctgg caagtgtagc ggtcacgctg cgcgtaacca    9120
ccacacccgc cgcgcttaat gcgccgctac agggcgcgtc ccattcgcca ttcaggctgc    9180
gcaactgttg ggaagggcga tcggtgcggg cctcttcgct attacgccag ctggcgaaag    9240
ggggatgtgc tgcaaggcga ttaagttggg taacgccagg gttttcccag tcacgacgtt    9300
gtaaaacgac ggccagtgag cgcgcgtaat acgactcact ataggcgaa ttgggtaccg    9360
ggccccccct cgatcgag                                                   9378
```

<210> SEQ ID NO 11
<211> LENGTH: 2211
<212> TYPE: DNA
<213> ORGANISM: Artificial Sequence
<220> FEATURE:
<223> OTHER INFORMATION: Adeno-associated virus capsid VP1 gene

<400> SEQUENCE: 11

```
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180
aagggggagc cggtcaacgc agcagacgcg gcggccctcg agcacgacaa ggcctacgac     240
cagcagctca aggccggaga caacccgtac ctcaagtaca accacgccga cgccgagttc     300
caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct      600
cttacaatgg cttcaggtgg tggcgcacca gtggcagaca taacgaagg tgccgatgga     660
gtgggtagtt cctcgggaaa ttggcattgc gattcccaat ggctggggga cagagtcatc     720
accaccagca cccgaacctg ggccctgccc acctacaaca tcacctcta caagcaaatc     780
tccaacagca catctggagg atcttcaaat gacaacgcct acttcggcta cagcaccccc     840
tgggggtatt ttgacttcaa cagattccac tgccacttct caccacgtga ctggcagcga     900
ctcatcaaca caactgggg attccggcct aagcgactca acttcaagct cttcaacatt     960
caggtcaaag aggttacgga caacaatgga gtcaagacca tcgccaataa ccttaccagc    1020
acggtccagg tcttcacgga ctcagactat cagctcccgt acgtgctcgg tcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttcctt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacgacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
```

```
tacacttcca actattacaa gtctaataat gttgaatttg ctgttaatac tgaaggtgta      2160
tatagtgaac cccgccccat tggcaccaga tacctgactc gtaatctgta a               2211

<210> SEQ ID NO 12
<211> LENGTH: 736
<212> TYPE: PRT
<213> ORGANISM: Artificial Sequence
<220> FEATURE:
<223> OTHER INFORMATION: Adeno-associated virus capsid protein G2B-13

<400> SEQUENCE: 12
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

```
Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Ile Gln Ser Ser Gln Thr Pro Arg Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 13
<211> LENGTH: 743
<212> TYPE: PRT
<213> ORGANISM: Artificial Sequence
<220> FEATURE:

<223> OTHER INFORMATION: Adeno-associated virus capsid protein G2B-26

<400> SEQUENCE: 13

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

Pro Ser Gln Met Leu Arg Thr Gly Asn Asn Phe Gln Phe Ser Tyr Glu
                    405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
                740

<210> SEQ ID NO 14
<211> LENGTH: 743
<212> TYPE: PRT
<213> ORGANISM: Artificial Sequence
<220> FEATURE:
<223> OTHER INFORMATION: Adeno-associated virus capsid protein TH1.1-32

<400> SEQUENCE: 14

Met Ala Ala Asp Gly Tyr Leu Pro Asp Trp Leu Glu Asp Asn Leu Ser
1               5                   10                  15

-continued

Glu Gly Ile Arg Glu Trp Trp Ala Leu Lys Pro Gly Ala Pro Gln Pro
         20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
     50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Leu Leu Glu Pro
         115                 120                 125

Leu Gly Leu Val Glu Glu Ala Ala Lys Thr Ala Pro Gly Lys Lys Arg
         130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
             165                 170                 175

Gly Asp Thr Glu Ser Val Pro Asp Pro Gln Pro Ile Gly Glu Pro Pro
             180                 185                 190

Ala Ala Pro Ser Gly Val Gly Ser Leu Thr Met Ala Ser Gly Gly Gly
         195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
             245                 250                 255

Tyr Lys Gln Ile Ser Asn Ser Thr Ser Gly Gly Ser Ser Asn Asp Asn
             260                 265                 270

Ala Tyr Phe Gly Tyr Ser Thr Pro Trp Gly Tyr Phe Asp Phe Asn Arg
         275                 280                 285

Phe His Cys His Phe Ser Pro Arg Asp Trp Gln Arg Leu Ile Asn Asn
         290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
             325                 330                 335

Asn Leu Thr Ser Thr Val Gln Val Phe Thr Asp Ser Asp Tyr Gln Leu
             340                 345                 350

Pro Tyr Val Leu Gly Ser Ala His Glu Gly Cys Leu Pro Pro Phe Pro
         355                 360                 365

Ala Asp Val Phe Met Ile Pro Gln Tyr Gly Tyr Leu Thr Leu Asn Asp
         370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
             405                 410                 415

Phe Glu Asn Val Pro Phe His Ser Ser Tyr Ala His Ser Gln Ser Leu
             420                 425                 430

Asp Arg Leu Met Asn Pro Leu Ile Asp Gln Tyr Leu Tyr Tyr Leu Ser

```
            435                 440                 445
Arg Thr Ile Ile Leu Gly Thr Gly Thr Ser Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Arg Thr Asn
            580                 585                 590

Pro Glu Ala Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 15
<211> LENGTH: 743
<212> TYPE: PRT
<213> ORGANISM: Artificial Sequence
<220> FEATURE:
<223> OTHER INFORMATION: Adeno-associated virus capsid protein TH1.1-35

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
```

```
              50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                     85                  90                  95

Asp Ala Glu Phe Gln Glu Arg Leu Lys Glu Asp Thr Ser Phe Gly Gly
                    100                 105                 110

Asn Leu Gly Arg Ala Val Phe Gln Ala Lys Lys Arg Leu Leu Glu Pro
                    115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                    165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Ile Ile Leu Gly Thr Gly Thr Ser Gln Thr Leu Lys Phe Ser
            450                 455                 460

Val Ala Gly Pro Ser Asn Met Ala Val Gln Gly Arg Asn Tyr Ile Pro
465                 470                 475                 480
```

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Asn Gly Gly Thr
            580                 585                 590

Ser Ser Ser Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
            610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
            645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
            725                 730                 735

Arg Tyr Leu Thr Arg Asn Leu
            740

<210> SEQ ID NO 16
<211> LENGTH: 27
<212> TYPE: DNA
<213> ORGANISM: Artificial Sequence
<220> FEATURE:
<223> OTHER INFORMATION: 9CapF primer

<400> SEQUENCE: 16
caggtcttca cggactcaga ctatcag                                    27

<210> SEQ ID NO 17
<211> LENGTH: 32
<212> TYPE: DNA
<213> ORGANISM: Artificial Sequence
<220> FEATURE:
<223> OTHER INFORMATION: CDF Primer

<400> SEQUENCE: 17
caagtaaaac tctacaaat gtggtaaaat cg                              32

<210> SEQ ID NO 18
<211> LENGTH: 36

```
<212> TYPE: DNA
<213> ORGANISM: Artificial Sequence
<220> FEATURE:
<223> OTHER INFORMATION: XF primer

<400> SEQUENCE: 18
actcatcgac caatacttgt actatctctc tagaac                              36

<210> SEQ ID NO 19
<211> LENGTH: 26
<212> TYPE: DNA
<213> ORGANISM: Artificial Sequence
<220> FEATURE:
<223> OTHER INFORMATION: AR Primer

<400> SEQUENCE: 19
ggaagtattc cttggttttg aaccca                                         26

<210> SEQ ID NO 20
<211> LENGTH: 23
<212> TYPE: DNA
<213> ORGANISM: Artificial Sequence
<220> FEATURE:
<223> OTHER INFORMATION: TF Primer

<400> SEQUENCE: 20
ggtcgcggtt cttgtttgtg gat                                            23

<210> SEQ ID NO 21
<211> LENGTH: 24
<212> TYPE: DNA
<213> ORGANISM: Artificial Sequence
<220> FEATURE:
<223> OTHER INFORMATION: TR Primer

<400> SEQUENCE: 21
gcaccttgaa gcgcatgaac tcct                                           24

<210> SEQ ID NO 22
<211> LENGTH: 85
<212> TYPE: DNA
<213> ORGANISM: Artificial Sequence
<220> FEATURE:
<223> OTHER INFORMATION: 7xNNK Primer
<220> FEATURE:
<221> NAME/KEY: MISC_FEATURE
<222> LOCATION: (38)..(39)
<223> OTHER INFORMATION: n indicates a, t, c or g
<220> FEATURE:
<221> NAME/KEY: MISC_FEATURE
<222> LOCATION: (41)..(42)
<223> OTHER INFORMATION: n indicates a, t, c or g
<220> FEATURE:
<221> NAME/KEY: MISC_FEATURE
<222> LOCATION: (44)..(45)
<223> OTHER INFORMATION: n indicates a, t, c or g
<220> FEATURE:
<221> NAME/KEY: MISC_FEATURE
<222> LOCATION: (47)..(48)
<223> OTHER INFORMATION: n indicates a, t, c or g
<220> FEATURE:
<221> NAME/KEY: MISC_FEATURE
<222> LOCATION: (50)..(51)
<223> OTHER INFORMATION: n indicates a, t, c or g
<220> FEATURE:
<221> NAME/KEY: MISC_FEATURE
<222> LOCATION: (53)..(54)
<223> OTHER INFORMATION: n indicates a, t, c or g
<220> FEATURE:
<221> NAME/KEY: MISC_FEATURE
<222> LOCATION: (56)..(57)
```

<223> OTHER INFORMATION: n indicates a, t, c or g

<400> SEQUENCE: 22
catcgaccaa tacttgtact atctctctag aactattnnk nnknnknnkn nknnknnkca    60
aacgctaaaa ttcagtgtgg ccgga    85

<210> SEQ ID NO 23
<211> LENGTH: 83
<212> TYPE: DNA
<213> ORGANISM: Artificial Sequence
<220> FEATURE:
<223> OTHER INFORMATION: 7xMNN Primer
<220> FEATURE:
<221> NAME/KEY: MISC_FEATURE
<222> LOCATION: (42)..(43)
<223> OTHER INFORMATION: n indicates a, t, c or g
<220> FEATURE:
<221> NAME/KEY: MISC_FEATURE
<222> LOCATION: (45)..(46)
<223> OTHER INFORMATION: n indicates a, t, c or g
<220> FEATURE:
<221> NAME/KEY: MISC_FEATURE
<222> LOCATION: (48)..(49)
<223> OTHER INFORMATION: n indicates a, t, c or g
<220> FEATURE:
<221> NAME/KEY: MISC_FEATURE
<222> LOCATION: (51)..(52)
<223> OTHER INFORMATION: n indicates a, t, c or g
<220> FEATURE:
<221> NAME/KEY: MISC_FEATURE
<222> LOCATION: (54)..(55)
<223> OTHER INFORMATION: n indicates a, t, c or g
<220> FEATURE:
<221> NAME/KEY: MISC_FEATURE
<222> LOCATION: (57)..(58)
<223> OTHER INFORMATION: n indicates a, t, c or g
<220> FEATURE:
<221> NAME/KEY: MISC_FEATURE
<222> LOCATION: (60)..(61)
<223> OTHER INFORMATION: n indicates a, t, c or g

<400> SEQUENCE: 23
gtattccttg gttttgaacc caaccggtct gcgcctgtgc mnnmnnmnnm nnmnnmnnmn    60
nttgggcact ctggtggttt gtg    83

<210> SEQ ID NO 24
<211> LENGTH: 21
<212> TYPE: DNA
<213> ORGANISM: Artificial Sequence
<220> FEATURE:
<223> OTHER INFORMATION: AAV varient

<400> SEQUENCE: 24
actttggcgg tgccttttaa g    21

<210> SEQ ID NO 25
<211> LENGTH: 21
<212> TYPE: DNA
<213> ORGANISM: Artificial Sequence
<220> FEATURE:
<223> OTHER INFORMATION: AAV varient

<400> SEQUENCE: 25
agtgtgagta agccttttt g    21

<210> SEQ ID NO 26
<211> LENGTH: 21
<212> TYPE: DNA
<213> ORGANISM: Artificial Sequence
<220> FEATURE:
<223> OTHER INFORMATION: AAV varient

<400> SEQUENCE: 26
tttacgttga cgacgcctaa g                                              21

<210> SEQ ID NO 27
<211> LENGTH: 21
<212> TYPE: DNA
<213> ORGANISM: Artificial Sequence
<220> FEATURE:
<223> OTHER INFORMATION: AAV varient

<400> SEQUENCE: 27
atgaatgcta cgaagaatgt g                                              21

<210> SEQ ID NO 28
<211> LENGTH: 7
<212> TYPE: PRT
<213> ORGANISM: Artificial Sequence
<220> FEATURE:
<223> OTHER INFORMATION: AAV varient

<400> SEQUENCE: 28

Ser Val Ser Lys Pro Phe Leu
1               5

<210> SEQ ID NO 29
<211> LENGTH: 7
<212> TYPE: PRT
<213> ORGANISM: Artificial Sequence
<220> FEATURE:
<223> OTHER INFORMATION: AAV varient

<400> SEQUENCE: 29

Phe Thr Leu Thr Thr Pro Lys
1               5

<210> SEQ ID NO 30
<211> LENGTH: 7
<212> TYPE: PRT
<213> ORGANISM: Artificial Sequence
<220> FEATURE:
<223> OTHER INFORMATION: AAV varient

<400> SEQUENCE: 30

Met Asn Ala Thr Lys Asn Val
1               5

<210> SEQ ID NO 31
<211> LENGTH: 6
<212> TYPE: PRT
<213> ORGANISM: Artificial Sequence
<220> FEATURE:
<223> OTHER INFORMATION: Target peptide

<400> SEQUENCE: 31

Leu Ala Val Pro Phe Lys
1               5

<210> SEQ ID NO 32
<211> LENGTH: 5
<212> TYPE: PRT
<213> ORGANISM: Artificial Sequence
<220> FEATURE:
<223> OTHER INFORMATION: Target peptide

```
<400> SEQUENCE: 32

Ala Val Pro Phe Lys
1               5

<210> SEQ ID NO 33
<211> LENGTH: 4
<212> TYPE: PRT
<213> ORGANISM: Artificial Sequence
<220> FEATURE:
<223> OTHER INFORMATION: Target peptide

<400> SEQUENCE: 33

Val Pro Phe Lys
1

<210> SEQ ID NO 34
<211> LENGTH: 6
<212> TYPE: PRT
<213> ORGANISM: Artificial Sequence
<220> FEATURE:
<223> OTHER INFORMATION: Target peptide

<400> SEQUENCE: 34

Thr Leu Ala Val Pro Phe
1               5

<210> SEQ ID NO 35
<211> LENGTH: 5
<212> TYPE: PRT
<213> ORGANISM: Artificial Sequence
<220> FEATURE:
<223> OTHER INFORMATION: Target peptide

<400> SEQUENCE: 35

Thr Leu Ala Val Pro
1               5

<210> SEQ ID NO 36
<211> LENGTH: 4
<212> TYPE: PRT
<213> ORGANISM: Artificial Sequence
<220> FEATURE:
<223> OTHER INFORMATION: Target peptide

<400> SEQUENCE: 36

Thr Leu Ala Val
1

<210> SEQ ID NO 37
<211> LENGTH: 49
<212> TYPE: DNA
<213> ORGANISM: Artificial Sequence
<220> FEATURE:
<223> OTHER INFORMATION: Primer

<400> SEQUENCE: 37
caaccggtaa tagttctaga gagatagtac aagtattggt cgatgagtg          49

<210> SEQ ID NO 38
<211> LENGTH: 46
<212> TYPE: DNA
<213> ORGANISM: Artificial Sequence
<220> FEATURE:
<223> OTHER INFORMATION: Primer

<400> SEQUENCE: 38
```

```
ctctctagaa ctattaccgg ttgggttcaa aaccaaggaa tacttc                         46

<210> SEQ ID NO 39
<211> LENGTH: 33
<212> TYPE: DNA
<213> ORGANISM: Artificial Sequence
<220> FEATURE:
<223> OTHER INFORMATION: Primer

<400> SEQUENCE: 39
gtccaaactc atcaatgtat cttatcatgt ctg                                      33

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
gagtcaatct ggaagttaac catcggca                                            28

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gatggttaac ttccagattg actcg                                               25

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
gactactcta caggcctctt ctatccag                                            28

<210> SEQ ID NO 43
<211> LENGTH: 28
<212> TYPE: DNA
<213> ORGANISM: Artificial Sequence
<220> FEATURE:
<223> OTHER INFORMATION: Primer

<400> SEQUENCE: 43
gatagaagag gcctgtagag tagtctcc                                            28

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
catcggcacc ttagttattg tctg                                                24

<210> SEQ ID NO 45
<211> LENGTH: 28
<212> TYPE: DNA
<213> ORGANISM: Artificial Sequence
```

```
<220> FEATURE:
<223> OTHER INFORMATION: Primer

<400> SEQUENCE: 45
gacaataact aaggtgccga tggagtgg                                          28

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46
gtctctgccg gtaccttgtt tgccaaaaat taaagatcca                             40

<210> SEQ ID NO 47
<211> LENGTH: 39
<212> TYPE: DNA
<213> ORGANISM: Artificial Sequence
<220> FEATURE:
<223> OTHER INFORMATION: Primer

<400> SEQUENCE: 47
gcaaacaagg taccggcaga gacaacgtgg atgcggaca                              39

<210> SEQ ID NO 48
<211> LENGTH: 21
<212> TYPE: DNA
<213> ORGANISM: Artificial Sequence
<220> FEATURE:
<223> OTHER INFORMATION: Varient G2B-13

<400> SEQUENCE: 48
cagtcgtcgc agacgcctag g                                                 21

<210> SEQ ID NO 49
<211> LENGTH: 21
<212> TYPE: DNA
<213> ORGANISM: Artificial Sequence
<220> FEATURE:
<223> OTHER INFORMATION: Varient G2B-26

<400> SEQUENCE: 49
actttggcgg tgccttttaa g                                                 21

<210> SEQ ID NO 50
<211> LENGTH: 21
<212> TYPE: DNA
<213> ORGANISM: Artificial Sequence
<220> FEATURE:
<223> OTHER INFORMATION: Varient TH 1-32

<400> SEQUENCE: 50
attctgggga ctggtacttc g                                                 21

<210> SEQ ID NO 51
<211> LENGTH: 21
<212> TYPE: DNA
<213> ORGANISM: Artificial Sequence
<220> FEATURE:
<223> OTHER INFORMATION: Varient TH 1-32

<400> SEQUENCE: 51
acgcggacta atcctgaggc t                                                 21
```

-continued

```
<210> SEQ ID NO 52
<211> LENGTH: 21
<212> TYPE: DNA
<213> ORGANISM: Artificial Sequence
<220> FEATURE:
<223> OTHER INFORMATION: Varient TH 1-35

<400> SEQUENCE: 52
attctgggga ctggtacttc g                                              21

<210> SEQ ID NO 53
<211> LENGTH: 21
<212> TYPE: DNA
<213> ORGANISM: Artificial Sequence
<220> FEATURE:
<223> OTHER INFORMATION: Varient TH 1-35

<400> SEQUENCE: 53
aatgggggga ctagtagttc t                                              21

<210> SEQ ID NO 54
<211> LENGTH: 7
<212> TYPE: PRT
<213> ORGANISM: Artificial Sequence
<220> FEATURE:
<223> OTHER INFORMATION: Varient G2B-13

<400> SEQUENCE: 54

Gln Ser Ser Gln Thr Pro Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Varient TH 1-32

<400> SEQUENCE: 55

Ile Leu Gly Thr Gly Thr Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Varient TH 1-32

<400> SEQUENCE: 56

Thr Arg Thr Asn Pro Glu Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Varient TH 1-35

<400> SEQUENCE: 57

Ile Leu Gly Thr Gly Thr Ser
1               5

<210> SEQ ID NO 58
<211> LENGTH: 7
```

```
<212> TYPE: PRT
<213> ORGANISM: Artificial Sequence
<220> FEATURE:
<223> OTHER INFORMATION: Varient TH 1-35

<400> SEQUENCE: 58

Asn Gly Gly Thr Ser Ser Ser
1               5

<210> SEQ ID NO 59
<211> LENGTH: 21
<212> TYPE: DNA
<213> ORGANISM: Artificial Sequence
<220> FEATURE:
<223> OTHER INFORMATION: Varient PHP-A

<400> SEQUENCE: 59
tatactttgt cgcagggttg g                                              21

<210> SEQ ID NO 60
<211> LENGTH: 7
<212> TYPE: PRT
<213> ORGANISM: Artificial Sequence
<220> FEATURE:
<223> OTHER INFORMATION: Varient PHP-A

<400> SEQUENCE: 60

Tyr Thr Leu Ser Gln Gly Trp
1               5
```